US012371675B2

(12) United States Patent
Yakunin et al.

(10) Patent No.: US 12,371,675 B2
(45) Date of Patent: Jul. 29, 2025

(54) PROCESS AND MICROORGANISM FOR SYNTHESIS OF ADIPIC ACID FROM CARBOXYLIC ACIDS

(71) Applicant: THE GOVERNING COUNCIL OF THE UNIVERSITY OF TORONTO, Toronto (CA)

(72) Inventors: Alexander Yakunin, Toronto (CA); Anna Khusnutdinova, Toronto (CA); Jeong Chan Joo, Toronto (CA); Radhakrishnan Mahadevan, Toronto (CA)

(73) Assignee: The Governing Council of the University of Toronto, Toronto (CA)

( * ) Notice: Subject to any disclaimer, the term of this patent is extended or adjusted under 35 U.S.C. 154(b) by 355 days.

(21) Appl. No.: 17/479,722

(22) Filed: Sep. 20, 2021

(65) Prior Publication Data

US 2022/0041998 A1   Feb. 10, 2022

Related U.S. Application Data

(63) Continuation of application No. 15/741,484, filed as application No. PCT/CA2016/050781 on Jul. 4, 2016, now Pat. No. 11,124,778.

(60) Provisional application No. 62/188,591, filed on Jul. 3, 2015.

(30) Foreign Application Priority Data

Jul. 3, 2015  (CA) ................................ CA 2897454

(51) Int. Cl.
*C12N 9/00* (2006.01)
*C12N 9/02* (2006.01)
*C12N 15/70* (2006.01)
*C12P 7/18* (2006.01)
*C12P 7/24* (2006.01)
*C12P 7/42* (2006.01)
*C12P 7/44* (2006.01)
*C12P 13/00* (2006.01)

(52) U.S. Cl.
CPC ............ *C12N 9/001* (2013.01); *C12N 15/70* (2013.01); *C12P 7/18* (2013.01); *C12P 7/24* (2013.01); *C12P 7/42* (2013.01); *C12P 7/44* (2013.01); *C12P 13/001* (2013.01); *C12Y 103/01031* (2013.01)

(58) Field of Classification Search
CPC .. C12P 7/42; C12P 13/001; C12P 7/24; C12P 13/02; C12P 41/002; C12P 7/26; C12N 9/0006; C12N 9/16; C12N 9/001; C12N 9/0016; C12Y 102/99006
USPC ......................................................... 435/146
See application file for complete search history.

(56) References Cited

U.S. PATENT DOCUMENTS

| | | |
|---|---|---|
| 8,097,439 B2 | 1/2012 | Alibhai |
| 11,124,778 B2 | 9/2021 | Yakunin et al. |
| 2011/0129899 A1 | 6/2011 | Haselbeck et al. |
| 2015/0167028 A1 | 6/2015 | Burgard et al. |
| 2020/0080064 A1 | 3/2020 | Yakunin et al. |

FOREIGN PATENT DOCUMENTS

| | | |
|---|---|---|
| CA | 2895867 A1 | 6/2014 |
| WO | 2005/005648 A1 | 1/2005 |
| WO | 2010/042664 A2 | 4/2010 |
| WO | 2017/004709 A1 | 1/2017 |

OTHER PUBLICATIONS

Genbank, "Fatty-acid-CoA ligase FadD9 [Mycolicibacterium smegmatis MC2 155]", Accession AFP42026; (Jan. 31, 2014) Obtained from https://www.ncbi.nlm.nih.gov/protein/AFP42026.
Bao et al. "2-enoate reductase [Clostridium acetobutylicum DSM 1731]," GenBank Accession No. AE132805.1, Feb. 18, 2015.
Bart et al., "Transiting from Adipic Acid to Bioadipic Acid. Part II. Biosynthetic Pathways," I & EC Research, pp. 567-576, 2015.
Biocatalysis, "Changing Paradigms in Catalysis, "Gordon Research Conference, Smithfield, Rhode Island, 10 pages, Jul. 6-11, 2014.
Devos, D. and Valencia, A., "Practical Limits of Function Prediction," Proteins: Structure, Function, and Genetics, vol. 41; 98-107 (2000).
Gao et al. "Biochemical characterization and substrate profiling of a new NADH-dependent enoate reductase from Lactobacillus casei," Enzyme Microb Technol, vol. 51, No. 1, pp. 26-34, Jun. 10, 2012.
GenBank No. AAK81302, "2-enoate reductase (Two distinct NAD(FAD)-dependent dehydrogenase domains) [Clostridium acetobutylicum ATCC 824]," Jan. 30, 2014, 2 pages.

(Continued)

*Primary Examiner* — Robert B Mondesi
*Assistant Examiner* — Mohammad Y Meah
(74) *Attorney, Agent, or Firm* — Hamilton, Brook, Smith & Reynolds, P.C.

(57) ABSTRACT

A method for biosynthesis of polymer precursors, including, adipic acid, 1,6-hexanediol, 6-hydroxyhexanoic and 6-aminocaproic acids from carboxylic acids is provided. A method for biosynthesis of adipic acid from six-carbon dicarboxylic acids having α, β-enoate reductase activity by treatment with an enzyme is provided. The biocatalytic conversion of aliphatic and hydroxycarboxylic acids to corresponding aldehydes, alcohols, and amines using novel carboxylate reductases, aldehyde reductases, and aminotransferases is described. Also provided are genetically engineered microorganisms for use in the biosynthetic processes.

20 Claims, 20 Drawing Sheets

Specification includes a Sequence Listing.

(56) References Cited

OTHER PUBLICATIONS

Kisselev, L., "Polypeptide Release Factors in Prokaryotes and Eukaryotes: Same Function, Different Structure," Structure, vol. 10; 2 pages (2002).

Nolling et al. 2-enoate reductase (Two distinct NAD(FAD)-dependent dehydrogenase domains) [Clostridium acetobutylicum ATCC824], GenBank Accession No. AAK81302.1, Jan. 30, 2014.

Rohdich et al. "Enoate reductase of Clostridia cloning, sequencing and expression," Journal of Biological Chemistry, vol. 276, No. 8, pp. 5779-5787, Feb. 23, 2001.

Uniparc, UPI000404C9FD, XP-002787549, Sequence, 2 pages, dated Dec. 18, 2018, retrieved from: https://www.uniprot.org/uniparc/UP1000404C9FD.

Witkowski, J.C. and Lesk, A.M., "Prediction of protein function from protein sequence and structure," Quarterly Reviews of Biophysics, vol. 36; No. 3; 307-340 (2003).

Whisstock, A. et al., "Conversion of a B-Ketoacyl Synthase to a Malonyl Decarboxylase by Replacement of the Active-Site Cysteine with Glutamine," Biochemistry, vol. 38; 11643-11650 (1999).

Yu et al., "Direct Biosynthesis of Adipic Acid From a Synthetic Pathway in Recombinant *Escherichia coli*," Biothechnology and Bioengineering, col. 111, No. 12, pp. 2580-2586, Dec. 2014.

International Preliminary Report on Patentability for International Application No. PCT/CA2016/050781, entitled "Process and Microorganism for Synthesis of Adipic Acid From Carboxylic Acids," mailed Jan. 18, 2018.

International Search Report and Written Opinion for International Application No. PCT/CA2016/050781, entitled "Process and Microorganism for Synthesis of Adipic Acid From Carboxylic Acids," mailed Oct. 19, 2016.

Non-Final Office Action for U.S. Appl. No. 15/741,484, mailed Nov. 3, 2020.

Notice of Allowance for U.S. Appl. No. 15/741,484, mailed May 19, 2021.

He, A. et al., "Nocardia sp. Carboxylic Acid Reductase: Cloning, Expression, and Characterization of a New Aldehyde Oxidoreductase Family," Applied and Environmental Microbiology, vol. 70; No. 3; 1874-1881 (2004).

Khusnutdinova, A.N. et al., "Exploring bacterial carboxylate reductases for the Reduction of Bifunctional Carboxylic Acids," Biotechnol., vol. 12; No. 11; 25 pages (2017).

PROCESS AND MICROORGANISM FOR SYNTHESIS OF ADIPIC ACID FROM CARBOXYLIC ACIDS

RELATED APPLICATION(S)

This application is a Continuation of U.S. application Ser. No. 15/741,484, filed on Jul. 4, 2016, which is the U.S. National Stage of International Application No. PCT/CA2016/050781, filed Jul. 4, 2016, which designates the U.S., published in English, and claims the benefit of U.S. Provisional Application No. 62/188,591, filed Jul. 3, 2015, and which claims priority under 35 U.S.C. §§ 119 or 365(c) to Canadian Application No. 2897454, filed Jul. 3, 2015. The entire teachings of the above applications are incorporated herein by reference.

INCORPORATION BY REFERENCE OF MATERIAL IN ASCII TEXT FILE

This application incorporates by reference the Sequence Listing contained in the following ASCII text file submitted on Jan. 2, 2018 in U.S. application Ser. No. 15/741,484:
  a) File name: 55331000001SEQLISTING.TXT; created Jan. 2, 2018, 474,634 bytes in size.

TECHNICAL FIELD

The present application includes as part of its description a sequence listing that includes 111 sequences and which was filed with this application in electronic form and this sequence listing is incorporated into the present application in its entirety.

This disclosure relates to enzymatic synthesis of polymer precursors from carboxylic acids.

BACKGROUND OF THE ART

Mono and dicarboxylic acids such as adipic, fumaric, glucaric, and succinic acids, diamines (cadaverine, putrescine, hexamethylenediamine), and diols (propanediols and butanediols) are the most common polymer precursors used in condensation polymerization reactions in the chemical industry. Polymeric materials find diverse application in a variety of industries, but most of them are still produced from petroleum.

Adipic acid is the most important commercial aliphatic dicarboxylic acid used for the synthesis of Nylon-6,6 polyamide (~$6 billion global market). 2.6 Million metric tonnes per year of adipic acid is produced from petroleum-derived benzene but known chemical processes can produce toxic by-products such as nitrous oxide ($N_2O$).

Other important polymer precursors typically manufactured from petroleum include 1,4-butanediol, 1,6-hexanediol, 6-hydroxyhexanoic and 6-aminocaproic acids.

There is a need for sustainable production of commodity chemicals from renewable biomass instead of petroleum due to growing concerns over climate change, energy security, and human health.

BRIEF SUMMARY

In one aspect, there is provided a host microorganism in which exogenous nucleic acids are introduced, wherein said exogenous nucleic acids encode an enzyme having α,β-enoate reductase activity, wherein the enzyme comprises an amino acid sequence of SEQ ID NO: 1 or active fragment or homologue thereof. In one embodiment, the enzyme comprises amino acids (363) to (382) of SEQ ID NO: 1. In one embodiment, the enzyme comprises an amino acid sequence that is at least 80%, 85%, 90%, 95% or 100% identical to the amino acid sequence of SEQ ID NO: 1.

In another aspect, there is provided a host microorganism in which exogenous nucleic acids are introduced, wherein said exogenous nucleic acids encode an enzyme having α,β-enoate reductase activity, wherein the enzyme comprises an amino acid sequence of SEQ ID NO: 2 or active fragment or homologue thereof.

In one embodiment, the enzyme having α,β-enoate reductase activity is derived from a microorganism of the genus *Bacillus, Clostridium*, or *Moorella*. In one embodiment, the microorganism is *Bacillus coagulans*.

In one embodiment, the host microorganism is *Escherichia coli*.

Also provided is a process for producing adipic acid comprising culturing a host microorganism as described above under conditions and for a sufficient period of time to produce adipic acid.

Also provided is a process for producing adipic acid comprising enzymatically converting a 6-carbon unsaturated dicarboxylic acid to adipic acid using a 2-enoate reductase. In one embodiment, the enzyme comprises the amino acid sequence of SEQ ID NO:1 or 2 or is a fragment or homologue of an enzyme comprising the amino acid sequence of SEQ ID NO: 1 or 2.

In one embodiment, the unsaturated 6-carbon dicarboxylic acid is muconic acid or 2-hexenedioic acid. In one embodiment, the 6-carbon unsaturated dicarboxylic acid is produced from biosynthetic methods.

In one embodiment, the process comprises culturing a host microorganism as described above under conditions and for a sufficient period of time to produce adipic acid.

In one embodiment of the process, the culture medium is substantially aerobic.

Also provided is a composition comprising a host microorganism as described above and muconic acid and/or 2-hexenedioic acid.

In another aspect, there is provided a host microorganism in which exogenous nucleic acids are introduced, wherein said exogenous nucleic acids encode an enzyme having carboxylate reductase activity, wherein the enzyme comprises an amino acid sequence of SEQ ID NO: 36 or active fragment or homologue thereof. In one embodiment, the enzyme comprises an amino acid sequence that is at least 80%, 85%, 90%, 95% or 100% identical to the amino acid sequence of SEQ ID NO:36. In one embodiment, the host microorganism is *Escherichia coli*.

Also provided, is a host microorganism comprising exogenous nucleic acids encoding an enzyme having carboxylate reductase activity wherein the enzyme comprises an amino acid sequence of any one of SEQ ID NOs: 35, 36, 37, 38 or 70 or active fragment or homologue thereof. In one embodiment, the host microorganism further co-expresses a gene encoding a phosphopantetheinyl transferase.

Also provided is a host microorganism comprising exogenous nucleic acids encoding an enzyme having aldehyde reductase activity, wherein the enzyme comprises an amino acid sequence of NOs:40-52, preferably an amino acid of one of SEQ ID NOs:47, 43, 50, 45, 46 or 52 or active fragment or homologue thereof.

Also provided is a host microorganism comprising exogenous nucleic acids encoding an enzyme having aminotransferase activity, wherein the enzyme comprises an amino acid sequence of one of SEQ ID NOs:53-65, preferably one of SEQ ID NOs: 53, 59, 55, 58 or 60 or active fragment or homologue thereof.

In another aspect, there is provided a process for producing a short chain aldehyde comprising enzymatically converting a carboxylic group of a C5-C8 saturated di-carboxylic acid to an aldehyde using a carboxylate reductase. In one embodiment, the carboxylate reductase comprises an amino acid sequence of any one of SEQ ID NOs: 35, 36, 37, 38 or 70 or active fragment or homologue thereof.

The process may further include enzymatically converting the aldehyde group to a hydroxy group using an aldehyde reductase. In one embodiment, the aldehyde reductase comprises an amino acid sequence of one of SEQ ID NOs:40-52, preferably an amino acid of one of SEQ ID NOs:47, 43, 50, 45, 46 or 52 or active fragment or homologue thereof.

The process can further include enzymatically coverting a second carboxylic acid group to an aldehyde using a carboxylate reductase, and optionally enzymatically converting said aldehyde to a hydroxyl group using an aldehyde reductase.

In another embodiment, the process further includes enzymatically converting the aldehyde to an amine using an aminotransferase. In one embodiment, the aminotransferase comprises an amino acid sequence of one of SEQ ID NOs:53-65, preferably one of SEQ ID NOs: 53, 59, 55, 58 or 60 or active fragment or homologue thereof. The process can further include enzymatically coverting a second carboxylic acid group to an aldehyde using a carboxylate reductase, and optionally enzymatically converting said aldehyde to an amine using an aminotransferase.

In the processes described above, the di-carboxylic acid may be adipic acid.

In one embodiment, the aldehyde is 6-oxohexanoic acid and the product of the enzymatic conversion is 6-hydroxyhexanoic acid.

In one embodiment, the product is 1,6-hexanediol.

In one embodiment, the product is 6-aminocaproic acid.

In one embodiment, the product is hexamethylenediamine.

In one embodiment, the di-carboxylic acid is adipic acid produced by a process described above.

Also provided is a process for producing 6-hydroxyhexanoic acid comprising culturing a host microorganism as described above under conditions and for a sufficient period of time to produce 6-hydroxyhexanoic acid.

Also provided is a process for producing 1,6-hexanediol comprising culturing a host microorganism as described above under conditions and for a sufficient period of time to produce 1,6-hexanediol.

Also provided is a process for producing 6-aminocaproic acid comprising culturing a host microorganism as described above under conditions and for a sufficient period of time to produce 6-aminocaproic acid.

Also provided is a process for producing hexamethylenediamine comprising culturing a host microorganism as described above under conditions and for a sufficient period of time to produce hexamethylenediamine.

Also provided is a process for producing 1,4-butanediol comprising culturing a host microorganism comprising exogenous nucleic acids encoding an enzyme having carboxylate reductase activity wherein the enzyme comprises an amino acid sequence of SEQ ID NO: 36 or active fragment or homologue thereof under conditions and for a sufficient period of time to produce 1,4-butanediol. In one embodiment, the enzyme comprises an amino acid sequence that is at least 80%, 85%, 90%, 95% or 100% identical to the amino acid sequence of SEQ ID NO: 36.

DETAILED DESCRIPTION

As used herein "enzyme" includes proteins produced by a cell capable of catalyzing biochemical reactions. Further, unless context dictates otherwise, as used herein "enzyme" includes protein fragments that retain the relevant catalytic activity, and may include artificial enzymes synthesized to retain the relevant catalytic activity.

In one aspect, the present disclosure provides novel enzymes for producing polymer precursors from renewable feedstocks and microorganisms for producing the same.

In one aspect, the present disclosure provides novel enzymes capable of reducing C=C bonds of unsaturated dicarboxylic acids and microorganisms for producing the same.

In one aspect, the present disclosure provides enzymes for converting hydroxycarboxylic acids, which may be produced from unsaturated dicarboxylic acids as described herein, to corresponding aldehydes, alcohols, and amines.

Figure 1:
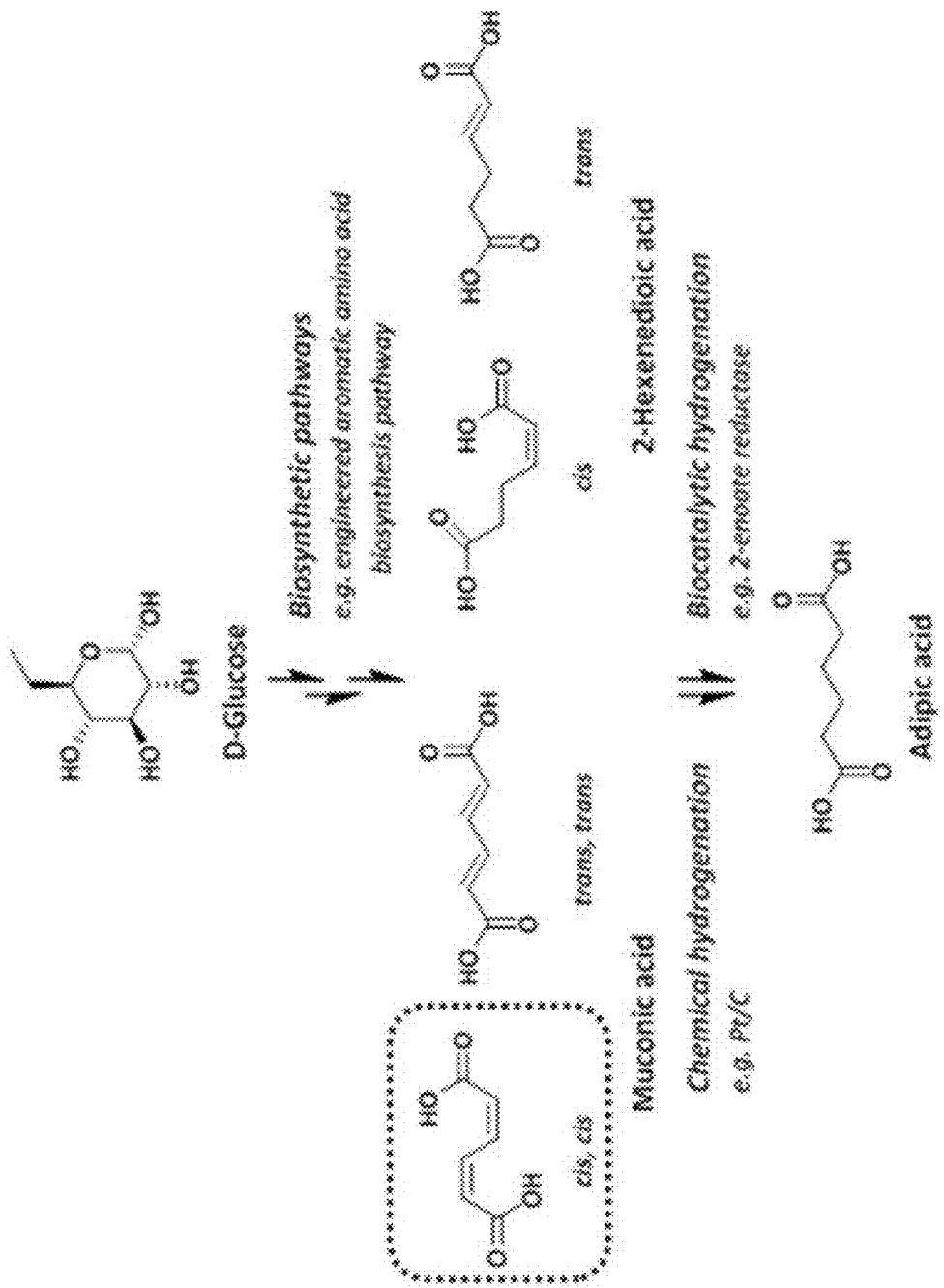
FIG. 1 shows chemocatalytic and biocatalytic hydrogenation of unsaturated six-carbon dicarboxylic acids into adipic acid using 2-enoate reductases (EREDs).

In one aspect, the present disclosure provides processes for producing cells and organisms for the biochemical synthesis of adipic acid from unsaturated six-carbon dicarboxylic acids using biocatalysts having hydrogenation activity toward α,β-enoate. In one embodiment, adipic acid can be produced from muconic acid or 2-hexenedioc acid using 2-enoate reductases as illustrated in FIG. 1.

In one embodiment, the biochemical synthesis of adipic acid is performed in a substantially aerobic environment.

In another aspect, the present disclosure provides processes for the enzymatic conversion of mono- and di-carboxylic acids to corresponding aldehydes, alcohols and amines.

Figure 2:
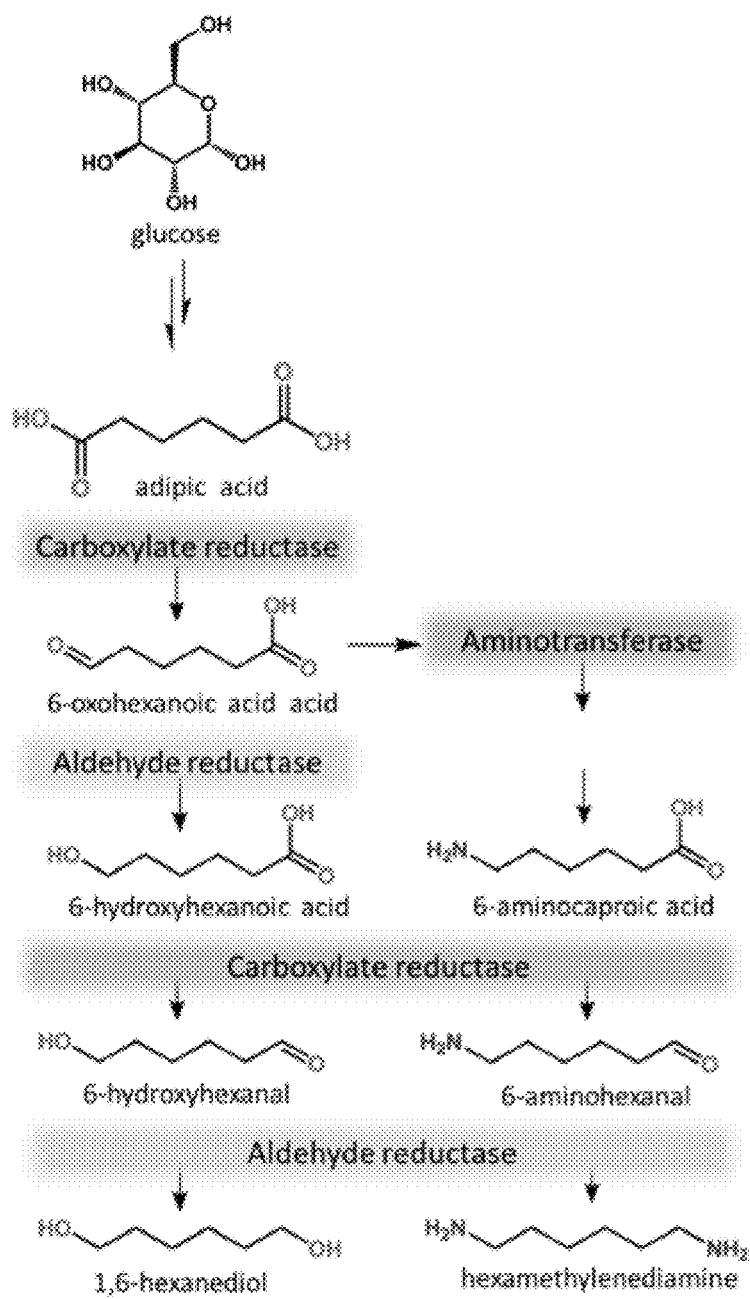
FIG. 2 shows enzymes and cascade enzymatic reactions for the bioconversion of carboxylic acids to 1,6-hexanediol, 6-hydroxyhexanoic and 6-aminocaproic acids.

In one aspect, the present disclosure provides processes for the enzymatic conversion of short chain saturated mono- and di-carboxylic acids, in one embodiment C3 to C8 saturated mono- and di-carboxylic acids, to corresponding aldehydes, alcohols and amines. In one embodiment, the carboxylic acid is a C5 to C7 dicarboxylic acid. In one embodiment, the carboxylic acid is a $C_6$ di-carboxylic acid, in one embodiment adipic acid. The product of the enzymatic conversion of adipic acid may be1-6-hexanediol, 6-hydroxyhexanoic and 6-aminocarpoic acids, as shown in FIG. 2.

Figure 3:
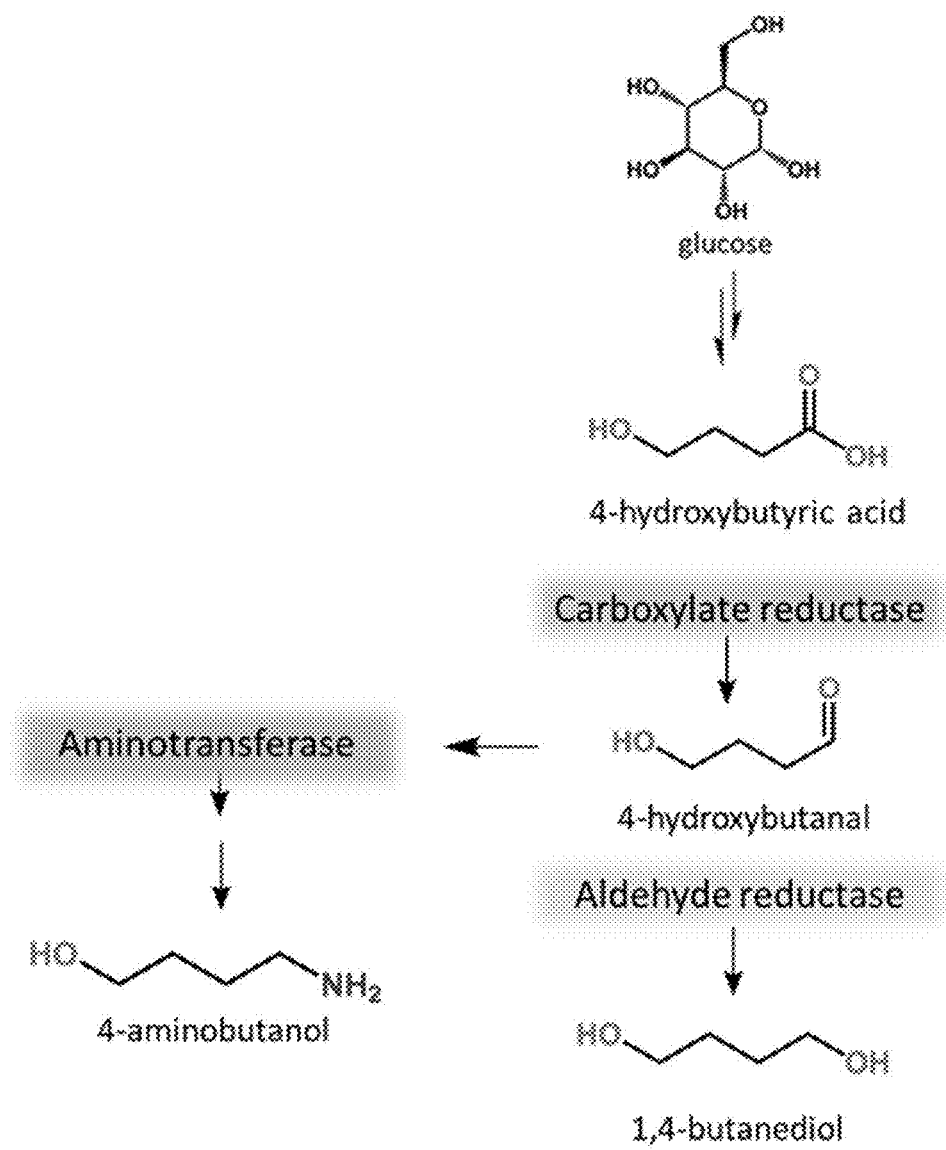
FIG. 3 shows enzymes and cascade enzymatic reactions for the bioconversion of 4-hydroxybutyric acid to 1,4-butanediol and 4-aminobutanol.
Figure 4:
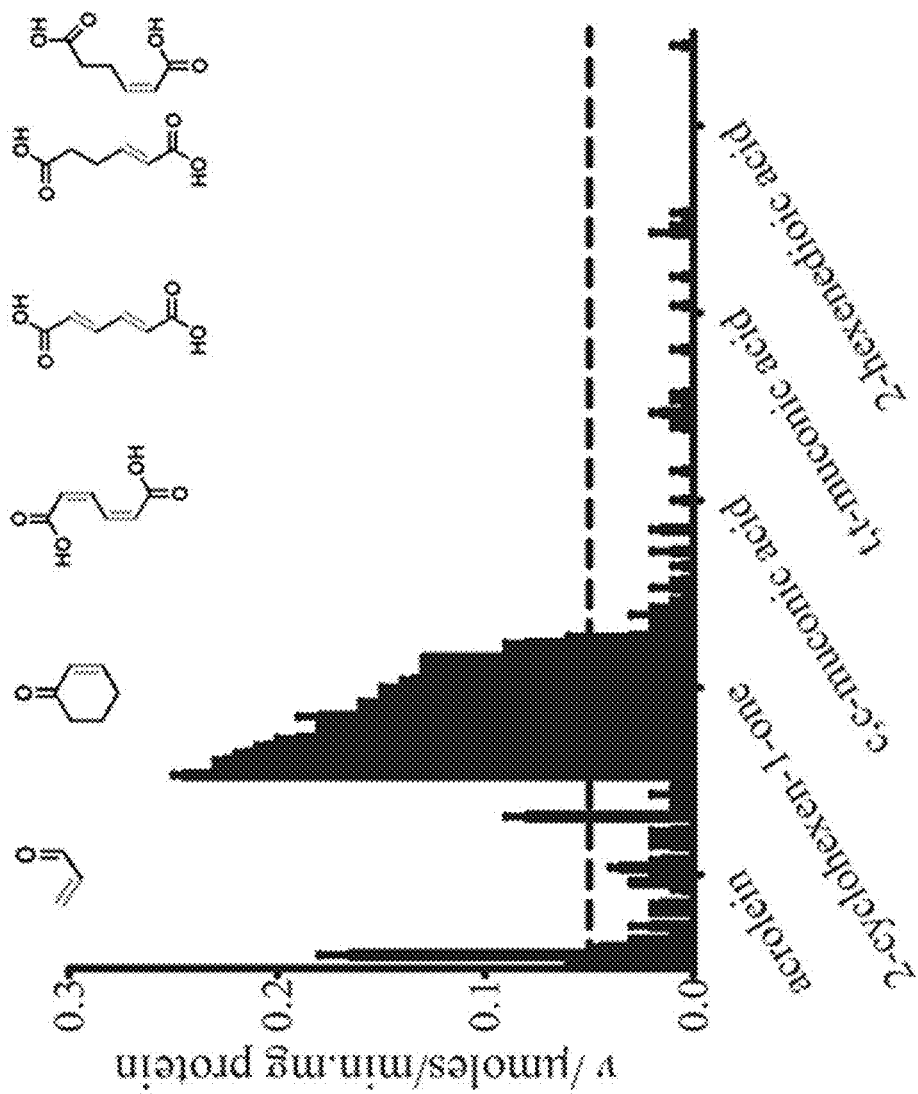
FIG. 4 shows activity profiles of 25 Old Yellow Enzymes (OYEs; EC 1.6.99.1). The cut-off value for enzyme activity of OYE is 0.05 U/mg protein. 1 mM of substrates, 0.25 mM of NADPH, and 2.5 µg of proteins were used in the reaction mixture (potassium phosphate 100 mM and pH 7.0). A mixture of cis- and trans-isomers of 2-hexenedioic acid was used as a substrate.

In another embodiment, there is described the enzymatic conversion of a monocarboxylic acid, which may be substituted with a terminal hydroxy group, in one embodiment, the carboxylic acid is a C3 or C4 monoacid, in one embodiment 4-hydroxybutyric acid (4-hydroxybutanoic acid) as shown in FIG. 3 to a corresponding aldehyde 4-hydroxybutanal, which may be enzymatically converted to 1,4-butanediol or 4-aminobutanol by aldehyde reductases and aminotransferases as described herein The enzymatic conversion of the carboxylic acids to corresponding aldehydes, alcohols and amines employ novel carboxylate reductases (CARs), aldehyde reductases (ARs) and/or aminotransferases (ATs). Also provided are processes for producing cells and organisms for the biochemical synthesis of these aldehydes, alcohols and amines.

There have been tremendous efforts to develop sustainable production of commodity chemicals from renewable biomass instead of petroleum due to growing concerns over climate change, energy security, and human health.

Production of polymer precursors using renewable feedstocks such as sugars, starch, lignin, cellulose and hemicellulose can help to overcome the depletion of fossil resources, without changing current technological processes of polymer synthesis. Recent development of engineered strains for dicarboxylic acids production using engineered shikimate [Curran K. A., Leavitt J. M., Karim A. S., Alper H. S. Metabolic engineering of muconic acid production in *Saccharomyces cerevisiae*. Metab. Eng. 15, 55-66 (2013)] or ketoadipate, reversed β-oxidation pathway [Yu J L., Xia X. X., Zhong J. J., Qian Z. G. Direct biosynthesis of adipic acid from a synthetic pathway in recombinant *Escherichia coli*. Biotechnol Bioeng, 111, 2580-2586 (2014)] enabled accumulating of fatty acids.

Bio-based adipic acid has been produced from glucose via sequential chemical reactions i.e., oxidation of glucose into glucaric acid and hydrodeoxygenation of glucaric acid into adipic acid, which can be only catalyzed by chemical catalysts (US20100317823 A1). Bio-based production of adipic acid has been also attempted using metabolic engineering approaches. Industrial microorganisms such as *E. coli* or *Saccharomyces cerevisiae* with engineered aromatic amino acid biosynthesis pathway can produce cis,cis-muconic acid from glucose, which is then hydrogenated into adipic acid using chemical catalysts (see e.g. Niu, W., Draths, K. M. & Frost, J. W. Benzene-free synthesis of adipic acid. Biotechnology Progress 18, 201-211 (2002).) However, a biosynthetic pathway to produce adipic acid from 2-hexenedioic acid or muconic acid has not been experimentally demonstrated.

The present disclosure provides for the biochemical synthesis of adipic acid from unsaturated six-carbon dicarboxylic acids using biocatalysts having hydrogenation activity toward α,β-enoate. In one embodiment, adipic acid is produced from muconic acid or 2-hexenedioc acid using 2-enoate reductases (ERED; EC 1.3.1.31). However, there are several known pathways to produce muconic acid and 2-hexenedioic acid starting from common renewable feedstocks, and in one embodiment, one or more of such pathways in suitably introduced into a host microorganism.

The present disclosure also provides for the biochemical synthesis of aldehydes, alcohols and amines hydroxycarboxylic acids using biocatalysts using novel carboxylate reductases (EC 1.2.1.30), aldehyde reductases (EC 1.1.1.-), and/or aminotransferases (EC 2.6.1.48; EC 2.6.1.19). In one embodiment, 1-6-hexanediol is produced from 6-hydroxyhexanal using AR (EC 1.1.1.-). In one embodiment, 6-hydroxyhexanoic is produced from 6-oxohexanoic acid using AR (EC 1.1.1.-). In one embodiment, 6-aminocarpoic acid is produced from 6-oxohexanoic acid using AT (EC 2.6.1.48; EC 2.6.1.19).

There have been efforts to produce 1,4-butanediol using the Carboxylic acid reductases as described in Burke et al. 2013 WO2013184602A2, in which CARs from *Nocardia iowensis, Mycobacterium smegmatis* mc(2)155, *Mycobacterium avium* subspecies paratuberculosis K-10, *Mycobacterium marinum* M (designated 892) were identified.

For the production of 1,4-butanediol, carboxylic reductases may be integrated into a 4-hydroxybutric acid producing host. 4 hydroxybuytric acid can be made either from 2-ketoglutarate through decarboxylation to succinate semialdehyde followed by reduction or from 4-aminobutyrate and 2-ketoglutarate via transamination resulting in 4-hydroxybutyrate and L-glutamate [Yim et al., Metabolic engineering of *Escherichia coli* for direct production of 1,4-butanediol. Nat Chem Biol. 2011 May 22; 7(7):445-52].

The expression "derived from" in relation to an enzyme or (poly)peptide denotes that the enzyme or poly(peptide) was isolated from a (micro)organism or that it includes all or a biologically active part of the amino acid sequence of an enzyme or (poly)peptide isolated or characterized from such a (micro)organism.

In certain embodiments, EREDs as provided herein are derived from organisms of the genus *Bacillus, Clostridium* or *Moorella*. In one embodiment, the ERED is derived from the species *Clostridium acetobutylicum*. In one embodiment, the ERED is derived from the genus *Bacillus*. In one embodiment, the ERED is derived from the species *Bacillus coagulans*.

In one embodiment, the ERED comprises or consists of the amino acid of SEQ ID NO: 1 or an active fragment or a homologue thereof.

In another embodiment, the ERED comprises or consists of the amino acid of SEQ ID NO: 2 or an active fragment or a homologue thereof.

In one aspect, the enzyme is at least 80%, 85%, 90%, 95% or 100% identical to the amino acid sequence of SEQ ID NO: 1 or SEQ ID NO: 2.

In certain embodiments, CARs as provided herein are derived from organisms of the genus *Mycobacterium*. In one embodiment, the CAR is derived from the species *Mycobacterium abscessus*. In one embodiment, the CAR is derived from the species *Mycobacterium* paratuberculosis. In one embodiment, the CAR is derived from the species *Mycobacterium smegmatis*.

In one embodiment, the CAR used comprises or consists of an amino acid of one of SEQ ID NOs: 35, 36, 37, 38 or 70 or an active fragment or a homologue thereof.

In one aspect, the enzyme is at least 80%, 85%, 90%, 95% or 100% identical to the amino acid sequence of one of SEQ ID NOs: 35, 36, 37, 38 or 70.

The present inventors surprisingly found that MAB_4714c from *M. abscessus* DSM444196 has high activity with respect to the conversion of both 4-hydroxybutyric acid and adipic acid to 4-hydroxybutanal and 6-oxohexanoic acid, respectively.

In one embodiment, the CAR used comprises or consists of an amino acid of SEQ ID NO: 36 or an active fragment or a homologue thereof.

In one embodiment, the enzyme is at least 80%, 85%, 90%, 95% or 100% identical to the amino acid sequence of SEQ ID NO: 36.

In one embodiment, an active fragment or homologue of a CAR as described herein includes the phosphopantetheine binding motif:

F-X(2)-L-G-G-D-S-X(2)-A wherein X(2) is any two amino acids.

Previously it has been shown that post-translational phosphopantetheinylation of CARs is required for their activity [P. Venkitasubramanian et al. Reduction of Carboxylic Acids by *Nocardia* Aldehyde Oxidoreductase Requires a Phosphopantetheinylated Enzyme, Jan. 5, 2007 *The Journal of Biological Chemistry*. 282, 478-485.]. Thus in one embodiment, CARs as described herein are co-expressed with a gene encoding a phosphopantetheinyl transferase. Suitable phosphopantetheinyl transferase genes will be known to those of skill in the art. Suitable phosphopantetheinyl transferase genes include e.g. BSU03570 and entD from *Bacillus subtilis* and *E. coli* K-12 genomic DNA.

In certain embodiments, ARs as provided herein are derived from organisms of the genus *Pseudomonas, Rhodococcus, Streptomyces* or *Thermotoga*. In one embodiment, the AR is derived from the species *Pseudomonas aeruginosa*. In one embodiment, the AR is derived from the species *Pseudomonas putida*. In one embodiment, the AR is derived from the species *Pseudomonas syringae*. In one embodiment, the AR is derived from the species *Rhodococcus jostii*. In one embodiment, the AR is derived from the species *Streptomyces coelicolor*. In one embodiment, the AR is derived from the species *Thermotoga maritima*.

In one embodiment, the AR comprises or consists of an amino acid of one of SEQ ID NOs: SEQ ID NOs:40-52 or an active fragment or a homologue thereof. In one aspect, the enzyme is at least 80%, 85%, 90%, 95% or 100% identical to the amino acid sequence of one of SEQ ID NOs: 40-52.

In one embodiment, the AR comprises or consists of an amino acid of one of SEQ ID NOs: SEQ ID NOs:47, 43, 50, 45, 46 or 52 or an active fragment or a homologue thereof.

In one aspect, the enzyme is at least 80%, 85%, 90%, 95% or 100% identical to the amino acid sequence of one of SEQ ID NOs: 47, 43, 50, 45, 46 or 52.

In one embodiment, an amino acid of SEQ ID NO: 43, 45, 47 or 50 is used for the enzymatic conversion of 6-oxohexanoic acid to 6-hydroxyhexanoic acid.

In certain embodiments, ATs as provided herein are derived from organisms of the genus *Escherichia, Sinorhizobium* or *Streptomyces* In one embodiment, the AT is derived from the species *Escherichia coli*. In one embodiment, the AT is derived from the species *Sinorhizobium meliloti*. In one embodiment, the AT is derived from the species *Streptomyces avermitilis*. In one embodiment, the AT is derived from the species *Sinorhizobium meliloti*.

In one embodiment, the AT comprises or consists of an amino acid of one of SEQ ID NOs: SEQ ID NOs:53-65 or an active fragment or a homologue thereof. In one aspect, the enzyme is at least 80%, 85%, 90%, 95% or 100% identical to the amino acid sequence of one of SEQ ID NOs: SEQ ID NOs:53-65

In one embodiment, the AT comprises or consists of an amino acid of one of SEQ ID NOs: 53, 59, 55, 58 or 60 or an active fragment or a homologue thereof.

In one aspect, the enzyme is at least 80%, 85%, 90%, 95% or 100% identical to the amino acid sequence of one of SEQ ID NOs: 53, 59, 55, 58 or 60.

CARs adenylation domain uses 2 phosphates of ATP for substrate activation, forming acyl-AMP intermediate transferred to reducing domain, where one molecule of NADPH is oxidised for aldehyde release. Application of CARs together with ARs for full reduction of carboxylic group to alcohol needs 2 molecules of NADPH and 1 ATP. Full biotransformation of adipic acid to 1,6-hexanediol will cost in total 4 NADPH and 2 ATP molecules. In vitro application of cofactor dependent enzymes such as oxidoreductases or transferases needs enzymatic systems for regeneration of consumed cofactors to make the system cost-effective.

In one embodiment, one or more of four enzymes commonly employed in the regeneration of ATP: pyruvate kinase (uses phosphoenolpyruvate), acetate kinase (uses acetylphosphate), creatine kinase (uses creatine phosphate), and polyphosphate kinase (uses polyphosphate) may be used. See Andexer and Richter, Emerging Enzymes for ATP Regeneration in Biocatalytic Process CHEMBIOCHEM 2015, 16, 380-386, for additional details. The majority of ATP-regenerating enzymes process only one step ADP phosphorylation. In one embodiment, polyphosphate kinases, in one embodiment, polyphosphate kinase family II; in one embodiment, for ATP regeneration SMc02148 from *Sinorhizobium meliloti* and PA3455 from *Pseudomonas aeruginosa*, may be used.

CARs, ARs and amino-donor regenerating enzymes use pyridine nucleotides as cofactors. Several enzymatic methods have been developed for the regeneration of NAD(P)H, such as reduction with formate dehydrogenase, glucose dehydrogenase, glucose-6-phosphate dehydrogenase, and alcohol dehydrogenase. In one embodiment, the host microorganism can be engineered to increase co-factor pools of NADH and/or NADPH. In one embodiment, the microorganism can be engineered to express a formate dehydrogenase. In one embodiment, a formate dehydrogenase of SEQ ID NO:108 or active fragment or homologue thereof.

In one embodiment, if *E. coli* is to be used as the host organism, glucosephosphate isomerase (pgi) gene can be deleted to divert flux towards the pentose phosphate pathway to increase NADPH pools. Other strategies may involve switching the endogenous NADH-dependent glyceraldehyde-3-phosphate dehydrogenase (GAPDH) to the host *E. coli* strain with an exogenous NADPH-dependent glyceraldehyde-3-phosphate dehydrogenase derived from *Clostridium acetobutylicum*. In another method, an NADH kinase (Pos5P) can be introduced from *S. cerevisiae* into the host *E. coli* strain. The latter was successfully used to increase several products that are produced through NADPH-dependent pathways [Lee, W.-H., Kim, M.-D., Jin, Y.-S., & Seo, J.-H. (2013). Engineering of NADPH regenerators in *Escherichia coli* for enhanced biotransformation. *Applied Microbiology and Biotechnology.* 97(7):2761-72]. As will be apparent to persons of skill in the art, if *E. coli* is chosen as the host organism, NADH pools can be increased by limiting competing pathways though the deletion of genes encoding NADH-dependent enzymes, including but not limited to: alcohol dehydrogenase (adhE), lactate dehydrogenase (ldhA) and pyruvate-formate lyase (pflB).

ATs disclosed herein consume alanine and/or glutamate as amino-group donors, which need to be regenerated. Accordingly, in one embodiment, a host microorganism can be engineered to increase the production of alanine and/or glutamate. In one embodiment, these host microorganism may be engineered to express a glutamate dehydrogenase or alanine dehydrogenase. Two enzymes were found suitable for this purposes—YOR375C, NADPH-dependent glutamate dehydrogenase from *Saccharomyces cerevisiae*, and BSU31930, NADH-dependent alanine dehydrogenase from *Bacillus subtilis*.

In various aspects, a homologue of each enzyme refers to a protein which has an identity of at least 25%, at least 50%, at least 60%, at least 70%, at least 80%, at least 85%, at least 90%, at least 95% or at least 99% with the amino acid sequence of SEQ ID NO corresponding to the enzyme and retains the activity of the enzyme. Algorithms for determining sequence identity are publicly available and include e.g. BLAST available through the National Center for Biotechnology Information (NCBI). One skilled in the art can determine if the sequences are similar to a degree that indicates homology and thus similar or identical function.

A person skilled in the art can obtain a polynucleotide encoding a homologue of each enzyme by appropriately introducing substitution, deletion, insertion, and/or addition to the DNA of the enzyme which is composed of a nucleotide sequence disclosed herein, using methods such as site-specific mutagenesis (Nucleic Acid Res. 10, pp. 6487 (1982), Methods in Enzymol. 100, pp. 448 (1983), Molecular Cloning 2nd Edt., Cold Spring Harbor Laboratory Press (1989), PCR A Practical Approach IRL Press pp. 200 (1991)). The polynucleotide encoding a homologue of each enzyme can be introduced and expressed in a host to obtain the homologue.

Enzymes as described herein may be produced by a non-naturally occurring microorganism.

As used herein, the term "microorganism" is intended to mean any organism that exists as a microscopic cell and encompasses prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "non-naturally occurring" when used in reference to a microorganism refers to a microorganism that has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon.

The term "endogenous" refers to a referenced molecule or activity that originates in a host microorganism. Similarly, the term when used in reference to expression of an encoding nucleic acid refers to expression of an encoding nucleic acid contained within the microorganism.

As used herein the term "exogenous" refers to molecules or activity that is introduced into a host microorganism. The molecule can be introduced, for example, by introduction of an encoding nucleic acid into the host genetic material such as by integration into a host chromosome or as non-chromosomal genetic material such as a plasmid. In reference to expression of an encoding nucleic acid the term refers to introduction of the encoding nucleic acid in an expressible form into the microorganism. When used in reference to a biosynthetic activity, the term refers to an activity that is introduced into a reference host organism. The source can be, for example, an encoding nucleic acid that expresses the activity following introduction into the host microorganism.

The term "heterologous" refers to a molecule or activity derived from a source other than the referenced species whereas "homologous" refers to a molecule or activity derived from the host microbial organism. Accordingly, exogenous expression of an encoding nucleic acid can use either or both a heterologous or homologous encoding nucleic acid.

As used herein, the term "isolated" when used in reference to a microorganism refers to an organism that is substantially free of at least one component as the referenced microorganism is found in nature. The term includes a microorganism that is removed from some or all components as it is found in its natural environment and includes substantially pure microbes and microbes cultured in a medium that is non-naturally occurring.

As used herein, the term "operably linked" refers to a linkage between one or more expression control sequences and the coding region in a polynucleotide to be expressed in such a way that expression is achieved under conditions compatible with the expression control sequence.

In one embodiment, the microorganism used in a process as described herein is a microorganism which is genetically modified so as to contain a nucleic acid molecule encoding a 2-enoate reductase as described herein.

Nucleic acid molecules encoding enzymes as described herein can be used alone or as part of a vector.

In one embodiment, the enzyme comprises an amino acid sequence of SEQ ID NO: 1 or active fragment or homologue thereof. In one embodiment, the enzyme comprises an amino acid sequence that is at least 80%, 85%, 90%, 95% or 100% identical to the amino acid sequence of SEQ ID NO: 1. In one aspect, the enzyme comprises amino acids (363) to (382) of SEQ ID NO: 1. In one embodiment, the enzyme comprises an amino acid sequence of SEQ ID NO: 2 or active fragment or homologue thereof. In one embodiment, the enzyme comprises an amino acid sequence that is at least 80%, 85%, 90%, 95% or 100% identical to the amino acid sequence of SEQ ID NO: 2. In another aspect, the enzyme comprises amino acids (363) to (382) of SEQ ID NO: 2.

In one embodiment, the enzyme comprises an 4Fe-4S cluster:

$CX_1SCX_2EGCMGRX_3QX_4YSX_5LX_6C$ wherein $X_1$ is any amino acid, preferably a hydrophobic amino acid, preferably leucine or isoleucine, preferably leucine;

$X_2$ is any amino acid, preferably a polar amino acid, preferably histidine or glutamine, preferably histidine;

$X_3$ is any amino acid, preferably a hydrophobic amino acid preferably isoleucine or valine, preferably isoleucine;

$X_4$ is any amino acid, preferably glutamic acid or histidine, preferably glutamic acid;

$X_5$ is any amino acid, preferably a polar amino acid, preferably serine or methionine, preferably serine;

$X_6$ is any amino acid, preferably glycine or asparagine, preferably glycine.

In one embodiment, the enzyme comprises or substantially comprises (>80%, >85%, >90%, >95% or >99%) of the consensus sequence as between SEQ ID NO: 1 and SEQ ID NO: 2.

In one embodiment, the enzyme is substantially aerostable, which in one embodiment comprises an enzyme that retains at least 20, at least 25 or at least 30% of its activity when stored in air for 3 days.

The nucleic acid molecules can further include expression control sequences operably linked to the polynucleotide comprised in the nucleic acid molecule. These expression control sequences may be suited to ensure transcription and synthesis of a translatable RNA in bacteria or fungi. Expression refers to the transcription of the heterologous DNA sequence, preferably into a translatable mRNA. Regulatory elements ensuring expression in bacteria, yeasts or fungi, cyanobacteria and algae are well known to those skilled in the art and encompass promoters, enhancers, termination signals, targeting signals and the like. Promoters for use in connection with the nucleic acid molecule may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used.

The polynucleotide introduced into a microorganism is expressed so as to lead to the production of a polypeptide having the enzymatic activity as described herein.

An overview of different expression systems is for instance contained in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antonie van Leuwenhoek 67 (1995), 261-279), Bussineau et al. (Developments in Biological Standardization 83 (1994), 13-19), Gellissen et al. (Antonie van Leuwenhoek 62 (1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072).

Expression vectors have been widely described in the literature. Generally, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms, including *E. coli* and *S. cerevisiae*, are described in the literature known to those of skill in the art. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, New York, (1982), 462-481; DeBoer et al., Proc. Natl. Acad. Sci. USA (1983), 21-25), lp1, rac (Boros et al., Gene 42 (1986), 97-100).

Inducible promoters which may provide higher polypeptide yields than constitutive promoters can be used. Suitably, in one embodiment, a two-stage process is used: the host cells are first cultured under optimum conditions up to a relatively high cell density; and transcription is then induced.

Termination signals for transcription are also described in the literature.

In addition, it is possible to insert different mutations into the polynucleotides by methods well known in molecular biology (see for instance Sambrook and Russell (2001), *Molecular Cloning: A Laboratory Manual*, CSH Press, Cold Spring Harbor, N.Y., USA), enabling the synthesis of polypeptides having modified biological properties. In one embodiment, point mutations are introduced at positions at which a modification of the amino acid sequence increases the catalytic activity or stability of the enzyme.

Alternatively, the substrate preference of enzymes can also be changed using directed evolution. Enhancement in specific activity can be accomplished by using random mutagenesis over the whole length of the protein (Sheryl B. Rubin-Pitel et al. (2007), "Chapter 3: Directed Evolution Tools in Bioproduct and Bioprocess Development" in *Bioprocessing for Value-Added Products from Renewable Resources*, S.-T. Yang, Ed., Elsevier, Amsterdam, The Netherlands.) Protein solubility can be increased by site-directed mutagenesis to make hydrophobic to hydrophilic mutations on the protein surface (Saul R. Trevino et al. Journal of Molecular Biology 366 (2007), 449-460).

Furthermore, genes can be subjected to codon optimization with techniques well known in the art to achieve optimized expression of the proteins.

Appropriate modifications to a nucleic acid sequence to remove or include a targeting sequence can be incorporated into an exogenous nucleic acid sequence to impart desirable properties.

As will be understood by those of skill in the art, when two or more exogenous encoding nucleic acids are to be co-expressed, both nucleic acids may be inserted, for example, into one expression vector or into separate expression vectors. For single vector expression, the encoding nucleic acids can be operationally linked to a common expression control sequence or linked to different expression control sequences, such as one inducible promoter and one constitutive promoter.

It is to be understood that in one embodiment, a non-naturally occurring microorganism that produces a pathway intermediate or product, may be used in combination with another organism (or other organisms) expressing downstream or upstream pathway enzyme(s) to produce a desired product. For example, an engineered organism can be used to produce and accumulate adipic acid. The adipic acid can then be used as a substrate for another engineered organism expressing one or more of the pathway genes to convert adipic acid to 1,6-hexanediol, 6-hydroxyhexanoic or 6-aminocaproic acids.

Host microorganisms can be selected from, and the non-naturally occurring microorganisms generated in, for example, bacteria, yeast, fungus or any of a variety of other microorganisms applicable to fermentation processes.

Host microorganisms can be selected from, and the non-naturally occurring microorganisms generated in, for example, bacteria, yeast, fungus or any of a variety of other microorganisms may be used as a host organism. Suitable host microorganisms can be selected for example from Bacteria phylum like Proteobacteria, Firmicutes, Actinocacteria, Thermotogae, *Bacteroides*, Cyanobacteria. Archaea phyla Euryarchaeota, Fungi phylum Ascomycota and Zygomycota or Eukariota phylum like Chlorophyta, Dinoflagellata, Bacillariophyta, Eustigmatophyceae, Haptophyta and Heterokontophyta.

Suitable bacterial and archaeal species include:

*Escherichia coli, Bacillus subtilis, Bacillus licheniformis, Bacillus cereus, Bacillus megaterium, Bacillus brevis, Bacillus pumilus, Corynebacterium glutamicum, Zymomonas mobilis, Clostridium acetobutylicum, Clostridium butylicum, Clostridium kluyveri, Clostridium autoethanogenum, Moorella thermoacetica, Clostridium aceticum, Clostridium beijerinckii, Clostridium ljungdahlii, Clostridium saccharoperbutylacetonicum, Clostridium perfringens, Clostridium difficile, Clostridium botulinum, Clostridium tyrobutyricum, Clostridium tetanomorphum, Clostridium tetani, Clostridium propionicum, Clostridium aminobutyricum, Clostridium subterminale, Clostridium sticklandii, Ralstonia eutropha, Mycobacterium bovis, Mycobacterium tuberculosis, Porphyromonas gingivalis, Pseudomonas fluorescens, Pseudomonas putida, Pseudomonas aeruginosa, Pseudomonas* carboxidovorans (*Oligotropha* carboxidovorans), *Pseudomonas stutzeri, Klebsiella pneumonia, Klebsiella oxytoca, Anaerobiospirillum succiniciproducens, Actinobacillus succinogenes, Mannheimia succiniciproducens, Rhizobium etli, Gluconobacter oxydans, Lactococcus lactis, Lactobacillus plantarum, Streptomyces coelicolor, Citrobacter freundii, Citrobacter amalonaticus, Acinetobacter calcoaceticus, Acinetobacter baylyi, Thermotoga maritima, Halobacterium salinarum, Serratia marcescens, Rhodospirillum rubrum, Ideonella sp., Rhodobacter capsulatus, Methylococcus capsulatus, Methylosinus trichosporium, Methylobacterium extorquens, Methylocystis GB25, Methylotrophus capsulatus, Methylomonas sp. 16a, Pyrococcus furiosus.*

Suitable yeasts or fungi include: *Saccharomyces cerevisiae, Schizosaccharomyces pombe, Saccharomycopsis crataegensis, Kluyveromyces lactis, Kluyveromyces marxianus, Aspergillus terreus, Aspergillus niger, Pichia stipitis, Pichia pastoris, Rhizopus arrhizus, Rhizopus oryzae, Yarrowia lipolytica, Issatchenkia orientalis, Issatchenkia occidentalis, Candida lambica, Candida sorboxylosa, Candida zemplinina, Candida geochares, Pichia membranifaciens, Zygosaccharomyces kombuchaensis, Candida sorbosivorans, Candida vanderwaltii, Candida sorbophila, Zygosaccharomyces bisporus, Zygosaccharomyces lentus, Saccharomyces bayanus, Saccharomyces bulderi, Debaryomyces castellii, Candida boidinii, Candida etchellsii, Pichia jadinii, Pichia anomala, Penicillium chrysogenum, Candida tropicalis.*

In one embodiment, the host microorganism is an aerobic organism that can express an enzyme as described herein in an aerobic environment.

Suitable cyanobacteria include: Acaryochloris marina MBIC11017, Anabaena sp. PCC 7120, Anabaena variabilis ATCC 29413, Agmenellum quadruplicatum, Chlorobium tepidumTLS, Cyanothece sp. ATCC 51142, Gloeobacter violaceus PCC 7421, Microcystis aeruginosa NIES-843, Nostoc punctiforme ATCC 29133, Prochlorococcus marinus MED4, Prochlorococcus marinus MIT9313, Prochlorococcus marinus SS120, Prochlorococcus marinus str. AS9601, Prochlorococcus marinus str. MIT 9211, Prochlorococcus marinus str. MIT 9215, Prochlorococcus marinus str. MIT 9301, Prochlorococcus marinus str. MIT 9303, Prochlorococcus marinus str. MIT 9312, Prochlorococcus marinus str. MIT 9515, Prochlorococcus marinus str. NATL1A, Prochlorococcus marinus str. NATL2A, Rhodopseudomonas palustris CGA009, Synechococcus elongatus PCC 6301, Synechococcus elongatus PCC 7942, Synechococcus sp. CC9311, Synechococcus sp. CC9605, Synechococcus sp. CC9902, Synechococcus sp. JA-2-3BVa(2-13), Synechococcus sp. JA-3-3Ab, Synechococcus sp. PCC 7002, Synechococcus sp. RCC307, Synechococcus sp. WH 7803, Synechococcus sp. WH8102, Synechocystis sp. PCC 6803, Thermosynechococcus elongatus BP-1, Trichodesmium erythraeum IMS101.

Suitable algae include: Botryococcus braunii, Chlamydomonas reinhardii, Chlorella sp., Crypthecodinium cohnii, Cylindrotheca sp., Dunaliella primolecta, Isochrysis sp., Monallanthus salina, Nannochloris sp., Nannochloropsis sp., Neochloris oleoabundans, Nitzschia sp., Phaeodactylum tricornutum, Schizochytrium sp., Tetraselmis sueica.

In one embodiment, the host microorganism is an aerobic organism that can express an enzyme having α,β-enoate reductase activity in an aerobic environment. Expression of such an enzyme in an aerobic or a microaerobic environment may allow improved growth rate leading to improved productivity. Furthermore, this enzyme can be used to make chemicals from compounds that require aerobic biosynthesis pathways.

E. coli is a particularly useful host organism since it is a well characterized microorganism suitable for genetic engineering.

Methods for constructing and testing the expression levels of a non-naturally occurring host can be performed by recombinant and detection methods, with techniques which are well known in the art. Such methods can be found described in, for example, Sambrook et al., *Molecular Cloning: A Laboratory Manual*, Third Ed., Cold Spring Harbor Laboratory, New York (2001); and Ausubel et al., Current Protocols in *Molecular Biology*, John Wiley and Sons, Baltimore, Md. (1999). Specific methods for constructing and testing the expression levels of an E. coli host that produces one or more of the enzymes described herein are provided in the Examples.

When reference is made to more than one exogenous nucleic acid being included in a microorganism, it is to be understood that this refers to the referenced encoding nucleic acids or biochemical activities and not the number of separate nucleic acids introduced into the host organism. As will be understood by those of skill in the art, such exogenous nucleic acids may be introduced into the host organism on separate nucleic acid molecules, on polycistronic nucleic acid molecules, or a combination thereof. For example, where two or more exogenous nucleic acids encoding different enzymatic activities are introduced into a host organism, the two or more exogenous nucleic acids can be introduced as a single nucleic acid, for example, on a single plasmid, on separate plasmids, can be integrated into the host chromosome at a single site or multiple sites, and still be considered as two or more exogenous nucleic acids.

As will be apparent to persons of skill in the art, depending on the host microorganism selected, nucleic acids for the pathway enzyme(s) described can be introduced into the host organism. As will be apparent to persons of skill in the art, where a host microorganism expresses the pathway gene(s), the microorganism may be engineered such that the gene encoding the enzyme is overexpressed and/or genes encoding enzymes or proteins of competing pathways may be deleted.

In one embodiment, methods are carried out with live cells. In another embodiment, the process is carried out in vitro with lysed cells or with partially or completely purified enzyme or with permeabilized cells. In one embodiment, the method is carried out in vitro and the enzyme is immobilized. Means and methods for immobilizing enzymes on different supports are well-known to the person skilled in the art. Such in vitro process can be similar to the processes described in (1) Dudley, Q. M., Karim, A. S., and Jewett, M. C. 2014. Cell-Free Metabolic Engineering: Biomanufacturing beyond the cell. Biotechnology Journal. 10:69-82, 2) Zhang Y-HP*. 2014. Production of biofuels and biochemicals by in vitro synthetic biosystems: opportunities and challenges. Biotechnology Advances, Epub, DOI: 10.1016/j.biotechadv.2014.10.009)

In one embodiment, the methods are carried out in culture, with the host organism, producing the enzyme(s). The growth medium can include, for example, any inorganic or organic carbon source which can supply a source of carbohydrates or other precursors that the host organisms can naturally use or is engineered to use. In one embodiment, the host organism is provided with a feedstock of sugars. Such sources include, for example, sugars such as glucose, xylose, galactose, mannose, fructose and starch. Glucose can be obtained from various carbohydrate-containing sources including conventional biorenewable sources such as corn (maize), wheat, potato, cassava and rice as well as alternative sources such as energy crops, plant biomass, agricultural wastes, forestry residues, sugar processing residues and plant-derived household wastes.

Sources of carbohydrate include renewable feedstocks and biomass, e.g. cellulosic biomass, hemicellulosic biomass and lignin feedstocks. Such biomass feedstocks contain, for example, carbohydrate substrates that can yield through biosynthetic pathways, unsaturated six-carbon dicarboxylic acids, muconic acid and 2-hexendioic acid. In addition, the enzyme can be incorporated in host microbes capable of using other substrates such as methanol, syngas, glycerol, CO2 and producing muconic acid and 2-hexenedioic acid. Other renewable feedstocks and biomass will be known to persons of skill in the art.

Biorenewable feedstock sources that may be used in accordance with the present invention include any renewable organic matter that includes a source of carbohydrates. These include, for example, grasses, trees (hardwood and softwood), vegetation and crop residues. Other sources can include, for example, organic waste materials (e.g., spent paper, green waste, municipal waste, etc.). Suitable carbohydrates, including glucose, may be isolated from biorenewable materials using methods that are known in the art. See, for example, Centi and van Santen, *Catalysis for Renewables*, Wiley-VCH, Weinheim 2007; Kamm, Gruber and Kamm, *Biorefineries-Industrial Processes and Products*, Wiley-VCH, Weinheim 2006; Shang-Tian Yang, *Bio-* processing for Value-Added Products from Renewable Resources New Technologies and Applications, Elsevier B. V. 2007; Furia, Starch in the Food Industry, Chapter 8, CRC Handbook of Food Additives 2nd Edition CRC Press, 1973. See also chapters devoted to Starch, Sugar and Syrups within Kirk-Othmer Encyclopedia of Chemical Technology 5th Edition, John Wiley and Sons 2001. Processes to convert starch to glucose are also well known in the art, see, for example, Schenck, "Glucose and Glucose containing Syrups" in Ullmann's Encyclopedia of Industrial Chemistry, Wiley-VCH 2009. Furthermore, methods to convert cellulose to glucose are known in the art, see, for example, Centi and van Santen, Catalysis for Renewables, Wiley-VCH, Weinheim 2007; Kamm, Gruber and Kamm, Biorefineries-Industrial Processes and Products, Wiley-VCH, Weinheim 2006; Shang-Tian Yang, Bioprocessing for Value-Added Products from Renewable Resources New Technologies and Applications, Elsevier B. V. 2007.

In one embodiment, the processes as provided may be carried out in a fermenter.

The engineered organism can be cultivated in a variety of reactors systems, and the process can be carried out in different modes of operations. The most commonly used bioreactor is a stirred tank bioreactor or aerated fermenter. The fermenter is equipped with sterile air supply, the mixing of bubble dispersion is achieved by mechanical agitation, and the temperature may be maintained using a jacket or coil that circulates steam or cooling water. For aerated vessels, high height/diameter ratio (>3) may be chosen to increase the contact time between the bubbles and liquid phase. Other variations of bioreactors are airlift bioreactor where mixing is achieved without mechanical agitation, and packed bed or fluidized bed bioreactors which are used when the biocatalyst is immobilized.

The fermentation can be carried out in three different modes: batch, fed-batch and continuous mode. A standard batch bioreactor is considered a "closed" system. In batch mode, all the media components are added to bioreactor while ensuring the sterility. Once the medium has been prepared, the bioreactor is inoculated with an appropriate inoculum and the fermentation is allowed to proceed until the end without any changes to the medium, i.e., without feeding of any additional components. Components such as acid and/or base can, however, be added to maintain the pH, and air/oxygen can be added to maintain the dissolved oxygen levels. In batch fermentation biomass and product concentration change over time until the fermentation is complete. The cells undergo classical lag-phase, exponential growth-phase, stationary phase growth, followed by death phase.

A variation of the batch mode is fed-batch mode where the nutrients including the carbon source is added to the fermenter as the process progresses.

In addition to batch or fed-batch mode, continuous mode of fermentation can also be used. A continuous system is considered to be "open" system in contrast to the batch mode. In continuous mode, defined production medium is added continuously to the bioreactor and equal amounts of bioreactor contents are removed at the same rate. Continuous operation can be carried out in a chemostat where the vessel contents, including the cells are removed, or in a bioreactor that uses perfusion culture, which allows recycling of the viable cells back to the bioreactor, allowing high cell densities to be achieved.

The commonly used fermenter designs and different operation modes are very well-established in the literature [Biochemical Engineering Fundamentals, 2nd Ed. J. E. Bailey and D. F. Ollis, McGraw Hill, New York, 1986; Development of Sustainable Bioprocesses: Modeling and Assessment, E. Heinzle, A. P. Biwer and C. L. Cooney, John Wiley & Sons, Ltd., 2006; Bioprocess Engineering: Basic Concepts, 2nd Ed., M. L. Shuler and F. Kargi, Prentice Hall, 2001].

Batch, fed-batch or continuous fermentation procedures may be employed.

The organisms can be grown in any suitable medium for growth such as Luria-Bertani broth, Terrific broth or yeast extract-peptone-dextrose (YPD) medium. For production, depending up on the choice of the host, synthetic minimal media such as M9 minimal medium, yeast synthetic minimal medium, yeast nitrogen base, BG-11, or variations thereof can be used. A suitable minimal medium may contain at least one carbon source, at least one nitrogen source, salts, cofactors, buffers, and other components required to grow and maintain the recombinant microorganism. The carbon source can be one or more of the carbon sources described previously, the nitrogen source can be an ammonium salt or nitrate salt including but not limited to $(NH_4)2SO_4$, $NH_4Cl$, $(NH_4)_2HPO_4$, $NH_4OH$, $KNO_3$, $NaNO_3$. The medium may be supplemented with complex or organic nitrogen sources such as urea, yeast extract, casamino acids, peptone, tryptone, soy flour, corn steep liquor, or casein hydrolysate. Additionally, the minimal medium can be supplied with trace metals including but not limited to $H_3BO_3$, $MnCl_2$, $ZnSO_4$, $Na_2MoO_4$, $CuSO_4$, $Co(NO_3)_2$, $CuCl_2$, $ZnCl_2$, $CoCl_2$, $FeCl_3$, $KI$. The minimal medium may be supplemented with vitamins and/or non-vitamin compounds including but not limited to biotin, pantothanate, folic acid, inositol, nicotinic acid, p-aminobenzoic acid, pyridoxine, riboflavin, thiamine, cyanocobalamin, citric acid, ethylenediamine tetraacetic acid (EDTA), ferric ammonium citrate. The medium can be supplied by carbon dioxide either by direct sparging or in the form of $NaHCO_3$, or $Na_2CO_3$.

In one embodiment, the processes are conducted under substantially aerobic conditions.

As used herein the term "substantially aerobic" when used in reference to a culture or growth condition means, in one embodiment, that the amount of oxygen is equal to or greater than about 10% of saturation for dissolved oxygen in liquid media. In one embodiment, the term includes sealed chambers of liquid or solid medium maintained with an atmosphere greater than about 1% oxygen.

In one embodiment, the processes as described herein may suitably be performed at a pH range of between about 4 to about 8.

While in one embodiment, the temperature at which the methods as described herein are performed is not particularly restricted, generally, the processes as described herein may be performed at temperatures of between about 20° C. and about 60° C.

A person skilled in the art will be readily able to determine an effective amount of enzyme to be used per quantity of substrate and, in one embodiment, the effective amount is not particularly restricted. The present inventors have found that an enzyme ratio of 1 μg of enzyme per 200 μg of substrate effective, although higher (e.g. 1:100) and lower (e.g. 1:1000) ratios of enzyme to substrate may be effective and an appropriate ratio can be readily determined by a person of skill in the art in relation to the specific reaction conditions.

The amount of product in the medium can be determined using methods known in the art such as High Performance Liquid Chromatography (HPLC), Gas Chromatography (GC), Liquid Chromatography-Mass Spectrometry (LC-MS), Gas Chromatography-Mass Spectrometry (GC-MS).

Methods of assaying for the production of the polymer precursors described herein are known to those of skill in the art and further are exemplified below. For example, product, intermediate and byproduct formation can be analyzed by methods such as HPLC (High Performance Liquid Chromatography), GC-MS (Gas Chromatography-Mass Spectroscopy) and LC-MS (Liquid Chromatography-Mass Spectroscopy). Individual enzymatic activities from the exogenous DNA sequences can also be assayed using methods well known in the art.

In some embodiments, processes as disclosed herein further include purifying the product of the processes products of the methods described herein. Such methods of purification are known to those of skill in the art and include e.g. by filtration, distillation or evaporation. Isolation of compound from the fermentation broth depends on the final purity of the compound required. The separation techniques may include: centrifugation, microfiltration, ultrafiltration, nano-filtration, evaporation, crystallization, distillation, and ion-exchange. Typical downstream processing operation would include a series of processes including separation of cells using centrifugation or microfiltration, removal of additional solids in the broth using ultrafiltration, removal of salts from the broth using nanofiltration, ion-exchange, or evaporative crystallization, and finally purification of adipic acid using distillation.

INDUSTRIAL APPLICABILITY

Adipic acid has various uses as will be known to those of skill in the art. The majority of adipic acid produced is used as a monomer for the production of nylon by a polycondensation reaction with hexamethylene diamine forming 6,6-nylon. Other major applications also involve polymers: it is a monomer for production of polyurethane and its esters are used as plasticizers, especially in polyvinyl chloride (PVC).

The polymer precursors 1,4-butanediol, 1,6-hexanediol, 6-hydroxyhexanoic acid and 6-aminocaproic acid have diverse industrial uses.

1,4-Butanediol is used industrially as a solvent and in the manufacture of some plastics, elastic fibers and polyurethanes. 1,4-butanediol is also used for the synthesis of γ-butyrolactone (GBL) and in the presence of phosphoric acid and high temperature, it dehydrates to the solvent tetrahydrofuran.

1,6-Hexanediol is widely used for industrial polyester and polyurethane production. It is also an intermediate to acrylics, adhesives, and dyestuffs.

Aminocaproic acid is an intermediate in the polymerization of Nylon-6, where it is formed by ring-opening hydrolysis of caprolactam. It also finds uses in pharmaceutical and applications.

All documents referenced herein are incorporated by reference, however, it should be appreciated that any patent, publication, or other disclosure material, in whole or in part, that is incorporated by reference herein is incorporated only to the extent that the incorporated material does not conflict with definitions, statements, or other disclosure material set forth in this disclosure. As such, and to the extent necessary, the disclosure as explicitly set forth herein supersedes any conflicting material incorporated herein by reference.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

The embodiments of the invention described above are intended to be exemplary only. The scope of the invention is therefore intended to be limited solely by the scope of the appended claims.

EXAMPLES

The two families of flavoenzymes, Old Yellow Enzymes (OYES; EC 1.6.99.1) and 2-enoate reductases (EREDs; EC 1.3.1.31) have been studied for biocatalytic hydrogenation of alkenes and exhibited a broad substrate specificity toward α,β-unsaturated substrates bearing an electron-withdrawing group such as aldehyde, ketone, and carboxylic acid. The C=C reducing activity of OYEs and EREDs from different organisms was analyzed.

Example 1—Cloning, Expression, and Purification of Proteins

Genes encoding the selected OYE and ERED proteins were PCR-amplified from genomic DNAs and cloned into p15Tv-Lic plasmid via a ligation-independent method as described in D. Bonsor, S. F. Butz, J. Solomons, S. Grant, I. J. S. Fairlamb, M. J. Fogg, G. Grogan, Organic and Biomolecular Chemistry 2006, 4, 1252-1260

Recombinant ERED plasmids were transformed into the *E. coli* BL21 (DE3) ΔiscR strain for the overexpression of iron-sulfur containing proteins (per methods described in M. K. Akhtar, P. R. Jones, Applied Microbiology and Biotechnology 2008, 78, 853-862). *E. coli* transformants were cultured aerobically at 37° C. in Terrific Broth (TB) medium (1 L) supplemented with 100 μg/mL ampicillin until the optical density (OD 600 nm) reached 0.6-0.8. At this point cultures were transferred to tightly-closed flasks with a magnetic stir bar and protein expression was induced with 0.4 mM IPTG after a 30 min anaerobic pre-cultivation in the closed flasks. Cultures were also incubated with DMSO (50 mM) as the final electron acceptor for 15-19 h at room temperature on a magnetic stir plate. *E. coli* cells were harvested by centrifugation (9,000 g) and the cell pellets were stored in liquid $N_2$ protein purification. For the whole-cell biotransformation cells were used immediately. Protein purification was performed in an anaerobic glove-box (Coy Laboratory Products, Grass Lake, MI, USA) under an atmosphere of 80% $N_2$, 10% $H_2$, and 10% $CO_2$. All buffers were degassed and sparged with Ar before use. Cell pellets were resuspended in lysis buffer (400 mM NaCl, 50 mM HEPES, pH 7.5, 5% glycerol, 5 mM imidazole, 0.05% Tween-20, 1 mg/mL lysozyme, 3 U/mL benzonase, 0.5 mM EDTA, and 1 mM DTT) and incubated at room temperature for 30 min. Cell lysates were cleared by centrifugation and the supernatant was incubated with Ni-affinity resin (Qiagen, Valencia, CA, USA) at 4° C. for 1 h. The resin was then washed with 100 mL of washing buffer (400 mM NaCl, 50 mM HEPES, pH 7.5, 5% glycerol, 30 mM imidazole, 0.5 mM EDTA, and 1 mM DTT) and eluted with elution buffer (400 mM NaCl, 50 mM HEPES, pH 7.5, 5% glycerol, 250 mM imidazole, 0.5 mM EDTA, and 1 mM DTT). Purified EREDs were frozen and stored in liquid $N_2$. Protein concentration was determined using Bradford assay and protein purity was evaluated on 10% SDS-PAGE gels.

Recombinant OYE plasmids were transformed into the *E. coli* BL21-Gold (DE3) strain (Stratagene, La Jolla, CA, USA). *E. coli* transformants were cultured at 37° C. in TB medium supplemented with 100 µg/mL of ampicillin until the OD at 600 nm reached 0.6-0.8. Protein expression was induced with 0.4 mM IPTG and the *E. coli* cells were grown overnight at 16° C. The *E. coli* cells were harvested by centrifugation (9,000 g) and the pellets were resuspended in lysis buffer (400 mM NaCl, 50 mM HEPES, pH 7.5, 5% glycerol, and 5 mM imidazole) followed by sonication to break cells. Lysates were cleared by centrifugation and the supernatant was incubated with Ni-affinity resin at 4° C. for 30 min. The resin was then washed with washing buffer (400 mM NaCl, 50 mM HEPES, pH 7.5, 5% Glycerol, and 30 mM imidazole) and eluted with elution buffer (400 mM NaCl, 50 mM HEPES, pH 7.5, 5% Glycerol, and 250 mM imidazole). Purified OYES were frozen in liquid $N_2$ and stored at −80° C.

Example 2—Comparative Example

All results in this study are means from at least two independent determinations. Control experiments were performed in parallel to correct substrate-independent oxidation of cofactors for OYEs. All buffers and reagents used in anaerobic reactions were rigorously sparged with Ar to remove traces of oxygen before use.

OYEs do not contain an iron-sulfur cluster, but they can catalyze hydrogenation of activated alkenes by hydride transfer from NAD(P)H to FMN in a similar way to EREDs. 25 putative OYE genes (Table 1) were cloned based on the Pfam domain of the FMN oxidoreductase family PF00724. Purified OYEs were screened for hydrogenation activity against acrolein, 2-cyclohexn-1-one, cis,cis-muconic acid, trans,trans-muconic acid, and 2-hexenedioic acid. Substrate specificity was measured spectrophotometrically in 96-well plates by following incubation for 20 min at room temperature in the anaerobic chamber. Buffers and reagents were also degassed and sparged with Ar. Reaction mixtures contained potassium phosphate (50 mM and pH 7.0), NaCl (10 mM), NADPH (0.25 mM), various substrates (1 mM) and protein (2.5 µg) in a final volume of 200 µL. Enzyme reactions were monitored by following the decrease in absorbance at 340 nm ($\varepsilon 340$ nm=6,200/M·cm) as a measure of the conversion of the cofactor NADPH to NADP+.

TABLE 1

The OYE proteins tested for biocatalytic hydrogenation

| | | | | Activity [U/mg protein]* | |
|---|---|---|---|---|---|
| Protein ID | SEQ ID NO | GenBank ID | Microorganism | acrolein | 2-cyclohexen-1-one |
| BH1481 | 7 | BAB05200.1 | *Bacillus halodurans* C-125 | ND | 0.13 |
| BSU2381 | 8 | CAB14314.1 | *Bacillus subtilis* subsp. *subtilis* str. 168 | ND | 0.21 |
| CV3501 | 9 | AAQ61162.1 | *Chromobacterium violaceum* ATCC 12472 | ND | 0.07 |
| EC5625 | 10 | AAC74722.1 | *Escherichia coli* K12 | ND | 0.18 |
| LMO2471 | 11 | CAD00549.1 | *Listeria monocytogenes* EGD-e | ND | 0.08 |
| NE2398 | 12 | CAD86422.1 | *Nitrosomonas europaea* ATCC 19718 | ND | 0.19 |
| PA2932 | 13 | AAG06320.1 | *Pseudomonas aeruginosa* PAO1 | ND | 13 |
| PA4356 | 14 | AAG07744.1 | *Pseudomonas aeruginosa* PAO1 | ND | .15 |
| PP0911 | 15 | AAN66545.1 | *Pseudomonas putida* KT2440 | ND | 0.15 |
| PP1244 | 16 | AAN66878.1 | *Pseudomonas putida* KT2440 | 0.06 | 0.25 |
| PP1466 | 17 | AAN67100.1 | *Pseudomonas putida* KT2440 | ND | 0.14 |
| PS1143 | 18 | AAO54700.1 | *Pseudomonas syringae* pv. tomato str. DC3000 | ND | 0.18 |
| PS2358 | 19 | AAO55915.1 | *Pseudomonas syringae* pv. tomato str. DC3000 | ND | 0.13 |
| PS4251 | 20 | AAO57808.1 | *Pseudomonas syringae* pv. tomato str. DC3000 | ND | 0.09 |
| PSPH1060 | 21 | AAZ36642.1 | *Pseudomonas syringae* pv. phaseolicola 1448A | ND | 0.14 |
| PSPH1370 | 22 | AAZ33328.1 | *Pseudomonas syringae* pv. phaseolicola 1448A | ND | 0.18 |
| PSPH4058 | 23 | AAZ35385.1 | *Pseudomonas syringae* phaseolicola 1448A | ND | 0.22 |
| RHA03305 | 24 | ABG95009.1 | *Rhodococcus* sp. RHA1 | 0.08 | ND |
| RHA09668 | 25 | ABG99960.1 | *Rhodococcus* sp. RHA1 | ND | ND |
| SA0956 | 26 | BAB57118.1 | *Staphylococcus aureus* subsp. *aureus* Mu50 | ND | ND |
| SAV1511 | 27 | BAC69220.1 | *Streptomyces avermitilis* MA-4680 | 0.05 | 0.23 |
| SM4273 | 28 | AAK65532.1 | *Sinorhizobium mehloti* 1021 | ND | ND |
| SO4153 | 29 | AAN57126.1 | *Shewanella oneidensis* MR-1 | ND | ND |
| XCC0307 | 30 | AAM39626.1 | *Xanthomonas campestris* pv. campestris str. ATCC 33913 | ND | 0.15 |
| YST4373 | 31 | AAA83386.1 | *Saccharomyces cerevisiae* | 0.17 | 0.23 |

The cut-off value for enzyme activity of OYE is 0.05 U/mg protein.
ND = not detected.

25 putative OYEs were overexpressed in *E. coli* and purified using Ni-NTA resin. OYE activity of purified proteins was tested with typical substrates of OYEs, i.e., acrolein and 2-cyclohexen-1-one, and 21 out of 25 proteins showed OYE activity (Table 1). However, no purified OYEs could hydrogenate 2-hexenedioic acid or muconic acid. Similarly, whole-cell biotransformations with three *E. coli* strains over-expressing OYEs: EC5625 (SEQ ID NO: 10) from *E. coli* (YST4373 (SEQ ID NO: 31) from *S. cerevisiae*, and BSU2381 (SEQ ID NO: 8) from *Bacillus* subtillis, revealed no hydrogenation of 2-hexenedioic acid into adipic acid. This results are consistent with previous reports that OYEs cannot easily reduce α,β-unsaturated carboxylic acids without additional electron-withdrawing groups such as second acid- or -ester, a halogen or nitrile.

Example 3—Enzyme Screening: ERED Family (EC 1.3.1.31)

All results in this study are means from at least two independent determinations. Control experiments were performed in parallel to correct substrate-independent oxidation of cofactors and EREDs. All buffers and reagents used in anaerobic reactions were rigorously sparged with Ar to remove traces of oxygen before use.

The C═C reducing activity of EREDs was examined. Enzyme activity of purified EREDs was measured spectrophotometrically in 96-well plates by following incubation for 3-5 min at 30° C. in the anaerobic chamber as described in M. Buhler, H. Simon, Hoppe-Seyler's Zeitschrift fur Physiologische Chemie 1982, 363, 609-625. Buffers and reagents were degassed and sparged with Ar. Reaction mixture contained potassium phosphate (100 mM and pH 7.0), NADH (0.5 mM), indicated substrates, and proteins (0.1-50 μg) in a final volume of 200 μL. Enzyme reactions were monitored by following the decrease in absorbance at 340 nm (ε340 nm=6,220/M·cm) due to oxidation of NADH to NAD+.

Figure 5B:
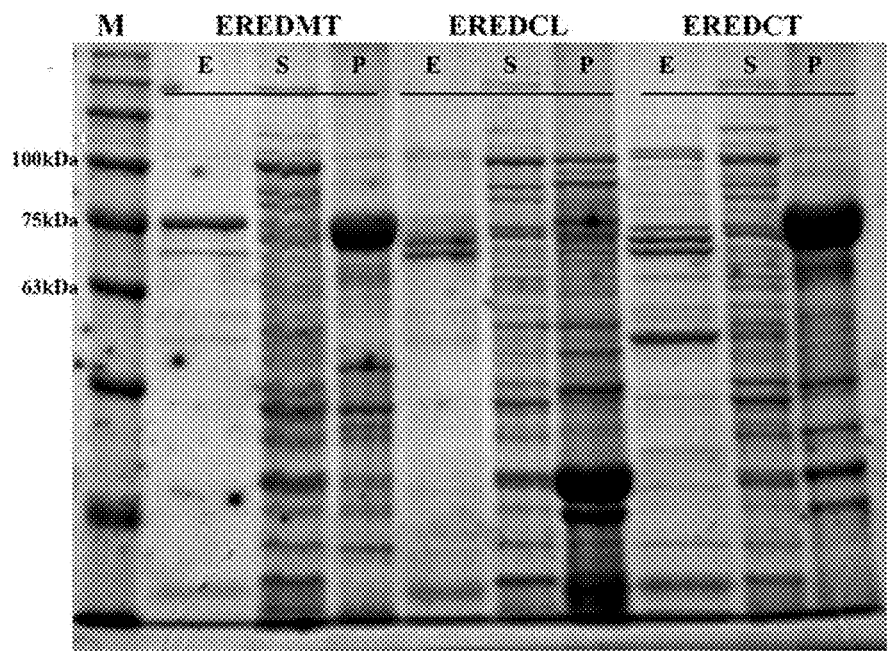
Figure 6:
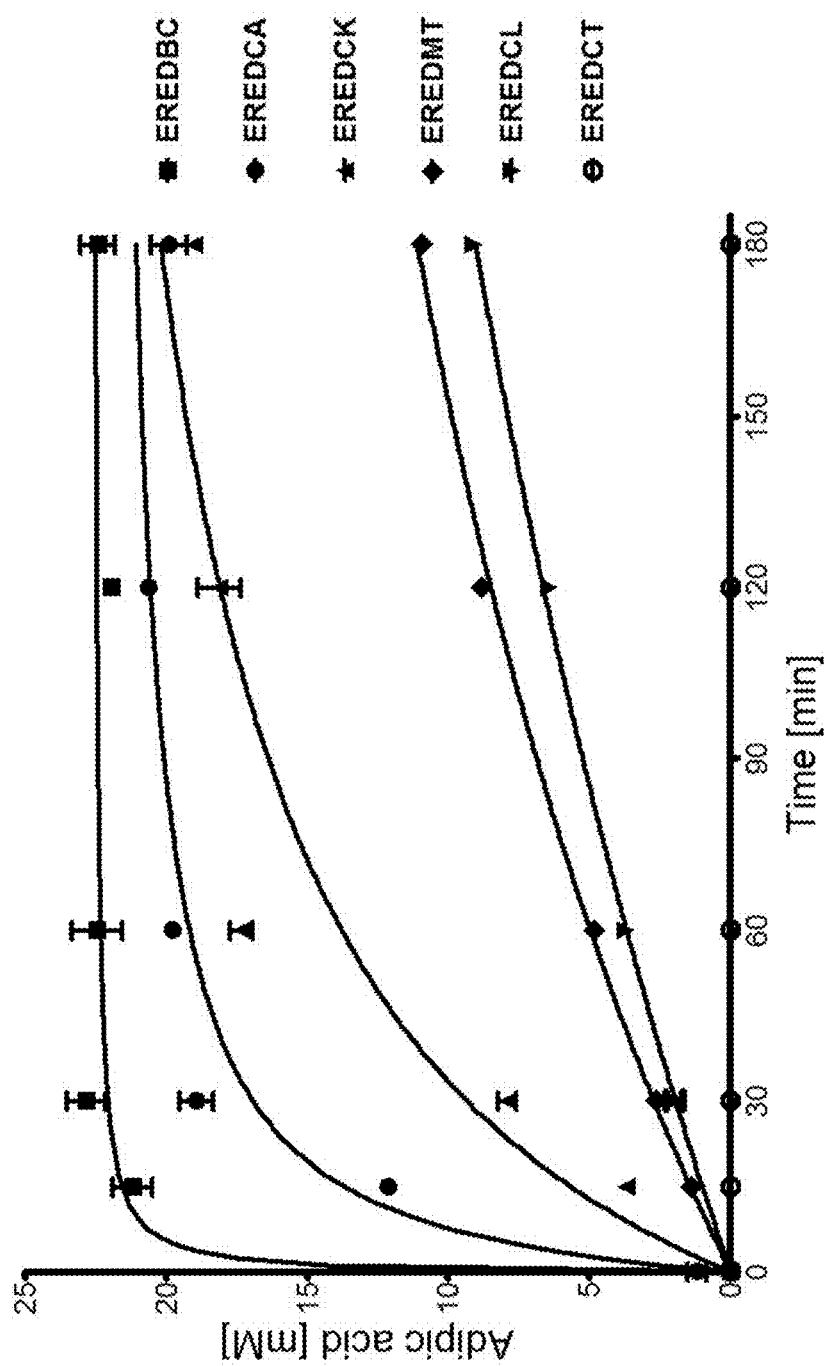
FIG. 6 shows time course of the anaerobic biotransformation of 2-hexenedioic acid into adipic acid by the *E. coli* cells expressing the recombinant EREDs. A mixture of cis- and trans-isomers of 2-hexenedioic acid was used as a substrate, and the results are means from at least two independent determinations. 20 mM 2-hexenedioic acid was used for the biotransformation.
Figure 7A:
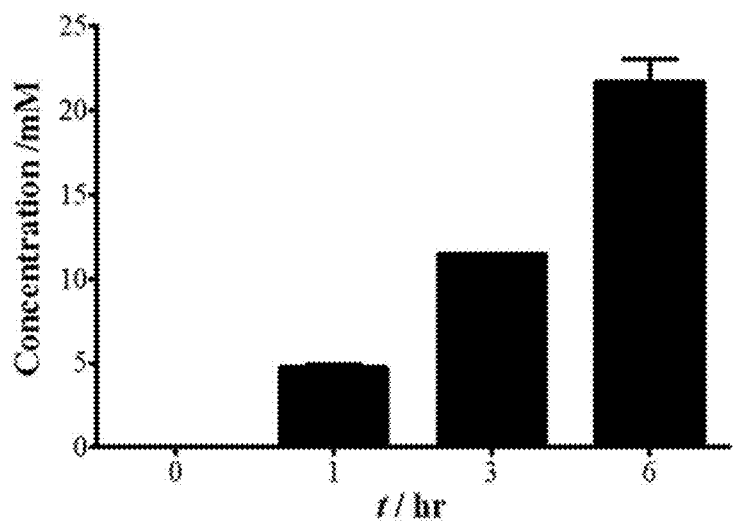
FIGS. 7A and 7B shows complete biotransformation of 2-hexenedioic acid into adipic acid by the *E. coli* cells expressing the recombinant a) EREDCL and b) EREDMT. 20 mM 2-hexenedioic acid was used for the biotransformation under anaerobic conditions.
Figure 7B:
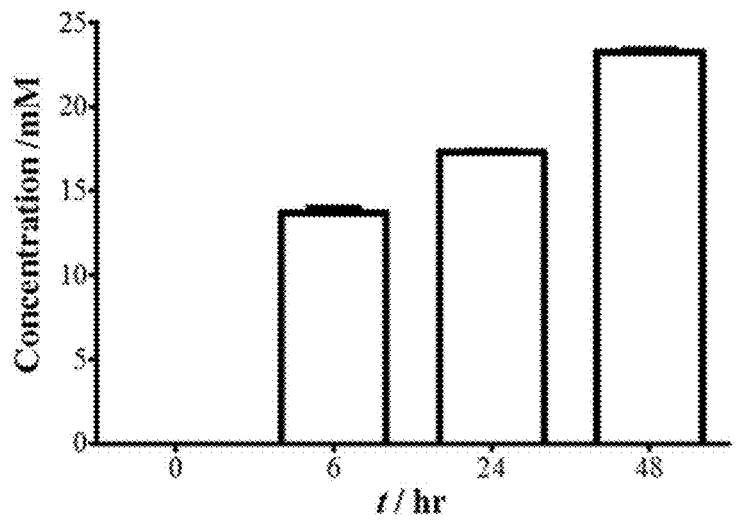
Figure 14:
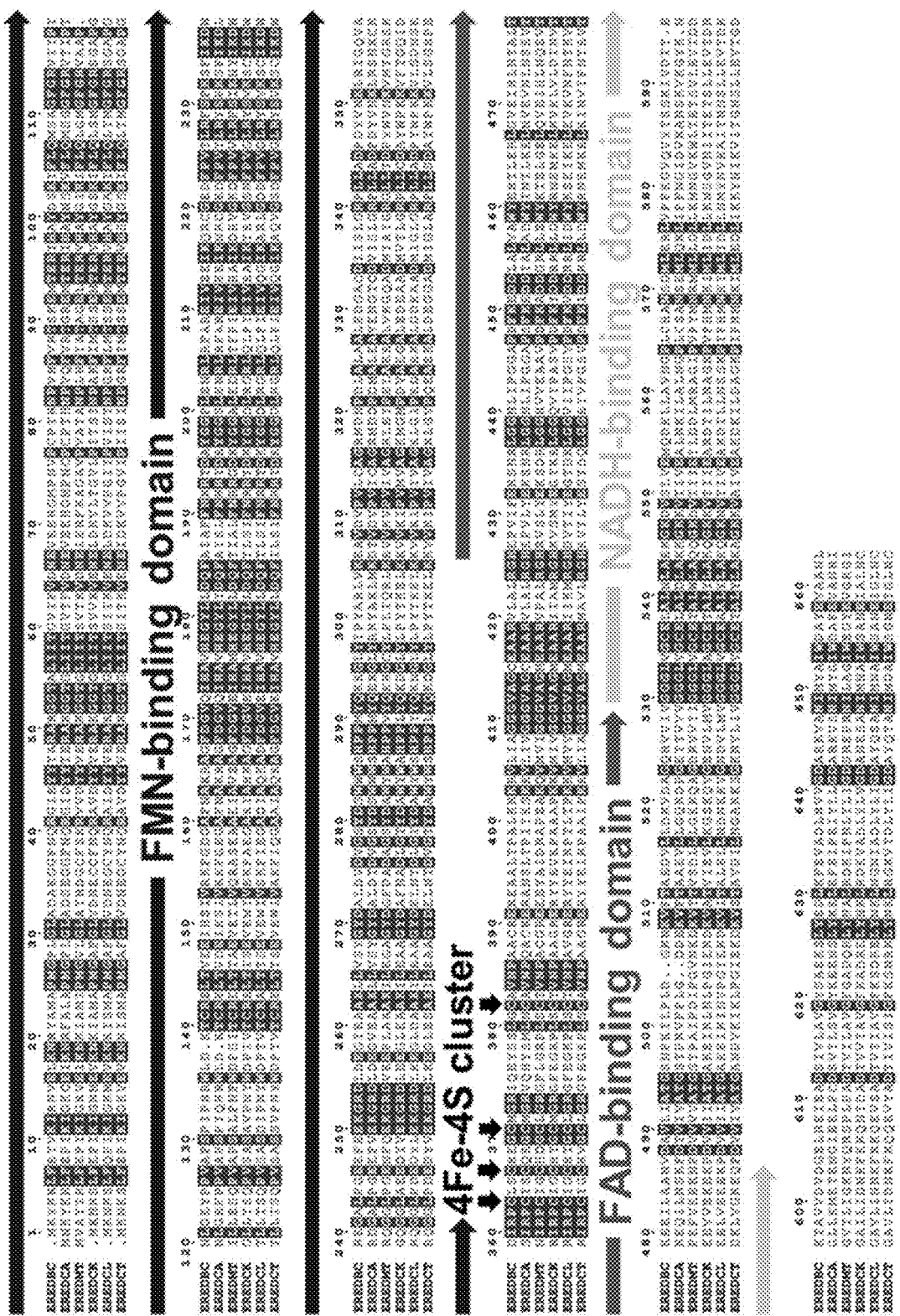
FIG. 14 shows multiple sequence alignment of EREDs studied. Multiple sequence alignment was performed and visualized by Cluster Omega and ESPript 3.0, respectively.
Figure 15:
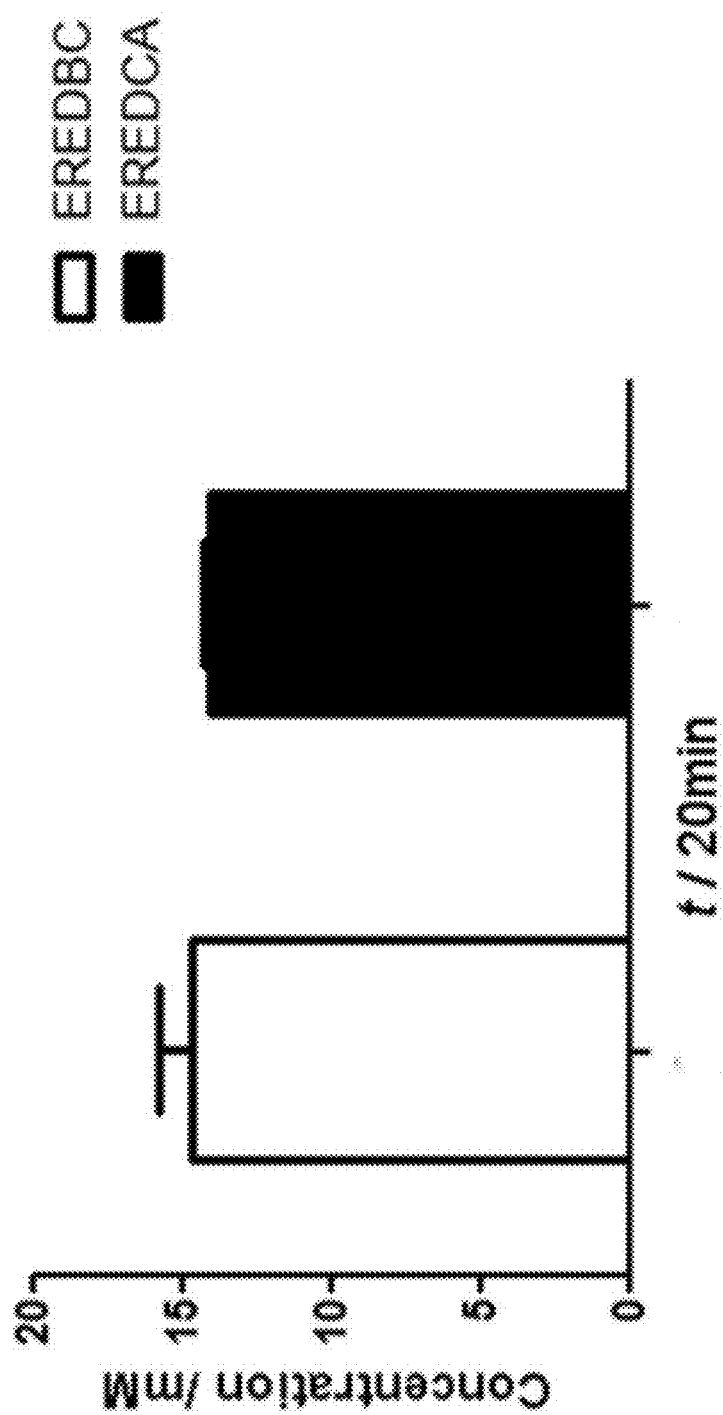
FIG. 15 shows whole-cell biotransformation of 2-hexenedioic acid (15 mM) into adipic acid by the $E.\ coli$ cells expressing recombinant EREDBC (black) and EREDCA (white) under aerobic conditions. The cells were grown and the proteins were expressed anaerobically.

It is known that ERED from *C. tyrobutyricum* (EREDCT, SEQ ID NO: 5 CAA71086.1) exhibits a broad substrate specificity toward α,β-unsaturated carboxylates in vivo. (Buhler and Simon 1982) EREDCT shows 50~82% sequence identity to EREDs (FIG. 14) from *Bacillus coagulans* 36D1 (EREDBC, SEQ ID NO: 1), *C. acetobutylicum* (EREDCA, SEQ ID NO: 2), *C. kluveri* (EREDCK, SEQ ID NO: 3), *C. ljungdahlii* (EREDCL, SEQ ID NO: 4) and *Moorella thermoacetica* (EREDMT, SEQ ID NO: 6). Whole-cell anaerobic biotransformation of 2-hexenedioic acid (20 mM) using these EREDs expressed in *E. coli* BL21 (DE3) zliscR (FIG. 3) revealed production of adipic acid by all EREDs (except EREDCT) (FIG. 6). EREDBC, EREDCA and EREDCK catalyzed a complete conversion of 2-hexenedioic acid to adipic acid within 3 hr, while EREDMT and EREDCL showed complete hydrogenation of 2-hexenedioic acid after 6 and 48 h, respectively (FIG. 7) The inactivity of EREDCT can be attributed to its low expression in *E. coli* (FIG. 5*b*), which can be improved using the established methods of codon optimization for recombinant protein expression in *E. coli*. Although the studied EREDCT is known to be an oxygen sensitive enzyme (Baler, M. & Simon, H. On the kinetics and mechanism of enoate reductase. *Hoppe-Seyler's Zeitschrift fur Physiologische Chemie* 363, 609-625 (1982)), for anaerobically grown EREDBC (SEQ ID NO: 1) and EREDCA (SEQ ID NO: 2) aerobic biotransformation of 2-hexenedioic acid (15 mM) was performed. All used buffers and solvents were prepared and stored under aerobic conditions. Under aerobic incubation conditions, both cultures catalyzed full conversion of 2-hexenedioic acid to adipic acid within 20 minutes (FIG. 15). This result can be explained by high cell density used for biotransformation (average—100 mg of dry cell biomass per ml) and *E. coli* high respiration rates in *E. coli* cells maintaining anaerobic conditions inside the cells.

TABLE 2

The ERED proteins tested for biocatalytic hydrogenation

| Protein ID | GenBank ID | Microorganism |
|---|---|---|
| EREDBC (SEQ ID NO: 1) | AEO99944.1 | *Bacillus coagulans* 36D1 |
| EREDCA (SEQ ID NO: 2) | AEI32805.1 | *Clostridium acetobutylicum* DSM 1731 |
| EREDCK (SEQ ID NO: 3) | EDK32796.1 | *Clostridium kluyveri* DSM 555 |
| EREDCL (SEQ ID NO: 4) | ADK16394.1 | *Clostridium ljungdahlii* DSM 13528 |
| EREDCT (SEQ ID NO: 5) | CAA71086.1 | *Clostridium tyrobutyricum* |
| EREDMT (SEQ ID NO: 6) | ABC20352.1 | *Moorella thermoacetica* ATCC 39073 |

Figure 8:
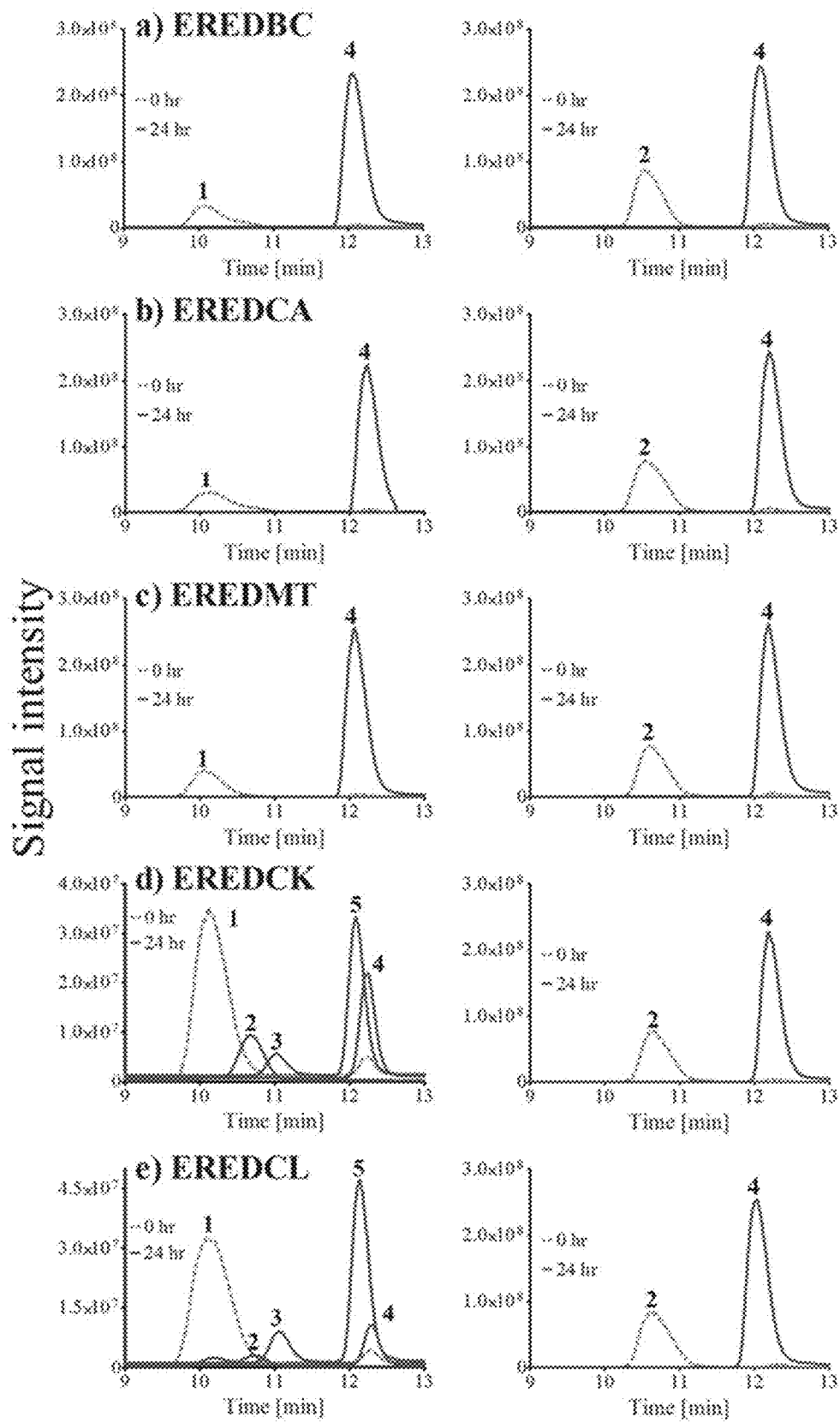
FIG. 8 shows 24 h anaerobic biotransformation of cis,cis-muconic acid to adipic acid by the *E. coli* cells expressing the recombinant a) EREDBC, b) EREDCA, c) EREDMT, d) EREDCK and e) EREDCL. The saturated cis,cis-muconic acid solution (0.7 mM) was used for the biotransformation. Substrates and products were detected by LC-MS. 1: cis,cis-muconic acid, 2: trans, trans-muconic acid, 3: 2-hexenedioic acid, 4: adipic acid, 5: 3-hexenedioic acid-like compound with m/z 143.0319.

Whole-cell biotransformation of cis,cis- and trans,trans-isomers of muconic acid (0.7 mM) revealed that EREDBC, EREDCA, and EREDMT also hydrogenated these substrates to adipic acid. After a 24-hr incubation, no muconic acid or 2-hexenedioic acid were detected in the culture, and a 99% yield of adipic acid was obtained (FIGS. 8*a*, 8*b*, and 8*c*). EREDCK and EREDCL also exhibited a 99% yield of adipic acid from trans,trans-muconic acid, but a lower yield (<35%) from the cis,cis-isomer (FIGS. 8*d* and 8*e*). Interestingly, with the latter substrate these EREDs produced three additional products identified as trans,trans-muconic acid, 2-hexenedioic acid, and 3-hexenedioic acid-like compound with m/z 143.0319 (FIGS. 8*d* and 8*e*). The formation of trans,trans-muconic acid from a cis,cis-isomer suggests the presence of cis-trans isomerase activity in EREDCK and EREDCL. The 3-hexenedioic acid-like compound appears to be an inefficient substrate for these EREDS. This is similar to the mutated 2,4-dienoyl-CoA reductases from *E. coli*, which catalyze hydrogenation of 2,4-dienoyl CoA into 3-enoyl CoA (Tu, X., Hubbard, P. A., Kim, J. J. P. & Schulz, H. Two distinct proton donors at the active site of *Escherichia coli* 2,4-dienoyl-CoA reductase are responsible for the formation of different products. Biochemistry 47, 1167-1175 (2008).). Thus, the results indicate that the studied EREDs can catalyze the sequential hydrogenations of two C═C bonds of the six-carbon dicarboxylic acids, but appear to have different isomeric preferences.

Example 4—Biochemical Characterization of EREDCA and EREDBC

Figure 5A:
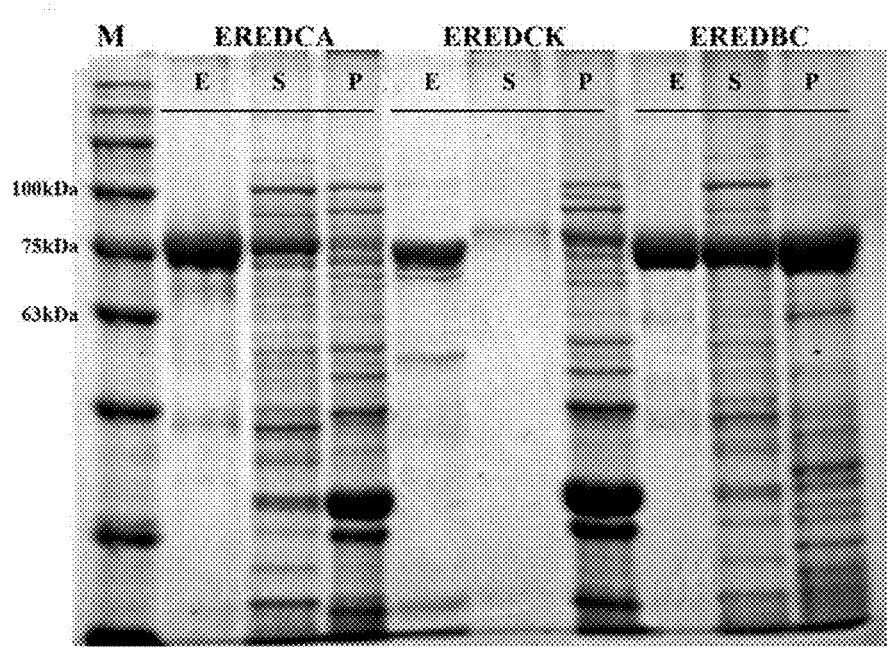
FIGS. 5A and 5B shows SDS-PAGE analysis of the ERED expression in *E. coli* and protein purification. a) EREDCA, EREDCK, and EREDBC. b) EREDMT, EREDCL, and EREDCT. LC-MS analysis revealed that soluble proteins at 75 kDa in the E lane of EREDCT are hypothetical protein ECD 02181 (74.2 kDA, GenBank: ACT44004.1), heat shock protein 90 (71.4 kDa, ACT42323.1), and molecular chaperone DnaK (69.1 kDa, ACT41916.1) (data not shown). M: marker, E: purified ERED, S: supernatant (soluble fraction), P: pellet (insoluble fraction).
Figure 9:
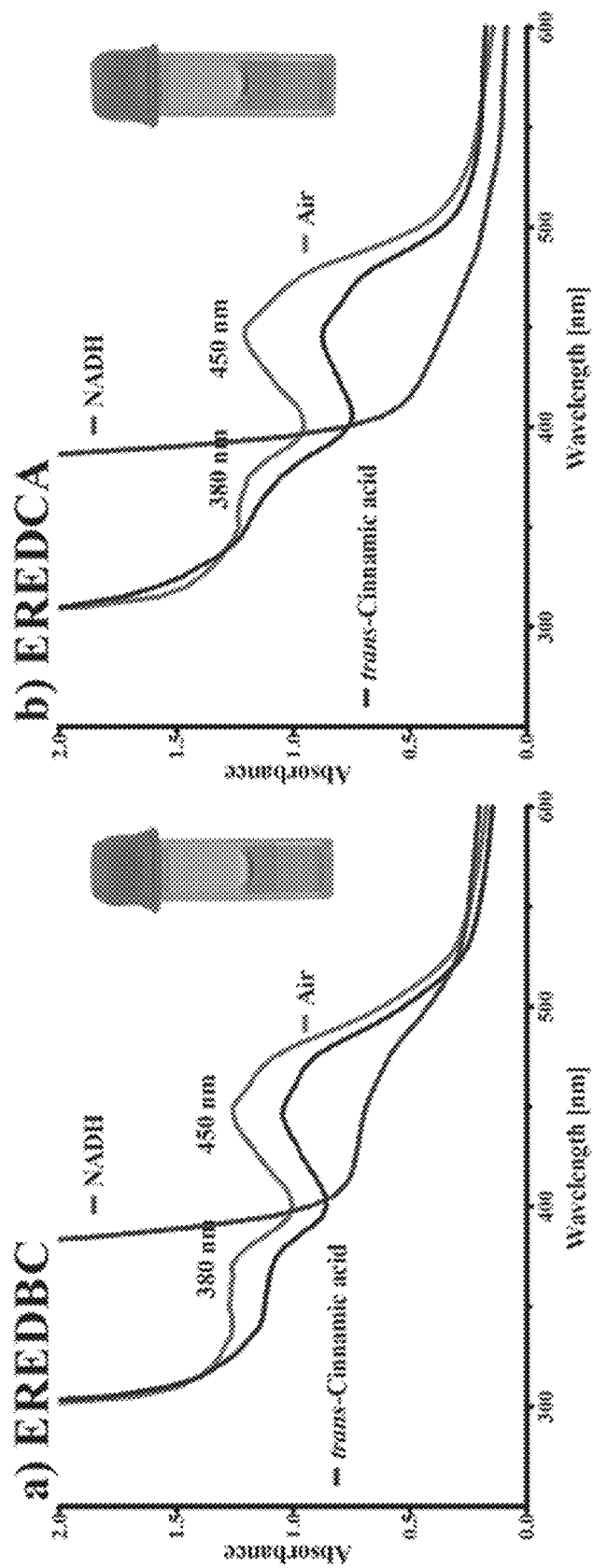
FIG. 9 shows UV-visible absorption spectra of purified EREDBC and EREDCA. Purified protein was kept on ice in the presence of air (oxidation, Air lines) or 3 mM NADH (reduction, NADH lines) under argon. Subsequent addition of 6 mM trans-cinnamic acid to the reduced protein resulted in partial re-oxidation (absorbance increase at 450 nm). The spectrophotometric cuvettes show brown-colored preparations of purified EREDBC and EREDCA used in these experiments.
Figure 10A:
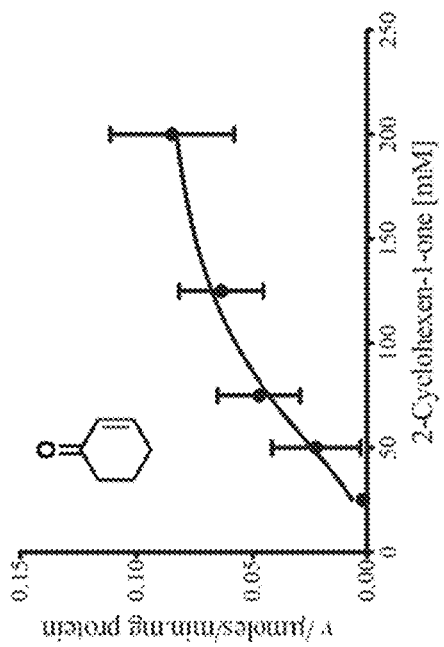
FIGS. 10A-10D shows in vitro biochemical characterization of purified EREDBC. Reductase activity of EREDBC as a function of a) 2-hexenedioic acid, b) 2-cyclohexen-1-one, c) 3-methyl-2-hexenone, and d) trans-cinnamic acid concentration.
Figure 10B:
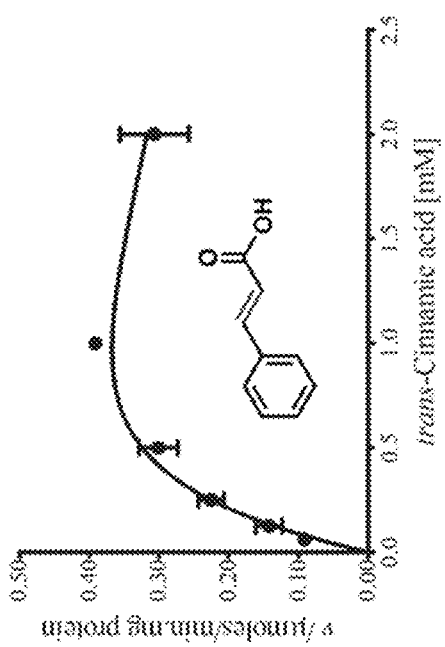
Figure 10C:
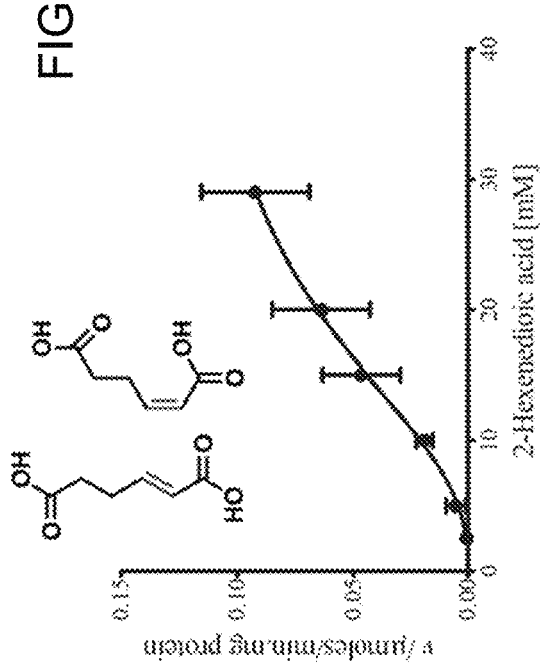
Figure 10D:
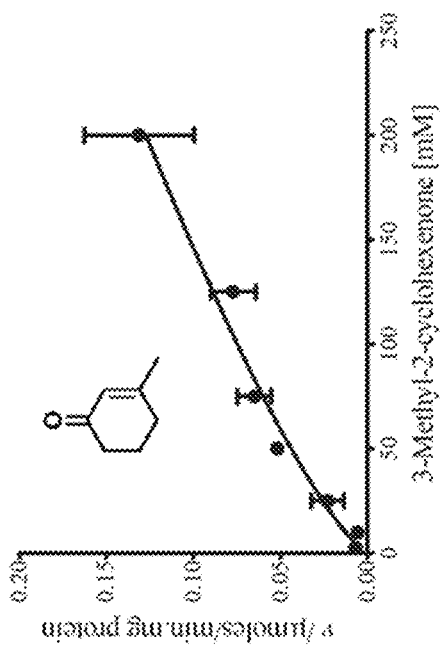

Anaerobic over-expression and affinity purification of six cloned EREDs produced significant amounts of soluble protein for EREDBC, EREDCA, and EREDCK (>5 mg/L), whereas the other three EREDs showed lower expression (FIG. 5). Purified EREDBC and EREDCA exhibited a brown colour in solution and an absorption spectrum with a shoulder at 380 nm and flavin-like maximum at 450 nm (FIG. 9). Both the brown colour of purified EREDBC and EREDCA and the 380 nm shoulder in its absorption spectrum suggest the presence of a functional [4Fe-4S] cluster.

Our spectral studies revealed that purified EREDBC and EREDCA can be completely oxidized by oxygen (in the presence of air), reduced with an excess of NADH (3 mM), and then partially re-oxidized by substrate addition (i.e. 6 mM trans-cinnamic acid).

For in vitro biochemical characterization, enzyme activities of purified EREDs were measured with 2-hexenedioic acid, cis-cis-muconic acid, trans-trans muconic acid, trans-cinnamic acid, trans-2-methyl-2-butenoic acid, trans-2-butenoic acid, acrolein, 2-cyclohexen-1-one, and 3-methyl-2-cyclohexenone. Purified EREDBC and EREDCA showed NADH-dependent reductase activity, while the other purified EREDs were inactive with the tested substrates, probably, due to the loss of the iron-sulfur cluster, or flavin cofactors, or different substrate preference. [Feng, J. et al. Discovery and Characterization of BlsE, a Radical S-Adenosyl-L-methionine Decarboxylase Involved in the Blasticidin S Biosynthetic Pathway. *PLoS ONE* 8 (2013)]. In the EREDBC and EREDCA spectra shown in FIG. 9, the peaks for the associated flavine and FeS cluster cofactors are clearly visible, which can help to differentiate between the active and inactive enzymes (while purifying).

Figures 11A, 11B:
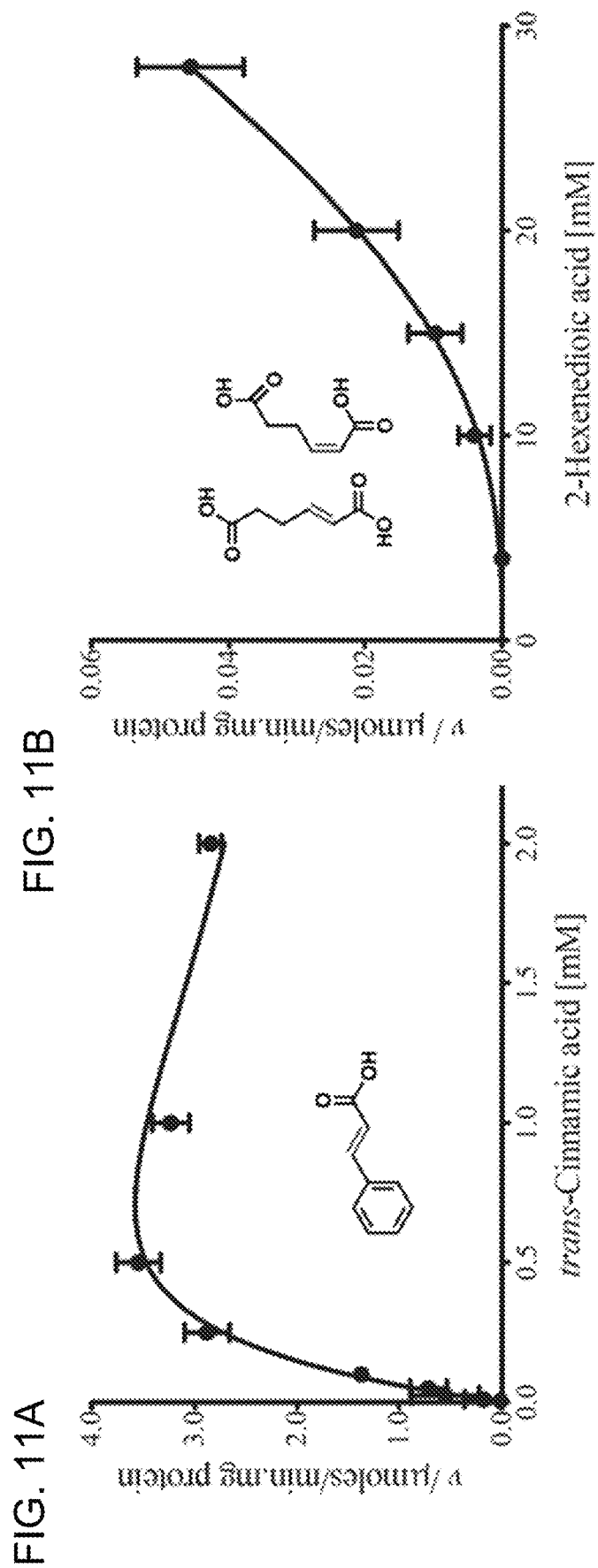
FIGS. 11A and 11B shows in vitro biochemical characterization of purified EREDCA. Reductase activity of EREDCA as a function of a) trans-cinnamic acid concentration or b) 2-hexenedioic acid concentration in the presence of NADH.

Enzymatic assays under anaerobic conditions revealed that purified EREDCA has high hydrogenation activity against trans-cinnamic acid (3.5 U/mg protein) and low activity with trans-2-butenoic acid (0.008 U/mg protein). The kinetic constants ($k_{cat}$ and $K_m$) for trans-cinnamic acid were 5.2 s$^{-1}$ and 0.17 mM respectively, and its specific activity was comparable to that of cinnamate reductase from *C. sporogenes* (5 U/mg protein). EREDCA exhibited substrate inhibition by trans-cinnamic acid at substrate concentrations higher than 0.5 mM with an inhibition constant ($K_i$) of 1.2 mM (FIG. 11a). Purified EREDCA was also active against 2-hexenedioic acid (up to 0.05 U/mg protein), but showed no saturation by this substrate in the concentration range from 4 to 28 mM (FIG. 11b).

Purified EREDBC exhibited significant reductase activity against 2-hexenedioic acid (0.09 U/mg protein), 2-cyclohexen-1-one (0.08 U/mg protein), 3-methyl-2-cyclohexenone (0.13 U/mg protein), and trans-cinnamic acid (0.39 U/mg protein) and detectable activity against trans-2-butenoic acid (crotonic acid, 0.036 U/mg protein) and acrolein (0.037 U/mg protein). EREDBC had a broad substrate specificity compared to EREDCA (Table 3). A biocompatible palladium catalyst was proposed for non-enzymatic hydrogenation of alkene metabolites in growth media including cinnamic acid variants and dicarboxylic acids. EREDBC exhibited a comparable substrate spectrum to that of the palladium catalyst (Sirasani, G., Tong, L. & Balskus, E. P. A biocompatible alkene hydrogenation merges organic synthesis with microbial metabolism. *Angew. Chem. Int. Ed.* (2014), providing evidence that EREDBC can be a good substitute for alkene hydrogenation in microbial production of biochemicals.

TABLE 3

| In vitro C=C reductase activity of EREDBC against unsaturated carbonyl substrates. | |
| --- | --- |
| Substrates | Activity [U/mg protein] |
| 2-Hexenedioic acid[a] | |
| [29 mM] | 0.09 ± 0.02 |
| [35 mM] | 2.3 ± 0.04 |
| trans-Cinnamic acid [1.0 mM][b] | 0.39 ± 0.001 |
| 3-Methyl-2-cyclohexenone [200 mM] | 0.13 ± 0.03 |
| 2-Cyclohexen-1-one [200 mM] | 0.08 ± 0.03 |

TABLE 3-continued

In vitro C=C reductase activity of EREDBC against unsaturated carbonyl substrates.

| Substrates | Activity [U/mg protein] |
|---|---|
| Acrolein [15 mM] | 0.036 ± 0.005 |
| trans-2-Butenoic acid [50 mM] | 0.037 ± 0.010 |
| Muconic acid [0.7 mM] cis,cis-isomer | ND[c] |
| trans,trans-isomer | ND[c] |

[a]2-Hexendioic acid was dissolved in aqueous buffer (29 mM) or in 0.25 mM isopropanol (35 mM).
[b]trans-Cinnamic acid titrated with 1N NaOH was used for enzyme assay.
[c]ND: not detected.

Kinetic studies of purified EREDBC were performed using 2-hexenedioic acid, 2-cyclohexen-1-one, 3-methyl-2-cyclohexenone, and trans-cinnamic acid as substrates (FIG. 10). EREDBC showed no saturation by 2-hexenedioic acid, 2-cyclohexen-1-one, and 3-methyl-2-cyclohexenone, but saturation kinetics was observed for trans-cinnamic acid (FIG. 10d). The kinetic constants ($k_{cat}$ and $K_m$) for trans-cinnamic acid were 0.50 s$^{-1}$ and 0.51 mM, respectively. EREDBC also exhibited moderate substrate inhibition by trans-cinnamic acid at substrate concentrations higher than 1.0 mM with the inhibition constant $K_1$ 1.4 mM. In contrast to trans-cinnamic acid, EREDBC showed a sigmoid-like profile for 2-hexenedioic acid dissolved in aqueous buffer solution but no saturation was observed despite its significant in vitro activity (0.09 U/mg protein) (FIG. 10a), which might be due to limited solubility of 2-hexenedioic acid in aqueous solutions.

Figure 12:
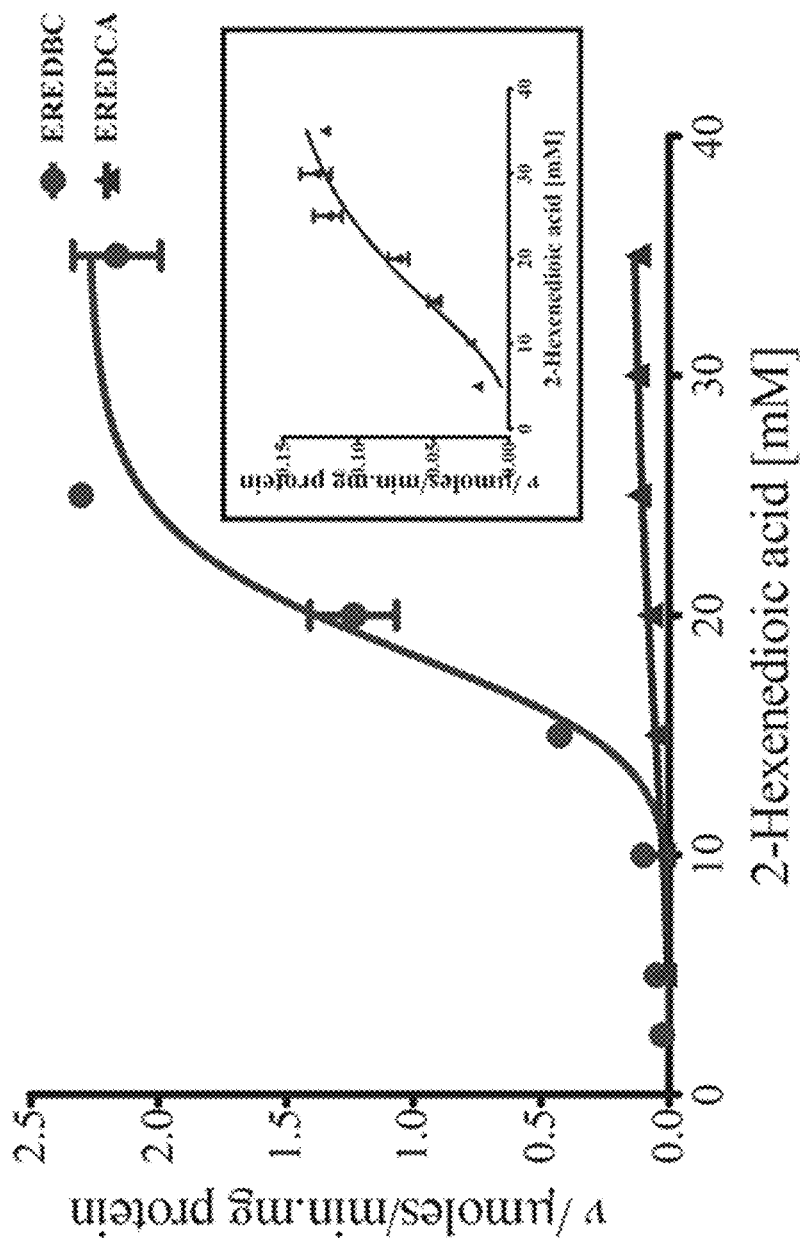
FIG. 12 shows in vitro biochemical characterization of purified EREDBC and EREDCA. Reductase activity as a function of 2-hexenedioic acid dissolved in a reaction mixture containing isopropanol in the presence of NADH.

To increase the dissolved substrate concentration, 2-hexenedioic acid was dissolved in a reaction mixture containing 0.25 mM (final concentration) isopropanol, and kinetic constants of EREDBC and EREDCA were determined. Both ERED enzymes showed sigmoidal kinetics in the concentration range from 2.5 to 35 mM (FIG. 12). Compared to EREDCA, EREDBC exhibited a higher turnover rate ($k_{cat}$, 1.86 vs. 0.138 s$^{-1}$) and similar affinity ($K_m$, 18.9 vs. 20.47 mM) for 2-hexenedioic acid, resulting in a 14.6-fold higher catalytic efficiency of EREDBC compared to EREDCA ($k_{cat}/K_m$, 0.984 vs. 0.0674 s$^{-1}$ mM$^{-1}$).

Example 5—Oxygen Tolerance

It is known that EREDs are oxygen-sensitive enzymes, which are rapidly inactivated by oxygen due to the presence of an oxygen sensitive [4Fe-4S] iron-sulfur cluster coordinated by four cysteine residues in strictly conserved motif C-2X-C-3X-C-11X-C (FIG. 14) [Gall, M. et al. Enzymatic conversion of flavonoids using bacterial chalcone isomerase and enoate reductase. Angewandte Chemie International Edition 53, 1439-1442 (2014).]. However, in the present experiments purified EREDBC exhibited significant resistance to inactivation by oxygen, whereas EREDCA was inactivated only after two days of incubation under air (FIG. 13).

Purified EREDs were placed in 5 mL glass tubes tightly capped with air-tight rubber stoppers. Anaerobic tubes were filled with anaerobic gas mixture (80% $N_2$, 10% $H_2$, and 10% $CO_2$) and aerobic tubes were filled with atmospheric air. The tubes were kept on ice for a week and a small aliquots of EREDs (5 ul) were withdrawn by a syringe every day to measure residual activity in a reaction mixture containing 100 mM potassium phosphate buffer (pH 7.0), 0.5 mM NADH, indicated substrates (0.25 mM 2-hexenedioic acid for EREDBC and 0.75 mM cinnamic acid for EREDCA, and protein (1 μg) in a final volume of 200 μL.

Figure 13A:
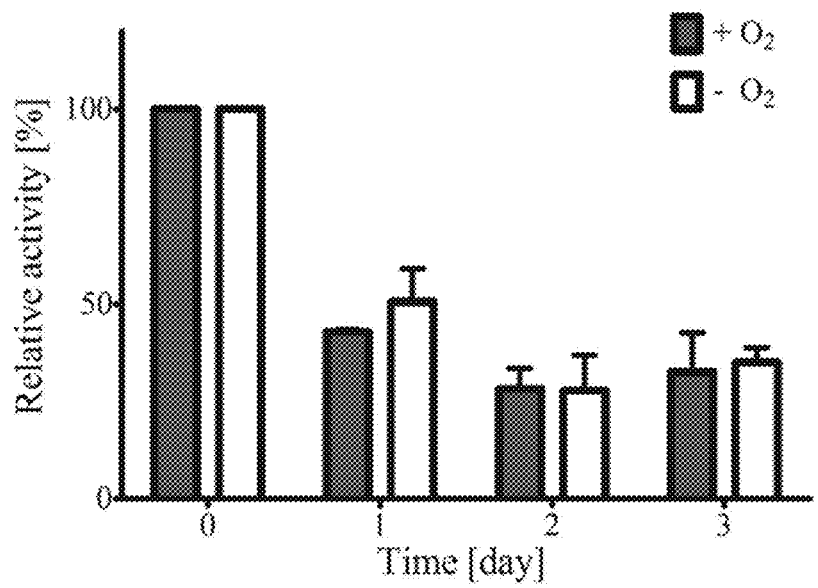
FIGS. 13A and 13B shows in vitro oxygen tolerance (residual activity) of purified a) EREDBC and b) EREDCA in the presence of 21% of oxygen.
Figure 13B:
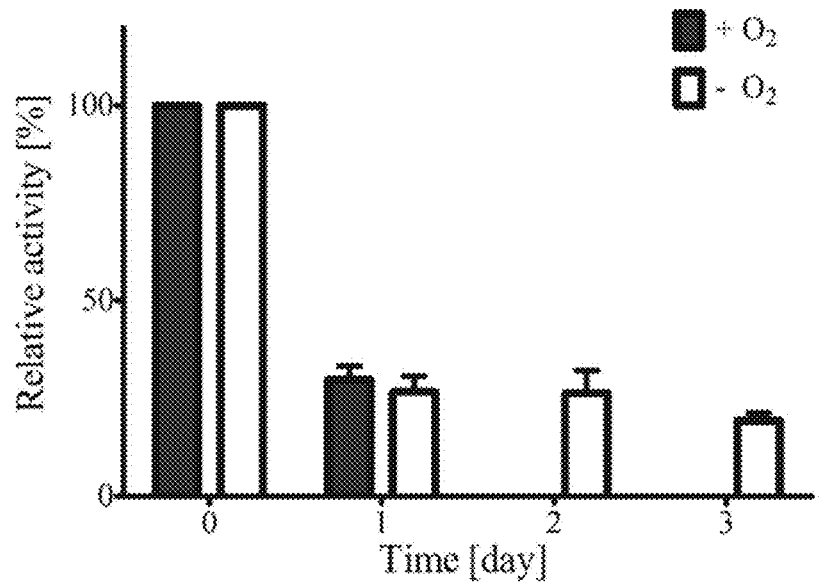

After three days of storage in the absence of oxygen at 4° C., both EREDBC and EREDCA retained 35 and 19% of initial activity, respectively. In the presence of air (21% oxygen), EREDBC showed significant oxygen tolerance (i.e. no oxygen inactivation after retaining 33% of initial activity after three days of storage) (FIG. 13a). In contrast, EREDCA exhibited 30% residual activity after one day of storage and then, was completely inactivated by oxygen after two additional days of storage (FIG. 13b). The oxygen tolerance of EREDBC and EREDCA may be associated with restricted access of oxygen to its [4Fe-4S]. [Jervis, A. J. et al. The $O_2$ sensitivity of the transcription factor FNR is controlled by Ser24 modulating the kinetics of [4Fe-4S] to [2Fe-2S] conversion. Proceedings of the National Academy of Sciences of the United States of America 106, 4659-4664 (2009)].

Materials—Examples 6 and 7

Adipaldehyde (≥95%) was purchased from Activate Scientific (UK), 6-hydroxyhexanoic acid was purchased from Alfa Aesar (Ward Hill, Massachusetts, USA), 4-hydroxybutyric acid was purchased from Arking Pharma (Guelph, ON, Canada), adipic acid (≥99.5%), butyraldehyde (≥99%), and aminocaproic acid (≥99%), 1,6-hexanediol (≥99%) were purchased from Sigma (St. Louis, MO, USA). Phusion® High-Fidelity DNA Polymerase and DpnI were purchased from New England Biolabs (Whitby, Ontario, Canada). In-Fusion HD plus EcoDry for a ligation-independent cloning was obtained from Clontech (Mountain View, CA, USA). All other chemicals were purchased from Sigma.

All results of in vitro experiments are means from at least three independent determinations. Control experiments were performed in parallel to correct substrate-independent oxidation of cofactors.

Product Analysis by HPLC and LC-MS—Examples 6 and 7

1.6-hexanediol, 1,4-butanediol, 6-hydroxyhexanoic and adipic acid standards and reaction samples were analyzed using a Varian ProStar HPLC system (Varian Medical Systems, Palo Alto, CA, USA) equipped with an Aminex HPX-87H column (300×7.8 mm) (Bio-Rad Laboratories Inc., Hercules, CA, USA). Samples were eluted with 5 mM $H_2SO_4$ at a flow rate of 0.6 ml/min, column temperature 50° C. The concentration of 1,6-hexanediol was determined by linear regression based on the peak areas at 210 nm UV or RI.

6-aminocaproic acid standards and reaction samples were prepared derivatised with o-phtalaldehyde according to Interchim website protocol for pre-column procedure of amines derivatisation (http://www.interchim.fr/ft/0/02727A.pdf). After 2 min 30° C. derivatisation, samples were analysed using a Varian ProStar HPLC system (Varian Medical Systems, Palo Alto, CA, USA) equipped with fluorescence detector (excitation—340 nm, emission—450 nm) and a Pursuit 5—C18 (150×4.0 mm) column. Samples were eluted with methanol/acetonitrile/water (45/45/10) (B)—40 mM phosphate buffer pH 7.6 (A) gradient. The solvent gradient was: 0 min, 0% B; 20 min, 60% B; 22 min, 60% B; 35 min, 0% B; followed by equilibration for 4 min with 0% B. The concentration of substrates and products was determined by linear regression based on the peak areas.

The LC-MS platform consists of a Dionex Ultimate 3000 UHPLC system and a Q-Exactive mass spectrometer equipped with a HESI source (all from Thermo Scientific). Control of the system and data handling was performed using Thermo XCalibur 2.2 software and Chromeleon 7.2 software. Separation by liquid chromatography was conducted on a Hypersil Gold C18 column (50 mm×2.1 mm, 1.9 μm particle size, Thermo Scientific) equipped with a guard column. The pump was run at a flow rate of 200 μL/min. Solvent A is water containing 0.1% formic acid; solvent B is acetonitrile. The gradient is 0min, 0% B; Detection of 4 min, 0% B; 15 min, 100% B; 24 min, 100% B; 25 min, 0% B; 30 min, 0% B; followed by equilibration for 5 min with 0% B. Autosampler temperature was maintained at 8° C. and injection volume was 10 μL. Data collection was done in positive ionization mode with a scan range m/z 100-300, resolution 70000 at 1 Hz, AGC target of 3e6 and a maximum injection time of 200 ms. Standard solutions of 1,6-hexanedioltime and m/z. (m/z 119.1062) and 6-hydroxycaproic acid (m/z 133.0864) were used for validation of retention time and m/z.

Example 6-6.1 Gene Cloning, Expression, and Purification of Proteins

Genes encoding the selected CARs, ARs, ATs, glutamate dehydrogenase YOR375C, alanine dehydrogenase BSU31930, polyphosphate kinases PA3455 and SMc02148 proteins were PCR-amplified from genomic DNA and cloned into a p15Tv-Lic plasmid with N-terminal 6His-tag via ligation-independent method as previously described [Bonsor D., Butz S. F., Solomons J., Grant S., Fairlamb I. J. S., Fogg M. J., Grogan G. Ligation independent cloning (LIC) as a rapid route to families of recombinant biocatalysts from sequenced prokaryotic genomes. Organic and Biomolecular Chemistry]. Previously it has been shown that post-translational phosphopantetheinylation of CARs is required for their activity [P. Venkitasubramanian et al. Reduction of Carboxylic Acids by Nocardia Aldehyde Oxidoreductase Requires a Phosphopantetheinylated Enzyme, Jan. 5, 2007 The Journal of Biological Chemistry. 282, 478-485.]. Hence, genes encoding phosphopantetheinyl transferase BSU03570 and entD were amplified from Bacillus subtilis and E. coli K-12 genomic DNA and cloned to pCDFDuet plasmid without tag using standard ligation-dependent protocol [Sambrook J, Russell D. Molecular Cloning—A Laboratory Manual. Cold Spring Harbor Laboratory Pres. (4th ed.) (2012)]. Formate dehydrogenase gene P33160 was cloned in pET23b with C-terminal tag. Site directed mutagenesis was performed using standard protocol [Kunkel T. A. Rapid and efficient site-specific mutagenesis without phenotypic selection. Proc Natl Acad Sci U.S.A. 82, 488-492 (1985)].

Recombinant plasmids were transformed into the E. coli BL21 (DE3) strain for the overexpression. Plasmids with phosphopantetheinyl transferase genes were co-transformed with CAR genes-containing plasmids. E. coli transformants were grown aerobically at 37° C. in Terrific Broth (TB) medium (1 L) supplemented with 100 μg/mL ampicillin (p15Tv-Lic, pET23b) and/or 50 μg/mL streptomycin (pCDFDuet) until the culture optical density (OD 600 nm) reached 0.8-1. At this point, cultivation temperature was decreased to 16° C., and protein expression was induced with 0.4 mM IPTG. E. coli cells after overnight induction were harvested by centrifugation (4,500 g), and the cell pellets were stored at −20° C. before protein purification. Cell pellets were resuspended in lysis buffer (400 mM NaCl, 50 mM HEPES, pH 7.5, 5% glycerol, 5 mM imidazole) and sonicated on ice for 20 minutes in 5 secon pulses, followed by 5 seconds cooling. Insoluble cell material was removed (40,000 g) and the supernatant was incubated with a Ni-affinity resin (Qiagen, Valencia, CA, USA) at 4° C. for 1 h. The resin was then washed with 100 mL of washing buffer (400 mM NaCl, 50 mM HEPES, pH 7.5, 5% glycerol, 20 mM imidazole) and eluted with elution buffer (400 mM NaCl, 50 mM HEPES, pH 7.5, 5% glycerol, 250 mM imidazole). Purified proteins were frozen in droplets in liquid $N_2$ and stored at −80° C. Protein concentration was determined using Bradford assay and protein purity was evaluated using 13% SDS-PAGE gels.

6.2. Enzyme Screening: CARs (1.2.1.30)

It has been shown that the N. iowensis CAR has a broad substrate range, though its maximal activity was usually observed with aromatic substrates such as benzoic and cinnamic acids. CARs gene sequences homologues to the N.

Figure 16:
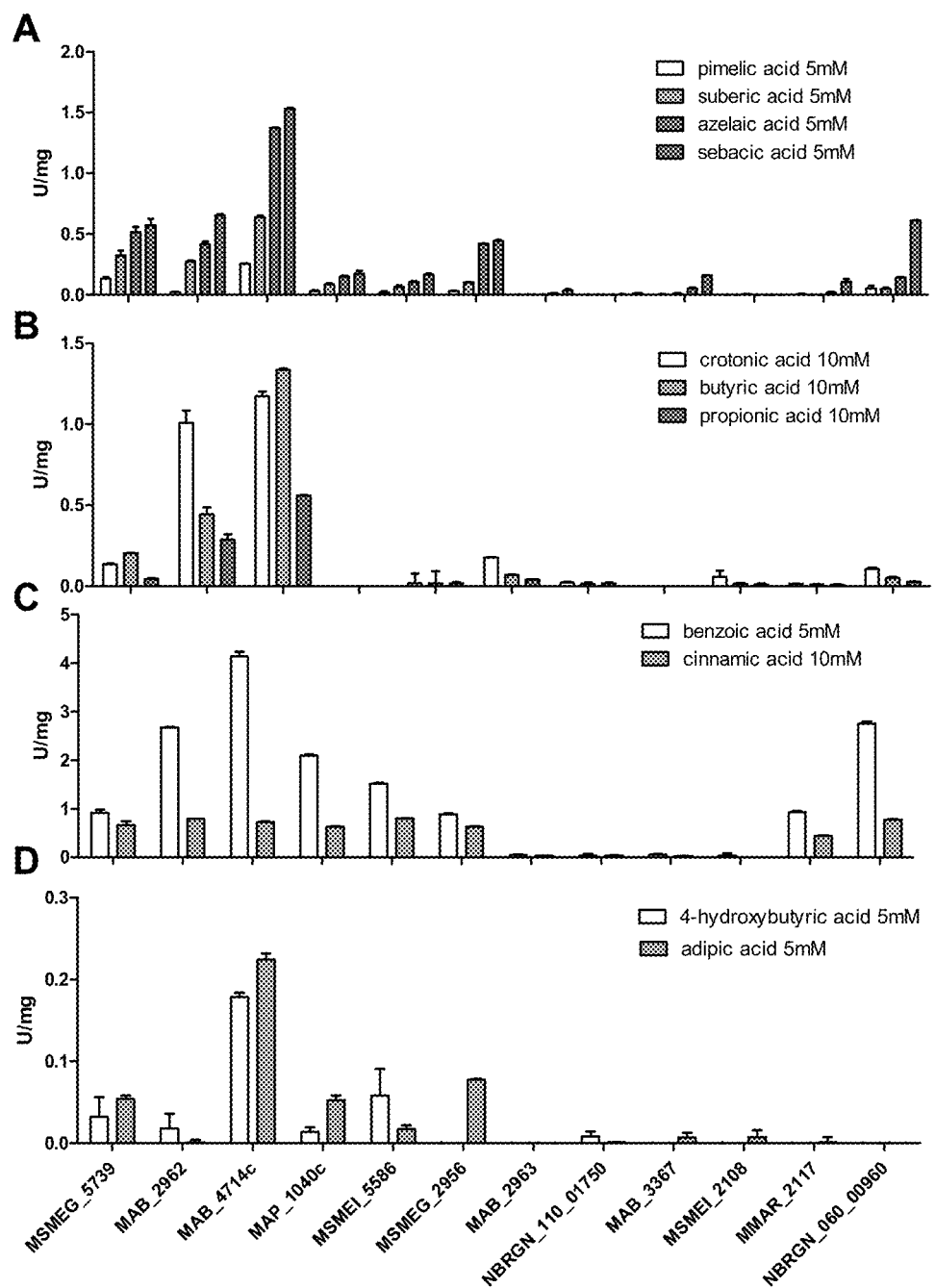
FIG. 16 shows substrate screening of purified carboxylate reductases (CARs): A—pimelic acid, suberic acid, azelaic acid (5 mM each); B—crotonic acid, butyric acid, propionic acid (10 mM each); C—benzoic acid (5 mM) and cinnamic acid (10 mM); D—adipic and 4-hydroxybutyric acid (5 mM each). Reductase activity was measured spectrophotometrically by following the oxidation of NADPH depletion at 340 nm.

*iowensis* CAR (Uniprot number: Q6RKB1), were selected from GenBank database. Based on presence of adenylation (AMP-binding PF00501) and reduction (NAD-binding PF07993) domains accompanied with phosphopantetheinyl binding motif (PF00530) 13 CAR genes (mostly from *Mycobacterium*) were cloned and expressed in *E. coli*. (Table 4). As CAR activation enzymes, phosphopantetheinyl transferases (PPTs) from *E. coli* (P19925) and *Bacillus subtilis* (P39135), were used which were co-expressed with the selected CAR genes from a separate plasmid. Using 1-liter *E. coli* cultures with overnight induction by IPTG, 12 soluble CAR proteins were purified using affinity chromatography on a Ni-NTA resin. Based on a NADPH-oxidation assay, 8 proteins exhibited reductase activity towards the two common CAR substrates: benzoic acid and cinnamic acid (FIG. 16-A). Screening of purified enzymes against aliphatic dicarboxylic acids revealed significant reductase activity towards longer chain (C6) dicarboxylic acids, whereas no detectable activity was found with the shorter chain diacids (malonic acid, succinic acid, and glutaric acid) (FIG. 16). However, monocarboxylic C3-C4 monoacids with similar chain lengths (e.g. 4-hydroxybutyric acid, crotonic acid, butyric acid, and propionic acid) were found to be positive substrates for these enzymes (FIG. 16-B,D). The five CAR enzymes with the highest reductase activity towards adipic acid and 4-hydroxybutyric acid (MSMEI_5586, MAB_4714c, MSMEG_5739, MAP_1040c and MSMEG_2956) SEQ ID NOs: 35-39 were selected for the biochemical characterization and biotransformation reactions.

highest reductase activity against these substrates, and they were selected for the biochemical characterization and biotransformations.

Enzyme activity of purified ARs was measured spectrophotometrically in 96-well plates Reaction mixtures contained 100 mM HEPES buffer (pH 7.5), 0.4 mM NADH/NADPH, 10 mM adipaldehyde or butylaldehyde, and proteins (10 µg for adipaldehyde screen, 2 µg for butyraldehyde screen) in a final volume of 200 µL Reaction mixture for adipaldehyde screening contained 1.8% DMSO. Enzyme reactions were monitored by following the decrease in absorbance at 340 nm ($\varepsilon 340$ nm=6,220/M·cm) due to oxidation of NAD(P)H to NAD(P)+.

28 PLP-dependent aminotransferases (from the classes I, II and III) were cloned and overexpressed in *E. coli* (Table 6). Enzymes were purified using affinity chromatography on a Ni-NTA resin and were screened for reductase activity towards adipaldehyde using alanine and glutamate as aminodonors. Enzyme activity was measured spectrophotometrically using a coupled reaction with the NADPH/NADH-dependent alanine and glutamate dehydrogenases in the presence of excess of ammonium chloride. The five AT enzymes (GabT (SEQ ID NO:53), SM2011 b20379 (SEQ ID NO:59), SAV2583 (SEQ ID NO:55), SM2011_c04388 (SEQ ID NO:58), and SM2011 b20423 (SEQ ID NO:60)) exhibited the highest activity with adipaldehyde/butyraldehyde, and they were used for biochemical characterization.

Enzyme activity of ATs was measured spectrophotometrically in 96-well plates, coupled with NAD(P)H-dependent

TABLE 4

The 13 CARS cloned, purified and tested for reductase activity with 4-hydroxybutyric acid (5 mM) and adipic acid (5 mM) as substrates.

| | | | Activity [U/mg protein]* | |
|---|---|---|---|---|
| Uniprot gene ID | SEQ ID NO | Microorganism | 4-hydroxybutyric acid, 5 mM | adipic acid, 5 mM |
| 1. MAB_2962 | 39 | *M. abscessus* DSM44196 | ND | ND |
| 2. MAB_2963 | 66 | *M. abscessus* DSM44196 | ND | ND |
| 3. MAB_3367 | 67 | *M. abscessus* DSM44196 | ND | ND |
| 4. MAB_4714c | 36 | *M. abscessus* DSM44196 | 0.178 ± 0.005 | 0.225 ± 0.007 |
| 5. MMAR_2117 | 68 | *M. marinum* ATCC BAA-535 | ND | ND |
| 6. MMAR_2936 | 69 | *M. marinum* ATCC BAA-535 | NS | NS |
| 7. MAP_1040c | 38 | *M. paratuberculosis* ATCC BAA-968 | 0.014 ± 0.006 | 0.053 ± 0.006 |
| 8. MSMEG_2956 | 70 | *M. smegmatis* ATCC 700084 | ND | 0.078 ± 0.001 |
| 9. MSMEG_5739 | 37 | *M. smegmatis* ATCC 700084 | 0.032 ± 0.024 | 0.054 ± 0.004 |
| 10. MSMEI_2108 | 71 | *M. smegmatis* ATCC 700084 | ND | ND |
| 11. MSMEI_5586 | 35 | *M. smegmatis* ATCC 700084 | 0.058 ± 0.033 | 0.017 ± 0.005 |
| 12. NBRGN_110_01750 | 72 | *N. brasiliensis* NBRC 14402 | ND | ND |
| 13. NBRGN_060_00960 | 73 | *N. brasiliensis* NBRC 14402 | ND | ND |

*ND = no activity was detected.
NS = no soluble protein was detected.

6.3—Enzyme Screening: ARs and ATs 28 aldehyde reductases from different bacteria were cloned and overexpressed in *E. coli*. Enzymes purified using affinity chromatography on Ni-NTA resin were screened for reductase activity with adipaldehyde and butyraldehyde in presence of both NADPH and NADH (Table 5). Butyraldehyde was used as a substrate substitute for 4-oxo-butanal, which is not commercially available. Reactions were followed spectrophotometrically, by cofactor oxidation at 340 nm. The six AR enzymes (RHA1_ro05279 (SEQ ID NO:47), PA1146 (SEQ ID NO:43), SC00229 (SEQ ID NO:50), PP_3370 (SEQ ID NO:45), PSPTO_2097 (SEQ ID NO:46), and TM_0111 (SEQ ID NO:52) demonstrated the alanine and glutamate dehydrogenases (YOR375C (SEQ ID NO:107) and BSU31930 (SEQ ID NO:106)). Reaction was monitored by following the decrease in absorbance of NAD(P)H to NAD(P)+ at 340 nm ($\varepsilon 340$ nm=6,220/M·cm). Coupled enzymes can aminate pyruvate/ketoglutarate produced by ATs in excess of NH$_4$Cl. Reaction mixtures contained 100 mM HEPES buffer (pH 7.5), 0.5 mM NADPH, 0.5 mM NADH, 1 mM alanine, 1 mM glutamate, 10 mM adipaldehyde, 5% ethanol, 37.5 mM NaCl, 50 mM ammonium chloride, 50 µM PLP, YOR375C and BSU31930 (2.5 µg each), and AT proteins (20 µg) in a final volume of 200 µL.

TABLE 5

The 28 ARs cloned, purified and tested for the reduction of adipaldehyde (10 mM) and butyraldehyde (10 mM).

| # | Uniprot protein ID | Uniprot gene ID | SEQ ID NO | Microorganism | Activity [U/mg protein] Adipaldehyde | Activity [U/mg protein] Butyraldehyde |
|---|---|---|---|---|---|---|
| 1 | A9CHP3 | Atu2528 | 40 | Agrobacterium fabrum | ND | 0.110 ± 0.089 |
| 2 | Q81MX9 | GBAA_3440 | 74 | Bacillus anthracis | ND | ND |
| 3 | Q81MP2 | GBAA_4204 | 75 | Bacillus anthracis | ND | ND |
| 4 | Q7W7H3 | BPP2546 | 76 | Bordetella parapertussis | ND | ND |
| 5 | Q9KA03 | BH2491 | 41 | Bacillus halodurans | ND | 0.108 ± 0.026 |
| 6 | Q7NW13 | CV_2177 | 42 | Chromobacterium violaceum | ND | 0.151 ± 0.054 |
| 7 | Q7NTS7 | CV_2976 | 77 | Chromobacterium violaceum | ND | ND |
| 8 | H9UZD7 | P12B_c4067 | 78 | Escherichia coli | ND | ND |
| 9 | I2UEY0 | EC40522_3924 | 79 | Escherichia coli | ND | ND |
| 10 | M9FUN8 | EC174750_0241 | 80 | Escherichia coli | ND | ND |
| 11 | G0FDU2 | UMNF18_1684 | 81 | Escherichia coli | ND | ND |
| 12 | Q9I4I9 | PA1146 | 43 | Pseudomonas aeruginosa | 0.696 ± 0.032 | 1.68 ± 0.144 |
| 13 | Q9HZS9 | PA2918 | 44 | Pseudomonas aeruginosa | ND | 0.137 ± 0.03 |
| 14 | Q88HI7 | PP_3370 | 45 | Pseudomonas putida | 0.437 ± 0.043 | 1.516 ± 1.382 |
| 15 | Q884J5 | PSPTO_2097 | 46 | Pseudomonas syringae | 1.046 ± 0.009 | 0.59 ± 0.597 |
| 16 | Q0S803 | RHA1_ro04547 | 82 | Rhodococcus jostii | ND | ND |
| 17 | Q0SFL7 | RHA1_ro01858 | 83 | Rhodococcus jostii | ND | ND |
| 18 | Q0S5X6 | RHA1_ro05279 | 47 | Rhodococcus jostii | 0.721 ± 0.026 | 0.905 ± 0.834 |
| 19 | Q0RYZ9 | RHA1_ro08443 | 48 | Rhodococcus jostii | ND | 0.188 ± 0.142 |
| 20 | Q0RYT2 | RHA1_ro08510 | 84 | Rhodococcus jostii | ND | ND |
| 21 | Q6NDT3 | RPA0021 | 49 | Rhodopseudomonas palustris | ND | 0.116 ± 0.031 |
| 22 | Q82LP0 | SAV_1970 | 85 | Streptomyces avermitilis | ND | ND |
| 23 | Q9S1R2 | SCO0229 | 50 | Streptomyces coelicolor | 0.362 ± 0.05 | 0.892 ± 0.847 |
| 24 | Q93S07 | SCO6282 | 86 | Streptomyces coelicolor | ND | ND |
| 25 | A0A0F6EBS9 | SFyv_1886 | 51 | Shigella flexneri | ND | 0.124 ± 0.042 |
| 26 | V1QPP4 | SEEPB585_09674 | 87 | Salmonella enterica | ND | ND |
| 27 | Q9WMV6 | TM_0111 | 52 | Thermotoga maritima | ND | 1.055 ± 0.43 |
| 28 | Q8P5A9 | XCC3431 | 88 | Xanthomonas campestris | ND | ND |

*ND = no activity was detected.

TABLE 6

The 28 ATs cloned, purified and tested for the amination of adipaldehyde (10 mM).

| # | Target | Uniprot prot ID | Uniprot gene ID | SEQ ID NO | Microorganism | Adipaldehyde 10 mM U/mg |
|---|---|---|---|---|---|---|
| 1 | BAS0499 | Q81YV0 | BAS0499 | 89 | Bacillus anthracis | ND |
| 2 | BAS4776 | Q81K67 | BASH2_00839 | 90 | Bacillus anthracis | ND |
| 3 | EC6020 | P22256 | gabT | 53 | Escherichia coli | 0.337 ± 0.008 |
| 4 | MAR0012 | A1TWJ6 | Maqu_0007 | 91 | Marinobacter hydrocarbonoclasticus | ND |
| 5 | PA0221 | Q9I6R7 | PA0221 | 92 | Pseudomonas aeruginosa | ND |
| 6 | PA4805 | Q9HV04 | PA4805 | 93 | Pseudomonas aeruginosa | ND |
| 7 | PA5313 | Q9HTP1 | PA5313 | 94 | Pseudomonas aeruginosa | ND |
| 8 | PP2159 | Q88KV9 | PP2180 | 95 | Pseudomonas putida | ND |
| 9 | PP3681 | Q88GK3 | PP3718 | 96 | Pseudomonas putida | ND |
| 10 | PP4364 | Q88EN3 | PP4421 | 54 | Pseudomonas putida | 0.061 ± 0.001 |
| 11 | PP5113 | Q88CJ8 | PP5182 | 97 | Pseudomonas putida | ND |
| 12 | RHA04845 | Q0S806 | RHA1_ro04544 | 98 | Rhodococcus sp (strain RHA1) | ND |
| 13 | RHA07987 | Q0S5M0 | RHA1_ro05386 | 99 | Rhodococcus sp (strain RHA1) | ND |
| 14 | SAV2585 | Q82K21 | SAV_2583 | 55 | Streptomyces avermitilis | 0.136 ± 0.011 |
| 15 | SAV2614 | Q82JZ2 | SAV_2612 | 100 | Streptomyces avermitilis | ND |
| 16 | SC5440 | O86823 | SCO5676 | 56 | Streptomyces coelicolor | 0.084 ± 0.015 |
| 17 | SM2404 | M4MUD8 | SM2011_c01534 | 57 | Sinorhizobium meliloti | 0.021 ± 0.003 |
| 18 | SM3293 | M4MWT5 | SM2011_c04388 | 58 | Sinorhizobium meliloti | 0.152 ± 0.001 |
| 19 | SM4420 | Q92Y66 | SMa1855 | 101 | Rhizobium meliloti | ND |
| 20 | SM4966 | M4MIX5 | SM2011_b20277 | 102 | Sinorhizobium meliloti | ND |
| 21 | SM5064 | M4MML9 | SM2011_b20379 | 59 | Sinorhizobium meliloti | 0.106 ± 0.008 |
| 22 | SM5108 | M4ML18 | SM2011_b20423 | 60 | Sinorhizobium meliloti | 0.162 ± 0.002 |

TABLE 6-continued

The 28 ATs cloned, purified and tested for the amination of adipaldehyde (10 mM).

| # | Target | Uniprot prot ID | Uniprot gene ID | SEQ ID NO | Microorganism | Adipaldehyde 10 mM U/mg |
|---|--------|----------------|-----------------|-----------|---------------|-------------------------|
| 23 | SM5551 | M4MKK7 | SM2011_b21186 | 61 | Sinorhizobium meliloti | 0.051 ± 0.014 |
| 24 | mesta | A3EYF7 | — | 103 | Mesorhizobium sp. LUK | ND |
| 25 | Spo3471 | Q5LMU1 | Spo3471 | 62 | Ruegeria pomeroyi | 0.021 ± 0.001 |
| 26 | Mll7127 | Q987B2 | Mll7127 | 63 | Rhizobium loti | 0.063 ± 0.001 |
| 27 | Syrb2 | Q9RBY6 | Syrb2 | 64 | Pseudomonas syringae | 0.040 ± 0.001 |
| 28 | Rsp3534 | Q3IWE9 | Rsp3534 | 65 | Rhodobacter sphaeroides | 0.034 ± 0.005 |

*ND = no activity was detected.

6.4 Regenerating Enzymes: NADPH, ATP, Glutamate and Alanine.

CARs adenylation domain uses 2 phosphates of ATP for substrate activation, forming acyl-AMP intermediate transferred to reducing domain, where one molecule of NADPH is oxidised for aldehyde release. Application of CARs together with ARs for full reduction of carboxylic group to alcohol needs 2 molecules of NADPH and 1 ATP. Full biotransformation of adipic acid to 1,6-hexanediol will cost in total 4 NADPH and 2 ATP molecules. In vitro application of cofactor dependent enzymes such as oxidoreductases or transferases needs enzymatic systems for regeneration of consumed cofactors to make the system cost-effective. There are four enzymes commonly employed in the regeneration of ATP: pyruvate kinase (uses phosphoenolpyruvate), acetate kinase (uses acetylphisphate), creatine kinase (uses creatine phosphate), and polyphosphate kinase (uses polyphosphate) [Donk W. A., Zhao H. Recent developments in pyridine nucleotide regeneration. Current Opinion in Biotechnology 14, 421-426 (2003)]. Majority of ATP-regenerating enzymes process only one step ADP phosphorylation. Taking into account price and stability of starting substrate for ATP regeneration, polyphosphate kinases was chosen. Polyphospate kinase family II comprises enzymes able to regenerate AMP to ATP in two steps. For ATP regeneration SMc02148 (SEQ ID NO:105) from Sinorhizobium meliloti and PA3455 (SEQ ID NO:104) from Pseudomonas aeruginosa, were applied (Table 7) [Nocek B., Kochinyan S., Proudfoot M., Brown G., Evdokimova E., Osipiuk J., Edwards A. M., Savchenko A., Joachimiak A., Yakunin A. F. Polyphosphate-dependent synthesis of ATP and ADP by the family-2 polyphosphate kinases in bacteria. Proc. Natl. Acad. Sci. U.S.A 388, 17730-17735 (2008)]. Enzymes were cloned and overexpressed in E. coli. Enzymes purified by affinity chromatography using Ni-NTA resin were applied for CARs+ARs/ATs coupled reactions. Their activity for separate steps of ATP regeneration and full AMP to ATP regeneration in presence of polyphosphate (10-14 phosphates chain length) was confirmed by HPLC reverse-phase chromatography.

Figure 17A:
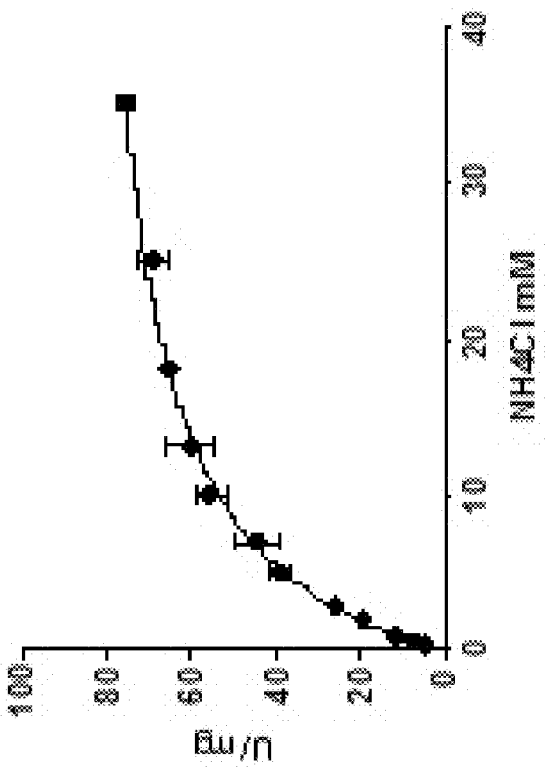
FIGS. 17A and 17B shows saturation with $NH_4Cl$ for A—BSU31930 in presence of 1 mM NADH, 1 mM pyruvate. B-YOR375C in presence of 1 mM NADPH, 1 mM ketoglutarate.
Figure 17B:
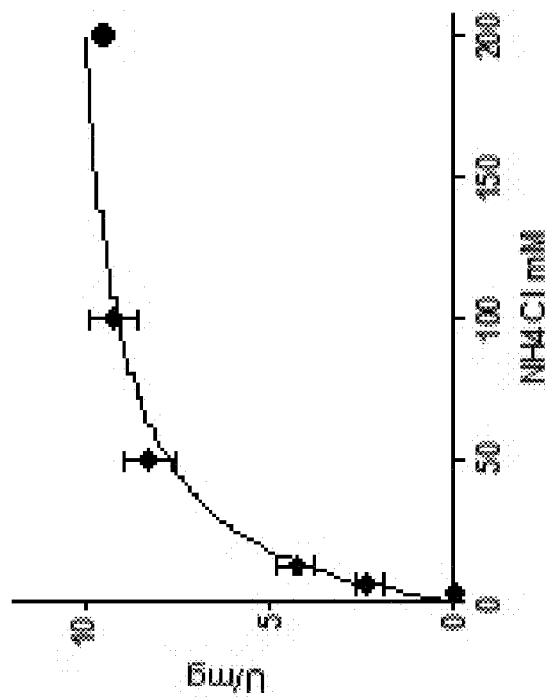

Screened ATs enzymes consume alanine and/or glutamate as amino-group donors, that also need to be regenerated. Two enzymes were found suitable for this purposes—YOR375C (SEQ ID NO:107), NADPH-dependent glutamate dehydrogenase from Saccharomyces cerevisiae, and BSU31930 (SEQ ID NO:106), NADH-dependent alanine dehydrogenase from Bacillus subtilis (Table 7). Enzymes were cloned and expressed in E. coli. After purification with affinity chromatography on Ni-NTA resin, enzymes were tested for alanine (FIG. 17 A) and glutamate regeneration (FIG. 17 B). Both enzymes were applied for primary ATs screening and ATs biochemical characterization as coupled enzymes, enabling pyruvate and ketoglutarate detection in presence of reduced cofactors NADH and NADPH and $NH_4Cl$ excess.

Formate dehydrogenase P33160 (D222Q/H224N) activity was measured spectrophotometrically in 96-well plates, monitored by increase in NAD+/NADP+ absorbance at 340 nm ($\epsilon 340$ nm=6,220/M·cm). Reaction mixture contained 100 mM Tris-HCl buffer (pH 8.0), 50 mM sodium formate, 1 µg of enzyme.

Polyphosphate kinase activity was measured using reverse phase Pursuit5-C18 column HPLC in linear gradient of Acetonitrile—50 mM $KH_2PO_4$ with 8 mM TBAH. Detecting wavelength—245 nm. Reaction mixture contains 100 mM Tris-HCl buffer (pH 8.0), 10 mM $MgCl_2$, 0.25 mM polyphosphate, 3 mM ADP/AMP, 0.5 µg enzyme.

Figure 18:
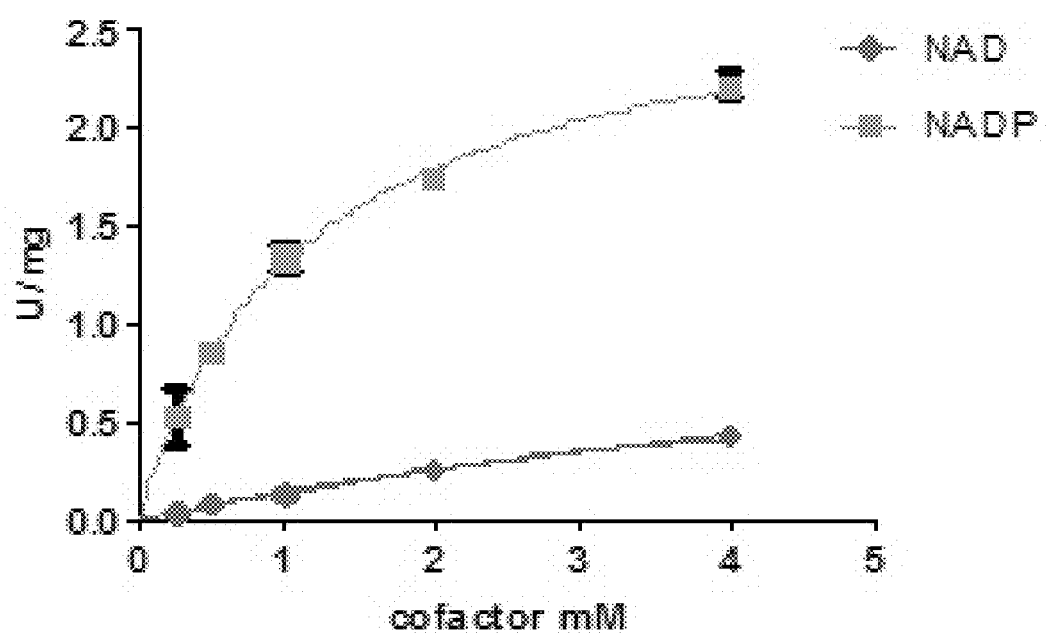
FIG. 18 shows PP33160 double mutant (D222Q/H224N) saturation with NADPH and NADH cofactors in presence of 50 mM formate.

CARs, ARs and amino-donor regenerating enzymes use pyridine nucleotides are as cofactors. Several enzymatic methods have been developed for the regeneration of NAD (P)H, such as reduction with formate dehydrogenase, glucose dehydrogenase, glucose-6-phosphate dehydrogenase, and alcohol dehydrogenase [Woodyer R. D., Johannes T., Zhao H. Cofactor Regeneration for Biocatalytic Applications. In Enzyme Technology, (A. Pandey, C. Webb, C. S. Soccol, and C. Larroche, Eds.) Chapter 5, Asiatech Publishers Inc., New Delhi, India, 83-101 (2004)]. Formate dehydrogenase are widely applied for regeneration of NADH and use cheap substrate—formate, releasing $CO_2$, that can be easily removed from reaction mixture. NADPH—dependent formate dehydrogenases are far less common, than NADH-dependent enzymes. Based on Masaki Ihara work [Ihara M., Okabe A., Kawano Y., and Urano M. Light Driven CO2 Fixation by using cyanobacterial photosystem I and NADPH-dependent formate dehydrogenase. Plos One. 8, e71581 (2013)] two mutations (D222Q and H224N) were introduced in adenine ribose binding loop of Pseudomonas aeruginosa formate dehydrogenase P33160, changing its specificity from NADH to NADPH (FIG. 18). Though NAD binding was significantly diminished, enzyme was still able to regenerate, what made it applicable for both cofactors regeneration.

TABLE 7

Cofactor regenerating enzymes, purified and tested for in vitro coupled reaction

| # | Uniprot protein ID | Uniprot gene ID | SEQ ID NO | Microorganism | Regenerating activity | Reaction |
|---|---|---|---|---|---|---|
| 1 | Q9HYF11 | PA3455 | 104 | Pseudomonas aeruginosa | Polyphosphate kinase | $AMP + PolyP_{(n)} = ADP + PolyP_{(n-1)}$ |
| 2 | Q925A62 | SMc02148 | 105 | Sinorhizobium meliloti | Polyphosphate kinase | $ADP + PolyP_{(n)} = ADP + PolyP_{(n-1)}$ |
| 3 | Q083523 | BSU31930 | 106 | Bacillus subtilis | Alanine dehydrogenase | Pyruvate + NH4Cl + NADH [1] Alanine + NAD |
| 4 | P072624 | YOR375C | 107 | Sccharomyces cerevisiae | Glutamate dehydrogenase | Ketoglutarate + $NH_4Cl$ + NADPH = Glutamate + NADP |
| 5 | P33160 | N/A | 108 | Pseudomonas sp. | Formate dehydrogenase | NaCOOH + NAD/NADP = [2] $CO_2$ + NADH/NADPH |

Example 7

7.1. In Vitro Biotransformation

In vitro enzymatic biotransformation was performed in 200ul reaction mixture 30° C., 800 rpm during 12 h.

CARs+PP 3370 reaction mixture contained 100 mM HEPES (pH 7.5), 1 mM NADPH, 2 mM ATP, 10 mM $MgCl_2$, 10 mM adipic or 4-hydroxybutyric acid, 50 mM sodium formate, 5 mM polyphosphate, 80 μg of CAR, 20 μg of PP 3370, 10 μg of P33160 (D222Q/H224N), 10 μg of PA3455, and 10 μg of SMc02148.

MAB 4714c+ATs reaction mixture contained 100 mM HEPES (pH 7.5), 0.5 mM NADPH, 1 mM glutamate, 2 mM ATP, 10 mM $MgCl_2$, 20 mM adipic, 50 mM sodium formate, 60 mM ammonium chloride, 5 mM polyphosphate, 80 μg of MAB 4714c, 20 μg of gabT or SAV2583, 10 μg of P33160 (D222Q/H224N), 5 μg YOR375C 10 μg of PA3455, and 10 μg of SMc02148.

After 12 h reactions were centrifuged (16,000 g), supernatant was filtered with 10 kDa filters, product formation was analyzed using HPLC.

Negative control experiment were performed with all enzymes, but not CARs.

7.2. Biochemical Characterization of CARs

Enzymes showing the highest activity from initial screening (FIG. 16) were characterized in vitro for adipic, and hydroxybutyric acids saturation (Table 8). The lowest Km for both substrates belongs to MAB 4714c (35.87±2.68 mM and 26.52±1.77 mM respectively) also as highest catalytic efficiency (89.55±3.07 M-1. s-1and 71±3 M-1·s-1). The specific activity of majority of CARs towards benzoic acid is in the same range as CAR from Nocardia iowensis (2 U/mg) [Akhtsr K. M., Turner N. J., Jones R. P. Carboxylic acid reductase is a versatile enzyme for the conversion of fatty acids into fuels and chemical commodities. Proc Natl Acad Sci USA. 110, 87-92 (2013)]. Taking into account sequential reduction of carboxylic groups of adipic acid and formation of 1,6-hexanoic acid as intermediate, CARs were also characterised for activity towards 6-hydroxyhexanoic acid.

TABLE 8

CARs kinetic parameters for ATP/NADPH dependent adipic and 4-hydroxybutyric acids reduction.

| | adipic acid | | |
|---|---|---|---|
| Enzymes | $k_{cat}$, $s^{-1}$ | $K_m$, mM | $k_{cat}/K_m$, $M^{-1} \cdot s^{-1}$ |
| MAB_4714c | 3.21 ± 0.11 | 35.87 ± 2.68 | 89.55 ± 3.07 |
| MSMEG_5739 | 2.40 ± 0.26 | 87.55 ± 16.20 | 27.39 ± 3.02 |
| MSMEG_2956 | 2.73 ± 0.20 | 108.2 ± 12.83 | 25.2 ± 1.83 |

TABLE 8-continued

| | 4-hydroxybutyric acid | | |
|---|---|---|---|
| Enzymes | $k_{cat}$, $s^{-1}$ | $K_m$, mM | $k_{cat}/K_m$, $M^{-1} \cdot s^{-1}$ |
| MAB_4714c | 1.878 ± 0.052 | 26.52 ± 1.77 | 70.81 ± 1.96 |
| MSMEG_5739 | 0.51 ± 0.017 | 37.84 ± 2.39 | 13.48 ± 0.45 |
| MSMEG_2956 | 0.513 ± 0.017 | 69.57 ± 4.16 | 7.37 ± 0.24 |
| MSMEI_5586 | 0.152 ± 0.013 | 19.63 ± 4.88 | 7.74 ± 0.66 |

TABLE 9

CARS kinetic parameters for ATP/NADPH dependent 6-hydroxyhexanoic acid reduction.

| | 6-hydroxyhexanoic acid | | |
|---|---|---|---|
| Enzymes | $k_{cat}$, $s^{-1}$ | $K_m$, mM | $k_{cat}/K_m$, $M^{-1} \cdot s^{-1}$ |
| MSMEG_2956 | 2.32 ± 0.22 | 66.15 ± 9.48 | 35.09 ± 3.29 |
| MSMEI_5586 | 1.20 ± 0.07 | 16.2 ± 2.11 | 74.18 ± 4.05 |
| MSMEG_5739 | 1.21 ± 0.04 | 8.33 ± 0.73 | 145.4 ± 4.4 |
| MAP_1040c | 2.91 ± 0.19 | 70.1 ± 7.04 | 41.58 ± 2.77 |
| MAB_4714c | 2.62 ± 0.03 | 2.64 ± 0.13 | 995.04 ± 13.02 |

7.3—Biochemical Characterization of ARs/ATs

ARs RHA1_ro05279, PA1146, SC00229, PP_3370 were characterised for saturation with adipaldehyde, PP_3370, PSPTO_2097, RHA1_ro05279, SC00229, TM_0111, PA1146 were characterised for butyraldehyde saturation (Table 10). Regarding CARs cofactor preference towards NADPH rather that NADH, ARs more active with NADPH were chosen. For both substrates maximal $k_{cat}/K_m$ with minimal $K_m$ values was shown by AR PP 3370 from Pseudomonas putida. Observed catalytic efficiency was determined as (2.08±0.09) $10^4 M^{-1} \cdot s^{-1}$ for adipaldehyde and (5.58±0.14)×$10^3 M^{-1} \cdot s^{-1}$ for butyraldehyde, $K_m$ values were estimated as 0.29±0.02 and 1.53±0.11 mM respectively.

ATs GabT, SM2011_b20379, SAV2583, SM2011_c04388, SM2011 b20423, that revealed highest activity with adipaldehyde were used for biochemical characterisation (Table 11). Maximal catalytic efficiency ($k_{cat}/K_m$) and lowest $K_m$ value was determined as (9.22±0.27)× $10^2 M^{-1} \cdot s^{-1}$ and 0.67 mM for E. coli gabT aminotransferase.

TABLE 10

ARs kinetic parameters for adipaldehyde and butyraldehyde reduction.

| Parameters | Cofactor | adipaldehyde* | | | |
|---|---|---|---|---|---|
| | | RHA1_ro05279 | PA1146 | SCO0229 | PP_3370 |
| $K_m$, mM | NADPH | ND | ND | 8.48 ± 0.58 | 0.29 ± 0.02 |
| $K_m$, mM | NADH | 6.89 ± 1.38 | 9.0 ± 1.99 | ND | 4.78 ± 0.49 |
| $k_{cat}$, s$^{-1}$ | NADPH | ND | ND | 3.79 ± 0.10 | 6.03 ± 0.25 |
| $k_{cat}$, s$^{-1}$ | NADH | 3.67 ± 0.31 | 5.45 ± 0.56 | ND | 1.74 ± 0.08 |
| $k_{cat}/K_m$, M$^{-1}$·s$^{-1}$ | NADPH | ND | ND | (4.47 ± 0.12) × 10$^2$ | (2.08 ± 0.09) × 10$^4$ |
| $k_{cat}/K_m$, M$^{-1}$·s$^{-1}$ | NADH | (5.33 ± 0.45) × 10$^2$ | (6.02 ± 0.06) × 10$^2$ | ND | (3.64 ± 0.16) × 10$^2$ |

| Parameters | Cofactor | butyraldehyde | | | | | |
|---|---|---|---|---|---|---|---|
| | | PP_3370 | PSPTO_2097 | RHA1_ro05279 | SCO0229 | TM_0111 | PA1146 |
| $K_m$, mM | NADPH | 1.53 ± 0.11 | 10.3 ± 1.06 | 1.53 ± 0.39 | 35.7 ± 10.5 | 2.72 ± 1.39 | 3.37 ± 0.9 |
| $K_m$, mM | NADH | 16.1 ± 1.89 | ND | 14.28 ± 0.88 | 6.56 ± 2.54 | 1.37 ± 0.31 | 15.6 ± 5.94 |
| $k_{cat}$, s$^{-1}$ | NADPH | 8.54 ± 0.22 | 12.2 ± 0.63 | 1.28 ± 0.09 | 21.9 ± 4.69 | 0.30 ± 0.06 | 0.84 ± 0.08 |
| $k_{cat}$, s$^{-1}$ | NADH | 10.7 ± 0.73 | ND | 25.77 ± 0.88 | 0.90 ± 0.05 | 0.90 ± 0.05 | 9.01 ± 01.9 |
| $k_{cat}/K_m$, NADPH | | (5.58 ± 0.14) × 10$^3$ | (1.18 ± 0.06) × 10$^3$ | (8.37 ± 0.59) × 10$^2$ | (6.15 ± 1.31) × 10$^2$ | (1.10 ± 0.22) × 10$^2$ | (2.49 ± 0.24) × 10$^2$ |
| $k_{cat}/K_m$, M$^{-1}$·s$^{-1}$ | NADH | (6.64 ± 0.45) × 10$^2$ | ND | (1.80 ± 0.06) × 10$^3$ | (1.07 ± 0.18) × 10$^2$ | (6.57 ± 0.36) × 10$^2$ | (5.76 ± 1.22) × 10$^2$ |

*reactions were supplemented with 1,8% DMSO to increase adipaldehyde solubility.

TABLE 11

ATs kinetic parameters for adipaldehyde

| Parameters | Amino-donor | sdipaldehyde | | | | |
|---|---|---|---|---|---|---|
| | | gabT | SM2011_b20379 | SAV2583 | SM2011_c04388 | SM2011_b20423 |
| $K_m$, mM | Ala/Glu | 0.67 ± 0.07 | 0.32 ± 0.10 | 1.35 ± 0.19 | 8.58 ± 3.34 | 2.64 ± 0.35 |
| $k_{cat}$, s$^{-1}$ | Ala/Glu | 0.61 ± 0.02 | 0.26 ± 0.05 | 0.39 ± 0.02 | 0.42 ± 0.09 | 0.28 ± 0.01 |
| $k_{cat}/K_m$, M$^{-1}$·s$^{-1}$ | Ala/Glu | (9.22 ± 0.27) × 10$^2$ | (8.08 ± 1.52) × 10$^2$ | (2.90 ± 0.13) × 10$^2$ | (4.86 ± 1.07) × 10$^2$ | (1.05 ± 0.06) × 10$^2$ |

7.4—Coupling CARs with ARs for Diol Production In Vitro and In Vivo

Figure 19:
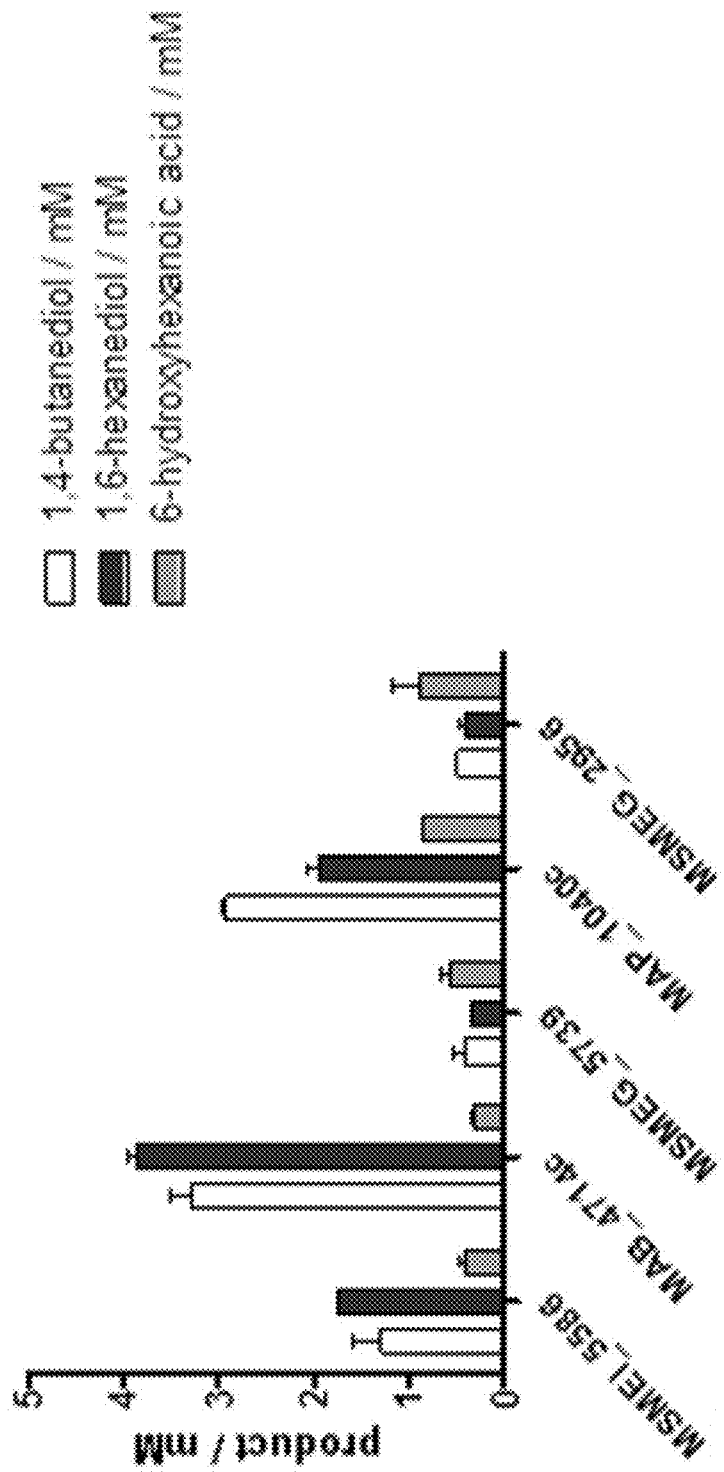
FIG. 19 shows in vitro CARs coupled with aldehyde reductase (AR) PP 3370 conversion of 10 mM adipic acid or 10 mM 4-hydroxybutyric acid (12 h). Reaction was supplied with ATP and NADPH—regenerating enzymes, supplied with 50 mM formate and 5 mM polyphosphate. A—graphical view of final product concentration. B—table of conversion efficiencies.

To investigate efficiency of adipic acid and 4-hydroxybutyric acid transformation to corresponding diols coupling CARs to ARs was tested. 10 mM of substrate was used for 12 h conversion. MSMEG_5739, MAB_4714c, MAP_1040c, MSMEI_5586 and MSMEG_2956 active with adipic acid and 4-hydroxybutyric acid, were tested for coupled reaction with PP_3370 AR (FIG. 19). ATP and NADPH-regenerating enzymes provided constant supply of reduced cofactors. Since PP_3370 substrate conversion yield is minimum 2 orders of magnitude higher than any CARs, its activity should not be a limiting step in coupled reaction. Product formation was analysed by HPLC, RI-detector, Aminex-87H column. MAB_4714c exhibited maximal 32.9±2.2% transformation of 4-hydroxybutanoic acid to 1,4-butanediol, and 38.7±0.9% transformation of adipic acid to 1,6 hexanediol. MMAB_4714c converted 3.2±0.2% of adipic acid to 6-hydroxyhexanoic acid (Table 12).

Figure 20:
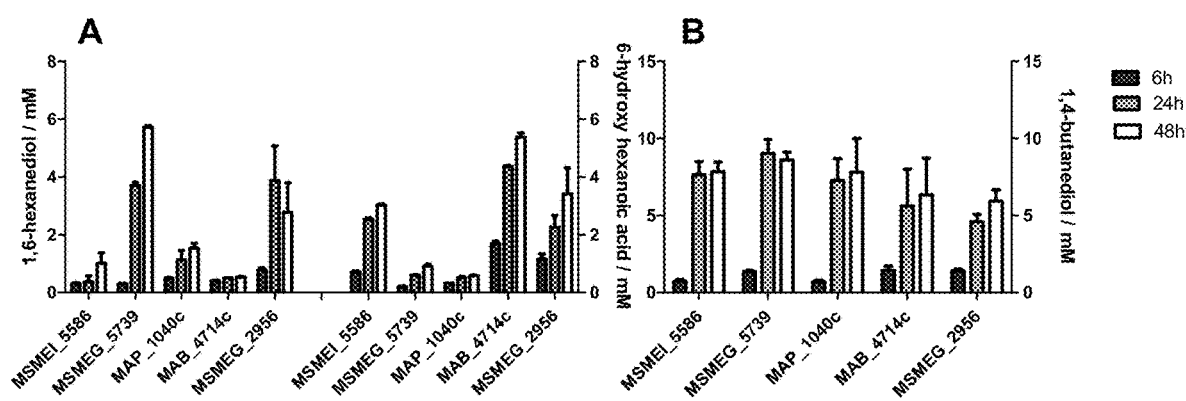
FIG. 20 shows in vivo conversion of 10 mM adipic acid or 10 mM 4-hydroxybutyric acid by $E.\ coli$ expressing CARs. A—Time course of final 1,6-hexanediol and 6-hydroxyhexanoic acid formation. B—Time course of final 1,4-butanediol formation C—Table of conversion efficiencies.

Next, a series of in vivo 4-hydroxybutyric and adipic acid biotransformation using E. coli cells expressing recombinant CARs were conducted. The same CARs, (coexpressed with BSU4205 PPTase) as used for in vitro transformation were chosen for whole cell biotransformation of 10 mM substrate. E. coli essentially possess several aldehyde reductases with different substrate preference. In the absence of additional ARs expression, second step of aldehyde reduction to alcohol was successfully fulfilled with endogenous E. coli ARs. Additional expression of PP_3370 for adipic acid biotransformation decreased transformation rates. Cells expressing MSMEG_5739 catalysed maximal conversion of 4-hydroxybutyric acid after 24 h-86.1±5.2% as well as adipic acid transformation to 1,6-hexanediol with 53.8±1.4% efficiency accompanied with minimal conversion to 6-hydroxyhexanoic acid—9.1%±0.7% (FIG. 20 B). MAB_4714c, characterised with highest conversion efficiencies towards all substrates in vivo converted 63.4±23.8% of 4-hydroxybutyric acid and 5.3±0.3% of adipic acid to 1,6-hexanediol, though saving intermediate 6-hydroxyhexanoic acid—53.8±1.4% (Table 13). Formation of 1,6-hexanediol, 1,4-butanediol and 6-hydroxyhexanoic acid was confirmed by LC-MS analysis.

E. coli cells expressing recombinant CARs with BSU03570 phosphopantetheinyl transferase were grown on LB media with 100 μM ampicillin, 50 μM streptomycin, supplemented with 2% glycerol aerobically on 37° C., until the culture optical density (OD 600 nm) reached 0.6-0.8. At this point protein expression was induced with 0.4 mM IPTG and substrate (adipic acid or 4-hydroxybutyric acid) for final 10 mM concentration was added. Samples were taken at 6 h, 24 h and 48 h, centrifuged, supernatant was filtered through 10 kDa centrifugal filters. Products were analyzed with HPLC or LC-MS. Negative control experiments were performed using E. coli cells harboring empty plasmids. All results of in vivo experiments are means from at least two independent determinations.

TABLE 12

Conversion efficiencies of 10 mM adipic aicd or
10 mM 4-hydroxybutyric acid (12 h)
in vitro by CARs coupled with aldehyde reductase
PP3370. Reaction was supplied with ATP
and NADPH-regenerating enzymes, supplied
with 50 mM formate and 5 mM polyphosphate.

| Enzyme | In vivo conversion efficiency (%) to: In vivo conversion efficiency % to: | | |
|---|---|---|---|
| | 1,4-butanediol | 1,6-hexanediol | 6-hydroxyhexanoic acid |
| MSMEI_5586 | 78.4 ± 6.2 | 10.2 ± 3.4 | 30.3 ± 0.4 |
| MAB_4713c | 63.4 ± 23.8 | 5.3 ± 0.3 | 53.8 ± 1.4 |
| MSMEG_5739 | 86.1 ± 5.2 | 57.2 ± 0.6 | 9.1 ± 0.7 |
| MAP_1040c | 81.6 ± 18.3 | 15.4 ± 1.7 | 5.8 ± 0.2 |
| MSMEG_2956 | 59.4 ± 7.3 | 27.7 ± 10.3 | 34.2 ± 9.1 |

TABLE 13

Conversion of efficiencies of 10 mM adipic
acid or 10 mM 4-hydroxybutyric acid
(24 h) in vivo by E. coli expressing CARs.

| Enzyme | In vivo conversion efficiency (%) to: | | |
|---|---|---|---|
| | 1,4-butanediol | 1,6-hexanediol | 6-hydroxyhexanoic acid |
| MSMEI_5586 | 78.4 ± 6.2 | 10.2 ± 3.4 | 30.3 ± 0.4 |
| MAB_4713c | 63.4 ± 23.8 | 5.3 ± 0.3 | 53.8 ± 1.4 |
| MSMEG_5739 | 86.1 ± 5.2 | 57.2 ± 0.6 | 9.1 ± 0.7 |
| MAP_1040c | 81.6 ± 18.3 | 15.4 ± 1.7 | 5.8 ± 0.2 |
| MSMEG_2956 | 59.4 ± 7.3 | 27.7 ± 10.3 | 34.2 ± 9.1 |

7.5—Coupling CARs with ATs for the In Vitro Adipic Acid Conversion to Aminocaproic Acid.

Screened CARs exhibited no activity towards aminated substrates. MAB_4714c $K_m$ value with adipic acid is 35.87±2.68 mM (Table 8). Under optimal conditions, the conversion yields for the characterized ATs with adipaldehyde are at least 10 times higher, than that with CARs's. In such case majority of monoaldehyde will be trapped by aminotransferases and excepted from catalytic transformation in form of 6-aminocaproic acid. MAB_4714c was coupled with GabT or SAV2583 ATs, glutamate was used as amino-donor. Reaction was supplied with ATP, NAD(P)H and glutamate regenerating enzymes and their substrates—5 mM polyphosphate (10-14 phosphates in chain length), 40 mM formate, 50 mM $NH_4Cl$. 20 mM of substrate was used for 12 h conversion. Product formation was analyzed by HPLC using C18 pre-column O-phtalaldehyde derivatization. Maximum transformation efficiency of adipic acid to 6-aminocaproic acid was estimated as 21.3±0.8% (Table 14).

TABLE 14

In vitro (12 h) conversion efficiency of
20 mM adipic acid to 6-aminocaproic
acid by coupled reaction of CARs with ATs in presence of
ATP, NAD(P)H and glutamate regenerating enzymes.

| Enzyme MAB_4714c + ATs: | In vitro conversion efficiency (%) to 6-aminocaproic acid |
|---|---|
| GabT | 21.3 ± 0.8 |
| SAV2583 | 19.5 ± 0.4 |

What is claimed is:

1. A process for producing a bifunctional aldehyde, as a product or an intermediate, the process comprising enzymatically converting a bifunctional carboxylic acid to a corresponding bifunctional aldehyde using a polypeptide having carboxylate reductase activity, wherein the polypeptide comprises an amino acid sequence at least 90% identical to the amino acid sequence of any one of SEQ ID NOs: 35, 36, 37, 38, or 70, wherein in addition to a first carboxyl functional group, the bifunctional carboxylic acid has an oxo-, a hydroxy-, an amino-, or a second carboxyl group as a second functional group, and wherein there are at least three carbons between the first carboxyl functional group and the second functional group.

2. The process of claim 1, wherein the bifunctional carboxylic acid-substrate is a C5-C10 dicarboxylic acid.

3. The process of claim 1, wherein:
  (a) the bifunctional carboxylic acid is adipic acid and the corresponding bifunctional aldehyde produced is 6-oxohexanoic acid;
  (b) the bifunctional carboxylic acid is 6-hydroxyhexanoic acid and the corresponding bifunctional aldehyde produced is 6-hydroxyhexanal;
  (c) the bifunctional carboxylic acid is 6-aminocaproic acid and the corresponding bifunctional aldehyde produced is 6-aminohexanal; or
  (d) the bifunctional carboxylic acid is 4-hydroxybutyric acid and the corresponding bifunctional aldehyde produced is 4-hydroxybutanal.

4. The process of claim 1, wherein the process further comprises enzymatically converting an aldehyde group of the bifunctional aldehyde produced to a hydroxy group using an aldehyde reductase.

5. The process of claim 3, wherein the process further comprises using an aldehyde reductase to enzymatically convert:
  (a) the 6-oxohexanoic acid to 6-hydroxyhexanoic acid;
  (b) the 6-hydroxyhexanal to 1,6-hexanediol;
  (c) the 6-aminohexanal to hexamethylenediamine; or
  (d) the 4-hydroxybutanal to 1,4-butanediol.

6. The process of claim 1, wherein the process further comprises enzymatically converting an aldehyde group of the bifunctional aldehyde produced to an amino group using an aminotransferase.

7. The process of claim 6, wherein the bifunctional carboxylic acid is adipic acid, the corresponding bifunctional aldehyde produced is 6-oxohexanoic acid, and the aminotransferase converts the 6-aminocaproic acid to 6-aminohexanal.

8. The process of claim 6, wherein the bifunctional carboxylic acid is 4-hydroxybutyric acid, the corresponding bifunctional aldehyde produced is 4-hydroxybutanal, and the aminotransferase converts the 4-hydroxybutanal to 4-aminobutanol.

9. The process of claim 1, which occurs in a host microorganism engineered to express the polypeptide.

10. The process of claim 4, which occurs in a host microorganism engineered to express the polypeptide and the aldehyde reductase.

11. The process of claim 6, which occurs in a host microorganism engineered to express the polypeptide and the aminotransferase.

12. The process of claim 1, wherein the polypeptide having carboxylate reductase activity comprises an amino acid sequence at least 99% identical to the amino acid sequence of any one of SEQ ID NOs: 35-38 or 70.

13. The process of claim 1, wherein the polypeptide having carboxylate reductase activity comprises an amino acid sequence that is identical to the amino acid sequence of any one of SEQ ID NOs: 35-38 or 70.

14. The process of claim 1, wherein the polypeptide having carboxylate reductase activity comprises an amino acid sequence at least 95% identical to the amino acid sequence of any one of SEQ ID NOs: 35-38 or 70.

15. A process for producing a bifunctional aldehyde, as a product or an intermediate, the process comprising enzymatically converting a bifunctional carboxylic acid to a corresponding bifunctional aldehyde using a polypeptide having carboxylate reductase activity, wherein the polypeptide comprises an amino acid sequence at least 90% identical to the amino acid sequence of SEQ ID NO: 35, 36, 37, or 38.

16. The process of claim 15, wherein:
  (a) the bifunctional carboxylic acid is a C5-C10 dicarboxylic acid;
  (b) the bifunctional carboxylic acid is adipic acid and the corresponding bifunctional aldehyde produced is 6-oxohexanoic acid;
  (c) the bifunctional carboxylic acid is 6-hydroxyhexanoic acid and the corresponding bifunctional aldehyde produced is 6-hydroxyhexanal;
  (d) the bifunctional carboxylic acid is 6-aminocaproic acid and the corresponding bifunctional aldehyde produced is 6-aminohexanal; or
  (e) the bifunctional carboxylic acid is 4-hydroxybutyric acid and the corresponding bifunctional aldehyde produced is 4-hydroxybutanal.

17. The process of claim 15, wherein the process further comprises enzymatically converting an aldehyde group of the bifunctional aldehyde produced to a hydroxy group using an aldehyde reductase.

18. The process of claim 15, wherein the process further comprises enzymatically converting an aldehyde group of the bifunctional aldehyde produced to an amino group using an aminotransferase.

19. The process of claim 15, wherein the polypeptide having carboxylate reductase activity comprises an amino acid sequence at least 95% identical to the amino acid sequence of SEQ ID NO: 35, 36, 37, or 38.

20. The process of claim 15, wherein the polypeptide having carboxylate reductase activity comprises an amino acid sequence at least 99% identical to the amino acid sequence of SEQ ID NO: 35, 36, 37, or 38.

\* \* \* \* \*

SEQUENCE LISTING

```
<160> NUMBER OF SEQ ID NOS: 111

<210> SEQ ID NO 1
<211> LENGTH: 663
<212> TYPE: PRT
<213> ORGANISM: Bacillus coagulans 36D1

<400> SEQUENCE: 1

Met Lys Tyr Lys Lys Leu Phe Glu Thr Val Lys Ile Arg Asn Val Glu
1               5                   10                  15

Leu Lys Asn Arg Tyr Ala Met Ala Pro Met Gly Pro Leu Gly Leu Ala
            20                  25                  30

Asp Ala Glu Gly Gly Phe Asn Gln Arg Gly Ile Glu Tyr Tyr Thr Ala
        35                  40                  45

Arg Ala Arg Gly Gly Thr Ala Leu Ile Ile Thr Gly Val Thr Phe Val
    50                  55                  60

Asp Asn Glu Val Glu His Gly Met Pro Asn Val Pro Cys Pro Thr
65                  70                  75                  80

His Asn Pro Val His Phe Val Arg Thr Ser Lys Glu Met Thr Glu Arg
                85                  90                  95

Ile His Ala Tyr Asp Ser Lys Ile Phe Leu Gln Met Ser Ala Gly Phe
            100                 105                 110

Gly Arg Val Thr Ile Pro Thr Asn Leu Gly Glu Tyr Pro Pro Val Ala
        115                 120                 125

Pro Ser Pro Ile Pro His Arg Trp Leu Asp Lys Thr Cys Arg Glu Leu
```

```
            130                 135                 140
Thr Val Glu Glu Ile His Ser Ile Val Arg Lys Phe Gly Asp Gly Ala
145                 150                 155                 160

Phe Asn Ala Lys Arg Ala Gly Phe Asp Gly Val Gln Ile His Ala Val
                165                 170                 175

His Glu Gly Tyr Leu Leu Asp Gln Phe Ala Ile Ala Phe Phe Asn Lys
            180                 185                 190

Arg Thr Asp Ala Tyr Gly Gly Pro Leu Glu Asn Arg Leu Arg Phe Ala
            195                 200                 205

Arg Glu Ile Val Glu Glu Ile Lys Gln Arg Cys Gly Glu Asp Phe Pro
210                 215                 220

Val Thr Leu Arg Phe Ser Pro Lys Ser Phe Ile Lys Asp Trp Arg Glu
225                 230                 235                 240

Gly Ala Leu Pro Gly Glu Glu Phe Glu Gly Lys Gly Arg Asp Leu Asp
                245                 250                 255

Glu Gly Ile Glu Ala Ala Lys Leu Leu Val Ser Tyr Gly Tyr Asp Ala
            260                 265                 270

Leu Asp Val Asp Val Gly Ser Tyr Asp Ser Trp Trp Trp Ser His Pro
            275                 280                 285

Pro Met Tyr Gln Lys Lys Gly Leu Tyr Ile Pro Tyr Ala Arg Leu Val
        290                 295                 300

Lys Glu Ala Val Asp Val Pro Val Leu Cys Ala Gly Arg Met Asp Asn
305                 310                 315                 320

Pro Asp Leu Ala Leu Ala Ala Leu Glu Asp Gly Ala Cys Asp Ile Ile
                325                 330                 335

Ser Leu Gly Arg Pro Leu Leu Ala Asp Pro Asp Tyr Val Asn Lys Leu
            340                 345                 350

Arg Ile Gly Gln Val Ala Asp Ile Arg Pro Cys Leu Ser Cys His Glu
            355                 360                 365

Gly Cys Met Gly Arg Ile Gln Glu Tyr Ser Ser Leu Gly Cys Ala Val
        370                 375                 380

Asn Pro Ala Ala Cys Arg Glu Lys Glu Ala Ala Leu Thr Pro Ala Leu
385                 390                 395                 400

Lys Lys Lys Arg Val Leu Ile Ala Gly Gly Val Ala Gly Cys Glu
                405                 410                 415

Ala Ala Arg Val Leu Ala Leu Arg Gly His Glu Pro Val Ile Phe Glu
            420                 425                 430

Lys Ser Asn Arg Leu Gly Gly Asn Leu Ile Pro Gly Gly Ala Pro Asp
            435                 440                 445

Phe Lys Glu Asp Asp Leu Ala Leu Val Ala Trp Tyr Glu His Thr Leu
450                 455                 460

Glu Arg Leu Gly Val Glu Ile His Leu Asn Thr Ala Leu Thr Lys Glu
465                 470                 475                 480

Glu Ile Leu Ala Ala Asn Val Asp Ala Val Leu Ile Ala Thr Gly Ser
                485                 490                 495

Asn Pro Lys Ile Leu Pro Leu Asp Gly Lys Asn Lys Val Phe Thr Ala
            500                 505                 510

Glu Asp Val Leu Leu Asp Lys Val Asp Ala Gly Gln His Val Val Ile
            515                 520                 525

Val Gly Gly Gly Leu Val Gly Cys Glu Leu Ala Leu Asn Leu Ala Glu
        530                 535                 540

Lys Gly Lys Asp Val Ser Leu Val Glu Met Gln Asp Lys Leu Leu Ala
545                 550                 555                 560
```

Val Asn Gly Pro Leu Cys His Ala Asn Ser Asp Met Leu Glu Arg Leu
                565                 570                 575

Val Pro Phe Lys Gly Val Gln Val Tyr Thr Ser Ser Lys Ile Val Asp
            580                 585                 590

Thr Thr Glu Lys Thr Ala Val Val Asp Val Asp Gly Glu Leu Arg Glu
        595                 600                 605

Ile Glu Ala Asp Ser Ile Val Leu Ala Val Gly Tyr Ser Ala Glu Lys
    610                 615                 620

Ser Leu Tyr Glu Asp Leu Lys Phe Glu Val Ala Asp Leu His Val Val
625                 630                 635                 640

Gly Asp Ala Arg Lys Val Ala Asn Ile Met Tyr Ala Ile Trp Asp Ala
                645                 650                 655

Tyr Glu Val Ala Ala Asn Leu
            660

<210> SEQ ID NO 2
<211> LENGTH: 664
<212> TYPE: PRT
<213> ORGANISM: Clostridium acetobutilicum DSM 1731

<400> SEQUENCE: 2

Met Asn Lys Tyr Lys Lys Leu Phe Glu Pro Ile Lys Ile Gly Lys Cys
1               5                   10                  15

Glu Ile Lys Asn Arg Phe Ala Leu Ala Pro Met Gly Pro Leu Gly Leu
            20                  25                  30

Ala Asp Ser Glu Gly Gly Phe Asn Gln Arg Gly Ile Asp Tyr Tyr Thr
        35                  40                  45

Glu Arg Ala Lys Gly Gly Thr Gly Leu Ile Ile Thr Gly Val Thr Phe
    50                  55                  60

Val Asp Asn Glu Val Glu His Gly Met Pro Asn Cys Pro Cys Pro
65                  70                  75                  80

Thr His Asn Pro Val Gln Phe Val Arg Thr Gly Arg Glu Met Thr Glu
                85                  90                  95

Arg Ile His Ala Tyr Asn Ser Lys Val Phe Leu Gln Met Ser Gly Gly
            100                 105                 110

Phe Gly Arg Val Thr Ile Pro Thr Asn Leu Gly Glu Phe Pro Pro Val
        115                 120                 125

Ala Pro Ser Pro Ile Gln His Arg Trp Leu Asp Lys Thr Cys Arg Glu
    130                 135                 140

Leu Thr Val Asp Glu Ile Lys Ser Ile Val Lys Lys Phe Gly Glu Gly
145                 150                 155                 160

Ala Phe Asn Ala Lys Arg Ala Gly Phe Asp Gly Val Gln Ile His Ala
                165                 170                 175

Val His Glu Gly Tyr Leu Ile Asp Gln Phe Ala Ile Ser Leu Phe Asn
            180                 185                 190

His Arg Thr Asp Glu Tyr Gly Gly Ser Leu Glu Asn Arg Leu Arg Phe
        195                 200                 205

Ala Arg Glu Ile Val Glu Glu Ile Lys Asn Arg Cys Gly Glu Asp Phe
    210                 215                 220

Pro Val Thr Leu Arg Tyr Ser Pro Lys Ser Phe Ile Lys Asp Leu Arg
225                 230                 235                 240

Asp Gly Ala Leu Pro Gly Glu Glu Phe Val Glu Lys Gly Arg Asp Leu
                245                 250                 255

Asp Glu Gly Val Glu Ala Ala Lys Leu Leu Val Ser Tyr Gly Tyr Asp

```
                260             265             270
Ala Leu Asp Thr Asp Val Gly Ser Tyr Asp Ser Trp Trp Trp Ser His
            275             280             285
Pro Pro Met Tyr Gln Glu Lys Gly Leu Tyr Arg Lys Tyr Ala Lys Leu
            290             295             300
Met Lys Asp Thr Val Asp Val Pro Val Ile Cys Ala Gly Arg Met Asp
305             310             315             320
Asp Pro Asp Met Ala Leu Glu Ala Val Glu Asn Gly Thr Cys Asp Val
                325             330             335
Ile Ser Leu Gly Arg Pro Leu Leu Ala Asp Pro Asp Tyr Val Asn Lys
            340             345             350
Leu Arg Ser Asn Lys Cys Lys Ser Ile Arg Pro Cys Ile Ser Cys Gln
            355             360             365
Glu Gly Cys Met Gly Arg Val Gln His Tyr Ser Met Leu Asn Cys Ala
            370             375             380
Val Asn Pro Gln Ala Cys Lys Glu Arg Ala Asn Ser Leu Thr Pro Ile
385             390             395             400
Ile Lys Ser Lys Lys Val Leu Ile Val Gly Gly Val Ala Gly Cys
            405             410             415
Glu Ala Ala Arg Val Leu Ala Leu Arg Gly His Glu Pro Val Leu Tyr
            420             425             430
Glu Lys Ser Asn Arg Leu Gly Gly Asn Leu Ile Pro Gly Gly Ala Pro
            435             440             445
Ser Phe Lys Glu Asp Asp Ile Ala Leu Ala Asp Trp Tyr Thr Asn Thr
            450             455             460
Leu Lys Glu Leu Asn Val Glu Val Asn Leu Asn Ser Glu Val Thr Lys
465             470             475             480
Glu Gln Ile Leu Asn Ser Lys Phe Asp Thr Val Ile Val Ala Thr Gly
                485             490             495
Ser Thr Pro Lys Val Phe Pro Leu Gly Asp Asp Glu Lys Val Phe Thr
            500             505             510
Ala Ala Glu Val Leu Leu Gly Gln Lys Asp Pro Gly Glu Thr Thr Val
            515             520             525
Val Val Gly Gly Gly Leu Val Gly Cys Glu Leu Ala Leu Asp Leu Ala
            530             535             540
Lys Lys Gly Lys Lys Val Thr Ile Val Glu Ala Leu Asn Lys Ile Leu
545             550             555             560
Ala Leu Asn Gly Pro Leu Cys Ser Ala Asn Ser Glu Met Leu Gln Lys
                565             570             575
Leu Ile Pro Phe Asn Gly Ile Asp Val Lys Ala Asn Ser Lys Val Lys
            580             585             590
Gly Tyr Lys Asn Gly Leu Leu Lys Met Glu Thr Glu Asn Gly Ile Glu
            595             600             605
Glu Leu Pro Cys Asp Ser Val Ile Leu Ser Val Gly Tyr Lys Glu Glu
            610             615             620
Asn Ser Leu Tyr Lys Glu Leu Glu Phe Glu Ile Pro Glu Ile Tyr Leu
625             630             635             640
Leu Gly Asp Ala Arg Lys Val Ser Asn Ile Met Tyr Gly Ile Trp Asp
            645             650             655
Ala Phe Glu Val Ala Asn His Ile
            660

<210> SEQ ID NO 3
```

```
<211> LENGTH: 667
<212> TYPE: PRT
<213> ORGANISM: Clostridium kluyveri DSM 555

<400> SEQUENCE: 3

Met Lys Asn Lys Ser Leu Phe Glu Pro Ile Lys Ile Gly Asn Met Glu
1               5                   10                  15

Val Lys Asn Lys Ile Ala Met Ala Pro Met Gly Ala Phe Gly Leu Val
            20                  25                  30

Asp Asn Glu Cys Cys Phe Asn Gln Arg Ala Val Asp Tyr Tyr Val Glu
        35                  40                  45

Arg Ala Lys Gly Gly Thr Gly Leu Ile Ile Thr Ser Val Val Lys Val
    50                  55                  60

Glu Asn Glu Leu Asp Lys Val Leu Thr Gly Val Leu Pro Ile Thr Ser
65                  70                  75                  80

Ile Asn Pro Ala Lys Phe Ile Met Thr Ser Glu Met Thr Glu Arg
                85                  90                  95

Val His Ala Tyr Gly Ser Lys Ile Phe Leu Gln Leu Ser Met Gly Phe
            100                 105                 110

Gly Arg Ser Gly Ala Pro Gly Gly Leu Leu Thr Ser Gln Pro Val Ser
        115                 120                 125

Ala Ser Ala Val Pro Asn Tyr Trp Asp Pro Thr Val Thr Cys Arg Glu
    130                 135                 140

Leu Thr Thr Ser Glu Val Glu Trp Ile Val Glu Lys Phe Ala Glu Gly
145                 150                 155                 160

Ala Lys Ile Ala His Lys Ala Gly Phe Asp Gly Val Glu Ile His Ala
                165                 170                 175

Val His Glu Gly Tyr Leu Leu Asp Gln Phe Thr Leu Ser Ile Phe Asn
            180                 185                 190

Arg Arg Thr Asp Lys Tyr Gly Gly Asp Leu Arg Gly Arg Leu Gln Leu
        195                 200                 205

Pro Ile Glu Ile Val Glu Ala Ile Lys Thr Glu Val Gly Ser Asn Phe
    210                 215                 220

Pro Val Gly Leu Arg Tyr Ser Val Lys Ser Cys Ile Lys Asp Trp Gly
225                 230                 235                 240

Gln Gly Gly Leu Ala Glu Glu Asp Tyr Val Glu Lys Gly Arg Asp Leu
                245                 250                 255

Glu Glu Gly Leu Glu Ala Ala Lys Ile Leu Glu Ala Ala Gly Tyr Asp
            260                 265                 270

Ala Phe Asn Ala Asp Leu Gly Thr Tyr Asp Ala Trp Tyr Trp Ala His
        275                 280                 285

Pro Pro Leu Tyr Gln Lys Asp Gly Leu Tyr Leu Pro Tyr Thr Lys Glu
    290                 295                 300

Leu Lys Lys Val Val Lys Ile Pro Val Met Val Ala Gly Lys Met Gly
305                 310                 315                 320

Met Pro Asp Val Ala Glu Gly Ala Leu Glu Asp Glu Ala Ala Asp Met
                325                 330                 335

Val Thr Leu Gly Arg Pro Leu Leu Cys Asp Ala Tyr Trp Pro Lys Lys
            340                 345                 350

Val Phe Thr Gly Gln Ile Asp Arg Ile Arg Pro Cys Ile Gly Cys His
        355                 360                 365

Thr Gly Cys Met Gly Arg Gly Phe Glu Gly Arg Pro Leu Ser Cys Thr
    370                 375                 380

Val Asn Pro Ala Ala Gly Arg Glu Arg Tyr Tyr Glu Val Lys Pro Ala
```

```
385                 390                 395                 400
Ala Ala Pro Lys Lys Val Met Ile Val Gly Gly Val Ala Gly Met
                405                 410                 415

Glu Ala Ala Arg Ile Thr Ala Met Arg Gly His Lys Val Ser Met Tyr
                420                 425                 430

Glu Gly Thr Lys Glu Leu Gly Gly Gln Val Ile Pro Ala Ser Val Pro
                435                 440                 445

Asp Phe Lys Ile Asp Asp Arg Arg Leu Leu Asp Trp Tyr Arg Asn Glu
            450                 455                 460

Met Lys Glu Leu Lys Val Lys Leu Val Leu Asp Thr Asn Val Thr Glu
465                 470                 475                 480

Glu Val Val Glu Lys Glu Lys Pro Asp Val Val Ile Ile Ala Thr Gly
                485                 490                 495

Ala Lys Glu Ile Lys Leu Asn Leu Pro Gly Ile Glu Lys Asp Lys Val
            500                 505                 510

Ala Thr Val Ile Glu Val Leu Lys Gly Ser Lys Gln Val Gly Glu Asn
            515                 520                 525

Val Leu Met Val Gly Gly Gly Leu Ala Gly Cys Glu Thr Ala Leu Tyr
        530                 535                 540

Leu Ala Lys Gln Gly Lys Lys Val Thr Ile Ile Glu Ala Arg Asp Thr
545                 550                 555                 560

Ile Leu Asn Ala Gly Lys Pro Val Pro His Met Asn Lys Ile Met Leu
                565                 570                 575

Ile Asp Leu Leu Lys Asn Ser Gly Val Asn Ile Ile Thr Glu Thr Ser
            580                 585                 590

Leu Leu Glu Val Thr Asp Arg Gly Ala Ile Leu Ile Asp Asn Lys Phe
        595                 600                 605

Lys Lys Gln Asn Ile Asp Ala Asp Thr Val Val Ile Ala Val Gly Phe
        610                 615                 620

Lys Ala Asp Arg Glu Leu Tyr Asn Lys Leu Arg Asp Lys Val Ala Asp
625                 630                 635                 640

Leu Tyr Leu Val Gly Asp Ala Asn Glu Ser Ala Asn Ile Met Asn Ala
                645                 650                 655

Ile Trp Ser Ala Asn Glu Ile Ala Leu Asn Cys
            660                 665

<210> SEQ ID NO 4
<211> LENGTH: 667
<212> TYPE: PRT
<213> ORGANISM: Clostridium ljungdahlii DSM 13528

<400> SEQUENCE: 4

Met Lys Asn Lys Ser Leu Phe Gln Pro Ile Lys Ile Gly Lys Met Glu
1               5                   10                  15

Val Lys Asn Lys Ile Ser Met Ala Pro Met Gly Ala Phe Gly Leu Val
                20                  25                  30

Asp Asn Glu Gly Cys Tyr Asn Gln Arg Ala Ile Asp Tyr Val Glu
            35                  40                  45

Arg Ala Lys Gly Gly Thr Gly Leu Ile Ile Thr Ser Ile Thr Lys Val
        50                  55                  60

Glu Asn Glu Leu Asp Lys Val Val Pro Gly Ile Ile Pro Val Ile Ser
65              70                  75                  80

Thr Asn Pro Gly Arg Phe Leu Met Thr Ser Ser Glu Met Thr Glu Arg
                85                  90                  95
```

```
Val His Ala Tyr Gly Ala Lys Ile Phe Leu Gln Leu Thr Met Gly Phe
                100                 105                 110

Gly Arg Ser Gly Ala Pro Gly Thr Leu Leu Thr Ser Gln Pro Val Ser
            115                 120                 125

Ala Ser Asp Ile Pro Asn Tyr Trp Asp Pro Thr Val Thr Cys Arg Ala
130                 135                 140

Leu Thr Thr Ser Glu Val Glu Trp Ile Val Ser Lys Phe Ile Glu Gly
145                 150                 155                 160

Ala Asp Ile Ala Gln Lys Ala Asp Phe Asp Gly Val Glu Ile His Ala
                165                 170                 175

Val His Glu Gly Tyr Leu Leu Asp Gln Phe Thr Leu Ser Ile Phe Asn
            180                 185                 190

Arg Arg Thr Asp Lys Tyr Gly Gly Asp Leu Arg Gly Arg Leu Gln Leu
        195                 200                 205

Pro Ile Glu Ile Val Gln Gly Ile Lys Ala Arg Leu Gly Asp Asp Phe
210                 215                 220

Pro Val Gly Leu Arg Tyr Ser Val Lys Ser Cys Ile Lys Asp Trp Arg
225                 230                 235                 240

Gln Gly Gly Leu Pro Asp Glu Asp Tyr Leu Glu Lys Gly Arg Asp Leu
                245                 250                 255

Lys Glu Gly Leu Asp Ala Ala Lys Ile Leu Glu Ala Ala Gly Tyr Asp
            260                 265                 270

Glu Leu Asn Thr Asp Leu Gly Thr Tyr Asp Ala Trp Tyr Trp Ser His
        275                 280                 285

Pro Pro Ile Tyr Gln Lys Asn Gly Leu Tyr Leu Pro Tyr Thr Lys Glu
290                 295                 300

Leu Lys Lys Val Val Lys Ile Pro Val Ile Val Ala Gly Lys Leu Gly
305                 310                 315                 320

Ile Pro Glu Asp Ala Glu Lys Ala Leu Asp Asp Lys Ala Ala Asp Met
                325                 330                 335

Ile Gly Leu Gly Arg Pro Leu Leu Ala Asp Pro Tyr Trp Pro Lys Lys
            340                 345                 350

Val Leu Ser Asp Asn Ser Glu Arg Ile Arg Pro Cys Ile Gly Cys His
        355                 360                 365

Thr Gly Cys Leu Gly Arg Gly Phe Glu Gly Lys Pro Leu Ser Cys Thr
370                 375                 380

Val Asn Pro Ala Val Gly Arg Glu Arg Tyr Tyr Glu Ile Lys Pro Thr
385                 390                 395                 400

Leu Thr Pro Lys Lys Val Met Val Val Gly Gly Gly Val Ala Gly Met
                405                 410                 415

Glu Ala Ala Arg Ile Ile Lys Met Arg Gly His Asp Val Thr Ile Tyr
            420                 425                 430

Glu Gly Thr Asp Lys Leu Gly Gly Val Ile Ile Pro Gly Ser Val Pro
        435                 440                 445

Asp Phe Lys Val Asp Arg Arg Leu Ile Asp Trp Tyr Lys Ser Glu
450                 455                 460

Ile Lys Glu Leu Glu Val Lys Val Asn Phe Asn Thr Lys Val Thr Glu
465                 470                 475                 480

Glu Leu Val Glu Glu Lys Pro Asp Val Val Ile Ile Ala Thr Gly
                485                 490                 495

Ala Lys Glu Ile Lys Ile Asn Val Pro Gly Ile Glu Lys Asp Lys Val
            500                 505                 510

Ile Thr Ala Leu Glu Leu Leu Asn Asp Asn Lys Lys Val Gly Asn Asp
```

```
            515                 520                 525
Val Leu Met Val Gly Gly Leu Val Gly Cys Glu Ala Ala Leu Tyr
        530                 535                 540

Leu Ala Lys Gln Gly Lys Asn Val Thr Ile Val Glu Ala Lys Asp Thr
545                 550                 555                 560

Leu Leu Asn Ser Ser Lys Pro Ile Pro His Met Asn Lys Ile Met Leu
                565                 570                 575

Ile Asp Leu Leu Asn Met Tyr Asn Val Lys Ala Ile Thr Asn Asn Ser
                580                 585                 590

Leu Leu Glu Val Thr Asp Lys Gly Ala Val Leu Ile Asn Asn Lys Phe
                595                 600                 605

Lys Lys Gln Glu Val Ser Ala Asp Thr Val Thr Ile Ala Val Gly Phe
610                 615                 620

Lys Ser Asp Arg Glu Leu Tyr Asn Lys Leu Asn Gly Asn Ile Ala Asp
625                 630                 635                 640

Leu Tyr Leu Ile Gly Asp Ala Tyr Gln Ser Ala Asn Ile Met Asn Ala
                645                 650                 655

Ile Trp Ser Ala Asn Glu Ile Gly Leu Asn Cys
                660                 665

<210> SEQ ID NO 5
<211> LENGTH: 667
<212> TYPE: PRT
<213> ORGANISM: Clostridium tyrobutyricum

<400> SEQUENCE: 5

Met Lys Asn Lys Ser Leu Phe Glu Pro Ile Lys Ile Gly Lys Val Glu
1               5                   10                  15

Val Lys Asn Lys Ile Ser Met Ala Pro Met Gly Ala Phe Gly Leu Val
                20                  25                  30

Asp Asn Glu Gly Cys Tyr Asn Gln Arg Ala Val Asp Tyr Tyr Val Glu
            35                  40                  45

Arg Ala Lys Gly Gly Thr Gly Leu Ile Ile Thr Ser Ile Thr Lys Val
        50                  55                  60

Glu Asn Glu Ile Asp Lys Val Val Pro Gly Val Ile Pro Ile Ile Ser
65                  70                  75                  80

Ile Asn Pro Gly Arg Phe Ile Met Thr Ser Ser Glu Met Thr Glu Arg
                85                  90                  95

Val His Ser Tyr Gly Ser Lys Ile Phe Leu Gln Leu Thr Met Gly Phe
            100                 105                 110

Gly Arg Ser Gly Ala Pro Gly Thr Leu Leu Thr Ser Gln Pro Val Ser
        115                 120                 125

Ala Ser Ser Val Pro Asn Tyr Trp Asp Pro Thr Val Thr Cys Arg Glu
    130                 135                 140

Leu Thr Thr Ser Glu Val Glu Trp Ile Val Ala Lys Phe Ile Gln Gly
145                 150                 155                 160

Ala Ala Ile Ala Gln Lys Ala Gly Phe Asp Gly Val Glu Ile His Ala
                165                 170                 175

Val His Glu Gly Tyr Leu Leu Asp Gln Phe Thr Leu Ser Ile Phe Asn
            180                 185                 190

Arg Arg Thr Asp Lys Tyr Gly Gly Asp Leu Arg Gly Arg Leu Gln Leu
        195                 200                 205

Pro Ile Glu Ile Val Gln Gly Ile Lys Ala Gln Val Gly Ser Asp Phe
    210                 215                 220
```

-continued

```
Pro Val Gly Leu Arg Tyr Ser Val Lys Ser Cys Ile Lys Asp Trp Arg
225                 230                 235                 240

Gln Gly Gly Leu Pro Asp Glu Asp Tyr Val Glu Lys Gly Arg Asp Leu
                245                 250                 255

Lys Glu Gly Leu Glu Ser Ala Lys Ile Leu Glu Ala Ala Gly Tyr Asp
            260                 265                 270

Glu Leu Asn Thr Asp Val Gly Thr Tyr Asp Ala Trp Tyr Trp Ser His
        275                 280                 285

Pro Pro Leu Tyr Gln Lys Asp Gly Leu Tyr Leu Pro Tyr Thr Lys Glu
    290                 295                 300

Leu Lys Lys Val Val Lys Ile Pro Val Ile Val Ala Gly Lys Leu Gly
305                 310                 315                 320

Val Pro Gln Glu Ala Glu Lys Ala Leu Asp Glu Gly Gly Ala Asp Met
                325                 330                 335

Ile Gly Leu Ala Arg Pro Leu Leu Ser Asp Ala Tyr Trp Pro Lys Lys
            340                 345                 350

Val Leu Ser Gly His Pro Glu Arg Ile Arg Pro Cys Ile Gly Cys His
        355                 360                 365

Val Gly Cys Leu Gly Arg Gly Phe Glu Gly Lys Pro Leu Ser Cys Ala
    370                 375                 380

Val Asn Pro Ala Ala Gly Arg Glu Arg Tyr Tyr Glu Ile Arg Pro Ala
385                 390                 395                 400

Ala Ile Pro Lys Lys Val Leu Ile Ala Gly Gly Val Ala Gly Met Glu
                405                 410                 415

Glu Ala Ala Arg Met Ala Val Leu Arg Gly His Lys Val Thr Leu Tyr
            420                 425                 430

Glu Ser Thr Asp Gln Leu Gly Gly Glu Ile Val Pro Gly Ser Val Pro
        435                 440                 445

Asp Phe Lys Ile Asp Asp Arg Arg Leu Leu Asp Trp Tyr Arg Asn Glu
    450                 455                 460

Met Lys Glu Leu Lys Ile Asn Val Ile Phe Asn Thr Glu Val Thr Asp
465                 470                 475                 480

Lys Leu Val Gly Lys Glu Gln Pro Asp Val Val Ile Val Ala Thr Gly
                485                 490                 495

Ala Asn Asp Val Lys Ile Lys Leu Pro Gly Ile Glu Lys Asp Lys Val
            500                 505                 510

Ser Thr Ala Val Asp Ile Leu Asn Gly Ala Lys Lys Ser Gly Lys Asn
        515                 520                 525

Val Leu Ile Val Gly Gly Leu Val Gly Cys Glu Thr Ala Leu Tyr
    530                 535                 540

Leu Ala Lys Ala Gly Lys Lys Val Ala Ile Val Glu Ala Lys Asp Lys
545                 550                 555                 560

Ile Leu Asp Ala Gly Lys Pro Ile Pro His Met Asn Lys Ile Met Leu
                565                 570                 575

Glu Asp Leu Ile Lys Lys Tyr Asn Ile Lys Val Ile Thr Gly Asn Ser
            580                 585                 590

Leu Leu Glu Val Thr Gly Asp Gly Ala Val Leu Ile Asp Asn Lys Phe
        595                 600                 605

Lys Gln Gln Glu Val Tyr Ala Asp Thr Ile Val Ile Ser Ile Gly Phe
    610                 615                 620

Lys Ser Asn Arg Lys Leu Tyr Asn Lys Leu His Gly Lys Val Thr Asp
625                 630                 635                 640

Leu Tyr Leu Ile Gly Asp Ala Tyr Gln Thr Ala Asn Ile Met Asp Ala
```

```
                    645                 650                 655

Ile Trp Ser Gly Asn Glu Ile Gly Leu Asn Cys
            660                 665

<210> SEQ ID NO 6
<211> LENGTH: 668
<212> TYPE: PRT
<213> ORGANISM: Moorella thermoacetica ATCC 39073

<400> SEQUENCE: 6

Met Val Val Ala Tyr Thr Arg Leu Phe Glu Pro Ile Lys Ile Gly Lys
1               5                   10                  15

Val Glu Ile Lys Asn Lys Ile Ala Met Ala Pro Met Gly Val Leu Gly
            20                  25                  30

Leu Ala Thr Gln Asp Gly Cys Phe Ser Lys Arg Val Val Asp Tyr Tyr
        35                  40                  45

Val Glu Arg Ala Lys Gly Gly Thr Gly Leu Ile Ile Thr Ser Val Thr
    50                  55                  60

Lys Val Asp Asn Glu Ile Glu Arg Phe Lys Ala Gly Ala Val Pro Val
65                  70                  75                  80

Ala Thr Ala Asn Pro Leu His Phe Ile Ala Thr Ala Gly Glu Leu Thr
                85                  90                  95

Glu Arg Val His Ala Tyr Gly Thr Lys Ile Phe Leu Gln Leu Gly Met
            100                 105                 110

Gly Phe Gly Arg Val Ala Ala Pro Ile Leu Leu Glu Ser His Pro Val
        115                 120                 125

Ala Pro Ser Ala Leu Pro Asn Phe Trp Asp Pro Ser Ile Thr Cys Arg
    130                 135                 140

Glu Leu Thr Thr Ala Glu Val Glu Thr Leu Val Gln Arg Ala Ser Glu
145                 150                 155                 160

Ala Ala Glu Ile Ala Val Glu Ala Gly Phe Asp Gly Val Glu Ile His
                165                 170                 175

Ala Met His Glu Gly Tyr Leu Leu Asp Gln Phe Thr Ile Ala Leu Phe
            180                 185                 190

Asn Arg Arg Gly Asp Lys Tyr Gly Gly Ala Leu Glu Asp Arg Leu Thr
        195                 200                 205

Phe Pro Ile Glu Ile Val Arg Ala Ile Lys Asp Arg Val Gly Lys Asp
    210                 215                 220

Phe Pro Val Val Leu Arg Phe Ser Ile Lys Asn Tyr Ile Lys Asp Trp
225                 230                 235                 240

Arg Gln Gly Gly Leu Pro Gly Glu Asn Phe Gln Glu Lys Gly Arg Asp
                245                 250                 255

Val Glu Glu Ala Leu Ala Ala Lys Ile Leu Glu Gly Ala Gly Tyr
            260                 265                 270

Asp Gly Phe Asp Ala Asp Ala Gly Ser Tyr Asp Ala Trp Tyr Trp Ala
        275                 280                 285

His Pro Pro Val Tyr Gln Lys His Gly Cys Tyr Leu Pro Leu Thr Gln
    290                 295                 300

Arg Leu Lys Glu Val Val Lys Val Pro Val Ile Val Ala Gly Arg Leu
305                 310                 315                 320

Glu Ile Pro Glu Leu Ala Glu Glu Ala Leu Val Lys Gly Gln Ala Asp
                325                 330                 335

Met Ile Ala Ile Gly Arg Gly Leu Leu Thr Asp Pro Tyr Trp Val Asn
            340                 345                 350
```

Lys Val Met Thr Gly Arg Ser Lys Asn Ile Arg Pro Cys Ile Gly Cys
            355                 360                 365

His Asp Gly Cys Leu Gly Arg Gly Phe Leu Gly Arg Pro Leu Ser Cys
    370                 375                 380

Thr Val Asn Pro Ala Cys Gly Arg Glu Glu Tyr Ala Ile Asp Arg
385                 390                 395                 400

Ala Pro Glu Ala Lys Gln Val Met Val Ile Gly Gly Val Ala Gly
                405                 410                 415

Met Glu Ala Ala Arg Val Ala Ala Leu Arg Gly His Arg Val Ser Leu
            420                 425                 430

Tyr Glu Lys Ser Asp Arg Leu Gly Gly His Val Val Glu Ala Ala Val
            435                 440                 445

Pro Asp Phe Lys Ala Asp Asp Gly Arg Leu Leu Glu Trp Tyr Lys Thr
    450                 455                 460

Glu Leu Gly Glu Leu Gln Val Glu Ile His Leu Asn Gln Glu Val Thr
465                 470                 475                 480

Pro Glu Phe Val Glu Glu Lys Asn Pro Asp Val Val Val Ala Thr
                485                 490                 495

Gly Ser Thr Pro Ala Ile Pro Asp Ile Pro Gly Val Asn Lys Asp Lys
            500                 505                 510

Val Thr Thr Val Ser Asp Leu Leu Gly Lys Lys Gln Ala Gly Asp
    515                 520                 525

Arg Val Val Ile Ile Gly Gly Gly Leu Ala Gly Cys Glu Thr Ala Leu
            530                 535                 540

Trp Leu Ala Gln Gln Gly Lys Asp Val Thr Ile Ile Glu Ile Leu Asp
545                 550                 555                 560

Asp Leu Met Arg Ala Gly Ile Pro Val Pro Tyr Met Asn Arg Met Met
            565                 570                 575

Leu Leu Asp Leu Leu Lys Met Asn Gly Val Lys Trp Leu Thr Glu Thr
            580                 585                 590

Ser Val Leu Glu Val Thr Asp Asp Gly Val Thr Leu Ile Gly Lys Thr
            595                 600                 605

Tyr Gln Arg Ser Pro Leu Pro Ala Asp Thr Val Ile Leu Ala Val Gly
    610                 615                 620

Phe Ala Ala Asp Gln Arg Leu Tyr Asn Ala Leu Arg Asp Lys Ile Pro
625                 630                 635                 640

Asn Leu Tyr Leu Ile Gly Asp Ser Arg Glu Pro Arg Asn Ile Leu Ala
            645                 650                 655

Ala Ile Trp Glu Gly Tyr Glu Val Gly Arg Gly Ile
            660                 665

<210> SEQ ID NO 7
<211> LENGTH: 338
<212> TYPE: PRT
<213> ORGANISM: Bacillus halodurans C-125

<400> SEQUENCE: 7

Met Glu His Lys Leu Phe Ser Ser Tyr Val Val Lys Gly Val Thr Leu
1               5                   10                  15

Lys Asn Arg Ile Val Met Ser Pro Met Cys Met Tyr Ser Ser Asp Gln
            20                  25                  30

Lys Asp Gly Lys Ile Arg Pro Phe His Ile Ser His Tyr Glu Ser Arg
        35                  40                  45

Ala Ala Gly Gln Val Gly Leu Ile Ile Val Glu Ala Thr Ala Val Thr
    50                  55                  60

```
Pro Gln Gly Arg Ile Ser Pro Tyr Asp Leu Gly Ile Trp Ser Asp Asp
 65                  70                  75                  80

His Ile Ser Gly Leu Thr Glu Thr Val Glu Arg Ile His Ala His Gly
                 85                  90                  95

Ala Lys Ala Ala Ile Gln Leu Ala His Ala Gly Arg Lys Ala Glu Leu
            100                 105                 110

Asp Gly Pro Ile Ile Ala Pro Ser Ala Ile Ser Tyr Asp Lys Met Lys
        115                 120                 125

Thr Pro Asp Ala Met Thr Glu Glu Gln Ile Ser Glu Thr Ile Glu Ala
    130                 135                 140

Phe Lys Leu Gly Ala Leu Arg Ala Lys Lys Ala Gly Phe Asp Ile Ile
145                 150                 155                 160

Glu Ile His Gly Ala His Gly Tyr Leu Ile Asn Glu Phe Leu Ser Pro
                165                 170                 175

Leu Thr Asn Lys Arg Thr Asp Ala Tyr Gly Gly Ser Leu Glu Asn Arg
            180                 185                 190

Tyr Arg Leu Leu Arg Glu Ile Ile Ser Glu Ile Gln Thr Val Trp Asp
        195                 200                 205

Gly Pro Leu Phe Val Arg Ile Ser Ala Ala Glu Tyr Ala Glu Gly Gly
    210                 215                 220

Asn Glu Leu Ser Asp Phe Ile Thr Leu Ala Lys Trp Met Lys Lys Gln
225                 230                 235                 240

Gly Ile Asp Leu Ile Asp Cys Ser Ser Gly Ala Val Val Pro Ala Pro
                245                 250                 255

Ile Pro Val Tyr Pro Gly Tyr Gln Val Pro Leu Ala Glu Ala Ile Arg
            260                 265                 270

His Glu Ala Asn Ile Ala Thr Gly Ala Val Gly Leu Ile Thr Ser Gly
        275                 280                 285

Ile Gln Ala Glu Glu Ile Leu Gln Asn Glu Arg Ala Asp Leu Ile Phe
    290                 295                 300

Val Ala Arg Glu Leu Leu Arg Asn Pro Tyr Trp Pro Arg Glu Ala Ala
305                 310                 315                 320

Leu Glu Leu Gly Thr Thr Ile Ser Gly Pro Ser Gln Tyr Asp Arg Ala
                325                 330                 335

Trp Leu

<210> SEQ ID NO 8
<211> LENGTH: 338
<212> TYPE: PRT
<213> ORGANISM: Bacillus subtilis subsp. subtilis str. 168

<400> SEQUENCE: 8

Met Ala Arg Lys Leu Phe Thr Pro Ile Thr Ile Lys Asp Met Thr Leu
 1               5                  10                  15

Lys Asn Arg Ile Val Met Ser Pro Met Cys Met Tyr Ser Ser His Glu
                 20                  25                  30

Lys Asp Gly Lys Leu Thr Pro Phe His Met Ala His Tyr Ile Ser Arg
            35                  40                  45

Ala Ile Gly Gln Val Gly Leu Ile Ile Val Glu Ala Ser Ala Val Asn
        50                  55                  60

Pro Gln Gly Arg Ile Thr Asp Gln Asp Leu Gly Ile Trp Ser Asp Glu
 65                  70                  75                  80

His Ile Glu Gly Phe Ala Lys Leu Thr Glu Gln Val Lys Glu Gln Gly
                 85                  90                  95
```

```
Ser Lys Ile Gly Ile Gln Leu Ala His Ala Gly Arg Lys Ala Glu Leu
            100                 105                 110

Glu Gly Asp Ile Phe Ala Pro Ser Ala Ile Ala Phe Asp Glu Gln Ser
        115                 120                 125

Ala Thr Pro Val Glu Met Ser Ala Glu Lys Val Lys Glu Thr Val Gln
    130                 135                 140

Glu Phe Lys Gln Ala Ala Arg Ala Lys Glu Ala Gly Phe Asp Val
145                 150                 155                 160

Ile Glu Ile His Ala Ala His Gly Tyr Leu Ile His Glu Phe Leu Ser
                165                 170                 175

Pro Leu Ser Asn His Arg Thr Asp Glu Tyr Gly Gly Ser Pro Glu Asn
            180                 185                 190

Arg Tyr Arg Phe Leu Arg Glu Ile Ile Asp Glu Val Lys Gln Val Trp
        195                 200                 205

Asp Gly Pro Leu Phe Val Arg Val Ser Ala Ser Asp Tyr Thr Asp Lys
    210                 215                 220

Gly Leu Asp Ile Ala Asp His Ile Gly Phe Ala Lys Trp Met Lys Glu
225                 230                 235                 240

Gln Gly Val Asp Leu Ile Asp Cys Ser Ser Gly Ala Leu Val His Ala
                245                 250                 255

Asp Ile Asn Val Phe Pro Gly Tyr Gln Val Ser Phe Ala Glu Lys Ile
            260                 265                 270

Arg Glu Gln Ala Asp Met Ala Thr Gly Ala Val Gly Met Ile Thr Asp
        275                 280                 285

Gly Ser Met Ala Glu Glu Ile Leu Gln Asn Gly Arg Ala Asp Leu Ile
    290                 295                 300

Phe Ile Gly Arg Glu Leu Leu Arg Asp Pro Phe Phe Ala Arg Thr Ala
305                 310                 315                 320

Ala Lys Gln Leu Asn Thr Glu Ile Pro Ala Pro Val Gln Tyr Glu Arg
                325                 330                 335

Gly Trp

<210> SEQ ID NO 9
<211> LENGTH: 364
<212> TYPE: PRT
<213> ORGANISM: Chromobacterium violaceum ATCC 12472

<400> SEQUENCE: 9

Met Asn Ala Asp Lys Leu Leu Thr Pro Leu Thr Met Gly Ala Val Ala
1               5                   10                  15

Leu Ser Asn Arg Val Val Met Ala Pro Leu Thr Arg Leu Arg Asn Ile
            20                  25                  30

Glu Pro Gly Asp Val Pro Gly Pro Leu Ala Lys Glu Tyr Tyr Arg Gln
        35                  40                  45

Arg Ala Ser Ala Gly Leu Ile Val Ala Glu Gly Thr His Ile Ser Pro
    50                  55                  60

Thr Ala Lys Gly Tyr Ala Gly Ala Pro Gly Ile Tyr Ser Glu Glu Gln
65                  70                  75                  80

Val Arg Ala Trp Ser Glu Val Thr Gly Ala Val His Gln Asp Gly Gly
                85                  90                  95

Lys Ile Ala Leu Gln Leu Trp His Thr Gly Arg Ile Ser His Arg Ser
            100                 105                 110

Leu Gln Pro Asn Gly Asp Ala Pro Val Gly Pro Ser Ala Ile Gln Ala
        115                 120                 125
```

Asp Ser Arg Thr Asn Ile Arg Ala Ala Asp Gly Ser Leu Val Arg Glu
            130                 135                 140

Gln Cys Asp Thr Pro Arg Ala Leu Glu Ile Glu Ile Glu Asp Ile
145                 150                 155                 160

Ile Glu Asp Tyr Arg Arg Ala Ala Asp Asn Ala Arg Arg Ala Gly Phe
                165                 170                 175

Asp Met Val Glu Ile His Gly Ala His Gly Tyr Leu Ile Asp Gln Phe
            180                 185                 190

Leu Ser Pro Ala Ala Asn Val Arg Thr Asp Gln Tyr Gly Gly Ser Val
            195                 200                 205

Glu Asn Arg Ala Arg Phe Leu Leu Glu Val Val Asp Ala Val Val Ala
            210                 215                 220

Glu Trp Asp Ala Asp His Val Gly Ile Arg Ile Ser Pro Leu Gly Ile
225                 230                 235                 240

Phe Asn Gly Val Ser Asn Thr Asp Gln Leu Asp Met Ala Leu Tyr Leu
                245                 250                 255

Ala Glu Gln Leu Ala Lys Arg Lys Leu Ala Phe Leu His Ile Ser Glu
            260                 265                 270

Pro Asp Trp Ala Gly Gly Pro Thr Leu Asp Asp Gly Phe Arg Ala Glu
            275                 280                 285

Leu Arg Gln Arg Tyr Pro Gly Val Ile Ile Gly Ala Gly Gly Tyr Ser
            290                 295                 300

Ala Glu Lys Ala Glu Thr Leu Leu Lys Lys Gly Phe Ile Asp Ala Ala
305                 310                 315                 320

Ala Phe Gly Arg Ser Tyr Ile Ala Asn Pro Asp Leu Val Glu Arg Leu
                325                 330                 335

Lys Gln Asn Ala Pro Leu Asn Pro Pro Lys Pro Asp Thr Phe Tyr Gly
            340                 345                 350

Gly Gly Ala Glu Gly Tyr Thr Asp Tyr Pro Thr Leu
            355                 360

<210> SEQ ID NO 10
<211> LENGTH: 365
<212> TYPE: PRT
<213> ORGANISM: Escherichia coli K12

<400> SEQUENCE: 10

Met Ser Ser Glu Lys Leu Tyr Ser Pro Leu Lys Val Gly Ala Ile Thr
1               5                   10                  15

Ala Ala Asn Arg Ile Phe Met Ala Pro Leu Thr Arg Leu Arg Ser Ile
            20                  25                  30

Glu Pro Gly Asp Ile Pro Thr Pro Leu Met Ala Glu Tyr Tyr Arg Gln
        35                  40                  45

Arg Ala Ser Ala Gly Leu Ile Ile Ser Glu Ala Thr Gln Ile Ser Ala
    50                  55                  60

Gln Ala Lys Gly Tyr Ala Gly Ala Pro Gly Ile His Ser Pro Glu Gln
65                  70                  75                  80

Ile Ala Ala Trp Lys Lys Ile Thr Ala Gly Val His Ala Glu Asn Gly
                85                  90                  95

His Met Ala Val Gln Leu Trp His Thr Gly Arg Ile Ser His Ala Ser
            100                 105                 110

Leu Gln Pro Gly Gly Gln Ala Pro Val Ala Pro Ser Ala Leu Ser Ala
            115                 120                 125

Gly Thr Arg Thr Ser Leu Arg Asp Glu Asn Gly Gln Ala Ile Arg Val

```
                130                 135                 140
Glu Thr Ser Met Pro Arg Ala Leu Glu Leu Glu Ile Pro Gly Ile
145                 150                 155                 160

Val Asn Asp Phe Arg Gln Ala Ile Ala Asn Ala Arg Glu Ala Gly Phe
                165                 170                 175

Asp Leu Val Glu Leu His Ser Ala His Gly Tyr Leu Leu His Gln Phe
                180                 185                 190

Leu Ser Pro Ser Ser Asn His Arg Thr Asp Gln Tyr Gly Gly Ser Val
                195                 200                 205

Glu Asn Arg Ala Arg Leu Val Leu Glu Val Val Asp Ala Gly Ile Glu
                210                 215                 220

Glu Trp Gly Ala Asp Arg Ile Gly Ile Arg Val Ser Pro Ile Gly Thr
225                 230                 235                 240

Phe Gln Asn Thr Asp Asn Gly Pro Asn Glu Glu Ala Asp Ala Leu Tyr
                245                 250                 255

Leu Ile Glu Gln Leu Gly Lys Arg Gly Ile Ala Tyr Leu His Met Ser
                260                 265                 270

Glu Pro Asp Trp Ala Gly Gly Glu Pro Tyr Thr Asp Ala Phe Arg Glu
                275                 280                 285

Lys Val Arg Ala Arg Phe His Gly Pro Ile Ile Gly Ala Gly Ala Tyr
                290                 295                 300

Thr Val Glu Lys Ala Glu Thr Leu Ile Gly Lys Gly Leu Ile Asp Ala
305                 310                 315                 320

Val Ala Phe Gly Arg Asp Trp Ile Ala Asn Pro Asp Leu Val Ala Arg
                325                 330                 335

Leu Gln Arg Lys Ala Glu Leu Asn Pro Gln Arg Ala Glu Ser Phe Tyr
                340                 345                 350

Gly Gly Gly Ala Glu Gly Tyr Thr Asp Tyr Pro Thr Leu
                355                 360                 365

<210> SEQ ID NO 11
<211> LENGTH: 338
<212> TYPE: PRT
<213> ORGANISM: Listeria monocytogenes EGD-e

<400> SEQUENCE: 11

Met Ser Lys Leu Phe Ser Glu Tyr Lys Leu Lys Asp Val Thr Leu Lys
1               5                   10                  15

Asn Arg Ile Val Met Ser Pro Met Cys Met Tyr Ser Val Glu Asn Lys
                20                  25                  30

Asp Gly Ile Ala Thr Asp Phe His Phe Ala His Tyr Val Ser Arg Ala
                35                  40                  45

Ala Gly Gly Thr Gly Leu Val Ile Leu Glu Ala Thr Ala Val Gln Glu
                50                  55                  60

Val Gly Arg Ile Ser Glu Phe Asp Leu Gly Leu Trp Asn Asp Glu Gln
65                  70                  75                  80

Val Pro Ala Leu Lys Lys Leu Val Gly Gly Leu His Tyr His Gly Ala
                85                  90                  95

Lys Ala Gly Ile Gln Leu Ala His Ala Gly Arg Lys Ala Val Leu Pro
                100                 105                 110

Gly Glu Ile Val Ala Pro Ser Ala Ile Ala Phe Asp Glu Lys Ser Asp
                115                 120                 125

Lys Pro Val Glu Leu Thr Lys Glu Ala Ile Lys Glu Val Val Ala Asp
                130                 135                 140
```

Phe Lys Arg Ala Ala Tyr Arg Ala Lys Glu Ala Gly Phe Asp Val Ile
145                 150                 155                 160

Glu Ile His Ala Ala His Gly Tyr Leu Ile His Gln Phe Leu Ser Pro
                165                 170                 175

Ile Thr Asn Arg Arg Glu Asp Asn Tyr Gly Gly Pro Ala Gly Asn Arg
            180                 185                 190

Tyr Lys Ile Leu Ser Asp Ile Ile Lys Ala Val Lys Glu Val Trp Asp
            195                 200                 205

Gly Pro Ile Ile Val Arg Val Ser Ala Thr Asp Tyr Ala His Gly Gly
            210                 215                 220

Leu Gln Leu Glu Asp His Ile Pro Phe Ala Lys Trp Met Lys Ala Asp
225                 230                 235                 240

Gly Val Glu Leu Ile Asp Val Ser Thr Gly Gly Leu Val Asn Val Ala
                245                 250                 255

Pro Pro Val Phe Pro Gly Tyr Gln Val Pro Phe Ala Asp Glu Ile Arg
                260                 265                 270

Arg Gly Ala Gly Ile Ala Thr Gly Ala Leu Gly Leu Ile Thr Arg Gly
                275                 280                 285

Glu Gln Ala Glu Glu Ile Leu Cys Asn Glu Arg Ala Asp Leu Ile Ile
290                 295                 300

Val Gly Arg Glu Leu Leu Arg Asn Pro Tyr Phe Ala Lys Asp Ala Ala
305                 310                 315                 320

Lys Gln Leu Gly Glu Thr Ile Glu Ala Pro Lys Gln Tyr Ser Arg Ala
                325                 330                 335

Trp Lys

<210> SEQ ID NO 12
<211> LENGTH: 354
<212> TYPE: PRT
<213> ORGANISM: Nitrosomonas europaea ATCC 19718

<400> SEQUENCE: 12

Met Leu Phe Asn Pro Leu Gln Val Gly Ser Leu Thr Leu Pro Asn Arg
1               5                   10                  15

Ile Leu Leu Ala Pro Leu Thr Arg Ala Arg Ala Asp Ala Gly His Met
                20                  25                  30

Pro Asn Ala Leu Met Ala Glu Tyr Tyr Ser Gln Arg Ala Thr Gly Gly
            35                  40                  45

Leu Leu Ile Ser Glu Cys Thr Met Val Ala Pro Gly Thr Ser Ala Phe
50                  55                  60

Val Asn Glu Pro Gly Ile Tyr Asn Asp Ala Gln Ile Ala Ala Trp Arg
65                  70                  75                  80

Gln Val Thr Asp Ala Val His Ala Lys Gly Gly Arg Ile Phe Met Gln
                85                  90                  95

Ile Trp His Ala Gly Arg Ala Ala Tyr Pro Gly Ala Ala Asp Gly Ala
            100                 105                 110

Pro Ile Val Ser Ser Ala Thr Ala Ile Glu Gly Glu Ile His Thr
            115                 120                 125

Pro Gln Gly Lys Val Pro His Ala Val Pro Arg Pro Leu Thr Val Asp
            130                 135                 140

Glu Ile Pro Gly Ile Val Ala Ala Phe Ala Gln Gly Ala Arg Asn Ala
145                 150                 155                 160

Ile Ala Ala Gly Phe Asp Gly Val Glu Val His Gly Ala Asn Gly Tyr
                165                 170                 175

Leu Ile Asp Gln Phe Leu Arg Asp Thr Pro Asn Gln Arg Thr Asp Ala
                180                 185                 190

Tyr Gly Gly Ser Leu Glu Asn Arg Ala Arg Leu Leu Phe Glu Val Leu
            195                 200                 205

Thr Ala Val Thr Gln Ala Ile Gly Ser Glu Arg Val Gly Leu Arg Leu
        210                 215                 220

Ser Pro Leu Asn Ser Phe Asn Ser Met Lys Asp Ser Asp Pro Leu Ala
225                 230                 235                 240

Leu Ile Gly Phe Leu Ala Asp Arg Leu Asn Ala Phe Lys Leu Ala Tyr
                245                 250                 255

Leu His Val Met Arg Ala Asp Phe Phe Gly Val Gln Lys Ala Asp Val
            260                 265                 270

Met Pro Val Ala Arg Glu Lys Tyr Lys Gly Val Leu Val Gly Asn Met
        275                 280                 285

Gly Tyr Ser Ala Asp Glu Ala Glu Ala Ala Ile Ala Glu Gly Arg Leu
    290                 295                 300

Asp Ala Val Ala Phe Gly Thr Ala Phe Leu Ala Asn Pro Asp Leu Pro
305                 310                 315                 320

Ala Arg Ile Arg Ala Lys Ala Pro Leu Asn Ala Pro Asp Ser Asn Thr
                325                 330                 335

Phe Tyr Ala Gly Gly Ala Lys Gly Tyr Thr Asp Tyr Pro Thr Leu Gln
            340                 345                 350

Leu Ala

<210> SEQ ID NO 13
<211> LENGTH: 369
<212> TYPE: PRT
<213> ORGANISM: Pseudomonas aeruginosa PAO1

<400> SEQUENCE: 13

Met Ser Asn Leu Leu Ser Pro Leu Ala Val Gly Asn Leu Ala Leu
1               5                   10                  15

Arg Asn Arg Ile Val Met Ala Pro Met Thr Arg Ser Arg Ala Gln Gln
                20                  25                  30

Pro Gly Asp Val Pro Thr Ala Leu Asn Ala Leu Tyr Tyr Ala Gln Arg
            35                  40                  45

Ala Gly Ala Gly Leu Ile Val Ser Glu Gly Thr Gln Ile Ser His Leu
        50                  55                  60

Gly Gln Gly Tyr Ala Tyr Thr Pro Gly Ile Tyr Ser Glu Ala Gln Leu
65                  70                  75                  80

Ala Gly Trp Arg Gln Val Thr Glu Ala Val His Ala Ala Gly Gly Leu
                85                  90                  95

Ile Ala Ala Gln Leu Trp His Val Gly Arg Met Ser His Arg Ser Leu
            100                 105                 110

Gln Ala Gly Gly Glu Ala Pro Ile Ala Pro Ser Pro Ile Gln Ala Lys
        115                 120                 125

Ala Gln Val Phe Ile Ala Asp Gly Gln Gly Gly Ser Met Ala Pro
    130                 135                 140

Ala Asp Ala Pro Arg Glu Met Thr Leu Glu Asp Ile Arg Arg Val Arg
145                 150                 155                 160

Asp Glu Phe Val Arg Ala Ala Arg Asn Ala Leu Asp Ala Gly Phe Asp
                165                 170                 175

Leu Val Glu Leu His Gly Ala Asn Gly Tyr Leu Ile Asp Gln Phe Leu
            180                 185                 190

```
Ala Ser Ala Ser Asn Arg Arg Ser Asp Ala Tyr Gly Gly Ser Leu Glu
            195                 200                 205

Asn Arg Ala Arg Phe Leu Leu Glu Ile Val Asp Ala Leu Val Ala Ala
210                 215                 220

Val Gly Ala Glu Arg Val Gly Leu Arg Leu Ser Pro Trp Gly Thr Ile
225                 230                 235                 240

Asn Asp Met His Asp Asp Glu Pro Glu Ala Met Thr Leu Tyr Leu Ala
                245                 250                 255

Glu Ala Leu Gln Arg Arg Gly Ile Ala Tyr Leu His Leu Ala Glu Trp
            260                 265                 270

Glu Trp Ser Gly Gly Pro Ala Tyr Pro Gln Gly Phe Arg Glu Arg Leu
            275                 280                 285

Arg Glu Arg Phe Arg Ala Pro Leu Ile Val Cys Gly Asn Tyr Asp Ala
290                 295                 300

Glu Arg Ala Glu Ala Ile Leu Gln Ala Gly Leu Ala Asp Ala Val Ala
305                 310                 315                 320

Ile Gly Arg Pro Phe Ile Ala Asn Pro Asp Leu Val Glu Arg Ile Arg
                325                 330                 335

Leu Gly Ala Pro Leu Ala Glu Ala Asn Gln Ala Arg Phe Tyr Gly Gly
            340                 345                 350

Asp Ala Ala Gly Tyr Thr Asp Tyr Pro Thr Leu Gly Gln Ser Ala Thr
            355                 360                 365

Ala

<210> SEQ ID NO 14
<211> LENGTH: 350
<212> TYPE: PRT
<213> ORGANISM: Pseudomonas aeruginosa PAO1

<400> SEQUENCE: 14

Met Ala Thr Leu Phe Asp Pro Ile Val Leu Gly Asp Leu Glu Leu Pro
1               5                   10                  15

Asn Arg Ile Val Met Ala Pro Leu Thr Arg Cys Arg Ala Asp Glu Gly
                20                  25                  30

Arg Val Pro Asn Ala Leu Met Ala Glu Tyr Tyr Ala Gln Arg Ala Asp
            35                  40                  45

Ala Gly Leu Ile Leu Ser Glu Ala Thr Ala Val Thr Pro Met Gly Val
        50                  55                  60

Gly Tyr Pro Asp Thr Pro Gly Ile Trp Ser Asp Asp Gln Val Arg Gly
65                  70                  75                  80

Trp Ser Asn Val Thr Lys Ala Val His Ala Gly Gly Arg Ile Phe
                85                  90                  95

Leu Gln Leu Trp His Val Gly Arg Ile Ser Asp Pro Leu Tyr Leu Asn
            100                 105                 110

Gly Glu Leu Pro Val Ala Pro Ser Ala Ile Ala Ala Glu Gly His Val
        115                 120                 125

Ser Leu Val Arg Pro Lys Arg Pro Tyr Val Thr Pro Arg Ala Leu Asp
    130                 135                 140

Thr Glu Glu Ile Ala Asp Ile Val Glu Ala Tyr Arg Gln Gly Ala Glu
145                 150                 155                 160

Arg Ala Lys Ala Ala Gly Phe Asp Gly Val Glu Ile His Gly Ala Asn
                165                 170                 175

Gly Tyr Leu Leu Asp Gln Phe Leu Gln Asp Ser Thr Asn Lys Arg Thr
            180                 185                 190
```

Asp Arg Tyr Gly Gly Ser Ile Glu Asn Arg Ala Arg Leu Leu Glu
            195                 200                 205

Val Thr Asp Ala Ala Ile Ser Val Trp Gly Ala Gln Arg Val Gly Val
210                 215                 220

His Leu Ala Pro Arg Ala Asp Ser His Asp Met Gly Asp Ser Asn Arg
225                 230                 235                 240

Leu Glu Thr Phe Ser His Val Ala Arg Glu Leu Gly Lys Arg Gly Ile
            245                 250                 255

Ala Phe Ile Cys Ala Arg Glu Ala Gln Ala Asp Asp Ser Ile Gly Val
            260                 265                 270

Ala Leu Lys Lys Ala Phe Gly Gly Pro Tyr Ile Ala Asn Glu Gln Phe
            275                 280                 285

Thr Leu Asp Ser Ala Asn Ala Ile Leu Ala Lys Gly Asp Ala Asp Ala
290                 295                 300

Val Ala Phe Gly Val Pro Phe Ile Ala Asn Pro Asp Leu Val Glu Arg
305                 310                 315                 320

Leu Arg Gln Gly Ala Glu Leu Asn Pro Pro Arg Pro Glu Thr Phe Tyr
            325                 330                 335

Thr Gly Gly Thr Glu Gly Tyr Leu Asp Tyr Pro Thr Leu Ala
            340                 345                 350

<210> SEQ ID NO 15
<211> LENGTH: 349
<212> TYPE: PRT
<213> ORGANISM: Pseudomonas putida KT2440

<400> SEQUENCE: 15

Met Thr Thr Leu Phe Asp Pro Ile Lys Leu Gly Asp Leu Gln Leu Pro
1               5                   10                  15

Asn Arg Ile Ile Met Ala Pro Leu Thr Arg Cys Arg Ala Asp Glu Gly
                20                  25                  30

Arg Val Pro Asn Ala Leu Met Ala Glu Tyr Tyr Val Gln Arg Ala Ser
            35                  40                  45

Ala Gly Leu Ile Leu Ser Glu Ala Thr Ser Val Ser Pro Met Gly Val
50                  55                  60

Gly Tyr Pro Asp Thr Pro Gly Ile Trp Asn Asp Glu Gln Val Arg Gly
65                  70                  75                  80

Trp Asn Asn Val Thr Lys Ala Val His Ala Ala Gly Gly Arg Ile Phe
                85                  90                  95

Leu Gln Leu Trp His Val Gly Arg Ile Ser His Pro Ser Tyr Leu Asn
            100                 105                 110

Gly Glu Leu Pro Val Ala Pro Ser Ala Ile Gln Pro Lys Gly His Val
            115                 120                 125

Ser Leu Val Arg Pro Leu Ser Asp Tyr Pro Thr Pro Arg Ala Leu Glu
130                 135                 140

Thr Glu Glu Ile Asn Asp Ile Val Glu Ala Tyr Arg Ser Gly Ala Glu
145                 150                 155                 160

Asn Ala Lys Ala Ala Gly Phe Asp Gly Val Glu Ile His Gly Ala Asn
                165                 170                 175

Gly Tyr Leu Leu Asp Gln Phe Leu Gln Ser Ser Thr Asn Gln Arg Thr
            180                 185                 190

Asp Arg Tyr Gly Gly Ser Leu Glu Asn Arg Ala Arg Leu Leu Leu Glu
            195                 200                 205

Val Thr Asp Ala Ala Ile Glu Val Trp Gly Ala Gln Arg Val Gly Val
210                 215                 220

His Leu Ala Pro Arg Ala Asp Ala His Asp Met Gly Asp Ala Asp Arg
225                 230                 235                 240

Ala Glu Thr Phe Thr Tyr Val Ala Arg Glu Leu Gly Lys Arg Gly Ile
            245                 250                 255

Ala Phe Ile Cys Ser Arg Glu Arg Glu Ala Asp Asp Ser Ile Gly Pro
        260                 265                 270

Leu Ile Lys Glu Ala Phe Gly Gly Pro Tyr Ile Val Asn Glu Arg Phe
    275                 280                 285

Asp Lys Ala Ser Ala Asn Ala Ala Leu Ala Ser Gly Lys Ala Asp Ala
290                 295                 300

Val Ala Phe Gly Val Pro Phe Ile Ala Asn Pro Asp Leu Pro Ala Arg
305                 310                 315                 320

Leu Ala Ala Asp Ala Pro Leu Asn Glu Ala His Pro Glu Thr Phe Tyr
                325                 330                 335

Gly Lys Gly Pro Val Gly Tyr Ile Asp Tyr Pro Arg Leu
            340                 345

<210> SEQ ID NO 16
<211> LENGTH: 363
<212> TYPE: PRT
<213> ORGANISM: Pseudomonas putida KT2440

<400> SEQUENCE: 16

Met Ser Ala Leu Phe Glu Pro Tyr Thr Leu Lys Asp Val Thr Leu Arg
1               5                   10                  15

Asn Arg Ile Ala Ile Pro Pro Met Cys Gln Tyr Met Ala Glu Asp Gly
            20                  25                  30

Met Ile Asn Asp Trp His His Val His Leu Ala Gly Leu Ala Arg Gly
        35                  40                  45

Gly Ala Gly Leu Leu Val Val Glu Ala Thr Ala Val Ala Pro Glu Gly
    50                  55                  60

Arg Ile Thr Pro Gly Cys Ala Gly Ile Trp Ser Asp Ala His Ala Gln
65                  70                  75                  80

Ala Phe Val Pro Val Val Gln Ala Ile Lys Ala Ala Gly Ser Val Pro
                85                  90                  95

Gly Ile Gln Ile Ala His Ala Gly Arg Lys Ala Ser Ala Asn Arg Pro
            100                 105                 110

Trp Glu Gly Asp Asp His Ile Ala Ala Asp Ala Arg Gly Trp Glu
        115                 120                 125

Thr Ile Ala Pro Ser Ala Ile Ala Phe Gly Ala His Leu Pro Lys Val
    130                 135                 140

Pro Arg Glu Met Thr Leu Asp Asp Ile Ala Arg Val Lys Gln Asp Phe
145                 150                 155                 160

Val Asp Ala Ala Arg Arg Ala Arg Asp Ala Gly Phe Glu Trp Ile Glu
                165                 170                 175

Leu His Phe Ala His Gly Tyr Leu Gly Gln Ser Phe Phe Ser Glu His
            180                 185                 190

Ser Asn Lys Arg Thr Asp Ala Tyr Gly Gly Ser Phe Asp Asn Arg Ser
        195                 200                 205

Arg Phe Leu Leu Glu Thr Ala Ala Val Arg Glu Val Trp Pro Glu
    210                 215                 220

Asn Leu Pro Leu Thr Ala Arg Phe Gly Val Leu Glu Tyr Asp Gly Arg
225                 230                 235                 240

Asp Glu Gln Thr Leu Glu Glu Ser Ile Glu Leu Ala Arg Arg Phe Lys

```
            245                 250                 255
Ala Gly Gly Leu Asp Leu Leu Ser Val Ser Val Gly Phe Thr Ile Pro
                260                 265                 270

Asp Thr Asn Ile Pro Trp Gly Pro Ala Phe Met Gly Pro Ile Ala Glu
            275                 280                 285

Arg Val Arg Arg Glu Ala Lys Leu Pro Val Thr Ser Ala Trp Gly Phe
        290                 295                 300

Gly Thr Pro Gln Leu Ala Glu Ala Leu Gln Ala Asn Gln Leu Asp
305                 310                 315                 320

Leu Val Ser Val Gly Arg Ala His Leu Ala Asp Pro His Trp Ala Tyr
                325                 330                 335

Phe Ala Ala Lys Glu Leu Gly Val Glu Lys Ala Ser Trp Thr Leu Pro
            340                 345                 350

Ala Pro Tyr Ala His Trp Leu Glu Arg Tyr Arg
        355                 360

<210> SEQ ID NO 17
<211> LENGTH: 368
<212> TYPE: PRT
<213> ORGANISM: Pseudomonas putida KT2440

<400> SEQUENCE: 17

Met Ser Leu Leu Leu Glu Pro Tyr Thr Leu Arg Gln Leu Thr Leu Pro
1               5                   10                  15

Asn Arg Ile Ala Val Ser Pro Met Cys Gln Tyr Ser Ala Ile Asp Gly
                20                  25                  30

Leu Ala Asn Asp Trp His Leu His Leu Gly Cys Arg Ala Val Gly
            35                  40                  45

Gly Ala Gly Leu Val Ile Ser Glu Ala Val Ala Val Thr Ala Asp Gly
        50                  55                  60

Arg Ile Thr Ala Glu Asp Leu Gly Leu Trp Asn Asp Asp Gln Ile Val
65                  70                  75                  80

Pro Leu Gln Arg Ile Thr Arg Phe Ile Thr Ala Gln Gly Ala Val Pro
                85                  90                  95

Gly Ile Gln Leu Ala His Ala Gly Arg Lys Ala Ser Thr Tyr Arg Pro
            100                 105                 110

Trp Leu Gly Lys Gln Gly Ser Val Lys Leu Glu Asp Gly Gly Trp Gln
        115                 120                 125

Pro Val Gly Pro Ser Lys Ile Ala Phe Asp Pro Gln His Thr Pro Pro
    130                 135                 140

Arg Glu Leu Ser Lys Asp Glu Ile Gln Asp Val Ile Asp Ala Phe Val
145                 150                 155                 160

Ala Ser Thr Glu Arg Ala Leu Lys Ala Gly Phe Lys Val Val Glu Ile
                165                 170                 175

His Ala Ala His Gly Tyr Leu Leu His Gln Phe Leu Ser Pro Leu Ser
            180                 185                 190

Asn Gln Arg Arg Asp Glu Tyr Gly Ser Cys Phe Glu Asn Arg Ile Arg
        195                 200                 205

Leu Thr Leu Gln Val Val Glu Ala Val Arg Lys Val Trp Pro Ala Glu
    210                 215                 220

Leu Pro Leu Phe Val Arg Val Ser Ala Thr Asp Trp Val Glu Asp Gly
225                 230                 235                 240

Trp Asn Pro Asp Glu Thr Val Glu Leu Ala Arg Arg Leu Arg Val Leu
                245                 250                 255
```

Gly Val Asp Leu Ile Asp Val Ser Ser Gly Thr Ser Val Asn Ala
                260                 265                 270

Glu Ile Pro Thr Gly Pro Gly Tyr Gln Thr Arg Phe Ala Glu Arg Val
            275                 280                 285

Arg Lys Glu Ala Glu Ile Ala Thr Gly Thr Val Gly Met Ile Thr Glu
        290                 295                 300

Pro Ala Gln Ala Glu His Ile Leu Arg Thr Gly Gln Ala Asp Val Ile
305                 310                 315                 320

Phe Leu Ala Arg Glu Leu Leu Arg Asp Pro Tyr Trp Pro Leu His Ala
                325                 330                 335

Asp Asp Asp Leu Gly Gly Asn Lys Ala Thr Trp Pro Ala Gln Tyr Gln
            340                 345                 350

Arg Ala Thr Ser Arg Ala Asn Pro Ile His Glu Ser Asp Leu Arg Asp
        355                 360                 365

<210> SEQ ID NO 18
<211> LENGTH: 367
<212> TYPE: PRT
<213> ORGANISM: Pseudomonas syringae pv. tomato str. DC3000

<400> SEQUENCE: 18

Met Ser Ala Ala Ala Leu Phe Thr Pro Phe Arg Leu Gly Gly Leu Glu
1               5                   10                  15

Leu Ser Ser Arg Val Val Met Ala Pro Met Thr Arg Ser Phe Ser Pro
            20                  25                  30

Gly His Val Pro Asn Ser Lys Val Ile Glu Tyr Tyr Arg Arg Arg Ala
        35                  40                  45

Ala Ala Gly Val Gly Leu Ile Ile Thr Glu Gly Thr Thr Val Asn His
    50                  55                  60

Pro Ala Ser Asn Gly Tyr Pro Asn Val Pro Gln Phe Phe Gly Asp Ala
65                  70                  75                  80

Pro Leu Ala Gly Trp Lys Lys Val Val Asp Ala Val His Ala Glu Gly
                85                  90                  95

Gly Lys Ile Ala Pro Gln Leu Trp His Val Gly Ala Val Arg Arg Leu
            100                 105                 110

Gly Thr Glu Pro Asp Gly Ser Ile Pro Ala Tyr Gly Pro Met Glu Lys
        115                 120                 125

Val Lys Asp Gly Gln Val Leu His Gly Met Ser Lys Gln Asp Ile
    130                 135                 140

Asp Glu Val Val Ala Ala Phe Ala Gln Ala Ala Asp Ala Lys Ala
145                 150                 155                 160

Ile Gly Met Asp Gly Val Glu Ile His Gly Ala His Gly Tyr Leu Val
                165                 170                 175

Asp Gln Phe Phe Trp Glu Gly Ser Asn Gln Arg Ser Asp Glu Tyr Gly
            180                 185                 190

Gly Ser Leu Ala Asn Arg Ser Arg Phe Ala Ile Glu Leu Ile Lys Ala
        195                 200                 205

Val Arg Ala Ala Val Gly Pro Asp Tyr Pro Ile Ile Phe Arg Phe Ser
    210                 215                 220

Gln Trp Lys Gln Gln Asp Tyr Ser Ala Arg Leu Val Gln Thr Pro Glu
225                 230                 235                 240

Ala Leu Gly Glu Phe Val Gln Pro Leu Ser Asp Ala Gly Val Asp Ile
                245                 250                 255

Phe His Cys Ser Thr Arg Arg Phe Trp Glu Pro Glu Phe Glu Gly Ser
            260                 265                 270

```
Glu Leu Asn Leu Ala Gly Trp Thr Arg Lys Leu Thr Gly Lys Pro Thr
            275                 280                 285

Ile Thr Val Gly Ser Val Gly Leu Asp Gly Glu Phe Leu Gln Phe Met
    290                 295                 300

Val Asn Thr Glu Lys Val Ala Gln Pro Ala Ser Leu Glu Asn Leu Leu
305                 310                 315                 320

Glu Arg Leu Gly Lys Asp Glu Phe Asp Leu Val Ala Val Gly Arg Ala
                325                 330                 335

Leu Leu Val Asp Pro Asp Trp Ala Val Lys Val Arg Glu Gly Arg Glu
                340                 345                 350

Gln Asp Ile Leu Pro Phe Ser Arg Glu Ala Leu Thr Thr Leu Val
            355                 360                 365

<210> SEQ ID NO 19
<211> LENGTH: 363
<212> TYPE: PRT
<213> ORGANISM: Pseudomonas syringae pv. tomato str. DC3000

<400> SEQUENCE: 19

Met Ser Ala Leu Phe Glu Pro Phe Lys Leu Lys Asp Val Thr Leu Arg
1               5                   10                  15

Asn Arg Ile Ala Ile Pro Pro Met Cys Gln Tyr Ser Ala Ile Asp Gly
            20                  25                  30

Val Val Asn Asp Trp His His Val His Leu Ala Ser Met Ala Arg Gly
        35                  40                  45

Gly Ala Gly Leu Leu Val Val Glu Ala Thr Ala Val Ala Pro Glu Gly
    50                  55                  60

Arg Ile Thr Pro Gly Cys Thr Gly Ile Trp Asn Asp Glu Gln Ala Gln
65                  70                  75                  80

Ala Phe Val Pro Ile Val Lys Ala Ile Lys Asp Ala Gly Cys Val Pro
                85                  90                  95

Gly Ile Gln Ile Ala His Ala Gly Arg Lys Ala Ser Ala Asn Arg Pro
            100                 105                 110

Trp Glu Gly Asp Asp His Ile Val Ala Ser Asp Ser Arg Gly Trp Asp
        115                 120                 125

Thr Ile Ala Pro Ser Ala Ile Ala Phe Gly Ala Asn Leu Pro Lys Val
    130                 135                 140

Pro Arg Ala Met Thr Leu Asp Asp Ile Ala Arg Val Arg Gln Asn Phe
145                 150                 155                 160

Val Asp Ala Ala Arg Arg Ala Arg Asp Ala Gly Phe Glu Trp Ile Glu
                165                 170                 175

Leu His Phe Ala His Gly Tyr Leu Gly Gln Ser Phe Phe Ser Glu His
            180                 185                 190

Ser Asn Gln Arg Thr Asp Glu Tyr Gly Gly Ser Phe Asp Asn Arg Ser
        195                 200                 205

Arg Phe Leu Leu Glu Thr Leu Ala Ala Val Arg Glu Val Trp Pro Glu
    210                 215                 220

Asn Leu Pro Leu Thr Ala Arg Phe Gly Val Leu Glu Tyr Asp Gly Arg
225                 230                 235                 240

Asp Glu Gln Thr Leu Thr Glu Ser Ile Glu Leu Ala Arg Arg Phe Lys
                245                 250                 255

Ala Gly Gly Leu Asp Leu Leu Ser Val Ser Val Gly Phe Ser Thr Pro
            260                 265                 270

Asp Ala Asn Ile Pro Trp Gly Pro Ala Phe Met Gly Pro Ile Ala Glu
```

```
            275                 280                 285
Arg Val Arg Arg Glu Ala Ala Ile Pro Val Thr Ser Ala Trp Gly Phe
        290                 295                 300

Gly Glu Pro Lys Leu Ala Glu Ala Val Lys Ser Gly Gln Leu Asp
305                 310                 315                 320

Leu Val Ser Ile Gly Arg Ala His Leu Ala Asp Pro His Trp Ala Tyr
                325                 330                 335

Phe Ala Ala Lys Glu Leu Gly Val Glu Lys Ser Ala Trp Thr Leu Pro
                340                 345                 350

Ala Pro Tyr Ala His Trp Leu Glu Arg Tyr Arg
                355                 360

<210> SEQ ID NO 20
<211> LENGTH: 349
<212> TYPE: PRT
<213> ORGANISM: Pseudomonas syringae pv. tomato str. DC3000

<400> SEQUENCE: 20

Met Thr Thr Ile Phe Asp Pro Ile Thr Leu Gly Asp Leu Gln Leu Pro
1               5                   10                  15

Asn Arg Ile Ile Leu Ala Pro Leu Thr Arg Cys Arg Ala Asp Glu Gly
            20                  25                  30

Arg Val Pro Asn Ala Leu Met Ser Glu Tyr Tyr Val Gln Arg Ala Ser
        35                  40                  45

Ala Gly Leu Ile Leu Thr Glu Ala Thr Ser Val Thr Pro Met Gly Val
    50                  55                  60

Gly Tyr Pro Asp Thr Pro Gly Ile Trp Ser Asn Asp Gln Val Arg Gly
65                  70                  75                  80

Trp Ser Asn Ile Thr Gln Ala Val His Asn Ala Gly Gly Arg Ile Val
                85                  90                  95

Leu Gln Leu Trp His Val Gly Arg Ile Ser His Pro Ser Tyr Leu Asn
            100                 105                 110

Gly Glu Thr Pro Val Ala Pro Ser Ala Ile Ala Ala Gln Gly His Val
        115                 120                 125

Ser Leu Met Arg Pro Ile Thr Pro Leu Pro Thr Pro Arg Ala Leu Glu
    130                 135                 140

Leu Ala Glu Ile Gly Asp Ile Val Glu Ala Tyr Arg Val Gly Ala Glu
145                 150                 155                 160

Asn Ala Lys Ala Ala Gly Phe Asp Gly Val Glu Val His Gly Ala Asn
                165                 170                 175

Gly Tyr Leu Leu Glu Gln Phe Leu Leu Thr Gly Ser Asn Gln Arg Thr
            180                 185                 190

Asp Gln Tyr Gly Gly Ser Leu Glu Asn Arg Ala Arg Leu Leu Leu Glu
        195                 200                 205

Val Thr Asp Ala Val Ile Asp Val Trp Gly Ala Gly Arg Val Gly Val
    210                 215                 220

His Leu Ser Pro Arg Phe Asp Met His Asn Met Ser Asp Glu Asn Arg
225                 230                 235                 240

Ala Glu Thr Phe Ser Tyr Val Ala Lys Glu Leu Gly Lys Arg Gly Ile
                245                 250                 255

Ala Phe Ile Cys Ala Arg Glu Arg Asp Ala Glu Asp Ser Leu Gly Pro
            260                 265                 270

Gln Leu Lys Lys Asp Phe Gly Gly Val Tyr Ile Ala Asn Glu Lys Phe
        275                 280                 285
```

```
Thr Lys Asp Ser Ala Asn Ala Trp Leu Ala Glu Gly Lys Ala Asp Ala
290                 295                 300

Phe Ala Phe Gly Val Pro Tyr Ile Ala Asn Pro Asp Leu Pro Glu Arg
305                 310                 315                 320

Leu Ala Ser Asp Ala Pro Leu Asn Glu Ala His Pro Glu Thr Phe Tyr
                325                 330                 335

Gly Lys Gly Pro Val Gly Tyr Ile Asp Tyr Pro Arg Leu
                340                 345

<210> SEQ ID NO 21
<211> LENGTH: 367
<212> TYPE: PRT
<213> ORGANISM: Pseudomonas syringae pv. phaseolicola 1448A

<400> SEQUENCE: 21

Met Ser Val Glu Ala Leu Phe Thr Pro Phe Arg Leu Gly Ser Leu Glu
1               5                   10                  15

Leu Ser Ser Arg Val Val Met Ala Pro Met Thr Arg Ser Phe Ser Pro
                20                  25                  30

Gly His Val Pro Asn Ser Lys Val Ile Glu Tyr Tyr Arg Arg Arg Ala
                35                  40                  45

Ala Ala Gly Val Gly Leu Ile Val Thr Glu Gly Thr Thr Val Asn His
    50                  55                  60

Lys Ala Ser Asn Gly Tyr Pro Asn Val Pro Gln Phe Phe Gly Asp Ala
65                  70                  75                  80

Pro Leu Ala Gly Trp Arg Lys Val Glu Ala Val His Ala Glu Gly Gly
                85                  90                  95

Gly Lys Ile Val Pro Gln Leu Trp His Val Gly Ala Val Arg Arg Pro
                100                 105                 110

Gly Thr Glu Pro Asp Gly Ser Val Pro Ala Tyr Gly Pro Met Glu Lys
                115                 120                 125

Val Lys Asp Gly Gln Val Leu Val His Gly Met Ser Lys Gln Asp Ile
            130                 135                 140

Asp Asp Val Val Ala Ala Phe Ala Gln Ala Val Asp Ala Lys Ala
145                 150                 155                 160

Ile Gly Met Asp Gly Val Glu Ile His Gly Ala His Gly Tyr Leu Ile
                165                 170                 175

Asp Gln Phe Phe Trp Glu Gly Ser Asn Gln Arg Ser Asp Glu Tyr Gly
                180                 185                 190

Gly Ser Leu Ala Lys Arg Ser Arg Phe Ala Ile Glu Leu Ile Lys Ala
                195                 200                 205

Val Arg Val Ala Val Gly Ala Asp Tyr Pro Ile Ile Phe Arg Phe Ser
    210                 215                 220

Gln Trp Lys Gln Gln Asp Tyr Thr Ala Arg Leu Val Gln Thr Pro Glu
225                 230                 235                 240

Ala Leu Gly Glu Phe Leu Gln Pro Leu Ala Asp Ala Gly Val Asp Ile
                245                 250                 255

Phe His Cys Ser Thr Arg Arg Phe Trp Glu Pro Glu Phe Glu Gly Ser
                260                 265                 270

Asp Leu Asn Leu Ala Gly Trp Thr Arg Lys Leu Thr Gly Lys Pro Thr
                275                 280                 285

Ile Thr Val Gly Ser Val Gly Leu Asp Gly Glu Phe Leu Gln Phe Met
            290                 295                 300

Val Asn Thr Asp Lys Val Ala Gln Pro Ala Ser Leu Glu Asn Leu Leu
305                 310                 315                 320
```

```
Lys Arg Leu Gly Asn Asp Glu Phe Asp Leu Val Ala Val Gly Arg Ala
                325                 330                 335

Leu Leu Val Asp Pro Asp Trp Ala Leu Lys Val Arg Glu Gly Arg Glu
                340                 345                 350

Gln Asp Ile Leu Pro Phe Ser Arg Glu Ala Leu Thr Thr Leu Val
            355                 360                 365

<210> SEQ ID NO 22
<211> LENGTH: 368
<212> TYPE: PRT
<213> ORGANISM: Pseudomonas syringae phaseolicola 1448A

<400> SEQUENCE: 22

Met Ser Leu Leu Leu Glu Pro Tyr Thr Leu Arg Gln Leu Thr Leu Arg
1               5                   10                  15

Asn Arg Ile Ala Val Ser Pro Met Cys Gln Tyr Ser Ser Val Asp Gly
                20                  25                  30

Leu Ala Asn Asp Trp His Leu Val His Leu Gly Ser Arg Ala Val Gly
            35                  40                  45

Gly Ala Gly Leu Val Ile Thr Glu Ala Met Ala Val Thr Pro Asp Gly
        50                  55                  60

Arg Ile Thr Pro Glu Asp Leu Gly Leu Trp Asn Asp Glu Gln Ile Glu
65                  70                  75                  80

Pro Leu Gln Arg Ile Thr Arg Phe Ile Asn Ala Gln Gly Ala Val Ala
                85                  90                  95

Gly Ile Gln Leu Ala His Ala Gly Arg Lys Ala Ser Thr Trp Arg Pro
            100                 105                 110

Trp Leu Gly Lys His Gly Ser Ile Ser Leu Asn Glu Gly Gly Trp Thr
        115                 120                 125

Pro Val Gly Pro Ser Ala Ile Ala Phe Asp Pro Gln His Thr Ala Pro
130                 135                 140

Val Gln Leu Ser Glu Thr Gln Ile Gln Glu Leu Ile Lys Ala Phe Val
145                 150                 155                 160

Asp Ser Ala Arg Arg Ala Leu Thr Ala Gly Phe Lys Val Val Glu Ile
                165                 170                 175

His Ala Ala His Gly Tyr Leu Leu His Gln Phe Leu Ser Pro Leu Ser
            180                 185                 190

Asn Gln Arg Thr Asp Gln Tyr Gly Gly Ser Phe Glu Asn Arg Ile Arg
        195                 200                 205

Leu Thr Leu Gln Val Thr Glu Ala Val Arg Ala Val Trp Pro Glu Glu
210                 215                 220

Leu Pro Leu Phe Val Arg Val Ser Ala Thr Asp Trp Val Glu Asp Gly
225                 230                 235                 240

Trp Asn Ala Asp Glu Thr Val Glu Leu Ala Arg Arg Leu Lys Ala Leu
                245                 250                 255

Gly Thr Asp Leu Ile Asp Val Ser Gly Gly Thr Ser Ala Asn Ala
            260                 265                 270

Glu Ile Pro Val Gly Pro Gly Tyr Gln Thr Arg Phe Ala Glu Arg Val
        275                 280                 285

Arg Lys Glu Ser Glu Ile Ala Thr Gly Thr Val Gly Met Ile Thr Asp
        290                 295                 300

Pro Ala Gln Ala Glu His Ile Leu Arg Thr Gly Gln Ala Asp Ile Ile
305                 310                 315                 320

Leu Leu Ala Arg Glu Leu Leu Arg Asp Pro Tyr Trp Pro Leu Arg Ala
```

```
                        325                 330                 335
Asp Glu Asp Leu Gly Gly Arg Leu Ala Thr Trp Pro Ala Gln Tyr Gln
                340                 345                 350
Arg Ala Thr His Arg Asp Gln Pro Ile His Glu Ser Asp Leu Arg Asp
            355                 360                 365

<210> SEQ ID NO 23
<211> LENGTH: 349
<212> TYPE: PRT
<213> ORGANISM: Pseudomonas syringae phaseolicola 1448A

<400> SEQUENCE: 23

Met Thr Thr Ile Phe Asp Pro Ile Thr Ile Gly Asp Leu Gln Leu Pro
1               5                   10                  15

Asn Arg Ile Ile Met Ala Pro Leu Thr Arg Cys Arg Ala Asp Glu Gly
                20                  25                  30

Arg Val Pro Asn Ala Leu Met Ser Glu Tyr Tyr Val Gln Arg Ala Ser
            35                  40                  45

Ala Gly Leu Ile Leu Thr Glu Ala Thr Ser Val Thr Pro Met Gly Val
        50                  55                  60

Gly Tyr Pro Asp Thr Pro Gly Ile Trp Ser Asn Asp Gln Val Arg Gly
65                  70                  75                  80

Trp Ser Asn Ile Thr Lys Ala Val His Thr Ala Gly Gly Arg Ile Val
                85                  90                  95

Leu Gln Leu Trp His Val Gly Arg Ile Ser His Pro Ala Tyr Leu Asn
            100                 105                 110

Gly Glu Thr Pro Val Ala Pro Ser Ala Ile Ala Ala Glu Gly His Val
        115                 120                 125

Ser Leu Met Arg Pro Ile Thr Pro Leu Pro Thr Pro Arg Ala Leu Glu
    130                 135                 140

Leu Ala Glu Ile Gly Asp Ile Val Glu Ala Tyr Arg Val Gly Ala Glu
145                 150                 155                 160

Asn Ala Lys Ala Ala Gly Phe Asp Gly Val Glu Val His Gly Ala Asn
                165                 170                 175

Gly Tyr Leu Leu Glu Gln Phe Leu Leu Thr Gly Ser Asn Gln Arg Thr
            180                 185                 190

Asp Glu Tyr Gly Gly Ser Val Glu Asn Arg Ala Arg Leu Leu Leu Glu
        195                 200                 205

Val Thr Asp Ala Val Ile Glu Val Trp Gly Ala Gly Arg Val Gly Val
    210                 215                 220

His Leu Ser Pro Arg Phe Asp Met His Asp Met Ser Asp Ala Asn Arg
225                 230                 235                 240

Thr Glu Thr Phe Ser Tyr Val Ala Lys Glu Leu Gly Lys Arg Gly Ile
                245                 250                 255

Ala Phe Ile Cys Ala Arg Glu Arg Asp Ala Glu Asp Ser Leu Gly Pro
            260                 265                 270

Gln Leu Lys Lys Asp Phe Gly Gly Val Tyr Ile Ala Asn Glu Lys Phe
        275                 280                 285

Thr Lys Asp Thr Ala Asn Thr Trp Leu Ala Glu Gly Lys Ala Asp Ala
    290                 295                 300

Ile Ala Phe Gly Val Pro Tyr Ile Ala Asn Pro Asp Leu Pro Glu Arg
305                 310                 315                 320

Leu Ala Ser Asp Ala Pro Leu Asn Glu Ala His Pro Glu Thr Phe Tyr
                325                 330                 335
```

Gly Lys Gly Pro Val Gly Tyr Ile Asp Tyr Pro Arg Leu
              340                 345

<210> SEQ ID NO 24
<211> LENGTH: 370
<212> TYPE: PRT
<213> ORGANISM: Rhodococcus sp. RHA1

<400> SEQUENCE: 24

Met Gln His Thr Ser Thr Thr Ala Ser Thr Leu Phe Ser Pro Leu Lys
1               5                   10                  15

Leu Gly Ser Thr Glu Leu Ala Asn Arg Val Ala Leu Ala Pro Met Thr
            20                  25                  30

Arg Val Ser Gly Asp Glu Asp Gly Ser Ala Asn Glu Ser Ile Ala Ser
        35                  40                  45

Tyr Tyr Glu Val Phe Ala Lys Gly Gly Phe Gly Leu Leu Ile Thr Glu
    50                  55                  60

Gly Ile Tyr Pro Asp Thr Lys Tyr Ser Gln Gly Tyr Leu Asn Gln Pro
65                  70                  75                  80

Gly Leu Ala Thr Ala Gln His Ala Asp Ser Trp Lys Pro Val Val Glu
                85                  90                  95

Arg Val His Thr Ala Gly Ala Arg Ile Phe Ala Gln Leu Met His Ala
            100                 105                 110

Gly Ala Gln Ser Gln Gly Asn Arg Tyr Val Thr Glu Thr Ile Ala Pro
        115                 120                 125

Ser Thr Thr Pro Pro Leu Gly Glu Gln Leu Gly Phe Tyr Gly Gly Thr
    130                 135                 140

Gly Pro Tyr Ala Thr Pro Arg Ala Leu Ser Leu Arg Asp Ile Asp Asp
145                 150                 155                 160

Val Cys Ala Gly Phe Ala Gln Ala Gln His Ala Val Ala Ala Gly
                165                 170                 175

Phe Asp Gly Val Glu Ile His Gly Ala Asn Gly Tyr Leu Leu Asp Gln
            180                 185                 190

Phe Leu Thr Asp Tyr Met Asn Gln Arg Asp Asp Glu Tyr Gly Gly Ser
        195                 200                 205

Leu Ala Asn Arg Leu Lys Ile Tyr Arg Glu Val Ile Ala Ala Val Arg
    210                 215                 220

Gln Val Val Gly Ser Lys Val Thr Val Gly Val Arg Ile Ser Gln Ser
225                 230                 235                 240

Lys Val Ser Asp Tyr Asn His Arg Trp Ala Gly Gly Glu Ser Asp Ala
                245                 250                 255

Ala Glu Ile Phe Gln Gly Leu Ala Glu Thr Gly Val Asp Tyr Ile His
            260                 265                 270

Thr Thr Glu Phe Asp Ala Thr Ala Pro Ala Phe Ala Asp Ser Gly Thr
        275                 280                 285

Thr Leu Ala Ala Phe Ala Thr Lys Tyr Ser Gly Leu Pro Val Ile Ala
    290                 295                 300

Asn Gly Gln Leu Gly Asp Pro Ala Ala Asp Ala Leu Ile Glu Asn
305                 310                 315                 320

Gly Ser Ala Gln Val Ile Ser Leu Gly Lys Pro Ala Leu Ala Asn Arg
                325                 330                 335

Asp Trp Pro Gln Arg Ala Leu Asp Ala Lys Pro Ile Gln Ser Asp Val
            340                 345                 350

Asp Pro Ser Val Phe Ser Pro Met Ala Thr Val Lys Ser Trp Glu Leu
        355                 360                 365

Ser Ala
    370

<210> SEQ ID NO 25
<211> LENGTH: 408
<212> TYPE: PRT
<213> ORGANISM: Rhodococcus sp. RHA1

<400> SEQUENCE: 25

```
Met Ser Arg Gln Ala Lys Trp Glu Glu Leu Ser Ser Pro Ile Glu Met
1               5                   10                  15

Arg Gly Val Lys Phe Lys Asn Arg Met Met Arg Ser Gly Met Tyr Glu
            20                  25                  30

Gly Met Ala Thr Glu Arg Gly Glu Val Thr Pro Glu Leu Glu Thr Trp
        35                  40                  45

Ile Ala Arg Gln Ala Ala Gly Ala Ala Cys Ile Phe Pro Gly Tyr
    50                  55                  60

Thr Asn Val Cys Leu Pro Arg Cys Met Pro Tyr Gln Thr Gly Ser Tyr
65                  70                  75                  80

Ser Asp Ser His Ile Pro Gly Leu Thr Lys Leu Ala Glu Ile Ile His
                85                  90                  95

Ser Tyr Gly Ala Val Ala Gly Leu Gln Leu Ala Ala Ala Gly Arg Gln
            100                 105                 110

Ala Asn Pro Asn Leu Phe Phe Ser Asp Ala Glu Ala Val Met Gly Pro
        115                 120                 125

Ser Ala Met Gly Pro Ser Pro Leu Tyr Gln Ala Ala Cys Arg Glu Met
    130                 135                 140

Thr Glu Ala Glu Ile Trp Gln Ala Val Glu Asp Gln Ala Ala Ala Ala
145                 150                 155                 160

Ala Arg Ala Lys Glu Ala Gly Phe Asp Ile Val Leu Pro Asn Ala Ala
                165                 170                 175

His Gly Tyr Met Leu Ala Gln Phe Leu Ser Pro His Thr Asn Lys Arg
            180                 185                 190

Thr Asp Ala Trp Gly Gly Thr Pro Glu Lys Arg Phe Lys Phe Phe Glu
        195                 200                 205

Glu Thr Phe Arg Ala Val Arg Glu Ala Val Gly Pro Glu Met Leu Val
    210                 215                 220

Trp Thr Lys Ile Ser Val Asp Glu Pro Trp Glu Asp Gly Ile Asn Leu
225                 230                 235                 240

Asp Glu Ala Arg Ile Phe Ile Pro Glu Val Ala Lys Leu Val Asp Ala
                245                 250                 255

Ile Glu Ile Ser Gly Gly Thr Ile Val Asp Asn Val Phe Met Met Thr
            260                 265                 270

Arg Gly Glu Ile Pro Ile Gly Thr Leu Arg Lys Gly Ile Gly Gly Pro
        275                 280                 285

Val Glu Gly Ile Ser Ala Glu Leu Val Glu Gly Leu Tyr Gly Ile Arg
    290                 295                 300

Asp Ser Val Lys Phe Glu Glu Thr Tyr Trp Tyr Asp His Ala Leu Ala
305                 310                 315                 320

Leu Lys Pro Leu Cys Gly Asp Thr Pro Leu Ile Leu Thr Gly Gly His
                325                 330                 335

Lys Tyr Pro Ala Thr Met Asn Gln Ile Ile Lys Glu Gly Thr Ala Asp
            340                 345                 350

Met Leu Ser Leu Ala Arg Val Leu Ala Ala Glu Pro Asn Phe Pro Asn
```

```
                355                 360                 365
Glu Val Val Ala Gly Arg Glu Asp Pro Gly Lys Cys Ser Asn Cys Asn
370                 375                 380

Lys Cys Leu Val Glu Val Val Leu Gly Asn Lys Leu Arg Cys Tyr Leu
385                 390                 395                 400

Pro Asp Pro Gly Tyr Thr Tyr Ala
                405

<210> SEQ ID NO 26
<211> LENGTH: 375
<212> TYPE: PRT
<213> ORGANISM: Staphylococcus aureus subsp. aureus Mu50

<400> SEQUENCE: 26

Met Lys Ser Lys Tyr Glu Pro Leu Phe Asp Lys Val Glu Leu Pro Asn
1               5                   10                  15

Gly Val Glu Leu Arg Asn Arg Phe Val Leu Ala Pro Leu Thr His Ile
                20                  25                  30

Ser Ser Asn Asp Asp Gly Thr Ile Ser Asp Val Glu Leu Pro Tyr Ile
            35                  40                  45

Glu Lys Arg Ser Gln Asp Val Gly Ile Thr Ile Asn Ala Ala Ser Asn
50                  55                  60

Val Ser Asp Val Gly Lys Ala Phe Pro Gly Gln Pro Ser Ile Ala His
65                  70                  75                  80

Asp Ser Asp Ile Glu Gly Leu Lys Arg Leu Ala Thr Ala Met Lys Lys
                85                  90                  95

Asn Gly Ala Lys Ala Leu Val Gln Ile His His Gly Gly Ala Gln Ala
            100                 105                 110

Leu Pro Glu Leu Ile Pro Asp Gly Asp Val Val Ala Pro Ser Pro Ile
        115                 120                 125

Ser Leu Lys Ser Phe Gly Gln Lys Gln Glu His Ser Ala Arg Glu Met
130                 135                 140

Thr Asn Glu Glu Ile Glu Gln Ala Ile Lys Asp Phe Gly Glu Ala Thr
145                 150                 155                 160

Arg Arg Ala Ile Glu Ala Gly Phe Asp Gly Val Glu Ile His Gly Ala
                165                 170                 175

Asn His Tyr Leu Ile His Gln Phe Val Ser Pro Tyr Tyr Asn Arg Arg
            180                 185                 190

Asn Asp Val Trp Ala Asn Gln Tyr Lys Phe Pro Val Ala Val Ile Glu
        195                 200                 205

Glu Val Leu Lys Ala Lys Glu Ala Tyr Gly Asn Lys Asp Phe Ile Val
210                 215                 220

Gly Tyr Arg Leu Ser Pro Glu Glu Ala Glu Ser Pro Gly Ile Thr Met
225                 230                 235                 240

Glu Ile Thr Glu Glu Leu Val Asn Lys Ile Ser His Met Pro Ile Asp
                245                 250                 255

Tyr Ile His Val Ser Met Met Asp Thr His Ala Thr Thr Arg Glu Gly
            260                 265                 270

Lys Tyr Ala Gly Gln Glu Arg Leu Pro Leu Ile His Lys Trp Ile Asn
        275                 280                 285

Gly Arg Met Pro Leu Ile Gly Ile Gly Ser Ile Phe Thr Ala Asp Glu
290                 295                 300

Ala Leu Asp Ala Val Glu Asn Val Gly Val Asp Leu Val Ala Ile Gly
305                 310                 315                 320
```

```
Arg Glu Leu Leu Leu Asp Tyr Gln Phe Val Glu Lys Ile Lys Asp Gly
                325                 330                 335

Arg Glu Asp Glu Ile Ile Asn Tyr Phe Asp Pro Glu Arg Glu Asp Asn
            340                 345                 350

His His Leu Thr Pro Asn Leu Trp His Gln Phe Asn Glu Gly Phe Tyr
        355                 360                 365

Pro Leu Pro Arg Lys Asp Lys
        370             375

<210> SEQ ID NO 27
<211> LENGTH: 359
<212> TYPE: PRT
<213> ORGANISM: Streptomyces avermitilis MA-4680

<400> SEQUENCE: 27

Met Ser Ala Leu Phe Glu Pro Tyr Ser Leu Arg Asp Leu Thr Ile Pro
1               5                   10                  15

Asn Arg Val Trp Met Ala Pro Met Cys Gln Tyr Ser Ala Ala Pro Gln
            20                  25                  30

Gly Pro Ala Ala Gly Ala Pro His Asp Trp His Phe Ala His Tyr Ala
        35                  40                  45

Ala Arg Ala Thr Gly Gly Thr Gly Leu Ile Val Val Glu Ala Thr Ala
    50                  55                  60

Val Ser Pro Glu Gly Arg Ile Ser Pro Tyr Asp Leu Gly Ile Trp Asn
65                  70                  75                  80

Asp Thr Gln Val Glu Ala Phe Arg Arg Ile Thr Arg Phe Leu Ala Ala
                85                  90                  95

Gln Gly Thr Val Pro Ala Ile Gln Leu Ala His Gly Gly Arg Lys Ala
            100                 105                 110

Ser Thr Asp Arg Pro Trp Lys Gly Gly Ala Pro Leu Ala Ala Asp Glu
        115                 120                 125

His Gly Trp Gln Pro Leu Gly Pro Ser Pro Val Ala Phe Asp Glu Arg
    130                 135                 140

His Pro Val Pro Thr Glu Leu Ser Val Ala Glu Ile Arg Gln Ile Val
145                 150                 155                 160

Gly Gln Phe Ala Asp Ala Ala Arg Arg Ala Leu Ala Ala Gly Phe Glu
                165                 170                 175

Ile Ala Glu Ile His Gly Ala His Gly Tyr Leu Ile Asn Glu Phe Leu
            180                 185                 190

Ser Pro His Ser Asn Arg Arg Thr Asp Glu Tyr Gly Gly Ser Tyr Glu
        195                 200                 205

Asn Arg Val Arg Phe Ala Leu Glu Val Val Asp Ala Val Arg Glu Val
    210                 215                 220

Trp Pro Ala Gly Lys Pro Leu Phe Phe Arg Val Ser Ala Thr Asp Trp
225                 230                 235                 240

Leu Asp Glu Gly Gly Trp Thr Ala Asp Thr Val Arg Phe Ala Ala
                245                 250                 255

Glu Leu Gln Ala His Gly Val Asp Leu Leu Asp Val Ser Thr Gly Gly
            260                 265                 270

Asn Ala Ser Gly Val Arg Ile Pro Thr Gly Pro Gly Tyr Gln Val Pro
        275                 280                 285

Phe Ala Ala Arg Val Lys Ala Gly Thr Ser Leu Pro Val Ala Ala Val
    290                 295                 300

Gly Leu Ile Thr Asp Ala Glu Gln Ala Glu Lys Ile Leu Ala Asn Gly
305                 310                 315                 320
```

Glu Ala Asp Ala Ile Leu Leu Gly Arg Glu Leu Leu Arg Asn Pro Ser
            325                 330                 335

Phe Ala Arg Leu Ala Ala Arg Glu Leu Gly Gly Asp Val His Val Pro
            340                 345                 350

Ala Gln Tyr His Arg Ser Val
        355

<210> SEQ ID NO 28
<211> LENGTH: 363
<212> TYPE: PRT
<213> ORGANISM: Sinorhizobium meliloti 1021

<400> SEQUENCE: 28

Met Glu Ile Pro Met Asn Pro Met Phe Thr Ser Val Arg Val Gly Arg
1               5                   10                  15

Tyr Met Leu Pro Asn Arg Leu Val Met Ala Pro Met Thr Arg Ser Arg
            20                  25                  30

Ala Ala Phe Asp Gly Thr Pro Gly Glu Leu Ala Thr Glu Tyr Tyr Val
        35                  40                  45

Gln Arg Ala Arg Leu Gly Leu Ile Val Thr Glu Gly Thr Gln Pro Ser
    50                  55                  60

Asp Asp Gly Gln Gly Tyr Leu Thr Thr Pro Gly Ile Tyr Thr Pro Ala
65                  70                  75                  80

His Ile Ala Gly Trp Arg Lys Ile Thr Ser Ala Val His Asp Lys Gly
                85                  90                  95

Gly His Ile Phe Ile Gln Leu Met His Ala Gly Arg Met Ser His Pro
            100                 105                 110

Asp Asn Thr Pro His His Arg Gln Gly Val Ala Pro Ser Ala Ile Ala
        115                 120                 125

Pro Gly Ala Gly Met Phe Thr Ala Thr Gly Met Gln Asp Ile Pro Thr
    130                 135                 140

Pro Arg Ala Leu Thr Thr Glu Glu Val Arg Arg Thr Val Ala Glu Phe
145                 150                 155                 160

Ser His Ala Ala Arg Ser Ala Ile Glu Ala Gly Ala Asp Gly Ile Glu
                165                 170                 175

Ile His Gly Ala Asn Ala Tyr Leu Val Gln Gln Phe Phe Ala Pro Ser
            180                 185                 190

Ala Asn Thr Arg Thr Asp Glu Tyr Gly Gly Ser Ile Glu Asn Arg Ala
        195                 200                 205

Arg Phe Ala Ile Glu Val Ala Thr Ala Ile Ala Glu Glu Val Gly Ala
    210                 215                 220

Asp Arg Thr Ala Ile Arg Leu Ser Pro Gly Thr Ala Leu Trp Gly Ile
225                 230                 235                 240

Asp Glu Gly Ala Glu Gly Pro Asp Leu Tyr Arg Tyr Leu Val Ala Glu
                245                 250                 255

Leu Asp Lys Leu Gly Leu Ala Tyr Val His Ile Leu His Gln Ser Asn
            260                 265                 270

Glu Pro Leu Leu Ala Asp Ile Arg Lys Leu Trp Arg Gln Pro Leu Ile
        275                 280                 285

Leu Asn Arg Pro Gly Arg Pro Arg Gly Gln Ile Gly Ala Asp Val Ala
    290                 295                 300

Ser Gly Leu Ala Asp Leu Glu Ala Phe Gly Gln Met Val Leu Ala Asn
305                 310                 315                 320

Pro Asp Phe Val Ala Arg Leu Lys Ala Asp Ala Ala Met Asn Glu Ser

```
                           325                 330                 335

Asp Pro Lys Thr Phe Tyr Gly Gly Ala Ala Lys Gly Tyr Ile Asp Tyr
            340                 345                 350

Pro Val Leu Ser Ala Arg Thr Asp Thr Ser Ser
        355                 360

<210> SEQ ID NO 29
<211> LENGTH: 378
<212> TYPE: PRT
<213> ORGANISM: Shewanella oneidensis MR-1

<400> SEQUENCE: 29

Met Ser Val Phe Thr Ala Tyr Glu Ser Gly Ala Leu Thr Leu Gln Asn
1               5                   10                  15

Arg Ile Val Met Ala Pro Met Thr Arg Ala Arg Thr Thr Gln Pro Gly
            20                  25                  30

Asn Ile Pro Asn Asp Leu Met Val Gln Tyr Tyr Ala Gln Arg Ser Ser
        35                  40                  45

Ala Gly Leu Ile Ile Thr Glu Ala Thr Gln Ile Ser Asn Asp Ser Gln
    50                  55                  60

Gly Tyr Ser Phe Thr Pro Gly Val Tyr Thr Glu Ala Gln Ile Asp Gly
65                  70                  75                  80

Trp Lys Lys Val Thr Ala Ala Val His Glu Ala Gly Gly Lys Ile Phe
                85                  90                  95

Asn Gln Ile Trp His Val Gly Arg Val Ser His Pro Ile Phe Gln Gln
            100                 105                 110

Gly Asn Ala Pro Ile Ala Pro Ser Ala Ile Ala Pro Val Gly Thr Lys
        115                 120                 125

Val Trp Ile Val Asp Glu Ala His Pro Glu Gly Gln Met Val Asp Cys
    130                 135                 140

Pro Glu Pro Arg Glu Met Thr Gln Ala Asp Ile Asp Arg Val Val Ala
145                 150                 155                 160

Asp Phe Ala Lys Ala Gly Ala Asn Ala Ile Ala Ala Gly Phe Asp Gly
                165                 170                 175

Ile Glu Ile His Gly Gly Asn Gly Tyr Leu Ile Asp Gln Phe Leu Arg
            180                 185                 190

Thr Asn Ser Asn His Arg Thr Asp Ala Tyr Gly Gly Ser Pro Glu Lys
        195                 200                 205

Arg Ile Arg Phe Leu Leu Glu Val Val Glu Ala Val Ser Ala Gln Ile
    210                 215                 220

Gly Ala Asp Lys Val Gly Val Arg Leu Ala Pro Tyr Val Thr Phe Lys
225                 230                 235                 240

Asp Met Ala Cys Pro Glu Ile Val Glu Thr Ile Leu Leu Ala Ala Lys
                245                 250                 255

Gln Leu Ser Ala Phe Gly Val Ala Tyr Leu His Leu Ser Glu Ala Asp
            260                 265                 270

Trp Asp Asp Ala Pro Gln Ile Pro Glu Ser Phe Arg Ile Glu Leu Arg
        275                 280                 285

Asn Val Phe Lys Gly Ser Ile Ile Val Ala Gly Arg Tyr Asp Val Glu
    290                 295                 300

Arg Ala Asn Asp Val Ile Glu Lys Gly Tyr Ala Asp Leu Val Ala Phe
305                 310                 315                 320

Gly Arg Ala Phe Ile Ala Asn Pro Asp Leu Pro Tyr Arg Leu Ala Asn
                325                 330                 335
```

```
Gln Leu Pro Leu Ser Pro Phe Asp Lys Gly Pro Leu Phe Gly Gly Ser
            340                 345                 350

Ala Ala Gly Tyr Thr Asp Tyr Pro Ser Tyr Gln Ala Ala Leu Arg Ala
        355                 360                 365

Val Ile Arg Ser Ser Asp Asp Glu Val Ala
    370                 375

<210> SEQ ID NO 30
<211> LENGTH: 365
<212> TYPE: PRT
<213> ORGANISM: Xanthomonas campestris pv. campestris str. ATCC 33913

<400> SEQUENCE: 30

Met Ser Gln Leu Phe Thr Pro Ile Asn Phe Gly Pro Leu Ala Leu Ala
1               5                   10                  15

Asn Arg Ile Val Ile Ala Pro Met Cys Gln Tyr Ser Ala Gln Asp Gly
            20                  25                  30

Arg Ala Thr Asp Trp His Arg Ile His Leu Gly Thr Leu Ser Gln Ser
        35                  40                  45

Gly Ala Ala Leu Leu Ile Leu Glu Ala Ala Ala Val Gln Pro Gln Gly
    50                  55                  60

Arg Ile Ser Tyr Ala Asp Leu Gly Leu Tyr Asp Asp Ala Thr Glu Gln
65                  70                  75                  80

Ala Leu Gly Glu Val Leu Ala Ser Val Arg Arg Trp Ser Pro Met Pro
                85                  90                  95

Ile Gly Ile Gln Leu Ala His Ala Gly Arg Lys Ala Ser Thr Asp Leu
            100                 105                 110

Pro Trp Lys Gly Gly Glu Ala Ile Ala Pro Asp His Ala Asn Gly Trp
        115                 120                 125

Gln Thr Val Ser Ala Ser Ala Leu Pro Phe Arg Asp Gly Gln Pro Leu
    130                 135                 140

Pro Gln Ala Leu Asp Ala Ala Gly Ile Asp Ala Val Val Glu Ala Phe
145                 150                 155                 160

Val Thr Ala Ala Lys Arg Ala Glu Arg Leu Glu Leu Gln Leu Ile Glu
                165                 170                 175

Leu His Ala Ala His Gly Tyr Leu Met His Gln Phe Leu Ser Pro Leu
            180                 185                 190

Ser Asn Gln Arg Ser Asp Ala Tyr Gly Gly Ser Leu Asp Asn Arg Met
        195                 200                 205

Arg Leu Thr Leu Arg Ile Phe Asp Ala Val Arg Ala Ala Val Ser Asp
    210                 215                 220

Gln Met Ala Ile Gly Val Arg Ile Ser Ala Thr Asp Trp Val Asp Gly
225                 230                 235                 240

Gly Trp Asp Leu Pro Gln Ser Ile Ala Leu Ser Lys Ala Leu Asp Ala
                245                 250                 255

Arg Gly Ala His Tyr Ile His Val Ser Ser Gly Gly Leu Asp Pro Arg
            260                 265                 270

Gln Gln Ile Pro Val Gln Ala Ser Tyr Gln Ile Pro Phe Ala Glu Ala
        275                 280                 285

Ile Arg Ala Gln Val Asp Thr Pro Val Ile Gly Val Gly Leu Ile Thr
    290                 295                 300

Glu Pro Gln Gln Ala Glu Ala Ile Leu Arg Asp Gly Gln Ala Asp Ala
305                 310                 315                 320

Ile Ala Leu Ala Arg Gly Ile Leu Tyr Asp Pro Arg Trp Pro Trp His
                325                 330                 335
```

Ala Ala Ala Ala Leu Gly Ala Ser Val Thr Pro Ala Pro Gln Tyr Gln
            340                 345                 350

Arg Cys Glu Pro Arg Glu Ala Arg Gly Val Phe Ala Ser
355                 360                 365

<210> SEQ ID NO 31
<211> LENGTH: 400
<212> TYPE: PRT
<213> ORGANISM: Saccharomyces cerevisiae

<400> SEQUENCE: 31

Met Pro Phe Val Lys Asp Phe Lys Pro Gln Ala Leu Gly Asp Thr Asn
1               5                   10                  15

Leu Phe Lys Pro Ile Lys Ile Gly Asn Asn Glu Leu Leu His Arg Ala
            20                  25                  30

Val Ile Pro Pro Leu Thr Arg Met Arg Ala Gln His Pro Gly Asn Ile
        35                  40                  45

Pro Asn Arg Asp Trp Ala Val Glu Tyr Tyr Ala Gln Arg Ala Gln Arg
    50                  55                  60

Pro Gly Thr Leu Ile Ile Thr Glu Gly Thr Phe Pro Ser Pro Gln Ser
65                  70                  75                  80

Gly Gly Tyr Asp Asn Ala Pro Gly Ile Trp Ser Glu Glu Gln Ile Lys
                85                  90                  95

Glu Trp Thr Lys Ile Phe Lys Ala Ile His Glu Asn Lys Ser Phe Ala
            100                 105                 110

Trp Val Gln Leu Trp Val Leu Gly Trp Ala Ala Phe Pro Asp Thr Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asn Pro Phe Leu Thr Glu Gly Glu Gly Glu
    290                 295                 300

Tyr Asn Gly Gly Ser Asn Lys Phe Ala Tyr Ser Ile Trp Lys Gly Pro
305                 310                 315                 320

Ile Ile Arg Ala Gly Asn Phe Ala Leu His Pro Glu Val Val Arg Glu
                325                 330                 335

Glu Val Lys Asp Pro Arg Thr Leu Ile Gly Tyr Gly Arg Phe Phe Ile

```
            340                 345                 350
Ser Asn Pro Asp Leu Val Asp Arg Leu Glu Lys Gly Leu Pro Leu Asn
            355                 360                 365

Lys Tyr Asp Arg Asp Thr Phe Tyr Lys Met Ser Ala Glu Gly Tyr Ile
            370                 375             380

Asp Tyr Pro Thr Tyr Glu Glu Ala Leu Lys Leu Gly Trp Asp Lys Asn
385                 390                 395                 400

<210> SEQ ID NO 32
<211> LENGTH: 660
<212> TYPE: PRT
<213> ORGANISM: Escherichia coli BL21-DE3

<400> SEQUENCE: 32

Met Lys Thr Val Val Phe Ala Tyr His Asp Met Gly Cys Leu Gly Ile
1               5                   10                  15

Glu Ala Leu Leu Ala Ala Gly Tyr Glu Ile Ser Ala Ile Phe Thr His
            20                  25                  30

Thr Asp Asn Pro Gly Glu Lys Ala Phe Tyr Gly Ser Val Ala Arg Leu
            35                  40                  45

Ala Ala Glu Arg Gly Ile Pro Val Tyr Ala Pro Asp Asn Val Asn His
50                  55                  60

Pro Leu Trp Val Glu Arg Ile Ala Gln Leu Ser Pro Asp Val Ile Phe
65                  70                  75                  80

Ser Phe Tyr Tyr Arg His Leu Ile Tyr Asp Glu Ile Leu Gln Leu Ala
                85                  90                  95

Pro Ala Gly Ala Phe Asn Leu His Gly Ser Leu Leu Pro Lys Tyr Arg
            100                 105                 110

Gly Arg Ala Pro Leu Asn Trp Val Leu Val Asn Gly Glu Thr Glu Thr
            115                 120                 125

Gly Val Thr Leu His Arg Met Val Lys Arg Ala Asp Ala Gly Ala Ile
            130                 135                 140

Val Ala Gln Leu Arg Ile Ala Ile Ala Pro Asp Asp Ile Ala Ile Thr
145                 150                 155                 160

Leu His His Lys Leu Cys His Ala Ala Arg Gln Leu Leu Glu Gln Thr
                165                 170                 175

Leu Pro Ala Ile Lys His Gly Asn Ile Leu Glu Ile Ala Gln Arg Glu
            180                 185                 190

Asn Glu Ala Thr Cys Phe Gly Arg Arg Thr Pro Asp Asp Ser Phe Leu
            195                 200                 205

Glu Trp His Lys Pro Ala Ser Val Leu His Asn Met Val Arg Ala Val
210                 215                 220

Ala Asp Pro Trp Pro Gly Ala Phe Ser Tyr Val Gly Asn Gln Lys Phe
225                 230                 235                 240

Thr Val Trp Ser Ser Arg Val His Pro His Ala Ser Lys Ala Gln Pro
                245                 250                 255

Gly Ser Val Ile Ser Val Ala Pro Leu Leu Ile Ala Cys Gly Asp Gly
            260                 265                 270

Ala Leu Glu Ile Val Thr Gly Gln Ala Gly Asp Gly Ile Thr Met Gln
            275                 280                 285

Gly Ser Gln Leu Ala Gln Thr Leu Gly Leu Val Gln Gly Ser Arg Leu
            290                 295                 300

Asn Ser Gln Pro Ala Cys Thr Ala Arg Arg Thr Arg Val Leu Ile
305                 310                 315                 320
```

```
Leu Gly Val Asn Gly Phe Ile Gly Asn His Leu Thr Glu Arg Leu Leu
                325                 330                 335

Arg Glu Asp His Tyr Glu Val Tyr Gly Leu Asp Ile Gly Ser Asp Ala
            340                 345                 350

Ile Ser Arg Phe Leu Asn His Pro His Phe His Phe Val Glu Gly Asp
        355                 360                 365

Ile Ser Ile His Ser Glu Trp Ile Glu Tyr His Val Lys Lys Cys Asp
    370                 375                 380

Val Val Leu Pro Leu Val Ala Ile Ala Thr Pro Ile Glu Tyr Thr Arg
385                 390                 395                 400

Asn Pro Leu Arg Val Phe Glu Leu Asp Phe Glu Glu Asn Leu Arg Ile
                405                 410                 415

Ile Arg Tyr Cys Val Lys Tyr Arg Lys Arg Ile Ile Phe Pro Ser Thr
            420                 425                 430

Ser Glu Val Tyr Gly Met Cys Ser Asp Lys Tyr Phe Asp Glu Asp His
        435                 440                 445

Ser Asn Leu Ile Val Gly Pro Val Asn Lys Pro Arg Trp Ile Tyr Ser
    450                 455                 460

Val Ser Lys Gln Leu Leu Asp Arg Val Ile Trp Ala Tyr Gly Glu Lys
465                 470                 475                 480

Glu Gly Leu Gln Phe Thr Leu Phe Arg Pro Phe Asn Trp Met Gly Pro
                485                 490                 495

Arg Leu Asp Asn Leu Asn Ala Ala Arg Ile Gly Ser Ser Arg Ala Ile
            500                 505                 510

Thr Gln Leu Ile Leu Asn Leu Val Glu Gly Ser Pro Ile Lys Leu Ile
        515                 520                 525

Asp Gly Gly Lys Gln Lys Arg Cys Phe Thr Asp Ile Arg Asp Gly Ile
    530                 535                 540

Glu Ala Leu Tyr Arg Ile Ile Glu Asn Ala Gly Asn Arg Cys Asp Gly
545                 550                 555                 560

Glu Ile Ile Asn Ile Gly Asn Pro Glu Asn Glu Ala Ser Ile Glu Glu
                565                 570                 575

Leu Gly Glu Met Leu Leu Ala Ser Phe Glu Lys His Pro Leu Arg His
            580                 585                 590

His Phe Pro Pro Phe Ala Gly Phe Arg Val Val Glu Ser Ser Ser Tyr
        595                 600                 605

Tyr Gly Lys Gly Tyr Gln Asp Val Glu His Arg Lys Pro Ser Ile Arg
    610                 615                 620

Asn Ala His Arg Cys Leu Asp Trp Glu Pro Lys Ile Asp Met Gln Glu
625                 630                 635                 640

Thr Ile Asp Glu Thr Leu Asp Phe Phe Leu Arg Thr Val Asp Leu Thr
                645                 650                 655

Asp Lys Pro Ser
            660

<210> SEQ ID NO 33
<211> LENGTH: 624
<212> TYPE: PRT
<213> ORGANISM: Escherichia coli BL21-DE3

<400> SEQUENCE: 33

Met Lys Gly Gln Glu Thr Arg Gly Phe Gln Ser Glu Val Lys Gln Leu
1               5                   10                  15

Leu His Leu Met Ile His Ser Leu Tyr Ser Asn Lys Glu Ile Phe Leu
                20                  25                  30
```

```
Arg Glu Leu Ile Ser Asn Ala Ser Asp Ala Asp Lys Leu Arg Phe
            35                  40                  45

Arg Ala Leu Ser Asn Pro Asp Leu Tyr Glu Gly Asp Gly Glu Leu Arg
 50                  55                  60

Val Arg Val Ser Phe Asp Lys Asp Lys Arg Thr Leu Thr Ile Ser Asp
 65                  70                  75                  80

Asn Gly Val Gly Met Thr Arg Asp Glu Val Ile Asp His Leu Gly Thr
                     85                  90                  95

Ile Ala Lys Ser Gly Thr Lys Ser Phe Leu Glu Ser Leu Gly Ser Asp
                100                 105                 110

Gln Ala Lys Asp Ser Gln Leu Ile Gly Gln Phe Gly Val Gly Phe Tyr
                115                 120                 125

Ser Ala Phe Ile Val Ala Asp Lys Val Thr Val Arg Thr Arg Ala Ala
            130                 135                 140

Gly Glu Lys Pro Glu Asn Gly Val Phe Trp Glu Ser Ala Gly Glu Gly
145                 150                 155                 160

Glu Tyr Thr Val Ala Asp Ile Thr Lys Glu Asp Arg Gly Thr Glu Ile
                165                 170                 175

Thr Leu His Leu Arg Glu Gly Glu Asp Glu Phe Leu Asp Asp Trp Arg
            180                 185                 190

Val Arg Ser Ile Ile Ser Lys Tyr Ser Asp His Ile Ala Leu Pro Val
            195                 200                 205

Glu Ile Glu Lys Arg Glu Glu Lys Asp Gly Glu Thr Val Ile Ser Trp
            210                 215                 220

Glu Lys Ile Asn Lys Ala Gln Ala Leu Trp Thr Arg Asn Lys Ser Glu
225                 230                 235                 240

Ile Thr Asp Glu Glu Tyr Lys Glu Phe Tyr Lys His Ile Ala His Asp
                245                 250                 255

Phe Asn Asp Pro Leu Thr Trp Ser His Asn Arg Val Glu Gly Lys Gln
                260                 265                 270

Glu Tyr Thr Ser Leu Leu Tyr Ile Pro Ser Gln Ala Pro Trp Asp Met
            275                 280                 285

Trp Asn Arg Asp His Lys His Gly Leu Lys Leu Tyr Val Gln Arg Val
            290                 295                 300

Phe Ile Met Asp Asp Ala Glu Gln Phe Met Pro Asn Tyr Leu Arg Phe
305                 310                 315                 320

Val Arg Gly Leu Ile Asp Ser Ser Asp Leu Pro Leu Asn Val Ser Arg
                325                 330                 335

Glu Ile Leu Gln Asp Ser Thr Val Thr Arg Asn Leu Arg Asn Ala Leu
            340                 345                 350

Thr Lys Arg Val Leu Gln Met Leu Glu Lys Leu Ala Lys Asp Asp Ala
            355                 360                 365

Glu Lys Tyr Gln Thr Phe Trp Gln Gln Phe Gly Leu Val Leu Lys Glu
            370                 375                 380

Gly Pro Ala Glu Asp Phe Ala Asn Gln Glu Ala Ile Ala Lys Leu Leu
385                 390                 395                 400

Arg Phe Ala Ser Thr His Thr Asp Ser Ser Ala Gln Thr Val Ser Leu
                405                 410                 415

Glu Asp Tyr Val Ser Arg Met Lys Glu Gly Gln Glu Lys Ile Tyr Tyr
                420                 425                 430

Ile Thr Ala Asp Ser Tyr Ala Ala Ala Lys Ser Ser Pro His Leu Glu
            435                 440                 445
```

-continued

```
Leu Leu Arg Lys Lys Gly Ile Glu Val Leu Leu Ser Asp Arg Ile
450                 455                 460

Asp Glu Trp Met Met Asn Tyr Leu Thr Glu Phe Asp Gly Lys Pro Phe
465                 470                 475                 480

Gln Ser Val Ser Lys Val Asp Glu Ser Leu Glu Lys Leu Ala Asp Glu
                485                 490                 495

Val Asp Glu Ser Ala Lys Glu Ala Glu Lys Ala Leu Thr Pro Phe Ile
            500                 505                 510

Asp Arg Val Lys Ala Leu Leu Gly Glu Arg Val Lys Asp Val Arg Leu
            515                 520                 525

Thr His Arg Leu Thr Asp Thr Pro Ala Ile Val Ser Thr Asp Ala Asp
530                 535                 540

Glu Met Ser Thr Gln Met Ala Lys Leu Phe Ala Ala Ala Gly Gln Lys
545                 550                 555                 560

Val Pro Glu Val Lys Tyr Ile Phe Glu Leu Asn Pro Asp His Val Leu
                565                 570                 575

Val Lys Arg Ala Ala Asp Thr Glu Asp Glu Ala Lys Phe Ser Glu Trp
            580                 585                 590

Val Glu Leu Leu Leu Asp Gln Ala Leu Leu Ala Glu Arg Gly Thr Leu
            595                 600                 605

Glu Asp Pro Asn Leu Phe Ile Arg Arg Met Asn Gln Leu Leu Val Ser
610                 615                 620

<210> SEQ ID NO 34
<211> LENGTH: 638
<212> TYPE: PRT
<213> ORGANISM: Escherichia coli BL21-DE3

<400> SEQUENCE: 34

Met Gly Lys Ile Ile Gly Ile Asp Leu Gly Thr Thr Asn Ser Cys Val
1               5                   10                  15

Ala Ile Met Asp Gly Thr Thr Pro Arg Val Leu Glu Asn Ala Glu Gly
                20                  25                  30

Asp Arg Thr Thr Pro Ser Ile Ile Ala Tyr Thr Gln Asp Gly Glu Thr
            35                  40                  45

Leu Val Gly Gln Pro Ala Lys Arg Gln Ala Val Thr Asn Pro Gln Asn
        50                  55                  60

Thr Leu Phe Ala Ile Lys Arg Leu Ile Gly Arg Arg Phe Gln Asp Glu
65                  70                  75                  80

Glu Val Gln Arg Asp Val Ser Ile Met Pro Phe Lys Ile Ile Ala Ala
                85                  90                  95

Asp Asn Gly Asp Ala Trp Val Glu Val Lys Gly Gln Lys Met Ala Pro
            100                 105                 110

Pro Gln Ile Ser Ala Glu Val Leu Lys Lys Met Lys Lys Thr Ala Glu
        115                 120                 125

Asp Tyr Leu Gly Glu Pro Val Thr Glu Ala Val Ile Thr Val Pro Ala
    130                 135                 140

Tyr Phe Asn Asp Ala Gln Arg Gln Ala Thr Lys Asp Ala Gly Arg Ile
145                 150                 155                 160

Ala Gly Leu Glu Val Lys Arg Ile Ile Asn Glu Pro Thr Ala Ala Ala
                165                 170                 175

Leu Ala Tyr Gly Leu Asp Lys Gly Thr Gly Asn Arg Thr Ile Ala Val
            180                 185                 190

Tyr Asp Leu Gly Gly Gly Thr Phe Asp Ile Ser Ile Ile Glu Ile Asp
        195                 200                 205
```

```
Glu Val Asp Gly Glu Lys Thr Phe Glu Val Leu Ala Thr Asn Gly Asp
    210                 215                 220

Thr His Leu Gly Gly Glu Asp Phe Asp Ser Arg Leu Ile Asn Tyr Leu
225                 230                 235                 240

Val Glu Glu Phe Lys Lys Asp Gln Gly Ile Asp Leu Arg Asn Asp Pro
                245                 250                 255

Leu Ala Met Gln Arg Leu Lys Glu Ala Ala Glu Lys Ala Lys Ile Glu
            260                 265                 270

Leu Ser Ser Ala Gln Gln Thr Asp Val Asn Leu Pro Tyr Ile Thr Ala
        275                 280                 285

Asp Ala Thr Gly Pro Lys His Met Asn Ile Lys Val Thr Arg Ala Lys
    290                 295                 300

Leu Glu Ser Leu Val Glu Asp Leu Val Asn Arg Ser Ile Glu Pro Leu
305                 310                 315                 320

Lys Val Ala Leu Gln Asp Ala Gly Leu Ser Val Ser Asp Ile Asp Asp
                325                 330                 335

Val Ile Leu Val Gly Gly Gln Thr Arg Met Pro Met Val Gln Lys Lys
            340                 345                 350

Val Ala Glu Phe Phe Gly Lys Glu Pro Arg Lys Asp Val Asn Pro Asp
        355                 360                 365

Glu Ala Val Ala Ile Gly Ala Ala Val Gln Gly Gly Val Leu Thr Gly
    370                 375                 380

Asp Val Lys Asp Val Leu Leu Leu Asp Val Thr Pro Leu Ser Leu Gly
385                 390                 395                 400

Ile Glu Thr Met Gly Gly Val Met Thr Thr Leu Ile Ala Lys Asn Thr
                405                 410                 415

Thr Ile Pro Thr Lys His Ser Gln Val Phe Ser Thr Ala Glu Asp Asn
            420                 425                 430

Gln Ser Ala Val Thr Ile His Val Leu Gln Gly Glu Arg Lys Arg Ala
        435                 440                 445

Ala Asp Asn Lys Ser Leu Gly Gln Phe Asn Leu Asp Gly Ile Asn Pro
    450                 455                 460

Ala Pro Arg Gly Met Pro Gln Ile Glu Val Thr Phe Asp Ile Asp Ala
465                 470                 475                 480

Asp Gly Ile Leu His Val Ser Ala Lys Asp Lys Asn Ser Gly Lys Glu
                485                 490                 495

Gln Lys Ile Thr Ile Lys Ala Ser Ser Gly Leu Asn Glu Asp Glu Ile
            500                 505                 510

Gln Lys Met Val Arg Asp Ala Glu Ala Asn Ala Glu Ala Asp Arg Lys
        515                 520                 525

Phe Glu Glu Leu Val Gln Thr Arg Asn Gln Gly Asp His Leu Leu His
    530                 535                 540

Ser Thr Arg Lys Gln Val Glu Glu Ala Gly Asp Lys Leu Pro Ala Asp
545                 550                 555                 560

Asp Lys Thr Ala Ile Glu Ser Ala Leu Thr Ala Leu Glu Thr Ala Leu
                565                 570                 575

Lys Gly Glu Asp Lys Ala Ala Ile Glu Ala Lys Met Gln Glu Leu Ala
            580                 585                 590

Gln Val Ser Gln Lys Leu Met Glu Ile Ala Gln Gln His Ala Gln
        595                 600                 605

Gln Gln Thr Ala Gly Ala Asp Ala Ser Ala Asn Asn Ala Lys Asp Asp
    610                 615                 620
```

Asp Val Val Asp Ala Glu Phe Glu Glu Val Lys Asp Lys Lys
625                 630                 635

<210> SEQ ID NO 35
<211> LENGTH: 1193
<212> TYPE: PRT
<213> ORGANISM: Mycobacterium smegmatis ATCC 700084

<400> SEQUENCE: 35

Met His Gln Leu Thr Val Thr Gly Met Asn Ile Cys Glu Val Gln Arg
1               5                   10                  15

Leu Phe Pro Arg Met Thr Ser Asp Val His Asp Ala Thr Asp Gly Val
                20                  25                  30

Thr Glu Thr Ala Leu Asp Asp Glu Gln Ser Thr Arg Arg Ile Ala Glu
            35                  40                  45

Leu Tyr Ala Thr Asp Pro Glu Phe Ala Ala Ala Pro Leu Pro Ala
    50                  55                  60

Val Val Asp Ala Ala His Lys Pro Gly Leu Arg Leu Ala Glu Ile Leu
65                  70                  75                  80

Gln Thr Leu Phe Thr Gly Tyr Gly Asp Arg Pro Ala Leu Gly Tyr Arg
                85                  90                  95

Ala Arg Glu Leu Ala Thr Asp Glu Gly Gly Arg Thr Val Thr Arg Leu
            100                 105                 110

Leu Pro Arg Phe Asp Thr Leu Thr Tyr Ala Gln Val Trp Ser Arg Val
        115                 120                 125

Gln Ala Val Ala Ala Ala Leu Arg His Asn Phe Ala Gln Pro Ile Tyr
    130                 135                 140

Pro Gly Asp Ala Val Ala Thr Ile Gly Phe Ala Ser Pro Asp Tyr Leu
145                 150                 155                 160

Thr Leu Asp Leu Val Cys Ala Tyr Leu Gly Leu Val Ser Val Pro Leu
                165                 170                 175

Gln His Asn Ala Pro Val Ser Arg Leu Ala Pro Ile Leu Ala Glu Val
            180                 185                 190

Glu Pro Arg Ile Leu Thr Val Ser Ala Glu Tyr Leu Asp Leu Ala Val
        195                 200                 205

Glu Ser Val Arg Asp Val Asn Ser Val Ser Gln Leu Val Val Phe Asp
    210                 215                 220

His His Pro Glu Val Asp Asp His Arg Asp Ala Leu Ala Arg Ala Arg
225                 230                 235                 240

Glu Gln Leu Ala Gly Lys Gly Ile Ala Val Thr Thr Leu Asp Ala Ile
                245                 250                 255

Ala Asp Glu Gly Ala Gly Leu Pro Ala Glu Pro Ile Tyr Thr Ala Asp
            260                 265                 270

His Asp Gln Arg Leu Ala Met Ile Leu Tyr Thr Ser Gly Ser Thr Gly
        275                 280                 285

Ala Pro Lys Gly Ala Met Tyr Thr Glu Ala Met Val Ala Arg Leu Trp
    290                 295                 300

Thr Met Ser Phe Ile Thr Gly Asp Pro Thr Pro Val Ile Asn Val Asn
305                 310                 315                 320

Phe Met Pro Leu Asn His Leu Gly Gly Arg Ile Pro Ile Ser Thr Ala
                325                 330                 335

Val Gln Asn Gly Gly Thr Ser Tyr Phe Val Pro Glu Ser Asp Met Ser
            340                 345                 350

Thr Leu Phe Glu Asp Leu Ala Leu Val Arg Pro Thr Glu Leu Gly Leu
        355                 360                 365

-continued

```
Val Pro Arg Val Ala Asp Met Leu Tyr Gln His His Leu Ala Thr Val
    370                 375                 380

Asp Arg Leu Val Thr Gln Gly Ala Asp Glu Leu Thr Ala Glu Lys Gln
385                 390                 395                 400

Ala Gly Ala Glu Leu Arg Glu Gln Val Leu Gly Gly Arg Val Ile Thr
                405                 410                 415

Gly Phe Val Ser Thr Ala Pro Leu Ala Ala Glu Met Arg Ala Phe Leu
            420                 425                 430

Asp Ile Thr Leu Gly Ala His Ile Val Asp Gly Tyr Gly Leu Thr Glu
            435                 440                 445

Thr Gly Ala Val Thr Arg Asp Gly Val Ile Val Arg Pro Pro Val Ile
    450                 455                 460

Asp Tyr Lys Leu Ile Asp Val Pro Glu Leu Gly Tyr Phe Ser Thr Asp
465                 470                 475                 480

Lys Pro Tyr Pro Arg Gly Glu Leu Leu Val Arg Ser Gln Thr Leu Thr
                485                 490                 495

Pro Gly Tyr Tyr Lys Arg Pro Glu Val Thr Ala Ser Val Phe Asp Arg
            500                 505                 510

Asp Gly Tyr Tyr His Thr Gly Asp Val Met Ala Glu Thr Ala Pro Asp
            515                 520                 525

His Leu Val Tyr Val Asp Arg Arg Asn Asn Val Leu Lys Leu Ala Gln
    530                 535                 540

Gly Glu Phe Val Ala Val Ala Asn Leu Glu Ala Val Phe Ser Gly Ala
545                 550                 555                 560

Ala Leu Val Arg Gln Ile Phe Val Tyr Gly Asn Ser Glu Arg Ser Phe
                565                 570                 575

Leu Leu Ala Val Val Pro Thr Pro Glu Ala Leu Glu Gln Tyr Asp
            580                 585                 590

Pro Ala Ala Leu Lys Ala Ala Leu Ala Asp Ser Leu Gln Arg Thr Ala
            595                 600                 605

Arg Asp Ala Glu Leu Gln Ser Tyr Glu Val Pro Ala Asp Phe Ile Val
    610                 615                 620

Glu Thr Glu Pro Phe Ser Ala Ala Asn Gly Leu Leu Ser Gly Val Gly
625                 630                 635                 640

Lys Leu Leu Arg Pro Asn Leu Lys Asp Arg Tyr Gly Gln Arg Leu Glu
                645                 650                 655

Gln Met Tyr Ala Asp Ile Ala Ala Thr Gln Ala Asn Gln Leu Arg Glu
            660                 665                 670

Leu Arg Arg Ala Ala Ala Thr Gln Pro Val Ile Asp Thr Leu Thr Gln
    675                 680                 685

Ala Ala Ala Thr Ile Leu Gly Thr Gly Ser Glu Val Ala Ser Asp Ala
    690                 695                 700

His Phe Thr Asp Leu Gly Gly Asp Ser Leu Ser Ala Leu Thr Leu Ser
705                 710                 715                 720

Asn Leu Leu Ser Asp Phe Phe Gly Phe Glu Val Pro Val Gly Thr Ile
                725                 730                 735

Val Asn Pro Ala Thr Asn Leu Ala Gln Leu Ala Gln His Ile Glu Ala
            740                 745                 750

Gln Arg Thr Ala Gly Asp Arg Arg Pro Ser Phe Thr Thr Val His Gly
            755                 760                 765

Ala Asp Ala Thr Glu Ile Arg Ala Ser Glu Leu Thr Leu Asp Lys Phe
    770                 775                 780
```

```
Ile Asp Ala Glu Thr Leu Arg Ala Ala Pro Gly Leu Pro Lys Val Thr
785                 790                 795                 800

Thr Glu Pro Arg Thr Val Leu Leu Ser Gly Ala Asn Gly Trp Leu Gly
                805                 810                 815

Arg Phe Leu Thr Leu Gln Trp Leu Glu Arg Leu Ala Pro Val Gly Gly
            820                 825                 830

Thr Leu Ile Thr Ile Val Arg Gly Arg Asp Ala Ala Arg Ala
        835                 840                 845

Arg Leu Thr Gln Ala Tyr Asp Thr Asp Pro Glu Leu Ser Arg Arg Phe
    850                 855                 860

Ala Glu Leu Ala Asp Arg His Leu Arg Val Val Ala Gly Asp Ile Gly
865                 870                 875                 880

Asp Pro Asn Leu Gly Leu Thr Pro Glu Ile Trp His Arg Leu Ala Ala
                885                 890                 895

Glu Val Asp Leu Val Val His Pro Ala Ala Leu Val Asn His Val Leu
                900                 905                 910

Pro Tyr Arg Gln Leu Phe Gly Pro Asn Val Val Gly Thr Ala Glu Val
            915                 920                 925

Ile Lys Leu Ala Leu Thr Glu Arg Ile Lys Pro Val Thr Tyr Leu Ser
        930                 935                 940

Thr Val Ser Val Ala Met Gly Ile Pro Asp Phe Glu Glu Asp Gly Asp
945                 950                 955                 960

Ile Arg Thr Val Ser Pro Val Arg Pro Leu Asp Gly Tyr Ala Asn
                965                 970                 975

Gly Tyr Gly Asn Ser Lys Trp Ala Gly Glu Val Leu Leu Arg Glu Ala
            980                 985                 990

His Asp Leu Cys Gly Leu Pro Val Ala Thr Phe Arg Ser Asp Met Ile
        995                 1000                1005

Leu Ala His Pro Arg Tyr Arg Gly Gln Val Asn Val Pro Asp Met
    1010                1015                1020

Phe Thr Arg Leu Leu Leu Ser Leu Leu Ile Thr Gly Val Ala Pro
    1025                1030                1035

Arg Ser Phe Tyr Ile Gly Asp Gly Glu Arg Pro Arg Ala His Tyr
    1040                1045                1050

Pro Gly Leu Thr Val Asp Phe Val Ala Glu Ala Val Thr Thr Leu
    1055                1060                1065

Gly Ala Gln Gln Arg Glu Gly Tyr Val Ser Tyr Asp Val Met Asn
    1070                1075                1080

Pro His Asp Asp Gly Ile Ser Leu Asp Val Phe Val Asp Trp Leu
    1085                1090                1095

Ile Arg Ala Gly His Pro Ile Asp Arg Val Asp Asp Tyr Asp Asp
    1100                1105                1110

Trp Val Arg Arg Phe Glu Thr Ala Leu Thr Ala Leu Pro Glu Lys
    1115                1120                1125

Arg Arg Ala Gln Thr Val Leu Pro Leu Leu His Ala Phe Arg Ala
    1130                1135                1140

Pro Gln Ala Pro Leu Arg Gly Ala Pro Glu Pro Thr Glu Val Phe
    1145                1150                1155

His Ala Ala Val Arg Thr Ala Lys Val Gly Pro Gly Asp Ile Pro
    1160                1165                1170

His Leu Asp Glu Ala Leu Ile Asp Lys Tyr Ile Arg Asp Leu Arg
    1175                1180                1185

Glu Phe Gly Leu Ile
```

<210> SEQ ID NO 36
<211> LENGTH: 1178
<212> TYPE: PRT
<213> ORGANISM: Mycobacterium abscessus DSM44196

<400> SEQUENCE: 36

```
Met Thr Glu Thr Ile Ser Thr Ala Ala Val Pro Thr Thr Asp Leu Glu
1               5                   10                  15

Glu Gln Val Lys Arg Arg Ile Glu Gln Val Val Ser Asn Asp Pro Gln
            20                  25                  30

Leu Ala Ala Leu Leu Pro Glu Asp Ser Val Thr Glu Ala Val Asn Glu
        35                  40                  45

Pro Asp Leu Pro Leu Val Glu Val Ile Arg Arg Leu Leu Glu Gly Tyr
    50                  55                  60

Gly Asp Arg Pro Ala Leu Gly Gln Arg Ala Phe Glu Phe Val Thr Gly
65                  70                  75                  80

Asp Asp Gly Ala Thr Val Ile Ala Leu Lys Pro Glu Tyr Thr Thr Val
                85                  90                  95

Ser Tyr Arg Glu Leu Trp Glu Arg Ala Glu Ala Ile Ala Ala Ala Trp
            100                 105                 110

His Glu Gln Gly Ile Arg Asp Gly Asp Phe Val Ala Gln Leu Gly Phe
        115                 120                 125

Thr Ser Thr Asp Phe Ala Ser Leu Asp Val Ala Gly Leu Arg Leu Gly
    130                 135                 140

Thr Val Ser Val Pro Leu Gln Thr Gly Ala Ser Leu Gln Gln Arg Asn
145                 150                 155                 160

Ala Ile Leu Glu Glu Thr Arg Pro Ala Val Phe Ala Ala Ser Ile Glu
                165                 170                 175

Tyr Leu Asp Ala Ala Val Asp Ser Val Leu Ala Thr Pro Ser Val Arg
            180                 185                 190

Leu Leu Ser Val Phe Asp Tyr His Ala Glu Val Asp Ser Gln Arg Glu
        195                 200                 205

Ala Leu Glu Ala Val Arg Ala Arg Leu Glu Ser Ala Gly Arg Thr Ile
    210                 215                 220

Val Val Glu Ala Leu Ala Glu Ala Leu Ala Arg Gly Arg Asp Leu Pro
225                 230                 235                 240

Ala Ala Pro Leu Pro Ser Ala Asp Pro Asp Ala Leu Arg Leu Leu Ile
                245                 250                 255

Tyr Thr Ser Gly Ser Thr Gly Thr Pro Lys Gly Ala Met Tyr Pro Gln
            260                 265                 270

Trp Leu Val Ala Asn Leu Trp Gln Lys Lys Trp Leu Thr Asp Asp Val
        275                 280                 285

Ile Pro Ser Ile Gly Val Asn Phe Met Pro Met Ser His Leu Ala Gly
    290                 295                 300

Arg Leu Thr Leu Met Gly Thr Leu Ser Gly Gly Thr Ala Tyr Tyr
305                 310                 315                 320

Ile Ala Ser Ser Asp Leu Ser Thr Phe Phe Glu Asp Ile Ala Leu Ile
                325                 330                 335

Arg Pro Ser Glu Val Leu Phe Val Pro Arg Val Val Glu Met Val Phe
            340                 345                 350

Gln Arg Phe Gln Ala Glu Leu Asp Arg Ser Leu Ala Pro Gly Glu Ser
        355                 360                 365
```

```
Asn Ser Glu Ile Ala Glu Arg Ile Lys Val Arg Ile Arg Glu Gln Asp
    370                 375                 380

Phe Gly Gly Arg Val Leu Ser Ala Gly Ser Gly Ser Ala Pro Leu Ser
385                 390                 395                 400

Pro Glu Met Thr Glu Phe Met Glu Ser Leu Leu Gln Val Pro Leu Arg
                405                 410                 415

Asp Gly Tyr Gly Ser Thr Glu Ala Gly Gly Val Trp Arg Asp Gly Val
                420                 425                 430

Leu Gln Arg Pro Pro Val Thr Asp Tyr Lys Leu Val Asp Val Pro Glu
            435                 440                 445

Leu Gly Tyr Phe Thr Thr Asp Ser Pro His Pro Arg Gly Glu Leu Arg
    450                 455                 460

Leu Lys Ser Glu Thr Met Phe Pro Gly Tyr Tyr Lys Arg Pro Glu Thr
465                 470                 475                 480

Thr Ala Asp Val Phe Asp Glu Gly Tyr Tyr Lys Thr Gly Asp Val
                485                 490                 495

Val Ala Glu Leu Gly Pro Asp His Leu Lys Tyr Leu Asp Arg Val Lys
            500                 505                 510

Asn Val Leu Lys Leu Ala Gln Gly Glu Phe Val Ala Val Ser Lys Leu
            515                 520                 525

Glu Ala Ala Tyr Thr Gly Ser Pro Leu Val Arg Gln Ile Phe Val Tyr
            530                 535                 540

Gly Asn Ser Glu Arg Ser Phe Leu Leu Ala Val Val Pro Thr Pro
545                 550                 555                 560

Glu Val Leu Glu Arg Tyr Ala Asp Ser Pro Asp Ala Leu Lys Pro Leu
                565                 570                 575

Ile Gln Asp Ser Leu Gln Gln Val Ala Lys Asp Ala Glu Leu Gln Ser
            580                 585                 590

Tyr Glu Ile Pro Arg Asp Phe Ile Val Glu Thr Val Pro Phe Thr Val
            595                 600                 605

Glu Ser Gly Leu Leu Ser Asp Ala Arg Lys Leu Arg Pro Lys Leu
    610                 615                 620

Lys Asp His Tyr Gly Glu Arg Leu Glu Ala Leu Tyr Ala Glu Leu Ala
625                 630                 635                 640

Glu Ser Gln Asn Glu Arg Leu Arg Gln Leu Ala Arg Glu Ala Ala Thr
                645                 650                 655

Arg Pro Val Leu Glu Thr Val Thr Asp Ala Ala Ala Leu Leu Gly
            660                 665                 670

Ala Ser Ser Ser Asp Leu Ala Pro Asp Val Arg Phe Ile Asp Leu Gly
            675                 680                 685

Gly Asp Ser Leu Ser Ala Leu Ser Tyr Ser Glu Leu Leu Arg Asp Ile
    690                 695                 700

Phe Glu Val Asp Val Pro Val Gly Val Ile Asn Ser Val Ala Asn Asp
705                 710                 715                 720

Leu Ala Ala Ile Ala Arg His Ile Glu Ala Gln Arg Thr Gly Ala Ala
                725                 730                 735

Thr Gln Pro Thr Phe Ala Ser Val His Gly Lys Asp Ala Thr Val Ile
                740                 745                 750

Thr Ala Gly Glu Leu Thr Leu Asp Lys Phe Leu Asp Glu Ser Leu Leu
            755                 760                 765

Lys Ala Ala Lys Asp Val Gln Pro Ala Thr Ala Asp Val Lys Thr Val
770                 775                 780

Leu Val Thr Gly Gly Asn Gly Trp Leu Gly Arg Trp Leu Val Leu Asp
```

```
            785                 790                 795                 800
Trp Leu Glu Arg Leu Ala Pro Asn Gly Gly Lys Val Tyr Ala Leu Ile
                805                 810                 815
Arg Gly Ala Asp Ala Glu Ala Ala Arg Ala Arg Leu Asp Ala Val Tyr
                820                 825                 830
Glu Ser Gly Asp Pro Lys Leu Ser Ala His Tyr Arg Gln Leu Ala Gln
                835                 840                 845
Gln Ser Leu Glu Val Ile Ala Gly Asp Phe Gly Asp Gln Asp Leu Gly
                850                 855                 860
Leu Ser Gln Glu Val Trp Gln Lys Leu Ala Lys Asp Val Asp Leu Ile
865                 870                 875                 880
Val His Ser Gly Ala Leu Val Asn His Val Leu Pro Tyr Ser Gln Leu
                885                 890                 895
Phe Gly Pro Asn Val Ala Gly Thr Ala Glu Ile Ile Lys Leu Ala Ile
                900                 905                 910
Ser Glu Arg Leu Lys Pro Val Thr Tyr Leu Ser Thr Val Gly Ile Ala
                915                 920                 925
Asp Gln Ile Pro Val Thr Glu Phe Glu Glu Asp Ser Asp Val Arg Val
930                 935                 940
Met Ser Ala Glu Arg Gln Ile Asn Asp Gly Tyr Ala Asn Gly Tyr Gly
945                 950                 955                 960
Asn Ser Lys Trp Ala Gly Glu Val Leu Leu Arg Glu Ala His Asp Leu
                965                 970                 975
Ala Gly Leu Pro Val Arg Val Phe Arg Ser Asp Met Ile Leu Ala His
                980                 985                 990
Ser Asp Tyr His Gly Gln Leu Asn Val Thr Asp Val Phe Thr Arg Ser
                995                 1000                1005
Ile Gln Ser Leu Leu Leu Thr Gly Val Ala Pro Ala Ser Phe Tyr
                1010                1015                1020
Glu Leu Asp Ala Asp Gly Asn Arg Gln Arg Ala His Tyr Asp Gly
                1025                1030                1035
Val Pro Gly Asp Phe Thr Ala Ser Ile Thr Ala Ile Gly Gly
                1040                1045                1050
Val Asn Val Val Asp Gly Tyr Arg Ser Phe Asp Val Phe Asn Pro
                1055                1060                1065
His His Asp Gly Val Ser Met Asp Thr Phe Val Asp Trp Leu Ile
                1070                1075                1080
Asp Ala Gly Tyr Lys Ile Ala Arg Ile Asp Asp Tyr Asp Gln Trp
                1085                1090                1095
Leu Ala Arg Phe Glu Leu Ala Leu Lys Gly Leu Pro Glu Gln Gln
                1100                1105                1110
Arg Gln Gln Ser Val Leu Pro Leu Leu Lys Met Tyr Glu Lys Pro
                1115                1120                1125
Gln Pro Ala Ile Asp Gly Ser Ala Leu Pro Thr Ala Glu Phe Ser
                1130                1135                1140
Arg Ala Val His Glu Ala Lys Val Gly Asp Ser Gly Glu Ile Pro
                1145                1150                1155
His Val Thr Lys Glu Leu Ile Leu Lys Tyr Ala Ser Asp Ile Gln
                1160                1165                1170
Leu Leu Gly Leu Val
                1175

<210> SEQ ID NO 37
```

<211> LENGTH: 1173
<212> TYPE: PRT
<213> ORGANISM: Mycobacterium smegmatis ATCC 700084

<400> SEQUENCE: 37

```
Met Thr Ser Asp Val His Asp Ala Thr Asp Gly Val Thr Glu Thr Ala
1               5                   10                  15

Leu Asp Asp Glu Gln Ser Thr Arg Arg Ile Ala Glu Leu Tyr Ala Thr
                20                  25                  30

Asp Pro Glu Phe Ala Ala Ala Pro Leu Pro Ala Val Val Asp Ala
            35                  40                  45

Ala His Lys Pro Gly Leu Arg Leu Ala Glu Ile Leu Gln Thr Leu Phe
    50                  55                  60

Thr Gly Tyr Gly Asp Arg Pro Ala Leu Gly Tyr Arg Ala Arg Glu Leu
65                  70                  75                  80

Ala Thr Asp Glu Gly Arg Thr Val Thr Arg Leu Leu Pro Arg Phe
                85                  90                  95

Asp Thr Leu Thr Tyr Ala Gln Val Trp Ser Arg Val Gln Ala Val Ala
            100                 105                 110

Ala Ala Leu Arg His Asn Phe Ala Gln Pro Ile Tyr Pro Gly Asp Ala
        115                 120                 125

Val Ala Thr Ile Gly Phe Ala Ser Pro Asp Tyr Leu Thr Leu Asp Leu
    130                 135                 140

Val Cys Ala Tyr Leu Gly Leu Val Ser Val Pro Leu Gln His Asn Ala
145                 150                 155                 160

Pro Val Ser Arg Leu Ala Pro Ile Leu Ala Glu Val Glu Pro Arg Ile
                165                 170                 175

Leu Thr Val Ser Ala Glu Tyr Leu Asp Leu Ala Val Glu Ser Val Arg
            180                 185                 190

Asp Val Asn Ser Val Ser Gln Leu Val Val Phe Asp His His Pro Glu
        195                 200                 205

Val Asp Asp His Arg Asp Ala Leu Ala Arg Ala Arg Glu Gln Leu Ala
    210                 215                 220

Gly Lys Gly Ile Ala Val Thr Thr Leu Asp Ala Ile Ala Asp Glu Gly
225                 230                 235                 240

Ala Gly Leu Pro Ala Glu Pro Ile Tyr Thr Ala Asp His Asp Gln Arg
                245                 250                 255

Leu Ala Met Ile Leu Tyr Thr Ser Gly Ser Thr Gly Ala Pro Lys Gly
            260                 265                 270

Ala Met Tyr Thr Glu Ala Met Val Ala Arg Leu Trp Thr Met Ser Phe
        275                 280                 285

Ile Thr Gly Asp Pro Thr Pro Val Ile Asn Val Asn Phe Met Pro Leu
    290                 295                 300

Asn His Leu Gly Gly Arg Ile Pro Ile Ser Thr Ala Val Gln Asn Gly
305                 310                 315                 320

Gly Thr Ser Tyr Phe Val Pro Glu Ser Asp Met Ser Thr Leu Phe Glu
                325                 330                 335

Asp Leu Ala Leu Val Arg Pro Thr Glu Leu Gly Leu Val Pro Arg Val
            340                 345                 350

Ala Asp Met Leu Tyr Gln His His Leu Ala Thr Val Asp Arg Leu Val
        355                 360                 365

Thr Gln Gly Ala Asp Glu Leu Thr Ala Glu Lys Gln Ala Gly Ala Glu
    370                 375                 380

Leu Arg Glu Gln Val Leu Gly Gly Arg Val Ile Thr Gly Phe Val Ser
```

-continued

```
            385                 390                 395                 400
        Thr Ala Pro Leu Ala Ala Glu Met Arg Ala Phe Leu Asp Ile Thr Leu
                        405                 410                 415

Gly Ala His Ile Val Asp Gly Tyr Gly Leu Thr Glu Thr Gly Ala Val
                        420                 425                 430

Thr Arg Asp Gly Val Ile Val Arg Pro Val Ile Asp Tyr Lys Leu
                        435                 440                 445

Ile Asp Val Pro Glu Leu Gly Tyr Phe Ser Thr Asp Lys Pro Tyr Pro
                        450                 455                 460

Arg Gly Glu Leu Leu Val Arg Ser Gln Thr Leu Thr Pro Gly Tyr Tyr
        465                 470                 475                 480

Lys Arg Pro Glu Val Thr Ala Ser Val Phe Asp Arg Asp Gly Tyr Tyr
                        485                 490                 495

His Thr Gly Asp Val Met Ala Glu Thr Ala Pro Asp His Leu Val Tyr
                        500                 505                 510

Val Asp Arg Arg Asn Asn Val Leu Lys Leu Ala Gln Gly Glu Phe Val
                        515                 520                 525

Ala Val Ala Asn Leu Glu Ala Val Phe Ser Gly Ala Ala Leu Val Arg
                        530                 535                 540

Gln Ile Phe Val Tyr Gly Asn Ser Glu Arg Ser Phe Leu Leu Ala Val
        545                 550                 555                 560

Val Val Pro Thr Pro Glu Ala Leu Glu Gln Tyr Asp Pro Ala Ala Leu
                        565                 570                 575

Lys Ala Ala Leu Ala Asp Ser Leu Gln Arg Thr Ala Arg Asp Ala Glu
                        580                 585                 590

Leu Gln Ser Tyr Glu Val Pro Ala Asp Phe Ile Val Glu Thr Glu Pro
                        595                 600                 605

Phe Ser Ala Ala Asn Gly Leu Leu Ser Gly Val Gly Lys Leu Leu Arg
                        610                 615                 620

Pro Asn Leu Lys Asp Arg Tyr Gly Gln Arg Leu Glu Gln Met Tyr Ala
        625                 630                 635                 640

Asp Ile Ala Ala Thr Gln Ala Asn Gln Leu Arg Glu Leu Arg Arg Ala
                        645                 650                 655

Ala Ala Thr Gln Pro Val Ile Asp Thr Leu Thr Gln Ala Ala Ala Thr
                        660                 665                 670

Ile Leu Gly Thr Gly Ser Glu Val Ala Ser Asp Ala His Phe Thr Asp
                        675                 680                 685

Leu Gly Gly Asp Ser Leu Ser Ala Leu Thr Leu Ser Asn Leu Leu Ser
                        690                 695                 700

Asp Phe Phe Gly Phe Glu Val Pro Val Gly Thr Ile Val Asn Pro Ala
        705                 710                 715                 720

Thr Asn Leu Ala Gln Leu Ala Gln His Ile Glu Ala Gln Arg Thr Ala
                        725                 730                 735

Gly Asp Arg Arg Pro Ser Phe Thr Thr Val His Gly Ala Asp Ala Thr
                        740                 745                 750

Glu Ile Arg Ala Ser Glu Leu Thr Leu Asp Lys Phe Ile Asp Ala Glu
                        755                 760                 765

Thr Leu Arg Ala Ala Pro Gly Leu Pro Lys Val Thr Thr Glu Pro Arg
                        770                 775                 780

Thr Val Leu Leu Ser Gly Ala Asn Gly Trp Leu Gly Arg Phe Leu Thr
        785                 790                 795                 800

Leu Gln Trp Leu Glu Arg Leu Ala Pro Val Gly Gly Thr Leu Ile Thr
                        805                 810                 815
```

Ile Val Arg Gly Arg Asp Asp Ala Ala Arg Ala Arg Leu Thr Gln
            820                 825                 830

Ala Tyr Asp Thr Asp Pro Glu Leu Ser Arg Arg Phe Ala Glu Leu Ala
            835                 840                 845

Asp Arg His Leu Arg Val Ala Gly Asp Ile Gly Asp Pro Asn Leu
850                 855                 860

Gly Leu Thr Pro Glu Ile Trp His Arg Leu Ala Ala Glu Val Asp Leu
865                 870                 875                 880

Val Val His Pro Ala Ala Leu Val Asn His Val Leu Pro Tyr Arg Gln
                885                 890                 895

Leu Phe Gly Pro Asn Val Val Gly Thr Ala Glu Val Ile Lys Leu Ala
            900                 905                 910

Leu Thr Glu Arg Ile Lys Pro Val Thr Tyr Leu Ser Thr Val Ser Val
            915                 920                 925

Ala Met Gly Ile Pro Asp Phe Glu Glu Asp Gly Asp Ile Arg Thr Val
930                 935                 940

Ser Pro Val Arg Pro Leu Asp Gly Gly Tyr Ala Asn Gly Tyr Gly Asn
945                 950                 955                 960

Ser Lys Trp Ala Gly Glu Val Leu Leu Arg Glu Ala His Asp Leu Cys
            965                 970                 975

Gly Leu Pro Val Ala Thr Phe Arg Ser Asp Met Ile Leu Ala His Pro
            980                 985                 990

Arg Tyr Arg Gly Gln Val Asn Val Pro Asp Met Phe Thr Arg Leu Leu
            995                 1000                1005

Leu Ser Leu Leu Ile Thr Gly Val Ala Pro Arg Ser Phe Tyr Ile
    1010                1015                1020

Gly Asp Gly Glu Arg Pro Arg Ala His Tyr Pro Gly Leu Thr Val
    1025                1030                1035

Asp Phe Val Ala Glu Ala Val Thr Thr Leu Gly Ala Gln Gln Arg
    1040                1045                1050

Glu Gly Tyr Val Ser Tyr Asp Val Met Asn Pro His Asp Asp Gly
    1055                1060                1065

Ile Ser Leu Asp Val Phe Val Asp Trp Leu Ile Arg Ala Gly His
    1070                1075                1080

Pro Ile Asp Arg Val Asp Asp Tyr Asp Asp Trp Val Arg Arg Phe
    1085                1090                1095

Glu Thr Ala Leu Thr Ala Leu Pro Glu Lys Arg Arg Ala Gln Thr
    1100                1105                1110

Val Leu Pro Leu Leu His Ala Phe Arg Ala Pro Gln Ala Pro Leu
    1115                1120                1125

Arg Gly Ala Pro Glu Pro Thr Glu Val Phe His Ala Ala Val Arg
    1130                1135                1140

Thr Ala Lys Val Gly Pro Gly Asp Ile Pro His Leu Asp Glu Ala
    1145                1150                1155

Leu Ile Asp Lys Tyr Ile Arg Asp Leu Arg Glu Phe Gly Leu Ile
    1160                1165                1170

<210> SEQ ID NO 38
<211> LENGTH: 1173
<212> TYPE: PRT
<213> ORGANISM: Mycobacterium paratuberculosis ATCC BAA-968

<400> SEQUENCE: 38

Met Ser Thr Ala Thr His Asp Glu Arg Leu Asp Arg Arg Val His Glu

```
1               5                   10                  15
Leu Ile Ala Thr Asp Pro Gln Phe Ala Ala Gln Pro Asp Pro Ala
                20                  25                  30
Ile Thr Ala Ala Leu Glu Gln Pro Gly Leu Arg Leu Pro Gln Ile Ile
                35                  40                  45
Arg Thr Val Leu Asp Gly Tyr Ala Asp Arg Pro Ala Leu Gly Gln Arg
        50                  55                  60
Val Val Glu Phe Val Thr Asp Ala Lys Thr Gly Arg Thr Ser Ala Gln
65                  70                  75                  80
Leu Leu Pro Arg Phe Glu Thr Ile Thr Tyr Ser Glu Val Ala Gln Arg
                85                  90                  95
Val Ser Ala Leu Gly Arg Ala Leu Ser Asp Asp Ala Val His Pro Gly
                100                 105                 110
Asp Arg Val Cys Val Leu Gly Phe Asn Ser Val Asp Tyr Ala Thr Ile
                115                 120                 125
Asp Met Ala Leu Gly Ala Ile Gly Ala Val Ser Val Pro Leu Gln Thr
            130                 135                 140
Ser Ala Ala Ile Ser Ser Leu Gln Pro Ile Val Ala Glu Thr Glu Pro
145                 150                 155                 160
Thr Leu Ile Ala Ser Ser Val Asn Gln Leu Ser Asp Ala Val Gln Leu
                165                 170                 175
Ile Thr Gly Ala Glu Gln Ala Pro Thr Arg Leu Val Val Phe Asp Tyr
                180                 185                 190
His Pro Gln Val Asp Asp Gln Arg Glu Ala Val Gln Asp Ala Ala Ala
                195                 200                 205
Arg Leu Ser Ser Thr Gly Val Ala Val Gln Thr Leu Ala Glu Leu Leu
            210                 215                 220
Glu Arg Gly Lys Asp Leu Pro Ala Val Ala Glu Pro Ala Asp Glu
225                 230                 235                 240
Asp Ser Leu Ala Leu Leu Ile Tyr Thr Ser Gly Ser Thr Gly Ala Pro
                245                 250                 255
Lys Gly Ala Met Tyr Pro Gln Ser Asn Val Gly Lys Met Trp Arg Arg
                260                 265                 270
Gly Ser Lys Asn Trp Phe Gly Glu Ser Ala Ala Ser Ile Thr Leu Asn
            275                 280                 285
Phe Met Pro Met Ser His Val Met Gly Arg Ser Ile Leu Tyr Gly Thr
            290                 295                 300
Leu Gly Asn Gly Gly Thr Ala Tyr Phe Ala Ala Arg Ser Asp Leu Ser
305                 310                 315                 320
Thr Leu Leu Glu Asp Leu Glu Leu Val Arg Pro Thr Glu Leu Asn Phe
                325                 330                 335
Val Pro Arg Ile Trp Glu Thr Leu Tyr Gly Glu Phe Gln Arg Gln Val
                340                 345                 350
Glu Arg Arg Leu Ser Glu Ala Gly Asp Ala Gly Glu Arg Arg Ala Val
            355                 360                 365
Glu Ala Glu Val Leu Ala Glu Gln Arg Gln Tyr Leu Leu Gly Gly Arg
            370                 375                 380
Phe Thr Phe Ala Met Thr Gly Ser Ala Pro Ile Ser Pro Glu Leu Arg
385                 390                 395                 400
Asn Trp Val Glu Ser Leu Leu Glu Met His Leu Met Asp Gly Tyr Gly
                405                 410                 415
Ser Thr Glu Ala Gly Met Val Leu Phe Asp Gly Glu Ile Gln Arg Pro
            420                 425                 430
```

-continued

Pro Val Ile Asp Tyr Lys Leu Val Asp Val Pro Asp Leu Gly Tyr Phe
        435                 440                 445

Ser Thr Asp Arg Pro His Pro Arg Gly Glu Leu Leu Leu Arg Thr Glu
    450                 455                 460

Asn Met Phe Pro Gly Tyr Tyr Lys Arg Ala Glu Thr Thr Ala Gly Val
465                 470                 475                 480

Phe Asp Glu Asp Gly Tyr Tyr Arg Thr Gly Asp Val Phe Ala Glu Ile
                485                 490                 495

Ala Pro Asp Arg Leu Tyr Val Asp Arg Arg Asn Asn Val Leu Lys
        500                 505                 510

Leu Ala Gln Gly Glu Phe Val Thr Leu Ala Lys Leu Glu Ala Val Phe
            515                 520                 525

Gly Asn Ser Pro Leu Ile Arg Gln Ile Tyr Val Tyr Gly Asn Ser Ala
        530                 535                 540

Gln Pro Tyr Leu Leu Ala Val Val Pro Thr Glu Glu Ala Leu Ala
545                 550                 555                 560

Ser Gly Asp Pro Glu Thr Leu Lys Pro Lys Ile Ala Asp Ser Leu Gln
                565                 570                 575

Gln Val Ala Lys Glu Ala Gly Leu Gln Ser Tyr Glu Val Pro Arg Asp
            580                 585                 590

Phe Ile Ile Glu Thr Thr Pro Phe Ser Leu Glu Asn Gly Leu Leu Thr
        595                 600                 605

Gly Ile Arg Lys Leu Ala Trp Pro Lys Leu Lys Gln His Tyr Gly Glu
    610                 615                 620

Arg Leu Glu Gln Met Tyr Ala Asp Leu Ala Ala Gly Gln Ala Asn Glu
625                 630                 635                 640

Leu Ala Glu Leu Arg Arg Asn Gly Ala Gln Ala Pro Val Leu Gln Thr
                645                 650                 655

Val Ser Arg Ala Ala Gly Ala Met Leu Gly Ser Ala Ala Ser Asp Leu
            660                 665                 670

Ser Pro Asp Ala His Phe Thr Asp Leu Gly Gly Asp Ser Leu Ser Ala
        675                 680                 685

Leu Thr Phe Gly Asn Leu Leu Arg Glu Ile Phe Asp Val Asp Val Pro
    690                 695                 700

Val Gly Val Ile Val Ser Pro Ala Asn Asp Leu Ala Ala Ile Ala Ser
705                 710                 715                 720

Tyr Ile Glu Ala Glu Arg Gln Gly Ser Lys Arg Pro Thr Phe Ala Ser
                725                 730                 735

Val His Gly Arg Asp Ala Thr Val Val Arg Ala Ala Asp Leu Thr Leu
            740                 745                 750

Asp Lys Phe Leu Asp Ala Glu Thr Leu Ala Ala Pro Asn Leu Pro
        755                 760                 765

Lys Pro Ala Thr Glu Val Arg Thr Val Leu Leu Thr Gly Ala Thr Gly
    770                 775                 780

Phe Leu Gly Arg Tyr Leu Ala Leu Glu Trp Leu Glu Arg Met Asp Met
785                 790                 795                 800

Val Asp Gly Lys Val Ile Ala Leu Val Arg Ala Arg Ser Asp Glu Glu
                805                 810                 815

Ala Arg Ala Arg Leu Asp Lys Thr Phe Asp Ser Gly Asp Pro Lys Leu
            820                 825                 830

Leu Ala His Tyr Gln Gln Leu Ala Ala Asp His Leu Glu Val Ile Ala
        835                 840                 845

```
Gly Asp Lys Gly Glu Ala Asn Leu Gly Leu Gly Gln Asp Val Trp Gln
850                 855                 860

Arg Leu Ala Asp Thr Val Asp Val Ile Val Asp Pro Ala Ala Leu Val
865                 870                 875                 880

Asn His Val Leu Pro Tyr Ser Glu Leu Phe Gly Pro Asn Ala Leu Gly
                885                 890                 895

Thr Ala Glu Leu Ile Arg Leu Ala Leu Thr Ser Lys Gln Lys Pro Tyr
            900                 905                 910

Thr Tyr Val Ser Thr Ile Gly Val Gly Asp Gln Ile Glu Pro Gly Lys
        915                 920                 925

Phe Val Glu Asn Ala Asp Ile Arg Gln Met Ser Ala Thr Arg Ala Ile
930                 935                 940

Asn Asp Ser Tyr Ala Asn Gly Tyr Gly Asn Ser Lys Trp Ala Gly Glu
945                 950                 955                 960

Val Leu Leu Arg Glu Ala His Asp Leu Cys Gly Leu Pro Val Ala Val
                965                 970                 975

Phe Arg Cys Asp Met Ile Leu Ala Asp Thr Thr Tyr Ala Gly Gln Leu
            980                 985                 990

Asn Leu Pro Asp Met Phe Thr Arg Leu Met Leu Ser Leu Val Ala Thr
        995                 1000                1005

Gly Ile Ala Pro Gly Ser Phe Tyr Glu Leu Asp Ala Asp Gly Asn
    1010                1015                1020

Arg Gln Arg Ala His Tyr Asp Gly Leu Pro Val Glu Phe Ile Ala
    1025                1030                1035

Ala Ala Ile Ser Thr Leu Gly Ser Gln Ile Thr Asp Ser Asp Thr
    1040                1045                1050

Gly Phe Gln Thr Tyr His Val Met Asn Pro Tyr Asp Asp Gly Val
    1055                1060                1065

Gly Leu Asp Glu Tyr Val Asp Trp Leu Val Asp Ala Gly Tyr Ser
    1070                1075                1080

Ile Glu Arg Ile Ala Asp Tyr Ser Glu Trp Leu Arg Arg Phe Glu
    1085                1090                1095

Thr Ser Leu Arg Ala Leu Pro Asp Arg Gln Arg Gln Tyr Ser Leu
    1100                1105                1110

Leu Pro Leu Leu His Asn Tyr Arg Thr Pro Glu Lys Pro Ile Asn
    1115                1120                1125

Gly Ser Ile Ala Pro Thr Asp Val Phe Arg Ala Ala Val Gln Glu
    1130                1135                1140

Ala Lys Ile Gly Pro Asp Lys Asp Ile Pro His Val Ser Pro Pro
    1145                1150                1155

Val Ile Val Lys Tyr Ile Thr Asp Leu Gln Leu Leu Gly Leu Leu
    1160                1165                1170

<210> SEQ ID NO 39
<211> LENGTH: 1184
<212> TYPE: PRT
<213> ORGANISM: Mycobacterium abscessus DSM44196

<400> SEQUENCE: 39

Met Thr Val Thr Asn Glu Thr Asn Pro Gln Gln Glu Gln Leu Ser Arg
1               5                   10                  15

Arg Ile Glu Ser Leu Arg Glu Ser Asp Pro Gln Phe Arg Ala Ala Gln
            20                  25                  30

Pro Asp Pro Ala Val Ala Glu Gln Val Leu Arg Pro Gly Leu His Leu
        35                  40                  45
```

```
Ser Glu Ala Ile Ala Ala Leu Met Thr Gly Tyr Ala Glu Arg Pro Ala
 50                  55                  60

Leu Gly Glu Arg Ala Arg Glu Leu Val Thr Asp Gln Asp Gly Arg Thr
 65                  70                  75                  80

Thr Leu Arg Leu Leu Pro Arg Phe Asp Thr Thr Thr Tyr Gly Glu Leu
                     85                  90                  95

Trp Ser Arg Thr Thr Ser Val Ala Ala Ala Trp His His Asp Ala Ala
                100                 105                 110

His Pro Val Lys Ala Gly Asp Leu Val Ala Thr Leu Gly Phe Thr Ser
            115                 120                 125

Ile Asp Tyr Thr Val Leu Asp Leu Ala Ile Met Ile Leu Gly Gly Val
            130                 135                 140

Ala Val Pro Leu Gln Thr Ser Ala Pro Ala Ser Gln Trp Thr Thr Ile
145                 150                 155                 160

Leu Ala Glu Ala Glu Pro Asn Thr Leu Ala Val Ser Ile Glu Leu Ile
                165                 170                 175

Gly Ala Ala Met Glu Ser Val Arg Ala Thr Pro Ser Ile Lys Gln Val
                180                 185                 190

Val Val Phe Asp Tyr Thr Pro Glu Val Asp Asp Gln Arg Glu Ala Phe
            195                 200                 205

Glu Ala Ala Ser Thr Gln Leu Ala Gly Thr Gly Ile Ala Ile Glu Thr
            210                 215                 220

Leu Asp Ala Val Ile Ala Arg Gly Ala Ala Leu Pro Ala Ala Pro Leu
225                 230                 235                 240

Tyr Ala Pro Ser Ala Gly Asp Pro Leu Ala Leu Leu Ile Tyr Thr
                245                 250                 255

Ser Gly Ser Thr Gly Ala Pro Lys Gly Ala Met His Ser Glu Asn Ile
                260                 265                 270

Val Arg Arg Trp Trp Ile Arg Glu Asp Val Met Ala Gly Thr Glu Asn
            275                 280                 285

Leu Pro Met Ile Gly Leu Asn Phe Met Pro Met Ser His Ile Met Gly
            290                 295                 300

Arg Gly Thr Leu Thr Ser Thr Leu Ser Thr Gly Gly Thr Gly Tyr Phe
305                 310                 315                 320

Ala Ala Ser Ser Asp Met Ser Thr Leu Phe Glu Asp Met Glu Leu Ile
                325                 330                 335

Arg Pro Thr Ala Leu Ala Leu Val Pro Arg Val Cys Asp Met Val Phe
                340                 345                 350

Gln Arg Phe Gln Thr Glu Val Asp Arg Arg Leu Ala Ser Ser Asp Thr
            355                 360                 365

Ala Ser Ala Glu Ala Val Ala Ala Glu Val Lys Ala Asp Ile Arg Asp
370                 375                 380

Asn Leu Phe Gly Gly Arg Val Ser Ala Val Met Val Gly Ser Ala Pro
385                 390                 395                 400

Leu Ser Glu Glu Leu Gly Glu Phe Ile Glu Ser Cys Phe Glu Leu Asn
                405                 410                 415

Leu Thr Asp Gly Tyr Gly Ser Thr Glu Ala Gly Met Val Phe Arg Asp
                420                 425                 430

Gly Ile Val Gln Arg Pro Val Ile Asp Tyr Lys Leu Val Asp Val
            435                 440                 445

Pro Glu Leu Gly Tyr Phe Ser Thr Asp Lys Pro His Pro Arg Gly Glu
450                 455                 460
```

```
Leu Leu Leu Lys Thr Asp Gly Met Phe Leu Gly Tyr Tyr Lys Arg Pro
465                 470                 475                 480

Glu Val Thr Ala Gly Val Phe Asp Ala Asp Gly Phe Tyr Met Thr Gly
                485                 490                 495

Asp Ile Val Ala Glu Leu Ala His Asp Asn Ile Glu Ile Ile Asp Arg
            500                 505                 510

Arg Asn Asn Val Leu Lys Leu Ser Gln Gly Glu Phe Val Ala Val Ala
        515                 520                 525

Thr Leu Glu Ala Glu Tyr Ala Asn Ser Pro Val Val His Gln Ile Tyr
    530                 535                 540

Val Tyr Gly Ser Ser Glu Arg Ser Tyr Leu Leu Ala Val Val Val Pro
545                 550                 555                 560

Thr Pro Glu Ala Val Ala Ala Ala Lys Gly Asp Ala Ala Ala Leu Lys
                565                 570                 575

Thr Thr Ile Ala Asp Ser Leu Gln Asp Ile Ala Lys Glu Ile Gln Leu
            580                 585                 590

Gln Ser Tyr Glu Val Pro Arg Asp Phe Ile Ile Glu Pro Gln Pro Phe
        595                 600                 605

Thr Gln Gly Asn Gly Leu Leu Thr Gly Ile Ala Lys Leu Ala Arg Pro
    610                 615                 620

Asn Leu Lys Ala His Tyr Gly Pro Arg Leu Glu Gln Met Tyr Ala Glu
625                 630                 635                 640

Ile Ala Glu Gln Gln Ala Ala Glu Leu Arg Ala Leu His Gly Val Asp
                645                 650                 655

Pro Asp Lys Pro Ala Leu Glu Thr Val Leu Lys Ala Ala Gln Ala Leu
            660                 665                 670

Leu Gly Val Ser Ser Ala Glu Leu Ala Ala Asp Ala His Phe Thr Asp
        675                 680                 685

Leu Gly Gly Asp Ser Leu Ser Ala Leu Ser Phe Ser Asp Leu Leu Arg
    690                 695                 700

Asp Ile Phe Ala Val Glu Val Pro Val Gly Val Ile Val Ser Ala Ala
705                 710                 715                 720

Asn Asp Leu Ser Gly Val Ala Lys Phe Val Asp Glu Gln Arg Tyr Ser
                725                 730                 735

Gly Gly Thr Arg Pro Thr Ala Glu Thr Val His Gly Ala Gly His Thr
            740                 745                 750

Glu Ile Arg Ala Ala Asp Leu Thr Leu Asp Lys Phe Ile Asp Glu Ala
        755                 760                 765

Thr Leu His Ala Ala Pro Ser Leu Pro Lys Ala Val Gly Ile Pro His
    770                 775                 780

Thr Val Leu Leu Thr Gly Ser Asn Gly Tyr Leu Gly His Tyr Leu Ala
785                 790                 795                 800

Leu Glu Trp Leu Glu Arg Leu Asp Lys Thr Glu Gly Lys Leu Ile Ala
                805                 810                 815

Ile Val Arg Gly Lys Asn Ala Glu Ala Ala Tyr Arg Arg Leu Glu Glu
            820                 825                 830

Ala Phe Asp Thr Gly Asp Thr Gln Leu Leu Ala His Phe Arg Ser Leu
        835                 840                 845

Ala Asp Lys His Leu Glu Val Leu Ala Gly Asp Ile Gly Asp Pro Asn
    850                 855                 860

Leu Gly Leu Asp Ala Asp Thr Trp Gln Arg Leu Ala Asp Thr Val Asp
865                 870                 875                 880

Val Ile Val His Pro Ala Ala Leu Val Asn His Val Leu Pro Tyr Ser
```

885                 890                 895
Gln Leu Phe Gly Pro Asn Val Val Gly Thr Ala Glu Ile Ile Lys Leu
                900                 905                 910

Ala Ile Thr Thr Lys Ile Lys Pro Val Thr Tyr Leu Ser Thr Val Ala
            915                 920                 925

Val Ala Ala Tyr Val Asp Pro Thr Thr Phe Asp Glu Glu Ser Asp Ile
        930                 935                 940

Arg Leu Ile Ser Ala Val Arg Pro Val Asp Glu Leu Tyr Ala Asn Gly
945                 950                 955                 960

Tyr Gly Asn Ser Lys Trp Ala Gly Glu Val Leu Leu Arg Glu Ala His
                965                 970                 975

Asp Leu Cys Gly Leu Pro Val Ala Val Phe Arg Ser Asp Met Ile Leu
            980                 985                 990

Ala His Ser Arg Tyr Thr Gly Gln Leu Asn Val Pro Asp Gln Phe Thr
        995                 1000                1005

Arg Leu Ile Leu Ser Leu Ile Ala Thr Gly Ile Ala Pro Gly Ser
    1010                1015                1020

Phe Tyr Gln Ala His Ala Thr Gly Glu Arg Pro Leu Ala His Tyr
    1025                1030                1035

Asp Gly Leu Pro Gly Asp Phe Thr Ala Glu Ala Ile Thr Thr Leu
    1040                1045                1050

Gly Thr Gln Val Val Asp Ser Tyr Glu Thr Tyr Asp Cys Val Asn
    1055                1060                1065

Pro His Ala Asp Gly Val Ser Leu Asp Asn Phe Val Asp Trp Leu
    1070                1075                1080

Ile Glu Ala Gly Tyr Pro Ile Ala Arg Ile Asp Asn Tyr Thr Glu
    1085                1090                1095

Trp Phe Thr Arg Phe Asp Thr Ala Ile Arg Ser Leu Pro Glu Lys
    1100                1105                1110

Gln Lys Gln His Ser Leu Leu Pro Leu Leu His Ala Phe Glu Gln
    1115                1120                1125

Pro Ser Ala Ala Glu Asn His Gly Val Val Pro Ala Lys Arg Phe
    1130                1135                1140

Gln His Ala Val Gln Ala Ala Gly Ile Gly Pro Ala Gly Gln Asp
    1145                1150                1155

Gly Thr Thr Asp Ile Pro His Leu Ser Arg Arg Leu Ile Val Lys
    1160                1165                1170

Tyr Ala Lys Asp Leu Glu Gln Leu Gly Leu Leu
    1175                1180

<210> SEQ ID NO 40
<211> LENGTH: 351
<212> TYPE: PRT
<213> ORGANISM: Agrobacterium fabrum ATCC 33970

<400> SEQUENCE: 40

Met Gln Pro Phe Val Tyr Met Ala Ala Pro Ala Arg Ile Val Phe Ser
1               5                   10                  15

Ala Gly Ser Ser Ala Asp Val Ala Glu Glu Ile Arg Arg Leu Gly Leu
                20                  25                  30

Ser Arg Ala Leu Val Leu Ser Thr Pro Gln Gln Lys Gly Asp Ala Glu
            35                  40                  45

Ala Leu Ala Ser Arg Leu Gly Arg Leu Ala Ala Gly Val Phe Ser Glu
        50                  55                  60

Ala Ala Met His Thr Pro Val Glu Val Thr Lys Thr Ala Val Glu Ala
65                  70                  75                  80

Tyr Arg Ala Ala Gly Ala Asp Cys Val Val Ser Leu Gly Gly Gly Ser
                85                  90                  95

Thr Thr Gly Leu Gly Lys Ala Ile Ala Leu Arg Thr Asp Ala Ala Gln
            100                 105                 110

Ile Val Ile Pro Thr Thr Tyr Ala Gly Ser Glu Val Thr Pro Ile Leu
            115                 120                 125

Gly Gln Thr Glu Asn Gly Val Lys Thr Thr Met Arg Gly Pro Glu Ile
            130                 135                 140

Leu Pro Glu Val Val Ile Tyr Asp Ala Glu Leu Thr Leu Gly Leu Pro
145                 150                 155                 160

Val Ala Ile Ser Met Thr Ser Gly Leu Asn Ala Met Ala His Ala Ala
                165                 170                 175

Glu Ala Leu Tyr Ala Arg Asp Arg Asn Pro Ile Ala Ser Met Met Ala
                180                 185                 190

Val Glu Gly Leu Arg Ala Met Ile Glu Ala Leu Pro Val Val Arg Gln
                195                 200                 205

Ala Pro His Asp Ile Gly Ala Arg Glu Thr Ala Leu Tyr Gly Ala Trp
210                 215                 220

Leu Cys Gly Thr Val Leu Gly Ala Val Gly Met Ser Leu His His Lys
225                 230                 235                 240

Leu Cys His Thr Leu Gly Gly Ser Leu Asp Leu Pro His Ala Glu Thr
                245                 250                 255

His Ala Val Leu Leu Pro His Thr Ile Ala Tyr Val Glu Glu Ala Ala
                260                 265                 270

Pro Asn Leu Leu Ala Pro Leu Ala Ala Leu Val Gly Gly Arg Ala Gly
                275                 280                 285

Ala Gly Leu Phe Asp Phe Ala Ala Arg Leu Gly Ala Pro Ser Ser Leu
            290                 295                 300

Ala Ala Leu Gly Val Gly Ala Asp Asp Leu Asp Pro Met Ala Glu Leu
305                 310                 315                 320

Ala Thr Ala Asn Pro Tyr Trp Cys Pro Arg Pro Ile Glu Lys Thr Ala
                325                 330                 335

Ile Arg Asp Leu Leu Gln Arg Ala Phe Glu Gly Ala Arg Pro Ala
            340                 345                 350

<210> SEQ ID NO 41
<211> LENGTH: 246
<212> TYPE: PRT
<213> ORGANISM: Bacillus halodurans ATCC BAA-125

<400> SEQUENCE: 41

Met Leu Gln Gly Lys Thr Ala Ile Val Thr Gly Ala Ser Arg Gly Ile
1               5                   10                  15

Gly Arg Ala Thr Ala Met Glu Leu Ala Arg His Gly Ala Asn Val Val
                20                  25                  30

Val Asn Tyr Ala Gly Asn Lys Glu Lys Ala Glu Lys Val Val Ala Glu
            35                  40                  45

Ile Lys Glu Leu Gly Val Glu Ala Ile Ala Ile Gln Ala Asp Val Ala
        50                  55                  60

Asp Ser Glu Ser Val Gln Ala Met Val Lys Glu Thr Ile Asp Thr Phe
65                  70                  75                  80

Gly Ala Val Asp Ile Leu Val Asn Asn Ala Gly Ile Thr Arg Asp Asn
                85                  90                  95

-continued

Leu Phe Met Arg Met Lys Glu Glu Asp Trp Asp Ala Val Ile Asp Thr
            100                 105                 110

Asn Leu Lys Gly Val Phe His Cys Ser Lys Ala Val Thr Arg Pro Met
            115                 120                 125

Met Lys Gln Arg Phe Gly Arg Ile Ile Asn Val Ser Ser Val Val Gly
        130                 135                 140

Ala Ile Gly Asn Ala Gly Gln Ala Asn Tyr Val Ala Ala Lys Ala Gly
145                 150                 155                 160

Val Ile Gly Leu Thr Lys Thr Leu Ala Arg Glu Leu Ala Asn Arg Asn
                165                 170                 175

Ile Thr Val Asn Ala Val Ala Pro Gly Phe Ile Glu Thr Asp Met Thr
            180                 185                 190

Gly Glu Leu Pro Glu Asp Val Lys Ala Gln Met Leu Gly Gln Ile Pro
        195                 200                 205

Leu Ala Arg Leu Gly Gln Pro Glu Glu Val Ala Lys Ala Val Arg Phe
    210                 215                 220

Leu Ala Ser Asp Asp Ala Ser Tyr Leu Thr Gly Gln Thr Ile His Val
225                 230                 235                 240

Asn Gly Gly Met Val Met
                245

<210> SEQ ID NO 42
<211> LENGTH: 250
<212> TYPE: PRT
<213> ORGANISM: Chromobacterium violaceum ATCC 12472

<400> SEQUENCE: 42

Met Arg Arg Leu Glu Gly Lys Gln Ala Leu Ile Thr Gly Gly Thr Ser
1               5                   10                  15

Gly Ile Gly Leu Glu Thr Ala Lys Gln Phe Leu Ala Glu Gly Ala Lys
            20                  25                  30

Val Ala Ile Thr Gly Arg Ser Glu Ala Gly Leu Ala Gln Ala Asn Glu
        35                  40                  45

Val Leu Gly Gly Arg Ala Leu Leu Leu Lys Ser Asp Ala Gly Ser Leu
    50                  55                  60

Asp Asp Gln Arg Ala Leu Pro Ala Gln Leu Arg Ser His Gly Trp Ser
65                  70                  75                  80

Arg Leu Asp Ala Ala Tyr Leu Asn Ala Gly Asp Val Thr His Leu Pro
                85                  90                  95

Leu Ala Asp Trp Ser Glu Ala Asp Phe Asp Arg Val Met Ala Val Asn
            100                 105                 110

Leu Lys Gly Pro Phe Phe Leu Leu Gln Ala Leu Ser Pro Leu Leu Ala
        115                 120                 125

Asn Pro Ser Ser Val Ile Leu Cys Gly Ser Val Gly Ala Arg Ile Gly
    130                 135                 140

Val Pro Ser Ser Ser Ala Tyr Ala Ala Ser Lys Ala Gly Leu Leu Ser
145                 150                 155                 160

Leu Ala Arg Thr Leu Ser Ala Glu Trp Leu Asp Arg Gly Ile Arg Val
                165                 170                 175

Asn Gly Leu Ser Pro Gly Pro Thr His Thr Pro Ala Phe Gly Lys Leu
            180                 185                 190

Gly Met Pro Glu Asp Glu Leu Pro Ala Leu Arg Asp Arg Ile Arg Lys
        195                 200                 205

Leu Val Pro Leu Gly Arg Leu Gly Arg Pro Glu Glu Leu Ala Lys Ala

```
            210                 215                 220
Ala Val Phe Leu Ala Ser Asp Glu Ser Ser Tyr Met Leu Gly Ser Glu
225                 230                 235                 240

Leu Leu Val Asp Gly Val Gly Asn Val
                245                 250

<210> SEQ ID NO 43
<211> LENGTH: 393
<212> TYPE: PRT
<213> ORGANISM: Pseudomonas aeruginosa ATCC 15692

<400> SEQUENCE: 43

Met Ser Asp Leu His Tyr Trp Asn Tyr Pro Thr Asp Ile Leu Cys Gly
1               5                   10                  15

Val Gly Ala Leu Glu Gln Leu Pro Arg Arg Cys Ala Leu Ala Gly Ala
                20                  25                  30

Arg Arg Pro Leu Leu Val Thr Asp Pro Gly Met Arg Ala Leu Glu Pro
            35                  40                  45

Leu Arg Leu Val Arg Glu Cys Leu Glu Arg Ala Gly Ile Asp His Asp
    50                  55                  60

Leu Phe His Glu Leu Ser Ser Asn Pro Ser Leu Ala Glu Val Gln Gly
65                  70                  75                  80

Gly Ala Arg Arg Phe Glu Ala Gly Gly His Asp Ala Leu Ile Ala Leu
                85                  90                  95

Gly Gly Gly Ser Ala Leu Asp Ala Ala Lys Gly Ile Ala Leu Leu Ser
                100                 105                 110

Arg Asp Pro His Gly Leu Glu Arg Phe Glu Trp Thr Gln Thr Leu Arg
            115                 120                 125

Ser Tyr Pro Thr Leu Ala Asp Tyr Pro Pro Leu Gly Leu Pro Pro Leu
    130                 135                 140

Leu Ala Leu Pro Thr Thr Ala Gly Thr Gly Ser Glu Leu Gly Arg Glu
145                 150                 155                 160

Ala Val Leu Thr Asp Thr Gln Leu Gly Ile Lys Arg Val Val Gly His
                165                 170                 175

Arg Glu Leu Leu Ala Ala Cys Val Phe Leu Asp Pro Arg Leu Thr Arg
            180                 185                 190

Gly Leu Pro Pro Ala Leu Ser Ala Ala Thr Gly Met Asp Ala Leu Thr
        195                 200                 205

His His Leu Glu Ala Leu Phe Ser Pro Leu Tyr His Pro Met Ser Ala
    210                 215                 220

Gly Ile Ala Leu Glu Gly Val Arg Leu Val Arg Gln His Leu Glu Asn
225                 230                 235                 240

Ala Val Arg Asp Gly Asn Asp Leu Ala Ala Arg Glu Gly Met Leu Val
                245                 250                 255

Ala Ser Ala Ser Ala Ala Val Ala Phe Gln Lys Gly Leu Gly Gly Val
            260                 265                 270

His Ala Leu Ala His Pro Leu Gly Ala Arg His His Leu His His Gly
        275                 280                 285

Leu Leu Asn Ala Val Leu Leu Pro Tyr Val Leu Leu Ala Asn Arg Pro
    290                 295                 300

Ala Ile Glu Ala Asp Ala Ala Arg Leu Ala Arg Tyr Leu Glu Leu Asp
305                 310                 315                 320

Glu Ala Ser Phe Asp Gly Leu Leu Ala Trp Ile Leu Glu Leu Arg Ala
                325                 330                 335
```

```
Arg Ile Gly Ile Pro Ala Asn Leu Ala Ala Leu Gly Leu Asp Gly Glu
                340                 345                 350

Asp Ala Gln Trp Val Gly Glu Gln Ala Leu Ala Asp Leu Ser Ser Ser
            355                 360                 365

Ala Thr Asn Ala Leu Pro Leu Asp Ala Arg Asp Tyr Ala Arg Ile Tyr
        370                 375                 380

Arg Gln Ala Val Ala Gly Thr Leu Ala
385                 390

<210> SEQ ID NO 44
<211> LENGTH: 257
<212> TYPE: PRT
<213> ORGANISM: Pseudomonas aeruginosa ATCC 15692

<400> SEQUENCE: 44

Met Val Asp His Ser Ile Lys Gly Lys Thr Val Leu Ile Thr Gly Gly
1               5                   10                  15

Ala Lys Asn Leu Gly Gly Leu Ile Ala Arg Asp Leu Ala Ala His Gly
            20                  25                  30

Ala Lys Ala Ile Thr Ile His Tyr Asn Ser Ala Ala Ser Lys Ala Asp
        35                  40                  45

Ala Asp Ala Thr Val Ala Ala Leu Gln Ala Ala Gly Ala Lys Ala Val
    50                  55                  60

Ala Leu Gln Gly Asp Leu Thr Ser Ala Ala Ala Met Glu Lys Leu Phe
65                  70                  75                  80

Ala Asp Ala Ile Ala Ala Val Gly Lys Pro Asp Ile Ala Ile Asn Thr
                85                  90                  95

Val Gly Lys Val Leu Lys Lys Pro Ile Thr Glu Ile Ser Glu Thr Glu
            100                 105                 110

Tyr Asp Glu Met Ser Ala Val Asn Ser Lys Ser Ala Phe Phe Phe Leu
        115                 120                 125

Arg Glu Ala Gly Lys His Val Asn Asp Asn Gly Lys Ile Cys Thr Leu
    130                 135                 140

Val Thr Ser Leu Leu Gly Ala Tyr Thr Pro Tyr Tyr Ala Ala Tyr Ala
145                 150                 155                 160

Gly Thr Lys Ala Pro Val Glu His Phe Thr Arg Ala Ala Ser Lys Glu
                165                 170                 175

Phe Gly Ala Arg Gly Ile Ser Val Thr Ala Val Gly Pro Gly Pro Met
            180                 185                 190

Asp Thr Pro Phe Phe Tyr Pro Ala Glu Gly Ala Asp Ala Val Asp Tyr
        195                 200                 205

Leu Lys Asn Ala Ala Ala Leu Ser Pro Phe Ser Lys Thr Gly Leu Thr
    210                 215                 220

Asp Ile Asp Asp Val Val Pro Phe Ile Arg His Leu Val Ser Glu Gly
225                 230                 235                 240

Trp Trp Ile Thr Gly Gln Thr Ile Leu Ile Asn Gly Gly Phe Ser Thr
                245                 250                 255

Lys

<210> SEQ ID NO 45
<211> LENGTH: 331
<212> TYPE: PRT
<213> ORGANISM: Pseudomonas putida KT2440

<400> SEQUENCE: 45

Met Gln Tyr Val Lys Leu Gly Ser Thr Gly Leu Asp Ile Ser Arg Leu
```

-continued

```
              1               5                  10                 15
            Cys Leu Gly Cys Met Thr Phe Gly Glu Pro Asp Ala Gly Thr His Pro
                             20                 25                 30

Trp Thr Leu Gly Glu Asp Ala Ser Arg Pro Ile Ile Arg His Ala Val
                         35                 40                 45

Glu Gln Gly Ile Asn Phe Phe Asp Thr Ala Asn Ser Tyr Ser Ala Gly
                     50                 55                 60

Thr Ser Glu Ile Ile Leu Gly Lys Leu Leu Arg Glu Phe Thr Arg Arg
             65                 70                 75                 80

Glu Glu Thr Val Ile Ala Thr Lys Val Phe Phe Pro Ala Asn Met Trp
                             85                 90                 95

Glu Gly Ala Ser Arg Pro Asn Glu Gln Gly Leu Ser Arg Lys Ala Ile
                            100                105                110

Met Ala Asn Ile Asp Ala Ser Leu Ser Arg Leu Gly Thr Asp Tyr Val
                            115                120                125

Asp Leu Tyr Gln Ile His Arg Trp Asp Tyr His Thr Pro Ile Glu Glu
                        130                135                140

Thr Met Glu Ala Leu His Asp Val Val Lys Ala Gly Lys Ala Arg Tyr
            145                150                155                160

Ile Gly Ala Ser Ser Met Tyr Ala Trp Gln Phe Ala Lys Ala Gln Gln
                            165                170                175

Val Ala Ala Asn His Gly Trp Ser Arg Phe Val Ser Met Gln Asn Tyr
                        180                185                190

Leu Asn Leu Ile Tyr Arg Glu Glu Arg Glu Met Ile Pro Leu Cys
                        195                200                205

Leu Asp Gln Gly Val Gly Leu Met Pro Trp Ser Pro Met Ala Arg Gly
                        210                215                220

Arg Leu Thr Arg Pro His Gly Gln Gln Thr Gln Arg Thr Arg Thr Asp
            225                230                235                240

Val Ser Gly Gln Ser Phe Tyr Glu Lys Thr Glu Val Glu Asp Gly Arg
                            245                250                255

Val Ile Asp Val Val Glu Gln Ile Ala Ser Glu Arg Gly Val Pro Met
                        260                265                270

Ala Gln Val Ala Leu Ala Trp Val Leu Gly Arg Ala Gly Val Ser Ala
                        275                280                285

Pro Ile Val Gly Ala Ser Lys Pro Ala His Leu Asp Asp Ala Leu Gly
                        290                295                300

Ala Leu Ser Leu Gln Leu Ser Glu Asp Glu Val Ala Arg Leu Gln Ala
            305                310                315                320

Pro Tyr Val Pro His Ala Val Thr Gly Phe Lys
                        325                330
```

<210> SEQ ID NO 46
<211> LENGTH: 249
<212> TYPE: PRT
<213> ORGANISM: Pseudomonas syringae pv. tomato DC3000

<400> SEQUENCE: 46

```
            Met Ile Glu His Leu Lys Leu Ala Gly Lys Val Ala Leu Val Gln Gly
             1               5                  10                 15

Gly Ser Arg Gly Ile Gly Ala Ala Ile Val Asn Arg Leu Ala Lys Glu
                             20                 25                 30

Gly Ala Ala Val Ala Phe Thr Tyr Ile Asn Ser Glu Val Asn Ala Leu
                         35                 40                 45
```

```
Glu Ile Gln Asp Ser Ile Asn Ala Asn Gly Gly Arg Ala Leu Ala Ile
 50                  55                  60

Arg Ala Asp Ser Ala Asp Glu Lys Ala Ile Arg Gln Ala Val Gln Thr
 65                  70                  75                  80

Thr Ala Glu Thr Leu Gly Arg Leu Asp Ile Leu Val Asn Asn Ala Gly
                 85                  90                  95

Val Leu Ala Ile Ala Pro Leu Asn Glu Phe Ser Met Gln Asp Phe Asp
                100                 105                 110

Lys Thr Leu Ala Ile Asn Val Arg Ser Val Phe Ile Ala Ser Gln Glu
                115                 120                 125

Ala Ala Arg His Met Glu Glu Gly Arg Ile Ile Asn Ile Gly Ser
130                 135                 140

Thr Asn Ala Glu Arg Met Pro Phe Ala Gly Gly Ala Thr Tyr Ala Met
145                 150                 155                 160

Ser Lys Ser Ala Leu Ile Gly Leu Thr Lys Gly Met Ala Arg Asp Leu
                165                 170                 175

Gly Pro Gln Gly Ile Thr Val Asn Asn Val Gln Pro Gly Pro Val Asp
                180                 185                 190

Thr Asp Met Asn Pro Ala Gln Gly Glu Phe Ala Glu Ser Leu Lys Ala
                195                 200                 205

Leu Met Ala Leu Pro Arg Tyr Gly Lys Ser Glu Glu Ile Ala Ser Phe
210                 215                 220

Val Ala Tyr Leu Ala Gly Pro Glu Ala Gly Tyr Ile Thr Gly Ala Ser
225                 230                 235                 240

Leu Thr Ile Asp Gly Gly Phe Ser Ala
                245

<210> SEQ ID NO 47
<211> LENGTH: 259
<212> TYPE: PRT
<213> ORGANISM: Rhodococcus jostii strain RHA1

<400> SEQUENCE: 47

Met Ser Ile Lys Gly Lys Val Ala Leu Val Thr Gly Ala Gly Gln Gly
 1                   5                  10                  15

Ile Gly Arg Ala Ile Ala Leu Arg Leu Ala Ser Asp Gly Ala Asp Ile
                 20                  25                  30

Ser Leu Val Asp Val Asn Gly Asp Arg Leu Asp Ala Val Ala Asp Glu
                 35                  40                  45

Val Arg Ala Val Gly Val Lys Ala Ile Ser Leu Val Ala Asp Val Thr
 50                  55                  60

Asp Arg Asp Gln Val Gln Ser Ala Val Asp Arg Thr Glu Arg Glu Leu
 65                  70                  75                  80

Gly Gly Phe Asp Ile Ile Val Asn Asn Ala Gly Ile Ala Gln Val Asn
                 85                  90                  95

Pro Ile Ala Asp Val Thr Pro Glu Glu Val Ser Arg Ile Leu Ala Val
                100                 105                 110

Asn Val Glu Gly Val Leu Trp Gly Ile Gln Val Gly Ala Ala Lys Phe
                115                 120                 125

Arg Glu Arg Gly His Gly Gly Lys Ile Ile Asn Ala Ser Ser Ile Ala
130                 135                 140

Gly His Glu Gly Phe Pro Met Leu Gly Val Tyr Ser Ala Thr Lys Phe
145                 150                 155                 160

Ala Val Arg Gly Leu Thr Gln Ala Ala Ala Lys Glu Tyr Ala Ala Asp
                165                 170                 175
```

```
Gly Ile Thr Val Asn Ala Tyr Cys Pro Gly Val Val Gly Thr Asp Met
            180                 185                 190

Trp Val Thr Ile Asp Glu Arg Phe Ala Ala Leu Thr Gly Ala Pro Lys
            195                 200                 205

Gly Ala Thr Phe Glu Lys Phe Val Gly Gly Ile Ala Leu Gly Arg Ala
            210                 215                 220

Gln Thr Pro Glu Asp Val Ala Ala Tyr Val Ser Tyr Leu Ala Gly Pro
225                 230                 235                 240

Asp Ser Asp Tyr Met Thr Gly Gln Ser Gly Leu Ile Asp Gly Gly Leu
                245                 250                 255

Val Tyr Arg

<210> SEQ ID NO 48
<211> LENGTH: 391
<212> TYPE: PRT
<213> ORGANISM: Rhodococcus jostii RHA1

<400> SEQUENCE: 48

Met Pro Glu Ile Val Lys Phe Glu Met Pro Arg Val Glu Thr Val Val
1               5                   10                  15

Gln Gly Val Gly Ala Val Arg Glu Ile Gly Ala Glu Leu Asp Arg Arg
            20                  25                  30

Asp Leu Lys Arg Val Phe Leu Val Thr Gly His Ser Val Gly Ser Ser
            35                  40                  45

Glu Ala Phe Ala Ala Leu Ala Ser Asp Leu Gly Asp Arg Val Val Gly
        50                  55                  60

Ile Phe Asp Gln Val Lys Ala His Asn Pro Val Glu Leu Ile Val Glu
65              70                  75                  80

Leu Ile Thr Ala Ala Lys Ser Ala Gln Ala Glu Ala Phe Val Ala Val
                85                  90                  95

Gly Gly Gly Ser Pro Val Asp Ala Ala Lys Leu Ala Ala Ile Gly Leu
            100                 105                 110

Cys Glu Gly Ser Glu Ser Val Glu Asp Leu Ala Arg Asn Tyr Leu Val
            115                 120                 125

Phe Glu Tyr Pro Asn Thr Ile His Gln Lys Pro Leu Thr Gly Thr Pro
        130                 135                 140

Met Pro Val Phe Ala Val Pro Thr Thr Leu Ser Ala Ala Glu Trp Asp
145                 150                 155                 160

Gly Phe Ala Gly Ser Val Asp His Thr Arg Asp Thr Lys Asp Leu Thr
                165                 170                 175

Val Tyr Leu Glu Ala Thr Pro Gln Val Val Phe Leu Asp Pro Glu Phe
            180                 185                 190

Cys Ala His Thr Pro Arg Asp Leu Trp Ala Thr Thr Gly Val Arg Ala
            195                 200                 205

Leu Asp His Ala Val Glu Thr Ala Tyr Ala Lys Asn Ala His Pro Phe
        210                 215                 220

Thr Thr Ala Leu Ala Asn Gly Ala Leu Thr Met Leu Ala Glu Asn Leu
225                 230                 235                 240

Pro Arg Ser Val Lys Asp Pro His Asp Tyr Asp Ala Ala Leu Lys Cys
                245                 250                 255

Leu Glu Ala Ala Trp Met Ser Ile Ile Gly Val His Asn Val Ser Leu
            260                 265                 270

Gly Leu Ser His Ala Ile Gly His Gln Leu Gly Ala Val Gly Ile Pro
            275                 280                 285
```

```
His Gly Val Thr Ser Cys Ile Met Leu Pro His Val Met Arg Phe Leu
    290                 295                 300

Glu Pro Val Thr Ser Ala Glu Gln Ala Arg Met Ala Gln Ser Leu Ala
305                 310                 315                 320

Gln Val Gln Gly Asp Gly Glu Asp Leu Pro Ala Ala Asp Arg Leu Glu
                325                 330                 335

Arg Ile Leu Asp Glu Leu Gly Val Pro Arg Arg Val Ser Glu Phe Gly
                340                 345                 350

Val Gly Arg Asp Lys Met Asp Gly Val Ala Arg Ala Thr Leu Gly Asp
            355                 360                 365

Ile Val Val Arg Glu Ser Pro Arg Pro Val Asp Glu Thr Val Val Tyr
    370                 375                 380

Gly Leu Leu Glu Thr Val Trp
385                 390

<210> SEQ ID NO 49
<211> LENGTH: 245
<212> TYPE: PRT
<213> ORGANISM: Rhodopseudomonas palustris ATCC BAA98

<400> SEQUENCE: 49

Met Thr Pro Arg Asn Ala Thr Val Ala Val Ile Gly Ala Gly Asp Tyr
1               5                   10                  15

Ile Gly Ala Glu Ile Ala Lys Lys Phe Ala Ala Glu Gly Phe Thr Val
            20                  25                  30

Phe Ala Gly Arg Arg Asn Gly Glu Lys Leu Ala Pro Leu Val Ala Glu
        35                  40                  45

Ile Glu Ala Ala Gly Gly Arg Ile Val Ala Arg Ser Leu Asp Ala Arg
    50                  55                  60

Asn Glu Asp Glu Val Thr Ala Phe Leu Asn Ala Ala Asp Ala His Ala
65                  70                  75                  80

Pro Leu Glu Val Thr Ile Phe Asn Val Gly Ala Asn Val Asn Phe Pro
                85                  90                  95

Ile Leu Glu Thr Thr Asp Arg Val Phe Arg Lys Val Trp Glu Met Ala
            100                 105                 110

Cys Trp Ala Gly Phe Val Ser Gly Arg Glu Ser Ala Arg Leu Met Leu
        115                 120                 125

Ala His Gly Gln Gly Lys Ile Phe Phe Thr Gly Ala Thr Ala Ser Leu
    130                 135                 140

Arg Gly Gly Ser Gly Phe Ala Ala Phe Ala Ser Ala Lys Phe Gly Leu
145                 150                 155                 160

Arg Ala Val Ala Gln Ser Met Ala Arg Glu Leu Met Pro Lys Asn Ile
                165                 170                 175

His Val Ala His Leu Ile Ile Asp Ser Gly Val Asp Thr Ala Trp Val
            180                 185                 190

Arg Glu Arg Arg Glu Gln Met Phe Gly Lys Asp Ala Leu Ala Asn Pro
        195                 200                 205

Asp Leu Leu Met Pro Pro Ala Ala Val Ala Gly Ala Tyr Trp Gln Leu
    210                 215                 220

Tyr Gln Gln Pro Lys Ser Ala Trp Thr Phe Glu Met Glu Ile Arg Pro
225                 230                 235                 240

Tyr Gly Glu Lys Trp
                245
```

<210> SEQ ID NO 50
<211> LENGTH: 282
<212> TYPE: PRT
<213> ORGANISM: Streptomyces coelicolor ATCC BAA471

<400> SEQUENCE: 50

Met Gln Arg Gln Asn Trp Leu Ile Thr Gly Val Ser Thr Gly Leu Gly
1               5                   10                  15

Arg Ala Phe Ala Gln Ala Ala Leu Ser Ala Gly His Thr Val Val Gly
            20                  25                  30

Thr Val Arg Ser Glu Asn Asp Val Arg Ala Phe Glu Glu Leu Gly Pro
        35                  40                  45

Gly His Ala His Gly Arg Ile Leu Asp Val Thr Asp Gly Gly Ala Val
    50                  55                  60

Asn Gly Val Val Ala Glu Val Glu Arg Ser Val Gly Pro Leu Asp Val
65                  70                  75                  80

Val Val Ala Asn Ala Gly Tyr Gly Leu Glu Gly Thr Phe Glu Glu Thr
                85                  90                  95

Pro Leu Ala Glu Val Arg Arg Gln Phe Asp Val Asn Val Phe Gly Ala
            100                 105                 110

Met Ala Thr Leu Gln Ala Ala Leu Pro His Met Arg Ala Arg Arg Arg
        115                 120                 125

Gly His Leu Met Ala Val Thr Ser Met Gly Gly Leu Met Ala Val Pro
    130                 135                 140

Gly Met Ser Ala Tyr Cys Gly Ser Lys Phe Ala Leu Glu Gly Ile Leu
145                 150                 155                 160

Glu Ala Leu Gly Lys Glu Val Ala Gln Phe Gly Ile His Val Thr Ala
                165                 170                 175

Ile Glu Pro Gly Ser Phe Arg Thr Asp Trp Ala Gly Arg Ser Met Thr
            180                 185                 190

Arg Ala Ala Arg Thr Val Ala Asp Tyr Asp Asp Leu Phe Ala Pro Ile
        195                 200                 205

Arg Glu Ala Arg Gln Lys Ala Ser Gly Asn Gln Leu Gly Asn Pro Ala
    210                 215                 220

Lys Ala Gly Glu Ala Val Val His Ile Thr Ser Val Asp Gln Pro Pro
225                 230                 235                 240

Ala His Leu Val Leu Gly Ser Asp Ala Leu Arg Leu Val Thr Ala Ala
                245                 250                 255

Arg Thr Ala Val Asp Glu Asp Ile Arg Ala Trp Glu Ala Leu Ser Arg
            260                 265                 270

Thr Thr Asp Phe Pro Gln Gly Ala Gln Leu
        275                 280

<210> SEQ ID NO 51
<211> LENGTH: 252
<212> TYPE: PRT
<213> ORGANISM: Shigella flexneri Shi06HN006

<400> SEQUENCE: 51

Met His Tyr Gln Pro Lys Gln Asp Leu Leu Asn Asp Arg Ile Ile Leu
1               5                   10                  15

Val Thr Gly Ala Ser Asp Gly Ile Gly Arg Glu Ala Ala Met Thr Tyr
            20                  25                  30

Ala Arg Tyr Gly Ala Thr Val Ile Leu Leu Gly Arg Asn Glu Glu Lys
        35                  40                  45

Leu Arg Gln Val Ala Ser His Ile Asn Glu Glu Thr Gly Arg Gln Pro

```
            50                  55                  60
Gln Trp Phe Ile Leu Asp Leu Leu Thr Cys Thr Ser Glu Asn Cys Gln
 65                  70                  75                  80

Gln Leu Ala Gln Arg Ile Val Val Asn Tyr Pro Arg Leu Asp Gly Val
                 85                  90                  95

Leu His Asn Ala Gly Leu Leu Gly Asp Val Cys Pro Met Ser Glu Gln
                100                 105                 110

Asn Pro Gln Val Trp Gln Asp Val Met Gln Ile Asn Val Asn Ala Thr
                115                 120                 125

Phe Met Leu Thr Gln Ala Leu Leu Pro Leu Leu Lys Ser Asp Ala
                130                 135                 140

Gly Ser Leu Val Phe Thr Ser Ser Val Gly Arg Gln Gly Arg Ala
145                 150                 155                 160

Asn Trp Gly Ala Tyr Ala Ala Ser Lys Phe Ala Thr Glu Gly Met Met
                165                 170                 175

Gln Val Leu Ala Asp Glu Tyr Gln Gln Arg Leu Arg Val Asn Cys Ile
                180                 185                 190

Asn Pro Gly Gly Thr Arg Thr Ala Met Arg Ala Ser Ala Phe Pro Thr
                195                 200                 205

Glu Asp Pro Gln Lys Leu Lys Thr Pro Ala Asp Ile Met Pro Leu Tyr
                210                 215                 220

Leu Trp Leu Met Gly Asp Asp Ser Arg Arg Lys Thr Gly Met Thr Phe
225                 230                 235                 240

Asp Ala Gln Pro Gly Arg Lys Pro Gly Ile Ser Gln
                245                 250
```

<210> SEQ ID NO 52
<211> LENGTH: 387
<212> TYPE: PRT
<213> ORGANISM: Thermotoga maritima ATCC 43589

<400> SEQUENCE: 52

```
Met Phe Lys Ile Ser Phe Tyr Leu Pro Thr Glu Ile Ile Phe Arg Val
 1               5                  10                  15

Gly Ala Val Asp Glu Leu Glu Glu Arg Ala Lys Lys Leu Gly Lys Lys
                20                  25                  30

Ala Leu Ile Val Thr Gly Arg Ser Ser Thr Lys Lys Thr Gly Leu Leu
                35                  40                  45

Gln Arg Val Val Asp Leu Leu Lys Lys Ala Gly Val Glu Ser Phe Val
 50                  55                  60

Phe Asp Lys Ile Val Pro Asn Pro Ile Ser Asp His Val Asp Glu Ala
 65                  70                  75                  80

Ala Glu Ile Val Arg Lys Glu Lys Ile Asp Phe Ile Ile Gly Leu Gly
                85                  90                  95

Gly Gly Ser Pro Ile Asp Ser Ala Lys Ala Ile Ser Ile Thr Ala Pro
                100                 105                 110

Asn Glu Gly Lys Phe Trp Asp Tyr Val Pro Val Gly Gly Lys Ile
                115                 120                 125

Pro Glu Lys Ser Ile Pro Val Val Ala Ile Pro Thr Thr His Gly Thr
                130                 135                 140

Gly Thr Glu Ala Asp Pro Phe Ala Val Ile Thr Asn Pro Gln Thr Lys
145                 150                 155                 160

Glu Lys Val Gly Ile Gly Tyr Arg Asn Thr Phe Pro Val Leu Ser Leu
                165                 170                 175
```

Val Asp Pro Glu Val Met Lys Thr Leu Pro Lys Asp Gln Thr Ala Tyr
            180                 185                 190

Thr Ser Met Asp Ala Phe Tyr His Ala Ile Glu Ala Phe Leu Asn Val
            195                 200                 205

Asn Ala Asn Pro Tyr Ser Asp Val Leu Ala Leu Asp Ala Met Lys Arg
            210                 215                 220

Ile Val Thr Tyr Leu Pro Val Ala Tyr Glu Asn Gly Glu Asp Met Glu
225                 230                 235                 240

Ala Arg Thr Asn Leu Ala Trp Ala Ser Thr Glu Ala Gly Ile Thr Glu
            245                 250                 255

Thr Leu Thr Gly Val Ile Ala Asn His Ala Leu Glu His Gly Leu Ser
            260                 265                 270

Gly Phe Tyr Pro Glu Ile Thr His Gly Leu Gly Leu Cys Ile Thr Gly
            275                 280                 285

Pro Tyr Leu Phe Glu Tyr Ile Phe Asp His Ala Tyr Glu Arg Leu Ala
            290                 295                 300

Ile Val Gly Arg Glu Val Phe Gly Val Tyr Glu Thr Asp Asp Arg Lys
305                 310                 315                 320

Ala Gly Arg Leu Ala Ile Lys Lys Leu Arg Asp Phe Gln Glu Met Phe
            325                 330                 335

Gly Leu Asn Lys Arg Leu Ser Glu Leu Gly Val Lys Lys Glu Asp Ile
            340                 345                 350

Pro Lys Met Ala Glu Thr Gly Tyr Arg Ile Leu Asn Gly Val Val Val
            355                 360                 365

Val Thr Pro Gly Asn Leu Thr Ala Lys Asp Met Glu Glu Ile Phe Asn
            370                 375                 380

Arg Cys Tyr
385

<210> SEQ ID NO 53
<211> LENGTH: 426
<212> TYPE: PRT
<213> ORGANISM: Escherichia coli K12

<400> SEQUENCE: 53

Met Asn Ser Asn Lys Glu Leu Met Gln Arg Ser Gln Ala Ile Pro
1               5                   10                  15

Arg Gly Val Gly Gln Ile His Pro Ile Phe Ala Asp Arg Ala Glu Asn
            20                  25                  30

Cys Arg Val Trp Asp Val Glu Gly Arg Glu Tyr Leu Asp Phe Ala Gly
            35                  40                  45

Gly Ile Ala Val Leu Asn Thr Gly His Leu His Pro Lys Val Val Ala
50                  55                  60

Ala Val Glu Ala Gln Leu Lys Lys Leu Ser His Thr Cys Phe Gln Val
65                  70                  75                  80

Leu Ala Tyr Glu Pro Tyr Leu Glu Leu Cys Glu Ile Met Asn Gln Lys
            85                  90                  95

Val Pro Gly Asp Phe Ala Lys Lys Thr Leu Leu Val Thr Thr Gly Ser
            100                 105                 110

Glu Ala Val Glu Asn Ala Val Lys Ile Ala Arg Ala Ala Thr Lys Arg
            115                 120                 125

Ser Gly Thr Ile Ala Phe Ser Gly Ala Tyr His Gly Arg Thr His
            130                 135                 140

Thr Leu Ala Leu Thr Gly Lys Val Asn Pro Tyr Ser Ala Gly Met Gly
145                 150                 155                 160

Leu Met Pro Gly His Val Tyr Arg Ala Leu Tyr Pro Cys Pro Leu His
                165                 170                 175

Gly Ile Ser Glu Asp Asp Ala Ile Ala Ser Ile His Arg Ile Phe Lys
            180                 185                 190

Asn Asp Ala Ala Pro Glu Asp Ile Ala Ala Ile Val Ile Glu Pro Val
        195                 200                 205

Gln Gly Glu Gly Gly Phe Tyr Ala Ser Ser Pro Ala Phe Met Gln Arg
    210                 215                 220

Leu Arg Ala Leu Cys Asp Glu His Gly Ile Met Leu Ile Ala Asp Glu
225                 230                 235                 240

Val Gln Ser Gly Ala Gly Arg Thr Gly Thr Leu Phe Ala Met Glu Gln
                245                 250                 255

Met Gly Val Ala Pro Asp Leu Thr Thr Phe Ala Lys Ser Ile Ala Gly
            260                 265                 270

Gly Phe Pro Leu Ala Gly Val Thr Gly Arg Ala Glu Val Met Asp Ala
        275                 280                 285

Val Ala Pro Gly Gly Leu Gly Gly Thr Tyr Ala Gly Asn Pro Ile Ala
    290                 295                 300

Cys Val Ala Ala Leu Glu Val Leu Lys Val Phe Glu Gln Glu Asn Leu
305                 310                 315                 320

Leu Gln Lys Ala Asn Asp Leu Gly Gln Lys Leu Lys Asp Gly Leu Leu
                325                 330                 335

Ala Ile Ala Glu Lys His Pro Glu Ile Gly Asp Val Arg Gly Leu Gly
            340                 345                 350

Ala Met Ile Ala Ile Glu Leu Phe Glu Asp Gly Asp His Asn Lys Pro
        355                 360                 365

Asp Ala Lys Leu Thr Ala Glu Ile Val Ala Arg Ala Arg Asp Lys Gly
    370                 375                 380

Leu Ile Leu Leu Ser Cys Gly Pro Tyr Tyr Asn Val Leu Arg Ile Leu
385                 390                 395                 400

Val Pro Leu Thr Ile Glu Asp Ala Gln Ile Arg Gln Gly Leu Glu Ile
                405                 410                 415

Ile Ser Gln Cys Phe Asp Glu Ala Lys Gln
            420                 425

<210> SEQ ID NO 54
<211> LENGTH: 463
<212> TYPE: PRT
<213> ORGANISM: Pseudomonas putida KT2440

<400> SEQUENCE: 54

Met Asp Lys Gln Lys Gln Asp Leu Ile Ser Gln Gln Asp Arg Gly Ala
1               5                   10                  15

Val Leu His Pro Phe Thr Gln Leu Lys Asp Phe Ala Ser Gly Lys Ala
            20                  25                  30

Gly Asp Pro Thr Ile Ile Glu Thr Ala Lys Gly Ile Thr Ile Thr Asp
        35                  40                  45

Ala Thr Gly Arg Glu Tyr Ile Asp Gly Phe Ala Gly Leu Tyr Cys Met
    50                  55                  60

Asn Val Gly Tyr Gly Arg Thr Glu Val Ala Glu Ala Ile Ser Lys Gln
65                  70                  75                  80

Ala His Lys Leu Ala Tyr Tyr His Thr Tyr Ala Ala His Thr Thr Glu
                85                  90                  95

Glu Leu Ala Arg Leu Ser Asp Arg Leu Val Lys Met Ala Pro Gly Lys

```
                    100                 105                 110
Met Ser Lys Val Phe Tyr Gly Met Ser Gly Asp Ala Asn Glu Thr
            115                 120                 125

Gln Ala Lys Leu Val Trp Tyr Tyr Asn Asn Leu Arg Gly Lys Pro Asn
        130                 135                 140

Lys Lys Lys Ile Ile Ala Arg Glu Arg Gly Tyr His Gly Cys Ser Val
145                 150                 155                 160

Val Ser Gly Ser Met Thr Gly Met Ser Phe Tyr His Asp His Met Asp
                165                 170                 175

Leu Pro Ile Ala Gly Ile Leu Arg Thr Gly Ala Pro His Tyr Tyr Trp
            180                 185                 190

Gly Ala Glu Pro Gly Glu Thr Glu Leu Glu Phe Ser Ala Arg Arg Ala
        195                 200                 205

Arg Glu Leu Glu Glu Leu Ile Leu Arg Gly Pro Asp Thr Ile Gly
    210                 215                 220

Ala Phe Ile Ala Glu Pro Val Leu Gly Thr Gly Ile Thr Pro Pro
225                 230                 235                 240

Pro Glu Gly Tyr Trp Ala Ala Val Gln Pro Val Leu Lys Tyr Asp
                245                 250                 255

Ile Leu Leu Ile Ala Asp Glu Val Ile Thr Gly Phe Gly Arg Thr Gly
            260                 265                 270

Ala Met Phe Gly Cys Asp Lys Tyr Gly Ile Glu Pro Asp Leu Ile Thr
        275                 280                 285

Val Ala Lys Gly Leu Thr Ser Ala Tyr Ala Pro Leu Ser Ala Ser Ile
    290                 295                 300

Val Gly Glu Lys Val Tyr Lys Val Met Glu Glu Gly Ala Asp Arg Val
305                 310                 315                 320

Gly Ala Phe Ser His Gly Tyr Thr Tyr Ser Gly His Pro Ile Gly Val
                325                 330                 335

Ala Ala Ala Asn Ala Val Leu Asp Ile Val Glu Gly Glu Asn Ile Pro
            340                 345                 350

Ala His Val Asp Lys Val Gly Gln Tyr Phe Gln Lys Ser Met Gln Glu
        355                 360                 365

Thr Phe Ser Ser Leu Pro Ile Val Gly Glu Val Arg Gly Val Gly Met
    370                 375                 380

Met Ala Ala Ile Glu Phe Val Ala Asp Pro Ala Thr Lys Lys Arg Phe
385                 390                 395                 400

Asp Pro Ala Leu Lys Val Gly Ala Arg Ile Ser Lys Ala Ala Arg Asp
                405                 410                 415

Arg Asn Leu Ile Ala Arg Ala Met Pro His Gly Glu Ile Leu Gly Phe
            420                 425                 430

Ala Pro Pro Leu Val Thr Thr Glu Gln Glu Val Asp Arg Ile Ile Ser
        435                 440                 445

Ile Ala His Glu Ala Val Leu Ser Val Leu Asp Glu Leu Lys Val
    450                 455                 460

<210> SEQ ID NO 55
<211> LENGTH: 444
<212> TYPE: PRT
<213> ORGANISM: Streptomyces avermitilis ATCC 31267

<400> SEQUENCE: 55

Met Ser Ala Leu Pro Gln Glu Arg Arg Val Val Thr Ala Ile Pro Gly
1               5                   10                  15
```

-continued

```
Pro Lys Ser Gln Glu Leu Gln Ala Arg Arg Thr Ala Val Val Ala Ala
            20                  25                  30
Gly Val Gly Ser Val Leu Pro Val Phe Thr Thr Arg Ala Gly Gly Gly
            35                  40                  45
Ile Ile Glu Asp Val Asp Gly Asn Arg Leu Ile Asp Phe Gly Ser Gly
50                  55                  60
Ile Ala Val Thr Ser Val Gly Ala Ser Ala Glu Ala Val Val Arg Arg
65                  70                  75                  80
Ala Ser Ala Gln Leu Gln Asp Phe Thr His Thr Cys Phe Met Val Thr
                85                  90                  95
Pro Tyr Glu Gly Tyr Val Ala Val Ala Glu Ala Leu Ala Glu Leu Thr
            100                 105                 110
Pro Gly Asp His Ala Lys Lys Ser Ala Leu Phe Asn Ser Gly Ala Glu
            115                 120                 125
Ala Val Glu Asn Ala Val Lys Ile Ala Arg Ala Tyr Thr Lys Arg Gln
130                 135                 140
Ala Val Val Val Phe Asp His Gly Tyr His Gly Arg Thr Asn Leu Thr
145                 150                 155                 160
Met Ala Leu Thr Ala Lys Asn Met Pro Tyr Lys Asn Gly Phe Gly Pro
                165                 170                 175
Phe Ala Pro Glu Val Tyr Arg Val Pro Val Ala Tyr Gly Tyr Arg Trp
            180                 185                 190
Leu Thr Gly Pro Glu Asn Ala Gly Ala Glu Ala Ser Ala Gln Ala Ile
            195                 200                 205
Asp Met Ile Asn Lys Gln Ile Gly Ala Asp Asn Val Ala Ala Ile Ile
210                 215                 220
Ile Glu Pro Val Leu Gly Glu Gly Gly Phe Ile Glu Pro Ala Lys Gly
225                 230                 235                 240
Phe Leu Pro Ala Ile Ser Lys Phe Ala Lys Asp Asn Gly Ile Val Phe
                245                 250                 255
Val Ala Asp Glu Ile Gln Ser Gly Phe Cys Arg Thr Gly Gln Trp Phe
            260                 265                 270
Ala Cys Glu Asp Glu Gly Ile Val Pro Asp Leu Ile Thr Thr Ala Lys
            275                 280                 285
Gly Ile Ala Gly Gly Leu Pro Leu Ala Ala Val Thr Gly Arg Ala Glu
290                 295                 300
Ile Met Asp Ala Ala His Ala Gly Gly Leu Gly Gly Thr Tyr Gly Gly
305                 310                 315                 320
Asn Pro Val Ala Cys Ala Gly Ala Leu Gly Ala Ile Glu Thr Met Lys
                325                 330                 335
Glu Leu Asp Leu Asn Ala Lys Ala Lys Asn Ile Glu Ala Val Met Lys
            340                 345                 350
Ala Arg Leu Gly Ala Met Ala Glu Lys Phe Asp Ile Ile Gly Asp Val
            355                 360                 365
Arg Gly Arg Gly Met Ile Ala Ile Glu Leu Val Lys Asp Arg Asp
370                 375                 380
Thr Lys Glu Pro Asn Pro Glu Ala Ala Gly Ala Leu Ala Lys Ala Cys
385                 390                 395                 400
His Gln Glu Gly Leu Leu Val Leu Thr Cys Gly Thr Tyr Gly Asn Val
                405                 410                 415
Leu Arg Phe Leu Pro Pro Leu Val Ile Gly Glu Asp Leu Leu Asn Glu
            420                 425                 430
Gly Leu Asp Ile Ile Glu Gln Ala Phe Ser Arg Ile
```

<210> SEQ ID NO 56
<211> LENGTH: 444
<212> TYPE: PRT
<213> ORGANISM: Streptomyces coelicolor ATCC BAA-471

<400> SEQUENCE: 56

Met Thr Ala Leu Pro Gln Glu Arg Arg Val Val Thr Ala Ile Pro Gly
1               5                   10                  15

Pro Lys Ser Gln Glu Leu Gln Ala Arg Arg Thr Ala Val Val Ala Gln
            20                  25                  30

Gly Val Gly Ser Thr Leu Pro Val Phe Val Ala Arg Ala Gly Gly Gly
        35                  40                  45

Val Ile Glu Asp Val Asp Gly Asn Arg Leu Ile Asp Phe Gly Ser Gly
    50                  55                  60

Ile Ala Val Thr Ser Val Gly Ala Ser Ala Glu Ala Val Val Arg Lys
65                  70                  75                  80

Ala Ser Ala Gln Leu Ala Asp Phe Thr His Thr Cys Phe Met Val Thr
                85                  90                  95

Pro Tyr Glu Gly Tyr Val Ala Val Ala Glu Ala Leu Ala Glu Leu Thr
            100                 105                 110

Pro Gly Asp His Ala Lys Lys Ser Ala Leu Phe Asn Ser Gly Ala Glu
        115                 120                 125

Ala Val Glu Asn Ala Val Lys Ile Ala Arg Ala Tyr Thr Lys Arg Gln
    130                 135                 140

Ala Val Val Val Phe Asp His Gly Tyr His Gly Arg Thr Asn Leu Thr
145                 150                 155                 160

Met Ala Leu Thr Ala Lys Asn Met Pro Tyr Lys His Gly Phe Gly Pro
                165                 170                 175

Phe Ala Pro Glu Val Tyr Arg Val Pro Val Ala Tyr Gly Tyr Arg Trp
            180                 185                 190

Pro Thr Gly Ala Glu Asn Ala Gly Pro Glu Ala Ala Gln Ala Ile
        195                 200                 205

Asp Gln Ile Ser Lys Gln Val Gly Ala Glu Asn Val Ala Ala Val Ile
    210                 215                 220

Ile Glu Pro Val Leu Gly Glu Gly Gly Phe Ile Glu Pro Ala Lys Gly
225                 230                 235                 240

Phe Leu Pro Ala Ile Arg Glu Phe Ala Ser Asp Asn Gly Ile Val Phe
                245                 250                 255

Val Ala Asp Glu Ile Gln Ser Gly Phe Cys Arg Thr Gly Gln Trp Phe
            260                 265                 270

Ala Cys Glu Asp Glu Gly Ile Val Pro Asp Leu Ile Thr Thr Ala Lys
        275                 280                 285

Gly Ile Ala Gly Gly Leu Pro Leu Ser Ala Val Thr Gly Arg Ala Glu
    290                 295                 300

Ile Met Asp Ala Ala His Ser Gly Gly Leu Gly Thr Tyr Gly Gly
305                 310                 315                 320

Asn Pro Val Ala Cys Ala Gly Ala Leu Gly Ala Ile Glu Thr Met Lys
                325                 330                 335

Glu Leu Asp Leu Asn Ala Arg Ala Lys Asp Ile Glu Ala Val Met Lys
            340                 345                 350

Ser Arg Leu Ala Ala Met Ala Glu Lys Phe Asp Val Ile Gly Asp Val
        355                 360                 365

Arg Gly Arg Gly Ala Met Ile Ala Ile Glu Leu Val Lys Asp Arg Glu
    370                 375                 380

Thr Lys Glu Pro Asn Pro Ala Thr Ala Ala Leu Ala Lys Ala Cys
385                 390                 395                 400

His Gln Glu Gly Leu Leu Val Leu Thr Cys Gly Thr Tyr Gly Asn Val
                405                 410                 415

Leu Arg Phe Leu Pro Pro Leu Val Ile Gly Glu Asp Leu Leu Asn Glu
                420                 425                 430

Gly Leu Asp Ile Ile Glu Gln Ala Phe Thr Arg Val
                435                 440

<210> SEQ ID NO 57
<211> LENGTH: 442
<212> TYPE: PRT
<213> ORGANISM: Sinorhizobium meliloti

<400> SEQUENCE: 57

Met Ser Asn Arg Leu Asn Thr Thr Pro Asn Asp Leu Ser Ala Phe Trp
1               5                   10                  15

Met Pro Phe Thr Ala Asn Arg Gln Phe Lys Lys Glu Pro Arg Leu Phe
                20                  25                  30

Val Gly Ala Lys Asp Met Tyr Tyr Thr Thr His Asp Gly Arg Thr Val
            35                  40                  45

Leu Asp Gly Thr Ala Gly Leu Trp Cys Val Asn Ala Gly His Cys Arg
        50                  55                  60

Pro Lys Ile Thr Glu Ala Ile Arg Glu Gln Ala Gly Glu Leu Asp Tyr
65                  70                  75                  80

Ala Pro Ala Phe Gln Leu Gly His Pro Lys Ala Phe Glu Leu Ala Asn
                85                  90                  95

Arg Leu Val Asp Ile Ala Pro Glu Gly Met Asn His Val Leu Tyr Thr
                100                 105                 110

Asn Ser Gly Ser Glu Ser Val Asp Thr Ala Leu Lys Val Ala Leu Ala
            115                 120                 125

Tyr His Arg Ala Lys Gly Asn Gly Ser Arg Phe Arg Leu Ile Gly Arg
    130                 135                 140

Glu Arg Gly Tyr His Gly Val Asn Phe Gly Gly Ile Ser Val Gly Gly
145                 150                 155                 160

Ile Val Ala Asn Arg Lys Met Phe Gly Thr Leu Leu Thr Gly Val Asp
                165                 170                 175

His Leu Pro His Thr His Leu Pro Ala Lys Asn Ala Phe Ser Arg Gly
                180                 185                 190

Glu Pro Glu His Gly Ala Asp Leu Ala Ala Glu Leu Glu Arg Ile Val
            195                 200                 205

Thr Leu His Asp Ala Ser Thr Val Ala Ala Val Ile Val Glu Pro Val
    210                 215                 220

Ala Gly Ser Thr Gly Val Leu Ile Pro Pro Lys Gly Tyr Leu Gln Lys
225                 230                 235                 240

Leu Arg Glu Ile Cys Thr Lys His Gly Ile Leu Leu Ile Phe Asp Glu
                245                 250                 255

Val Ile Thr Gly Tyr Gly Arg Leu Gly Thr Pro Phe Ala Ala Gln Tyr
            260                 265                 270

Phe Asp Val Lys Pro Asp Ile Ile Thr Thr Ala Lys Gly Leu Thr Asn
        275                 280                 285

Gly Val Ile Pro Met Gly Ala Val Phe Val Thr Ser Glu Ile His Asp
    290                 295                 300

Ala Phe Met Thr Gly Pro Glu His Leu Ile Glu Phe His Gly Tyr
305                 310                 315                 320

Thr Tyr Ser Gly Asn Pro Ile Ala Ser Ala Ala Leu Gly Thr Leu
            325                 330                 335

Asp Thr Tyr Arg Glu Glu Gly Leu Leu Thr Arg Ala Ala Glu Leu Ala
        340                 345                 350

Pro Tyr Trp Glu Glu Ala Leu His Ser Leu Lys Asp Cys Pro His Val
            355                 360                 365

Ile Asp Ile Arg Asn Ile Gly Leu Ile Gly Ala Val Glu Leu Glu Pro
370                 375                 380

Ile Ala Gly Glu Pro Thr Lys Arg Ala Phe Ser Ala Phe Leu Lys Ala
385                 390                 395                 400

Tyr Glu Lys Gly Leu Leu Ile Arg Thr Thr Gly Asp Ile Ile Ala Leu
                405                 410                 415

Ser Pro Pro Leu Ile Ile Glu Lys Arg Gln Ile Asp Glu Leu Phe Asp
                420                 425                 430

Lys Leu Arg Asp Val Leu Lys Asn Asn Ile
        435                 440

<210> SEQ ID NO 58
<211> LENGTH: 445
<212> TYPE: PRT
<213> ORGANISM: Sinorhizobium meliloti

<400> SEQUENCE: 58

Met Asn Ala His Asn Lys Pro Asn Ala Pro Val Leu Asp Ser Tyr Trp
1               5                   10                  15

Met Pro Phe Thr Ala Asn Arg Gln Phe Lys Ala Ala Pro Arg Leu Leu
            20                  25                  30

Ala Ala Ala Glu Gly Met His Tyr Thr Ser Val Asp Gly Arg Thr Val
            35                  40                  45

Leu Asp Gly Thr Ala Gly Leu Trp Cys Val Asn Ala Gly His Gly Arg
    50                  55                  60

Arg Gln Ile Ala Ala Ala Val Glu Arg Gln Leu Ser Thr Met Asp Phe
65                  70                  75                  80

Ala Pro Ser Phe Gln Met Gly His Pro Ile Ala Phe Asp Phe Ala Glu
                85                  90                  95

Arg Leu Ala Glu Ile Ala Pro Gly Pro Ala Gly Ala Lys Leu Asp Arg
            100                 105                 110

Val Phe Phe Thr Gly Ser Gly Ser Glu Ser Val Asp Thr Ala Leu Lys
        115                 120                 125

Met Ala Leu Ala Tyr Gln Arg Ser Ile Gly Gln Gly Thr Arg Thr Arg
130                 135                 140

Leu Ile Gly Arg Glu Arg Gly Tyr His Gly Val Gly Phe Gly Gly Ile
145                 150                 155                 160

Ser Val Gly Gly Ile Val Asn Asn Arg Arg Val Phe Pro Gln Leu Pro
                165                 170                 175

Gly Ser Asp His Leu Arg His Thr His Asp Pro Ala Lys Asn Ala Phe
            180                 185                 190

Val Lys Gly Gln Pro Glu His Gly Ala Glu Leu Ala Asp Asp Leu Glu
        195                 200                 205

Arg Leu Val Ala Leu His Gly Ala Glu Thr Ile Ala Ala Cys Ile Val
    210                 215                 220

Glu Pro Val Ala Gly Ser Thr Gly Val Leu Ile Pro Pro Lys Gly Tyr

```
                225                 230                 235                 240
Leu Glu Arg Leu Arg Ala Ile Cys Asp Lys His Gly Ile Leu Leu Ile
                245                 250                 255

Phe Asp Glu Val Ile Thr Gly Phe Gly Arg Leu Gly Ala Ala Phe Ala
                260                 265                 270

Thr Asp Tyr Phe Gly Val Thr Pro Asp Ile Val Thr Ala Lys Gly
                275                 280                 285

Leu Thr Asn Gly Ala Ile Pro Met Gly Ala Val Phe Ala Ser Arg Lys
                290                 295                 300

Val His Asp Ala Leu Met His Gly Pro Glu Gly Gln Ile Glu Leu Phe
305                 310                 315                 320

His Gly Tyr Thr Tyr Ser Gly His Pro Ala Ala Cys Ala Ala Gly Ile
                325                 330                 335

Ala Thr Leu Asp Ile Tyr Arg Asp Glu Gly Leu Met Thr Arg Ala Ala
                340                 345                 350

Glu Ile Glu Gly Asp Trp His Glu Ala Met His Ser Met Lys Gly Leu
                355                 360                 365

Pro His Val Ile Asp Ile Arg Thr Ile Gly Leu Ile Ala Gly Ile Glu
370                 375                 380

Leu Gln Ser Arg Asp Gly Ala Pro Gly Ala Arg Ala Tyr Asp Val Phe
385                 390                 395                 400

Val Asp Cys Phe Glu Arg Gly Leu Leu Ile Arg Val Thr Gly Asp Ile
                405                 410                 415

Ile Ala Phe Ser Pro Pro Leu Ile Ala Glu Lys Gln His Phe Gly Glu
                420                 425                 430

Ile Val Ser Ile Leu Ala Asp Ala Leu Lys Arg Val Lys
                435                 440                 445

<210> SEQ ID NO 59
<211> LENGTH: 461
<212> TYPE: PRT
<213> ORGANISM: Sinorhizobium meliloti

<400> SEQUENCE: 59

Met Asn Asp Arg Pro Asn Ser Leu His Ala Leu Asp Lys Gln Ser Leu
1               5                   10                  15

Val His Pro Tyr Thr Asn Leu Ala Val His Gln Glu Thr Gly Pro His
                20                  25                  30

Val Ile Thr Gly Gly Asp Gly Ile Tyr Val Val Asp Asp Glu Gly Lys
            35                  40                  45

Arg Tyr Ile Glu Gly Leu Ala Gly Leu Phe Cys Ala Gly Leu Gly Phe
        50                  55                  60

Ser Glu Gln Arg Leu Val Glu Ala Ala Thr Arg Gln Leu Lys Thr Met
65                  70                  75                  80

Pro Phe Tyr His Ser Phe Ala His Lys Ser Thr Glu Pro Gly Ile Arg
                85                  90                  95

Leu Ala Glu Lys Leu Leu Ser Ile Ala Pro Val Pro Met Ser Lys Val
                100                 105                 110

Phe Phe Ala Gly Ser Gly Ser Glu Ala Asn Asp Thr Ala Ile Lys Leu
            115                 120                 125

Ile Trp Tyr Tyr Asn Asn Ala Leu Gly Arg Pro Glu Lys Lys Lys Ile
        130                 135                 140

Ile Ser Arg Arg Lys Ala Tyr His Gly Val Thr Val Ala Thr Ala Ser
145                 150                 155                 160
```

```
Leu Thr Gly Leu Pro Phe Asn His Arg Asp Phe Asp Leu Pro Ile Ala
            165                 170                 175

Asn Ile Leu His Thr Asp Cys Pro His Tyr Trp Arg Phe Ala Glu Thr
        180                 185                 190

Gly Glu Thr Glu Glu Asp Phe Ala Thr Arg Met Ala Asn Asn Leu Glu
            195                 200                 205

Ala Ile Ile Leu Glu Glu Gly Pro Glu Thr Ile Ala Ala Phe Phe Ala
    210                 215                 220

Glu Pro Val Met Val Ser Gly Val Ile Thr Pro Lys Thr Tyr
225                 230                 235                 240

Phe Glu Lys Val Gln Ala Val Leu Arg Lys Tyr Asp Ile Leu Leu Ile
                245                 250                 255

Ala Asp Glu Val Ile Cys Gly Phe Gly Arg Thr Gly Asn Met Phe Gly
            260                 265                 270

Ser Glu Thr Tyr Gly Leu Lys Pro Asp Met Ile Ser Cys Ala Lys Gln
        275                 280                 285

Leu Ser Ala Ala Tyr Met Pro Ile Ser Ala Leu Met Ile Asn Ala Lys
    290                 295                 300

Ile Ala Asp Ala Leu Val Asp Gln Ser Arg Lys Ile Gly Thr Phe Ser
305                 310                 315                 320

His Gly Phe Thr Tyr Gly Gly His Pro Val Ala Ala Val Ala Leu
                325                 330                 335

Glu Ala Leu Thr Ile Tyr Glu Ile Asp Ile Val Gly His Val Arg
            340                 345                 350

Ser Val Ala Pro Ala Phe Gln Asp Arg Val Arg Lys Leu Gly Glu His
        355                 360                 365

Pro Leu Ile Gly Glu Ala Arg Gly Val Gly Leu Val Ala Gly Leu Glu
    370                 375                 380

Phe Val Lys Asp Lys Ala Thr Arg Glu Asn Phe Pro Pro Ala Trp Gln
385                 390                 395                 400

Val Ala Asn Gln Ala Gly Lys Phe Ala Thr Ala Arg Gly Val Leu Thr
                405                 410                 415

Arg Gly Leu Gly Asp Met Val Ser Leu Cys Pro Ala Met Ile Ile Asp
            420                 425                 430

Asp Glu Gln Ile Asp Asp Leu Met Thr Arg Met Gly Leu Ala Leu Asp
        435                 440                 445

Asp Thr Leu Ala Trp Ala Arg Ala Gln Gly His Val Gly
    450                 455                 460

<210> SEQ ID NO 60
<211> LENGTH: 458
<212> TYPE: PRT
<213> ORGANISM: Sinorhizobium meliloti

<400> SEQUENCE: 60

Met Leu Glu Arg Ser Asn Glu Leu Thr Ala Trp Asp Arg Asp His Phe
1               5                   10                  15

Phe His Pro Ser Thr His Met Gly Met His Ala Arg Gly Glu Thr Pro
            20                  25                  30

Thr Arg Val Ile Gly Gly Gly Glu Gly Val Tyr Ile Thr Asp Ile Ser
        35                  40                  45

Gly Lys Arg Ser Leu Asp Ala Phe Ala Gly Leu Tyr Cys Val Asn Val
    50                  55                  60

Gly Tyr Gly Arg Gln Lys Ile Ala Asp Ala Ile Ala Glu Gln Ala Lys
65                  70                  75                  80
```

```
Asn Leu Ala Tyr Tyr His Ala Tyr Val Gly His Gly Thr Glu Ala Ser
             85                  90                  95

Ile Arg Leu Ser Lys Met Ile Ile Asp Arg Ala Pro Glu Gly Met Ser
            100                 105                 110

Arg Val Tyr Phe Gly Leu Ser Gly Ser Asp Ala Asn Glu Thr Asn Ile
        115                 120                 125

Lys Leu Ile Trp Tyr Tyr Asn Asn Ile Leu Gly Arg Pro Glu Lys Lys
    130                 135                 140

Lys Ile Ile Ser Arg Trp Arg Gly Tyr His Gly Ser Gly Val Met Thr
145                 150                 155                 160

Gly Ser Leu Thr Gly Leu His Leu Phe His Asn Ala Phe Asp Leu Pro
                165                 170                 175

Arg Ala Pro Ile Leu His Thr Glu Ala Pro Tyr Tyr Phe Arg Arg Pro
            180                 185                 190

Asp Arg Ser Met Ser Glu Glu Gln Phe Ser Gln Tyr Cys Ala Asp Lys
        195                 200                 205

Leu Glu Glu Met Ile Leu Ala Glu Gly Pro Asp Thr Val Ala Ala Phe
    210                 215                 220

Ile Gly Glu Pro Ile Leu Gly Thr Gly Gly Ile Val Pro Pro Pro Lys
225                 230                 235                 240

Gly Tyr Trp Glu Lys Ile Gln Ala Val Leu Gln Lys Tyr Asp Ile Leu
                245                 250                 255

Leu Val Ala Asp Glu Val Val Thr Gly Phe Gly Arg Leu Gly Thr Met
            260                 265                 270

Phe Gly Ser Asp His Tyr Gly Ile Lys Pro Asp Leu Ile Thr Ile Ala
        275                 280                 285

Lys Gly Leu Thr Ser Ala Tyr Ala Pro Leu Ser Gly Thr Ile Val Ser
    290                 295                 300

Asp Lys Leu Trp Gln Val Leu Val Lys Gly Ser Asp Glu Leu Gly Ala
305                 310                 315                 320

Ile Gly His Gly Trp Thr Tyr Ser Ala His Pro Ile Cys Ala Ala Ala
                325                 330                 335

Gly Ile Ala Asn Leu Glu Leu Ile Asp Glu Leu Gly Ile Val Glu Asn
            340                 345                 350

Ala Gly Ser Thr Gly Ala Tyr Phe Arg Ala Glu Leu Gln Lys Ala Val
        355                 360                 365

Gly Asp His Arg His Val Gly Glu Val Arg Gly Asp Gly Leu Met Ala
    370                 375                 380

Ala Ile Glu Phe Val Glu Asp Arg Asp Arg Ala Phe Phe Asp Pro
385                 390                 395                 400

Gly Arg Lys Val Gly Pro Gln Val Ala Ala Leu Leu Glu Arg Gly
                405                 410                 415

Val Ile Gly Arg Ala Met Pro Gln Gly Asp Ile Leu Gly Phe Ala Pro
            420                 425                 430

Pro Leu Cys Leu Thr Arg Asp Glu Ala Asp Ile Val Val Lys Ala Ala
        435                 440                 445

Ala Asp Thr Ile Gln Ser Val Leu Gly Arg
    450                 455

<210> SEQ ID NO 61
<211> LENGTH: 422
<212> TYPE: PRT
<213> ORGANISM: Sinorhizobium meliloti
```

```
<400> SEQUENCE: 61

Met Thr Ser Leu Thr Asp Arg Lys Asn Ala Ala Ile Ser Arg Gly Val
1               5                   10                  15

Gly Met Thr Thr Gln Val Tyr Ala Asp Arg Ala Glu Asn Ala Glu Ile
            20                  25                  30

Trp Asp Lys Glu Gly Asn Arg Tyr Ile Asp Phe Ala Ala Gly Ile Ala
            35                  40                  45

Val Val Asn Thr Gly His Arg His Pro Lys Val Ile Ala Ala Val Lys
    50                  55                  60

Ala Gln Leu Asp Arg Phe Thr His Thr Cys His Gln Val Val Pro Tyr
65                  70                  75                  80

Glu Asn Tyr Val His Leu Ala Glu Arg Leu Asn Ala Ile Val Pro Gly
                85                  90                  95

Asp Phe Ala Lys Lys Thr Ile Phe Val Thr Thr Gly Ala Glu Ala Val
            100                 105                 110

Glu Asn Ala Val Lys Ile Ala Arg Ala Ala Thr Gly Arg Gln Ala Val
            115                 120                 125

Val Ala Phe Gly Gly Phe His Gly Arg Thr Phe Met Gly Met Ala
130                 135                 140

Leu Thr Gly Lys Val Val Pro Tyr Lys Val Gly Phe Gly Ala Met Pro
145                 150                 155                 160

Ala Asp Val Phe His Ala Pro Phe Pro Ile Glu Leu His Gly Val Thr
                165                 170                 175

Val Glu Gln Ser Leu Ser Ala Leu Lys Lys Leu Phe Ala Ala Asp Val
            180                 185                 190

Asp Pro Ala Arg Val Ala Ala Ile Ile Ile Glu Pro Val Gln Gly Glu
            195                 200                 205

Gly Gly Phe Tyr Pro Val Pro Thr Ala Phe Met Lys Ala Leu Arg Glu
    210                 215                 220

Val Cys Asp Gln His Gly Ile Leu Leu Ile Ala Asp Glu Val Gln Thr
225                 230                 235                 240

Gly Phe Ala Arg Thr Gly Lys Leu Phe Ala Met Glu His His Gly Val
                245                 250                 255

Ala Pro Asp Leu Thr Thr Met Ala Lys Ser Leu Ala Gly Gly Phe Pro
            260                 265                 270

Leu Ala Ala Val Thr Gly Arg Ala Glu Ile Met Asp Ala Pro Gly Pro
            275                 280                 285

Gly Gly Leu Gly Gly Thr Tyr Gly Gly Asn Pro Leu Gly Ile Ala Ala
    290                 295                 300

Ala His Ala Val Leu Asp Val Ile Ala Glu Glu Asn Leu Cys Glu Arg
305                 310                 315                 320

Ala Asn Gln Leu Gly Asn Arg Leu Lys Gln Arg Leu Ala Ala Ile Arg
            325                 330                 335

Glu Lys Ala Pro Glu Ile Val Asp Ile Arg Gly Pro Gly Phe Met Asn
            340                 345                 350

Ala Val Glu Phe Asn Asp Val Arg Thr Asn Leu Pro Ser Ala Glu Phe
            355                 360                 365

Ala Asn Lys Val Arg Leu Leu Ala Leu Glu Lys Gly Leu Ile Leu Leu
            370                 375                 380

Thr Cys Gly Val His Gly Asn Val Ile Arg Phe Leu Ala Pro Ile Thr
385                 390                 395                 400

Ile Gln Asp Glu Val Phe Ala Glu Ala Leu Asp Thr Ile Glu Ala Ser
            405                 410                 415
```

Ile Leu Glu Ala Arg Gly
            420

<210> SEQ ID NO 62
<211> LENGTH: 464
<212> TYPE: PRT
<213> ORGANISM: Ruegeria pomeroyi ATCC 700808

<400> SEQUENCE: 62

Met Ala Thr Ile Thr Asn His Met Pro Thr Ala Glu Leu Gln Ala Leu
1               5                   10                  15

Asp Ala Ala His His Leu His Pro Phe Ser Ala Asn Asn Ala Leu Gly
            20                  25                  30

Glu Glu Gly Thr Arg Val Ile Thr Arg Ala Arg Gly Val Trp Leu Asn
        35                  40                  45

Asp Ser Glu Gly Glu Glu Ile Leu Asp Ala Met Ala Gly Leu Trp Cys
    50                  55                  60

Val Asn Ile Gly Tyr Gly Arg Asp Glu Leu Ala Glu Val Ala Ala Arg
65                  70                  75                  80

Gln Met Arg Glu Leu Pro Tyr Tyr Asn Thr Phe Phe Lys Thr Thr His
                85                  90                  95

Val Pro Ala Ile Ala Leu Ala Gln Lys Leu Ala Glu Leu Ala Pro Gly
            100                 105                 110

Asp Leu Asn His Val Phe Phe Ala Gly Gly Ser Glu Ala Asn Asp
        115                 120                 125

Thr Asn Ile Arg Met Val Arg Thr Tyr Trp Gln Asn Lys Gly Gln Pro
130                 135                 140

Glu Lys Thr Val Ile Ile Ser Arg Lys Asn Ala Tyr His Gly Ser Thr
145                 150                 155                 160

Val Ala Ser Ser Ala Leu Gly Gly Met Ala Gly Met His Ala Gln Ser
                165                 170                 175

Gly Leu Ile Pro Asp Val His His Ile Asn Gln Pro Asn Trp Trp Ala
            180                 185                 190

Glu Gly Gly Asp Met Asp Pro Glu Glu Phe Gly Leu Ala Arg Ala Arg
        195                 200                 205

Glu Leu Glu Glu Ala Ile Leu Glu Leu Gly Glu Asn Arg Val Ala Ala
    210                 215                 220

Phe Ile Ala Glu Pro Val Gln Gly Ala Gly Gly Val Ile Val Ala Pro
225                 230                 235                 240

Asp Ser Tyr Trp Pro Glu Ile Gln Arg Ile Cys Asp Lys Tyr Asp Ile
                245                 250                 255

Leu Leu Ile Ala Asp Glu Val Ile Cys Gly Phe Gly Arg Thr Gly Asn
            260                 265                 270

Trp Phe Gly Thr Gln Thr Met Gly Ile Arg Pro His Ile Met Thr Ile
        275                 280                 285

Ala Lys Gly Leu Ser Ser Gly Tyr Ala Pro Ile Gly Gly Ser Ile Val
    290                 295                 300

Cys Asp Glu Val Ala His Val Ile Gly Lys Asp Glu Phe Asn His Gly
305                 310                 315                 320

Tyr Thr Tyr Ser Gly His Pro Val Ala Ala Val Ala Leu Glu Asn
                325                 330                 335

Leu Arg Ile Leu Glu Glu Glu Asn Ile Leu Asp His Val Arg Asn Val
            340                 345                 350

Ala Ala Pro Tyr Leu Lys Glu Lys Trp Glu Ala Leu Thr Asp His Pro

```
            355                 360                 365
Leu Val Gly Glu Ala Lys Ile Val Gly Met Met Ala Ser Ile Ala Leu
                370                 375                 380
Thr Pro Asn Lys Ala Ser Arg Ala Lys Phe Ala Ser Glu Pro Gly Thr
385                 390                 395                 400
Ile Gly Tyr Ile Cys Arg Glu Arg Cys Phe Ala Asn Asn Leu Ile Met
                405                 410                 415
Arg His Val Gly Asp Arg Met Ile Ile Ser Pro Pro Leu Val Ile Thr
                420                 425                 430
Pro Ala Glu Ile Asp Glu Met Phe Val Arg Ile Arg Lys Ser Leu Asp
                435                 440                 445
Glu Ala Gln Ala Glu Ile Glu Lys Gln Gly Leu Met Lys Ser Ala Ala
                450                 455                 460
```

<210> SEQ ID NO 63
<211> LENGTH: 459
<212> TYPE: PRT
<213> ORGANISM: Rhizobium loti MAFF303099

<400> SEQUENCE: 63

```
Met Leu Asn Gln Ser Asn Glu Leu Asn Ala Trp Asp Arg Asp His Phe
1               5                   10                  15
Phe His Pro Ser Thr His Met Gly Thr His Ala Arg Gly Glu Ser Pro
                20                  25                  30
Thr Arg Ile Met Ala Gly Gly Glu Gly Val Thr Val Trp Asp Asn Asn
                35                  40                  45
Gly Arg Lys Ser Ile Asp Ala Phe Ala Gly Leu Tyr Cys Val Asn Val
50                  55                  60
Gly Tyr Gly Arg Gln Lys Ile Ala Asp Ala Ile Ala Thr Gln Ala Lys
65                  70                  75                  80
Asn Leu Ala Tyr Tyr His Ala Tyr Val Gly His Gly Thr Glu Ala Ser
                85                  90                  95
Ile Thr Leu Ala Lys Met Ile Ile Asp Arg Ala Pro Lys Gly Met Ser
                100                 105                 110
Arg Val Tyr Phe Gly Leu Ser Gly Ser Asp Ala Asn Glu Thr Asn Ile
                115                 120                 125
Lys Leu Ile Trp Tyr Tyr Asn Asn Val Leu Gly Arg Pro Glu Lys Lys
                130                 135                 140
Lys Ile Ile Ser Arg Trp Arg Gly Tyr His Gly Ser Gly Val Met Thr
145                 150                 155                 160
Gly Ser Leu Thr Gly Leu Asp Leu Phe His Asn Ala Phe Asp Leu Pro
                165                 170                 175
Arg Ala Pro Val Leu His Thr Glu Ala Pro Tyr Tyr Phe Arg Arg Thr
                180                 185                 190
Asp Arg Ser Met Ser Glu Glu Gln Phe Ser Gln His Cys Ala Asp Lys
                195                 200                 205
Leu Glu Glu Met Ile Leu Ala Glu Gly Pro Glu Thr Ile Ala Ala Phe
                210                 215                 220
Ile Gly Glu Pro Ile Leu Gly Thr Gly Gly Ile Val Pro Pro Ala
225                 230                 235                 240
Gly Tyr Trp Glu Lys Ile Gln Ala Val Leu Lys Lys Tyr Asp Val Leu
                245                 250                 255
Leu Val Ala Asp Glu Val Val Thr Gly Phe Gly Arg Leu Gly Thr Met
                260                 265                 270
```

Phe Gly Ser Asp His Tyr Gly Ile Lys Pro Asp Leu Ile Thr Ile Ala
275 280 285

Lys Gly Leu Thr Ser Ala Tyr Ala Pro Leu Ser Gly Val Ile Val Ala
290 295 300

Asp Arg Val Trp Gln Val Leu Val Gln Gly Ser Asp Lys Leu Gly Ser
305 310 315 320

Leu Gly His Gly Trp Thr Tyr Ser Ala His Pro Ile Cys Val Ala Ala
325 330 335

Gly Val Ala Asn Leu Glu Leu Ile Asp Glu Met Asp Leu Val Thr Asn
340 345 350

Ala Gly Glu Thr Gly Ala Tyr Phe Arg Ala Glu Leu Ala Lys Ala Val
355 360 365

Gly Gly His Lys Asn Val Gly Glu Val Arg Gly Asp Gly Met Leu Ala
370 375 380

Ala Val Glu Phe Val Ala Asp Lys Asp Asp Arg Val Phe Phe Asp Ala
385 390 395 400

Ser Gln Lys Ile Gly Pro Gln Val Ala Thr Ala Leu Ala Ala Ser Gly
405 410 415

Val Ile Gly Arg Ala Met Pro Gln Gly Asp Ile Leu Gly Phe Ala Pro
420 425 430

Pro Leu Cys Leu Thr Arg Glu Gln Ala Asp Ile Val Val Ser Lys Thr
435 440 445

Ala Asp Ala Val Lys Ser Val Phe Ala Asn Leu
450 455

<210> SEQ ID NO 64
<211> LENGTH: 310
<212> TYPE: PRT
<213> ORGANISM: Pseudomonas syringae pv. syringae

<400> SEQUENCE: 64

Met Ser Lys Lys Phe Ala Leu Thr Ala Glu Gln Arg Ala Ser Phe Glu
1 5 10 15

Lys Asn Gly Phe Ile Gly Pro Phe Asp Ala Tyr Ser Pro Glu Glu Met
20 25 30

Lys Glu Thr Trp Lys Arg Thr Arg Leu Arg Leu Leu Asp Arg Ser Ala
35 40 45

Ala Ala Tyr Gln Asp Leu Asp Ala Ile Ser Gly Gly Thr Asn Ile Ala
50 55 60

Asn Tyr Asp Arg His Leu Asp Asp Asp Phe Leu Ala Ser His Ile Cys
65 70 75 80

Arg Pro Glu Ile Cys Asp Arg Val Glu Ser Ile Leu Gly Pro Asn Val
85 90 95

Leu Cys Trp Arg Thr Glu Phe Phe Pro Lys Tyr Pro Gly Asp Glu Gly
100 105 110

Thr Asp Trp His Gln Ala Asp Thr Phe Ala Asn Ala Ser Gly Lys Pro
115 120 125

Gln Ile Ile Trp Pro Glu Asn Glu Glu Phe Gly Gly Thr Ile Thr Val
130 135 140

Trp Thr Ala Phe Thr Asp Ala Asn Ile Ala Asn Gly Cys Leu Gln Phe
145 150 155 160

Ile Pro Gly Thr Gln Asn Ser Met Asn Tyr Asp Glu Thr Lys Arg Met
165 170 175

Thr Tyr Glu Pro Asp Ala Asn Asn Ser Val Val Lys Asp Gly Val Arg
180 185 190

Arg Gly Phe Phe Gly Tyr Asp Tyr Arg Gln Leu Gln Ile Asp Glu Asn
            195                 200                 205

Trp Lys Pro Asp Glu Ala Ser Ala Val Pro Met Gln Met Lys Ala Gly
    210                 215                 220

Gln Phe Ile Ile Phe Trp Ser Thr Leu Met His Ala Ser Tyr Pro His
225                 230                 235                 240

Ser Gly Glu Ser Gln Glu Met Arg Met Gly Phe Ala Ser Arg Tyr Val
            245                 250                 255

Pro Ser Phe Val His Val Tyr Pro Asp Ser Asp His Ile Glu Glu Tyr
            260                 265                 270

Gly Gly Arg Ile Ser Leu Glu Lys Tyr Gly Ala Val Gln Val Ile Gly
            275                 280                 285

Asp Glu Thr Pro Glu Tyr Asn Arg Leu Val Thr His Thr Thr Arg Gly
            290                 295                 300

Lys Lys Phe Glu Ala Val
305                 310

<210> SEQ ID NO 65
<211> LENGTH: 467
<212> TYPE: PRT
<213> ORGANISM: Rhodobacter sphaeroides ATCC 17023

<400> SEQUENCE: 65

Met Thr Arg Asn Asp Ala Thr Asn Ala Ala Gly Ala Val Gly Ala Ala
1               5                   10                  15

Met Arg Asp His Ile Leu Leu Pro Ala Gln Glu Met Ala Lys Leu Gly
            20                  25                  30

Lys Ser Ala Gln Pro Val Leu Thr His Ala Glu Gly Ile Tyr Val His
            35                  40                  45

Thr Glu Asp Gly Arg Arg Leu Ile Asp Gly Pro Ala Gly Met Trp Cys
        50                  55                  60

Ala Gln Val Gly Tyr Gly Arg Arg Glu Ile Val Asp Ala Met Ala His
65                  70                  75                  80

Gln Ala Met Val Leu Pro Tyr Ala Ser Pro Trp Tyr Met Ala Thr Ser
            85                  90                  95

Pro Ala Ala Arg Leu Ala Glu Lys Ile Ala Thr Leu Thr Pro Gly Asp
            100                 105                 110

Leu Asn Arg Ile Phe Phe Thr Thr Gly Gly Ser Thr Ala Val Asp Ser
            115                 120                 125

Ala Leu Arg Phe Ser Glu Phe Tyr Asn Asn Val Leu Gly Arg Pro Gln
        130                 135                 140

Lys Lys Arg Ile Ile Val Arg Tyr Asp Gly Tyr His Gly Ser Thr Ala
145                 150                 155                 160

Leu Thr Ala Ala Cys Thr Gly Arg Thr Gly Asn Trp Pro Asn Phe Asp
            165                 170                 175

Ile Ala Gln Asp Arg Ile Ser Phe Leu Ser Ser Pro Asn Pro Arg His
            180                 185                 190

Ala Gly Asn Arg Ser Gln Glu Ala Phe Leu Asp Asp Leu Val Gln Glu
            195                 200                 205

Phe Glu Asp Arg Ile Glu Ser Leu Gly Pro Asp Thr Ile Ala Ala Phe
            210                 215                 220

Leu Ala Glu Pro Ile Leu Ala Ser Gly Gly Val Ile Ile Pro Pro Ala
225                 230                 235                 240

Gly Tyr His Ala Arg Phe Lys Ala Ile Cys Glu Lys His Asp Ile Leu

```
                        245                 250                 255
Tyr Ile Ser Asp Glu Val Val Thr Gly Phe Gly Arg Cys Gly Glu Trp
            260                 265                 270

Phe Ala Ser Glu Lys Val Phe Gly Val Val Pro Asp Ile Ile Thr Phe
            275                 280                 285

Ala Lys Gly Val Thr Ser Gly Tyr Val Pro Leu Gly Gly Leu Ala Ile
            290                 295                 300

Ser Glu Ala Val Leu Ala Arg Ile Ser Gly Glu Asn Ala Lys Gly Ser
305                 310                 315                 320

Trp Phe Thr Asn Gly Tyr Thr Tyr Ser Asn Gln Pro Val Ala Cys Ala
                325                 330                 335

Ala Ala Leu Ala Asn Ile Glu Leu Met Glu Arg Gly Ile Val Asp
                340                 345                 350

Gln Ala Arg Glu Met Ala Asp Tyr Phe Ala Ala Leu Ala Ser Leu
                355                 360                 365

Arg Asp Leu Pro Gly Val Ala Glu Thr Arg Ser Val Gly Leu Val Gly
370                 375                 380

Cys Val Gln Cys Leu Leu Asp Pro Thr Arg Ala Asp Gly Thr Ala Glu
385                 390                 395                 400

Asp Lys Ala Phe Thr Leu Lys Ile Asp Glu Arg Cys Phe Glu Leu Gly
                405                 410                 415

Leu Ile Val Arg Pro Leu Gly Asp Leu Cys Val Ile Ser Pro Pro Leu
                420                 425                 430

Ile Ile Ser Arg Ala Gln Ile Asp Glu Met Val Ala Ile Met Arg Gln
                435                 440                 445

Ala Ile Thr Glu Val Ser Ala Ala His Gly Leu Thr Ala Lys Glu Pro
            450                 455                 460

Ala Ala Val
465

<210> SEQ ID NO 66
<211> LENGTH: 1183
<212> TYPE: PRT
<213> ORGANISM: Mycobacterium abscessus DSM44196

<400> SEQUENCE: 66

Met Thr Ile Asp Ala Thr Ala Asp Asn Thr Lys Glu Ala Arg Arg Gln
1               5                   10                  15

Arg Leu Gly Asp Arg Ile Arg Arg Leu Phe Thr Asp Asp Glu Gln Phe
                20                  25                  30

Arg Ala Ala Lys Pro Asp Thr Ala Val Asp Thr Ala Val Ala Gln Pro
            35                  40                  45

Gly Leu Arg Leu Ala Gln Val Val Ala Thr Ile Met Asn Gly Tyr Ala
        50                  55                  60

Asp Arg Pro Ala Leu Gly His Arg Val Gln Glu Leu Val Ala Asp Ala
65                  70                  75                  80

Ala Gly Arg Ser Thr Leu Arg Pro Leu Pro Glu Phe Glu Thr Val Thr
                85                  90                  95

Tyr Gly Glu Leu Trp Gly Met Ala Arg Ala Leu Ala Ser Thr Trp Tyr
            100                 105                 110

His Asp Pro Ala Ala Pro Val Arg Ala Gly Asp Phe Val Ala Met Leu
        115                 120                 125

Gly Phe Thr Ser Val Asp Tyr Thr Ala Val Asp Leu Ala Cys Ile His
    130                 135                 140
```

-continued

```
Leu Gly Ala Val Ala Val Pro Leu Gln Thr Ser Ala Ser Ala Ser Asn
145                 150                 155                 160

Trp Thr Ala Ile Leu Ala Glu Ser Glu Pro Ala Val Leu Ala Val Ser
                165                 170                 175

Ala Glu Leu Leu Asp Thr Ala Met Glu Ser Val Leu Ala Thr Pro Ser
            180                 185                 190

Leu Arg His Ile Thr Val Phe Asp Tyr His Pro Gly Val Asp Val Gln
        195                 200                 205

Arg Glu Ser Leu Glu Ser Ala Gln His Arg Ile Ala Glu Ala Gly Leu
    210                 215                 220

Pro Ile Ser Val Asp Pro Ile Pro Leu Ala Ile Gly His Gly Arg Ala
225                 230                 235                 240

Leu Pro Asp Ala Pro Leu Phe Thr Ala Glu Glu Gly Thr Asp Pro Leu
                245                 250                 255

Ala Leu Val Ile Tyr Thr Ser Gly Ser Thr Gly Thr Pro Lys Gly Ala
            260                 265                 270

Thr Tyr Ser Glu Lys Met Val Ala Lys Pro Trp Leu Arg Ala Asp Thr
        275                 280                 285

Leu Ser Ser Lys Ala Glu Ile Pro Leu Ile Asn Leu Asn Phe Met Pro
    290                 295                 300

Met Ser His Val Met Gly Arg Gly Ser Leu Val Thr Ala Leu Ala Cys
305                 310                 315                 320

Gly Gly Leu Ala Tyr Phe Ala Ala Ser Ser Asp Met Ser Thr Leu Phe
                325                 330                 335

Glu Asp Ile Thr Leu Thr Arg Pro Thr Val Val Thr Leu Val Pro Arg
            340                 345                 350

Val Cys Asp Met Leu Phe Gln Arg Tyr Arg Asn Glu Val Glu Arg Arg
        355                 360                 365

Thr Gly Leu Asp Pro Ala Ala Asp Leu Ala Thr Leu Asp Ala Asp Val
    370                 375                 380

Lys Thr Asp Ile Arg Glu Asn Leu Phe Gly Gly Arg Val Leu Thr Ile
385                 390                 395                 400

Val Cys Gly Ser Ala Pro Leu Ser Glu Glu Leu Ala Ala Phe Ile Glu
                405                 410                 415

Ser Cys Leu Asp Ala Arg Ile Thr Asp Gly Tyr Gly Ser Thr Glu Ala
            420                 425                 430

Gly Val Ile Val Arg Asn Gly Arg Ile Gln Arg Pro Pro Val Ile Asp
        435                 440                 445

Tyr Lys Leu Val Asp Val Pro Glu Leu Gly Tyr Phe Ser Thr Asp Lys
    450                 455                 460

Pro His Pro Arg Gly Glu Leu Leu Val Lys Ala Glu Ser Val Phe Gly
465                 470                 475                 480

Gly Tyr Phe Lys Arg Pro Asp Val Thr Ala Asp Val Phe Asp Pro Asp
                485                 490                 495

Gly Tyr Tyr Lys Thr Gly Asp Ile Val Ala Glu Leu Glu Pro Asp Lys
            500                 505                 510

Ile Gln Ile Val Asp Arg Arg Asn Asn Val Ile Lys Leu Ser Gln Gly
        515                 520                 525

Glu Phe Val Ala Ile Ala Asn Leu Glu Ala Glu Phe Ala Asn Ser Pro
    530                 535                 540

Leu Val His Gln Ile Cys Val Tyr Gly Ser Ser Glu Arg Ser Tyr Leu
545                 550                 555                 560

Leu Ala Val Val Val Pro Thr Ala Glu Ala Tyr Glu Gln Ser Gly Gly
```

-continued

```
                565                 570                 575
Asp Glu Asp Leu Leu Lys Arg Leu Ile Ala Asp Ser Leu Ala Gln Val
            580                 585                 590
Ala Arg Glu Ala Gln Leu Gln Ser Tyr Glu Val Pro Arg Asp Phe Leu
            595                 600                 605
Leu Glu Thr Glu Pro Phe Thr Ala Ala Asn Gly Leu Leu Thr Gly Ile
            610                 615                 620
Ala Lys Leu Ala Arg Pro Lys Leu His Glu Lys Tyr Gly Ala Arg Leu
625                 630                 635                 640
Glu Gln Leu Tyr Ser Asp Ile Ala Ala Gln Ala Leu Glu Leu Gln
                    645                 650                 655
Ala Leu His Ser Ala Gly His Glu Asp Lys Pro Val Leu Asp Thr Val
                660                 665                 670
Gln Arg Ala Val Thr Ala Leu Leu Gly Leu Ser Ala Ala Glu Val Ser
                675                 680                 685
Pro Asp Ala His Phe Ile Asp Leu Gly Gly Asp Ser Leu Ser Ala Leu
            690                 695                 700
Ala Phe Ser Asp Leu Leu Arg Asp Ile Phe Thr Val Glu Val Pro Val
705                 710                 715                 720
Gly Asp Ile Val Ser Ala Ala Asn Asp Leu Thr Ala Ile Ala Arg Ile
                    725                 730                 735
Val Glu Arg His Arg Glu Ala Asp Gly His Ser Val Thr Pro Thr Ala
                740                 745                 750
Glu Ser Val His Gly Ala Gly His Arg Glu Ile Arg Ala Ala Asp Leu
                755                 760                 765
Thr Leu Asp Lys Phe Ile Asp Ala Asp Thr Leu Arg Ala Ala Pro Ala
770                 775                 780
Leu Ser Thr Phe Thr Gly Thr Pro His Thr Val Leu Leu Thr Gly Ala
785                 790                 795                 800
Asn Gly Tyr Leu Gly Arg Phe Leu Ala Leu Glu Trp Leu Glu Arg Leu
                    805                 810                 815
Asp Lys Thr Asp Gly Lys Leu Ile Ala Ile Val Arg Gly Lys Asn Ala
                820                 825                 830
Glu Ala Ala Tyr Arg Arg Leu Glu Glu Ala Phe Asp Thr Gly Asp Thr
            835                 840                 845
Gln Leu Leu Ala His Phe Arg Ser Leu Ala Asp Lys His Leu Glu Val
            850                 855                 860
Leu Ala Gly Asp Ile Gly Asp Pro Asn Leu Gly Leu Asp Ala Asp Thr
865                 870                 875                 880
Trp Gln Arg Leu Ala Glu Thr Val Asp Val Ile Val His Pro Ala Ala
                    885                 890                 895
Leu Val Asn His Val Leu Pro Tyr Ser Gln Leu Phe Gly Pro Asn Val
                900                 905                 910
Val Gly Thr Ala Glu Ile Ile Lys Leu Ala Leu Thr Thr Lys Ile Lys
                915                 920                 925
Pro Ile Thr Tyr Leu Ser Thr Val Ala Val Ala Ile Ser Val Asp Pro
            930                 935                 940
Lys Val Phe Asp Glu Asp Ser Asp Ile Arg Thr Ile Ser Ala Val Arg
945                 950                 955                 960
Pro Ile Asn Asp Gly Tyr Ala Asn Gly Tyr Gly Asn Ala Lys Trp Ala
                    965                 970                 975
Gly Glu Val Leu Leu Arg Glu Ala His Asp Leu Cys Gly Leu Pro Val
                980                 985                 990
```

```
Ala Val Phe Arg Ser Asp Met Ile Leu Ala His Ser Arg Tyr Thr Gly
            995                 1000                1005

Gln Leu Asn Val Pro Asp Gln Phe Thr Arg Leu Ile Leu Ser Leu
        1010                1015                1020

Ile Ala Thr Gly Val Ala Pro Gly Ser Phe Tyr Gln Ala His Ala
        1025                1030                1035

Thr Gly Glu Arg Pro Leu Ala His Tyr Asp Gly Leu Pro Ala Asp
        1040                1045                1050

Phe Thr Ala Ser Ala Ile Thr Ala Leu Gly Pro Ile Glu Glu Phe
        1055                1060                1065

His Thr Tyr Asp Ser Val Asn Pro His Ala Asp Gly Ile Ser Leu
        1070                1075                1080

Asp Asn Phe Val Asp Trp Leu Ile Glu Ala Gly Tyr Pro Ile Ala
        1085                1090                1095

Arg Ile Asp Asn Tyr Thr Glu Trp Phe Thr Arg Phe Asp Thr Ala
        1100                1105                1110

Ile Arg Ser Leu Pro Glu Lys Gln Lys Gln His Ser Leu Leu Pro
        1115                1120                1125

Leu Leu His Ala Tyr Arg His Pro Gln His Pro His Asn Gly Ala
        1130                1135                1140

Phe Leu Pro Ala Ile Arg Phe Ser Glu Gly Val Gln Ala His Leu
        1145                1150                1155

Asn Ala Asp Ile Pro His Leu Thr Arg Glu Leu Ile Ala Lys Tyr
        1160                1165                1170

Ala Ala Asp Leu Lys Gln Leu Gly Leu Leu
        1175                1180

<210> SEQ ID NO 67
<211> LENGTH: 1163
<212> TYPE: PRT
<213> ORGANISM: Mycobacterium abscessus DSM44196

<400> SEQUENCE: 67

Met Thr Ala Gly Ala Ala Ala Arg Val Ala Lys Leu Phe Glu Ser Asp
1               5                   10                  15

Pro Gln Phe Arg Ala Ala Met Pro Asp Pro Ala Val Met Asp Ser Leu
            20                  25                  30

Leu Ala Pro Gly Leu Arg Leu Ser Gln Val Leu His Ala Leu Leu Ser
        35                  40                  45

Gly Tyr Ala Glu Arg Pro Val Met Gly Phe Arg Ser Arg Glu Ser Val
    50                  55                  60

Val Asp Thr Ala Thr Gly Arg Thr Val Asp Arg Leu Leu Pro Ala Phe
65                  70                  75                  80

Glu Thr Ile Thr Tyr Gly Gln Leu Leu Glu Asp Ile Ser Ala Ile Leu
                85                  90                  95

Ala Glu Trp Gln His Gly Asp Ile Pro Met Gly Ala Gly Asp Phe Ile
            100                 105                 110

Ala Thr Ile Gly Phe Ser Ser Pro Asp Tyr Val Thr Leu Asp Leu Ala
        115                 120                 125

Thr Leu Met Asn Gly Ser Val Ser Ile Pro Leu Gln His Asn Thr Ser
    130                 135                 140

Val Ala Gln Leu Arg Met Met Leu Glu Glu Thr Ser Pro Arg Leu Val
145                 150                 155                 160

Ala Ala Ser Ala Asp Cys Leu Asp Leu Ala Val Glu Ala Ala Val Gly
```

```
                    165                 170                 175
Leu Thr Asp Leu Arg Val Val Phe Asp Tyr Arg Ala Glu Thr
                180                 185                 190
Asp Asp His Arg Glu Lys Leu Ala Thr Ala Arg Glu Arg Leu His Ala
                195                 200                 205
Ala Gly Met Asp Val Val Glu Pro Leu Ala Glu Val Ile Gly Arg
            210                 215                 220
Gly Arg Asp Leu Pro Glu Pro Val Leu Tyr Thr Ala Gly Asp Gln
225                 230                 235                 240
Arg Thr Ala Leu Ile Met Tyr Thr Ser Gly Ser Thr Gly Ala Pro Lys
                    245                 250                 255
Gly Ala Met Phe Thr Glu Trp Thr Val Thr Arg Phe Trp Ser Ser Gly
                260                 265                 270
Ala Ala Pro Asn Arg Asp Thr Pro Ile Ile Asn Val Asn Phe Leu Pro
                275                 280                 285
Leu Asn His Leu Ala Gly Arg Val Gly Leu Leu Thr Ala Phe Ile Pro
                290                 295                 300
Gly Gly Thr Cys Tyr Phe Val Pro Glu Ser Asp Leu Ser Thr Leu Phe
305                 310                 315                 320
Glu Asp Trp Gln Leu Ala Arg Pro Thr His Met Gly Val Val Pro Arg
                    325                 330                 335
Val Val Asp Met Leu Phe Gln His Tyr Gln Thr Arg Val Asp Ala Leu
                340                 345                 350
Met Ala Gly Gly Thr Asp Val Asp Thr Ala Asp Arg Leu Ala Lys Thr
                355                 360                 365
Glu Leu Arg Glu Asp Val Leu Gly Gly Arg Val Val Ala Gly Met Leu
370                 375                 380
Ala Thr Ala Pro Leu Ser Pro Glu Met Lys Ala Phe Leu Glu Ser Ser
385                 390                 395                 400
Leu Asp Phe His Leu Leu Asp Leu Tyr Gly Leu Thr Glu Val Gly Gly
                    405                 410                 415
Val Phe Arg Asp Gly Lys Ile Ser Arg Pro Pro Val Leu Asp Tyr Lys
                420                 425                 430
Leu Val Asp Val Pro Glu Leu Gly Tyr Tyr Thr Thr Asp Lys Pro His
                435                 440                 445
Pro Arg Gly Glu Leu Leu Val Lys Ser Ala Thr Ala Thr Pro Gly Tyr
        450                 455                 460
Tyr Lys Arg Pro Asp Val Thr Ala Glu Val Phe Asp Ala Asp Gly Tyr
465                 470                 475                 480
Tyr Arg Thr Gly Asp Val Met Ala Glu Val Ala Pro Asp Gln Leu Val
                    485                 490                 495
Tyr Val Asp Arg Arg Asn Asn Val Ile Lys Leu Ala Gln Gly Glu Phe
                500                 505                 510
Val Ala Val Ala Asn Leu Glu Thr Val Tyr Val Gly Ala Pro Leu Val
                515                 520                 525
Arg Gln Ile Phe Val Tyr Gly Asn Ser Glu Arg Ala Tyr Leu Leu Ala
                530                 535                 540
Val Val Val Pro Thr Glu Glu Ala Leu Arg Ala His Pro Asp Pro Val
545                 550                 555                 560
Glu Leu Lys Asn Ser Ile Arg Glu Ser Leu Gln Arg Thr Ala Arg Ser
                    565                 570                 575
Asn His Leu His Ser Tyr Glu Leu Pro Ala Asp Phe Ile Ile Glu Thr
                580                 585                 590
```

```
Thr Pro Phe Thr Ile Glu Ser Gly Met Leu Ala Ala Val Gly Lys Pro
        595                 600                 605

Ile Arg Pro Lys Met Ile Glu His Tyr Gly Asp Arg Leu Glu Gln Leu
610                 615                 620

Tyr Val Asp Leu Ala Glu Ala Arg Val Gln Glu Leu Arg Gln Leu Arg
625                 630                 635                 640

Asp Thr Ala Gln Gln Arg Pro Val Leu Asp Thr Val Thr Glu Ala Ala
                645                 650                 655

Gln Ala Leu Leu Gly Met Ser Ala Asp Ala Val Arg Pro Asp His His
            660                 665                 670

Phe Ile Asp Leu Gly Gly Asp Ser Leu Ser Ala Leu Thr Phe Ser Asn
        675                 680                 685

Leu Leu Arg Asp Leu Phe Asp Val Glu Val Pro Val Gly Val Ile Thr
        690                 695                 700

Gly Pro Ala Ala Asp Leu Arg Lys Leu Ala Ala Tyr Ile Gln His Glu
705                 710                 715                 720

Arg Glu His Ser Thr Ala Thr Ala Ala Ser Val His Gly Leu Asp Thr
                725                 730                 735

Thr Val Ile Ser Ala Thr Glu Leu Thr Leu Asp Lys Phe Ile Asp Ala
            740                 745                 750

Glu Thr Leu His Asn Ala Ser Gln Leu Asp Val Pro Ala Gly Ala Val
        755                 760                 765

Ala Thr Val Leu Leu Thr Gly Ala Asn Gly Tyr Leu Gly Arg Phe Leu
        770                 775                 780

Cys Leu Glu Trp Leu Gln Arg Leu Ser Gln Thr Gly Gly Gln Leu Ile
785                 790                 795                 800

Cys Leu Val Arg Gly Asp Asn Ala Asp Gln Ala Leu Ala Arg Leu Val
                805                 810                 815

Ala Ala Tyr Gly Asp Thr Asp Arg Thr Leu Leu Glu Glu Phe His Thr
            820                 825                 830

Leu Ala Arg Arg His Leu Arg Val Ile Ala Ala Asp Ile Ala Gln Pro
        835                 840                 845

Arg Phe Gly Val Asp Asp Ala Thr Trp Glu Gln Leu Ala Arg Asp Val
850                 855                 860

Asp Lys Ile Val His Pro Ala Leu Val Asn His Val Leu Pro Tyr
865                 870                 875                 880

Asn Gln Leu Phe Gly Pro Asn Val Phe Gly Thr Ala Glu Val Ile Arg
            885                 890                 895

Leu Ala Leu Thr Thr Arg Ile Lys Pro Val Thr Tyr Leu Ser Thr Met
        900                 905                 910

Ala Val Ala Met Thr Val Pro Asp Phe Asp Glu Asp Gly Asp Ile Arg
        915                 920                 925

Thr Val Ser Pro Thr Arg His Ile Asp Pro Gly Tyr Ala Asn Gly Tyr
930                 935                 940

Ala Asn Ser Lys Trp Ala Gly Glu Val Leu Leu Arg Glu Ala His Asp
945                 950                 955                 960

Ile Cys Gly Leu Pro Val Ser Val Phe Arg Ser Asp Met Ile Leu Thr
                965                 970                 975

His Arg Arg Tyr Ser Gly Gln Leu Asn Val Thr Asp Ala Phe Thr Arg
            980                 985                 990

Met Leu Leu Ser Leu Val Leu Thr  Gly Ile Ala Pro Arg  Ser Phe Tyr
        995                 1000                1005
```

-continued

```
Gln Gly  Asp Gly Ser Gly Ala  Arg Pro Arg Ala His  Tyr Glu Gly
    1010                1015                1020

Leu Pro  Val Asp Phe Val Thr  Glu Ala Ile Thr Ser  Leu Gly Leu
    1025                1030                1035

Ser Ser  Ser Glu Gly Phe Arg  Ser Tyr Asp Val Met  Asn Pro His
    1040                1045                1050

Asp Asp  Gly Ile Ser Val Asp  Thr Phe Val Asp Trp  Leu Met Glu
    1055                1060                1065

Asp Gly  His Ser Ile Asp Ile  Ile Asp Asn Tyr Asp  Glu Trp Leu
    1070                1075                1080

Ser Arg  Phe Glu Thr Ala Leu  Arg Gly Leu Pro Asp  Glu Gln Arg
    1085                1090                1095

Arg Ala  Ser Val Leu Pro Leu  Leu Asp Ala Tyr Arg  Ile Pro Gly
    1100                1105                1110

Asn Pro  Arg Arg Ala Ala Ala  Thr Pro Asn His Val  Phe Arg Lys
    1115                1120                1125

Ala Val  Gln Glu Asn Asn Ile  Gly Gly Asp Gly Ala  Asp Ile Pro
    1130                1135                1140

Gln Ile  Asp Arg Ala Leu Ile  Ala Lys Tyr Ile Ala  Asp Leu Arg
    1145                1150                1155

Ala His  Arg Leu Leu
    1160

<210> SEQ ID NO 68
<211> LENGTH: 1174
<212> TYPE: PRT
<213> ORGANISM: Mycobacterium marinum ATCC BAA-535

<400> SEQUENCE: 68

Met Ser Pro Ile Thr Arg Glu Glu Arg Leu Glu Arg Arg Ile Gln Asp
1               5                   10                  15

Leu Tyr Ala Asn Asp Pro Gln Phe Ala Ala Ala Lys Pro Ala Thr Ala
            20                  25                  30

Ile Thr Ala Ala Ile Glu Arg Pro Gly Leu Pro Leu Pro Gln Ile Ile
        35                  40                  45

Glu Thr Val Met Thr Gly Tyr Ala Asp Arg Pro Ala Leu Ala Gln Arg
    50                  55                  60

Ser Val Glu Phe Val Thr Asp Ala Gly Thr Gly His Thr Thr Leu Arg
65                  70                  75                  80

Leu Leu Pro His Phe Glu Thr Ile Ser Tyr Gly Glu Leu Trp Asp Arg
                85                  90                  95

Ile Ser Ala Leu Ala Asp Val Leu Ser Thr Glu Gln Thr Val Lys Pro
            100                 105                 110

Gly Asp Arg Val Cys Leu Leu Gly Phe Asn Ser Val Asp Tyr Ala Thr
        115                 120                 125

Ile Asp Met Thr Leu Ala Arg Leu Gly Ala Val Ala Val Pro Leu Gln
    130                 135                 140

Thr Ser Ala Ala Ile Thr Gln Leu Gln Pro Ile Val Ala Glu Thr Gln
145                 150                 155                 160

Pro Thr Met Ile Ala Ala Ser Val Asp Ala Leu Ala Asp Ala Thr Glu
                165                 170                 175

Leu Ala Leu Ser Gly Gln Thr Ala Thr Arg Val Leu Val Phe Asp His
            180                 185                 190

His Arg Gln Val Asp Ala His Arg Ala Ala Val Glu Ser Ala Arg Glu
        195                 200                 205
```

```
Arg Leu Ala Gly Ser Ala Val Glu Thr Leu Ala Glu Ala Ile Ala
    210                 215                 220

Arg Gly Asp Val Pro Arg Gly Ala Ser Ala Gly Ser Ala Pro Gly Thr
225                 230                 235                 240

Asp Val Ser Asp Ser Leu Ala Leu Leu Ile Tyr Thr Ser Gly Ser
                245                 250                 255

Thr Gly Ala Pro Lys Gly Ala Met Tyr Pro Arg Arg Asn Val Ala Thr
                260                 265                 270

Phe Trp Arg Lys Arg Thr Trp Phe Glu Gly Gly Tyr Glu Pro Ser Ile
            275                 280                 285

Thr Leu Asn Phe Met Pro Met Ser His Val Met Gly Arg Gln Ile Leu
        290                 295                 300

Tyr Gly Thr Leu Cys Asn Gly Gly Thr Ala Tyr Phe Val Ala Lys Ser
305                 310                 315                 320

Asp Leu Ser Thr Leu Phe Glu Asp Leu Ala Leu Val Arg Pro Thr Glu
                325                 330                 335

Leu Thr Phe Val Pro Arg Val Trp Asp Met Val Phe Asp Glu Phe Gln
                340                 345                 350

Ser Glu Val Asp Arg Arg Leu Val Asp Gly Ala Asp Arg Val Ala Leu
            355                 360                 365

Glu Ala Gln Val Lys Ala Glu Ile Arg Asn Asp Val Leu Gly Gly Arg
370                 375                 380

Tyr Thr Ser Ala Leu Thr Gly Ser Ala Pro Ile Ser Asp Glu Met Lys
385                 390                 395                 400

Ala Trp Val Glu Glu Leu Leu Asp Met His Leu Val Glu Gly Tyr Gly
                405                 410                 415

Ser Thr Glu Ala Gly Met Ile Leu Ile Asp Gly Ala Ile Arg Arg Pro
            420                 425                 430

Ala Val Leu Asp Tyr Lys Leu Val Asp Val Pro Asp Leu Gly Tyr Phe
                435                 440                 445

Leu Thr Asp Arg Pro His Pro Arg Gly Glu Leu Leu Val Lys Thr Asp
    450                 455                 460

Ser Leu Phe Pro Gly Tyr Tyr Gln Arg Ala Glu Val Thr Ala Asp Val
465                 470                 475                 480

Phe Asp Ala Asp Gly Phe Tyr Arg Thr Gly Asp Ile Met Ala Glu Val
                485                 490                 495

Gly Pro Glu Gln Phe Val Tyr Leu Asp Arg Arg Asn Asn Val Leu Lys
                500                 505                 510

Leu Ser Gln Gly Glu Phe Val Thr Val Ser Lys Leu Glu Ala Val Phe
            515                 520                 525

Gly Asp Ser Pro Leu Val Arg Gln Ile Tyr Ile Tyr Gly Asn Ser Ala
    530                 535                 540

Arg Ala Tyr Leu Leu Ala Val Ile Val Pro Thr Gln Glu Ala Leu Asp
545                 550                 555                 560

Ala Val Pro Val Glu Glu Leu Lys Ala Arg Leu Gly Asp Ser Leu Gln
                565                 570                 575

Glu Val Ala Lys Ala Ala Gly Leu Gln Ser Tyr Glu Ile Pro Arg Asp
            580                 585                 590

Phe Ile Ile Glu Thr Thr Pro Trp Thr Leu Glu Asn Gly Leu Leu Thr
        595                 600                 605

Gly Ile Arg Lys Leu Ala Arg Pro Gln Leu Lys Lys His Tyr Gly Glu
610                 615                 620
```

-continued

```
Leu Leu Glu Gln Ile Tyr Thr Asp Leu Ala His Gly Gln Ala Asp Glu
625                 630                 635                 640

Leu Arg Ser Leu Arg Gln Ser Gly Ala Asp Pro Val Leu Val Thr
            645                 650                 655

Val Cys Arg Ala Ala Ala Ala Leu Leu Gly Gly Ser Ala Ser Asp Val
                660                 665                 670

Gln Pro Asp Ala His Phe Thr Asp Leu Gly Gly Asp Ser Leu Ser Ala
            675                 680                 685

Leu Ser Phe Thr Asn Leu Leu His Glu Ile Phe Asp Ile Glu Val Pro
690                 695                 700

Val Gly Val Ile Val Ser Pro Ala Asn Asp Leu Gln Ala Leu Ala Asp
705                 710                 715                 720

Tyr Val Glu Ala Ala Arg Lys Pro Gly Ser Ser Arg Pro Thr Phe Ala
                725                 730                 735

Ser Val His Gly Ala Ser Asn Gly Gln Val Thr Glu Val His Ala Gly
            740                 745                 750

Asp Leu Ser Leu Asp Lys Phe Ile Asp Ala Ala Thr Leu Ala Glu Ala
            755                 760                 765

Pro Arg Leu Pro Ala Ala Asn Thr Gln Val Arg Thr Val Leu Leu Thr
770                 775                 780

Gly Ala Thr Gly Phe Leu Gly Arg Tyr Leu Ala Leu Glu Trp Leu Glu
785                 790                 795                 800

Arg Met Asp Leu Val Asp Gly Lys Leu Ile Cys Leu Val Arg Ala Lys
                805                 810                 815

Ser Asp Thr Glu Ala Arg Ala Arg Leu Asp Lys Thr Phe Asp Ser Gly
            820                 825                 830

Asp Pro Glu Leu Leu Ala His Tyr Arg Ala Leu Ala Gly Asp His Leu
            835                 840                 845

Glu Val Leu Ala Gly Asp Lys Gly Glu Ala Asp Leu Gly Leu Asp Arg
850                 855                 860

Gln Thr Trp Gln Arg Leu Ala Asp Thr Val Asp Leu Ile Val Asp Pro
865                 870                 875                 880

Ala Ala Leu Val Asn His Val Leu Pro Tyr Ser Gln Leu Phe Gly Pro
                885                 890                 895

Asn Ala Leu Gly Thr Ala Glu Leu Leu Arg Leu Ala Leu Thr Ser Lys
            900                 905                 910

Ile Lys Pro Tyr Ser Tyr Thr Ser Thr Ile Gly Val Ala Asp Gln Ile
            915                 920                 925

Pro Pro Ser Ala Phe Thr Glu Asp Ala Asp Ile Arg Val Ile Ser Ala
930                 935                 940

Thr Arg Ala Val Asp Asp Ser Tyr Ala Asn Gly Tyr Ser Asn Ser Lys
945                 950                 955                 960

Trp Ala Gly Glu Val Leu Leu Arg Glu Ala His Asp Leu Cys Gly Leu
                965                 970                 975

Pro Val Ala Val Phe Arg Cys Asp Met Ile Leu Ala Asp Thr Thr Trp
            980                 985                 990

Ala Gly Gln Leu Asn Val Pro Asp Met Phe Thr Arg Met Ile Leu Ser
            995                 1000                1005

Leu Ala Ala Thr Gly Ile Ala Pro Gly Ser Phe Tyr Glu Leu Ala
    1010                1015                1020

Ala Asp Gly Ala Arg Gln Arg Ala His Tyr Asp Gly Leu Pro Val
    1025                1030                1035

Glu Phe Ile Ala Glu Ala Ile Ser Thr Leu Gly Ala Gln Ser Gln
```

```
                1040                1045                1050
Asp Gly Phe His Thr Tyr His Val Met Asn Pro Tyr Asp Asp Gly
        1055                1060                1065

Ile Gly Leu Asp Glu Phe Val Asp Trp Leu Asn Glu Ser Gly Cys
        1070                1075                1080

Pro Ile Gln Arg Ile Ala Asp Tyr Gly Asp Trp Leu Gln Arg Phe
        1085                1090                1095

Glu Thr Ala Leu Arg Ala Leu Pro Asp Arg Gln Arg His Ser Ser
        1100                1105                1110

Leu Leu Pro Leu Leu His Asn Tyr Arg Gln Pro Glu Arg Pro Val
        1115                1120                1125

Arg Gly Ser Ile Ala Pro Thr Asp Arg Phe Arg Ala Ala Val Gln
        1130                1135                1140

Glu Ala Lys Ile Gly Pro Asp Lys Asp Ile Pro His Val Gly Ala
        1145                1150                1155

Pro Ile Ile Val Lys Tyr Val Ser Asp Leu Arg Leu Leu Gly Leu
        1160                1165                1170

Leu

<210> SEQ ID NO 69
<211> LENGTH: 1180
<212> TYPE: PRT
<213> ORGANISM: Mycobacterium marinum ATCC BAA-535

<400> SEQUENCE: 69

Met Ser Ile Thr Cys Val Asp Thr Arg Ala Gln Arg Ser Ala Arg Arg
1               5                   10                  15

Ile Glu Gln Leu Tyr Ser Thr Asp Ala Gln Phe Ala Ala Ala Arg Pro
            20                  25                  30

Ser Thr Ala Val Gly Ile Ala Ile Ser Lys Ser Gly Leu Gly Leu Pro
        35                  40                  45

Gln Ile Ile Gln Thr Val Met Asp Gly Tyr Pro Gln Arg Pro Ala Leu
    50                  55                  60

Gly Gln Arg Ala Thr Arg Val Val Thr Asp Pro Asn Thr Gly Arg Ser
65                  70                  75                  80

Ser Ala Gln Leu Leu Ala Glu Phe Glu Thr Ile Thr Tyr Arg Glu Leu
                85                  90                  95

Trp Asn Arg Thr Asn Ala Leu Thr Asn Ala Phe Ala Ala Glu Ala Leu
            100                 105                 110

Ala Asp Arg Gly Gln Arg Val Cys Val Leu Gly Phe Ala Ser Ile Asp
        115                 120                 125

Tyr Ala Thr Ile Asp Leu Ala Leu Met Leu Leu Gly Ala Val Ser Val
    130                 135                 140

Pro Leu Pro Thr Asn Ala Ala Arg Ala Gln Leu Cys His Ile Val Ser
145                 150                 155                 160

Glu Thr Gln Pro Ser Leu Ile Ala Ser Ser Thr Glu Asn Leu Pro Asp
                165                 170                 175

Ala Ile Ser Leu Val Leu Ser His Arg Ala Pro His Arg Val Val
            180                 185                 190

Phe Asp Tyr Arg Pro Glu Leu Asp Ala His Arg Glu Ala Leu Glu Ala
        195                 200                 205

Ala Arg Ala Arg Leu Ala Ala Ile Pro Val Thr Val Glu Thr Leu Thr
    210                 215                 220

Ala Ile Ile Ala Arg Gly Arg Thr Val Arg Pro Ala Glu Ala Asp Cys
```

```
            225                 230                 235                 240

Gly Ala Gln Ser Ala Asp Ala Pro Ala Leu Leu Ile Tyr Thr Ser Gly
                        245                 250                 255

Ser Thr Gly Ala Pro Lys Gly Val Val Tyr Thr Arg Asn Arg Val Ala
                        260                 265                 270

Asp Phe Trp Arg Thr Ser Lys Ala Glu Val Glu Ala Thr Glu Gln Arg
                        275                 280                 285

Thr Ala Pro Ser Ile Thr Leu Asn Phe Met Pro Met Ser His Ala Asn
                    290                 295                 300

Gly Arg Gln Val Leu Tyr Gly Thr Leu Ser Asn Gly Thr Ala Tyr
        305                 310                 315                 320

Phe Thr Ala Arg Ser Asp Leu Ser Thr Leu Phe Asp Asp Leu Ala Leu
                        325                 330                 335

Val Arg Pro Thr Glu Leu Gly Phe Pro Pro Arg Ile Trp Asp Met Leu
                        340                 345                 350

Leu Glu Arg Phe Gly Arg Glu Val Asp Arg Arg Leu Arg Asp Gly Thr
                        355                 360                 365

Ala Glu Gly Ala Asp Pro Gly Ala Leu Lys Ala Arg Val Ala Ala Asp
                    370                 375                 380

Leu Arg Gln Val Leu Leu Gly Gly Arg Tyr Ala Leu Ala Met Met Gly
        385                 390                 395                 400

Ser Ala Pro Ile Ser Glu Gln Met Lys Ala Ser Val Glu Ser Leu Leu
                        405                 410                 415

Asp Leu Asp Val Met Glu Gly Tyr Gly Ser Thr Glu Ala Gly Thr Val
                        420                 425                 430

Ile Ile Asn Asn Glu Val Gln Arg Pro Gln Val Ile Asp Tyr Lys Leu
                        435                 440                 445

Val Asp Val Ala Glu Leu Gly Tyr Phe Leu Thr Asp Arg Pro Tyr Pro
                    450                 455                 460

Arg Gly Glu Leu Leu Val Lys Thr Arg Thr Leu Phe Ser Gly Tyr Tyr
        465                 470                 475                 480

Arg Asp Pro Glu Asp Gly Ala Gln Val Phe Asp Pro Asp Gly Phe Tyr
                        485                 490                 495

Arg Thr Gly Asp Ile Met Ala Gln Val Gly Pro Asp Arg Leu Ala Tyr
                        500                 505                 510

Leu Asp Arg Arg Asn Asn Val Leu Lys Leu Ser Gln Gly Glu Phe Val
                        515                 520                 525

Ala Val Ser Arg Leu Glu Ala Ile Phe Ala Asn Ser Pro Leu Val Arg
                    530                 535                 540

Gln Ile Phe Val Tyr Ala Asn Gly Ala Arg Ala Tyr Pro Leu Ala Val
        545                 550                 555                 560

Val Val Pro Thr Gln Asp Ala Gln Ser Arg His Gly Arg Ala Glu Leu
                        565                 570                 575

Lys Ala Glu Leu His Thr Ser Leu His Arg Val Ala Met Ser Ala Gly
                        580                 585                 590

Leu Ala Pro Tyr Glu Ile Pro Arg Asp Phe Ile Val Glu Thr Thr Pro
                        595                 600                 605

Phe Thr Pro Gln Asn Gly Leu Leu Thr Ala Ile His Lys Leu Ala Arg
                    610                 615                 620

Pro His Leu Thr Gln Arg Tyr Gly Ala Arg Leu Glu Leu Leu Tyr Thr
        625                 630                 635                 640

Glu Leu Ala Asp Ser Gln Thr Arg Arg Leu His Arg Leu Arg Gln Thr
                        645                 650                 655
```

```
Gly Gly Arg Leu Pro Ala Leu Glu Thr Ile Arg Arg Ala Ala Gly Ala
            660                 665                 670

Leu Leu Gly Thr Glu Thr Thr Glu Pro Arg Pro Glu Ala His Phe Lys
            675                 680                 685

Asp Leu Gly Gly Asp Ser Val Ser Ala Val Thr Phe Ser Asn Leu Leu
            690                 695                 700

His Asp Ile Tyr Gly Phe Asp Val Pro Val Gly Val Ile Leu Gly Pro
705                 710                 715                 720

Ala Thr Asp Leu Arg Ala Leu Ala Ser His Val Glu Ser Arg Arg Gly
                    725                 730                 735

Ala Gly Trp Ser Gly Pro Ser Phe Ala Ser Val His Val Pro Arg Ala
            740                 745                 750

Thr Ser Val His Ala Gly Asp Leu Lys Leu Ala Lys Phe Leu Asp Thr
            755                 760                 765

Lys Thr Leu Ala Ala Ala Thr Ser Leu Pro Ala Ala Asp Ala Arg Ala
            770                 775                 780

Arg Thr Val Leu Leu Thr Gly Ala Thr Gly Phe Leu Gly Arg Tyr Leu
785                 790                 795                 800

Val Leu Glu Trp Leu Arg Arg Leu Arg Ala Val Gly Gly Lys Leu Ile
                    805                 810                 815

Cys Leu Val Arg Ala Ala Ser Asp Glu Gln Ala Arg Val Arg Leu Asp
                    820                 825                 830

Thr Ala Phe Asp Ser Gly Asp Pro Gln Leu Pro Glu His Phe Arg Gln
                    835                 840                 845

Leu Ala Val Asp Arg Leu Glu Val Leu Ala Gly Asp Lys Ser Glu Pro
            850                 855                 860

Gly Leu Gly Leu Asp Gly Pro Thr Trp Gln Arg Leu Ala Asp Thr Val
865                 870                 875                 880

Asp Leu Ile Val Asp Pro Ala Thr Leu Val Asn His Val Leu Ser Tyr
                    885                 890                 895

Arg Gln Leu Phe Ala Pro Asn Val Ala Gly Thr Ala Glu Leu Leu Arg
                    900                 905                 910

Leu Ala Leu Thr Thr Lys Arg Lys Pro Tyr Ala Tyr Val Ser Thr Val
            915                 920                 925

Ser Val Ala Asn Gln Ile Glu Pro Ser Ala Phe Thr Glu Asp Ala Asp
            930                 935                 940

Ile Arg Glu Ile Ser Arg Thr Arg Thr Ile Asp Asp Ser Phe Ala Asn
945                 950                 955                 960

Gly Tyr Thr Thr Ser Lys Trp Ala Ser Glu Val Leu Leu Arg Glu Ala
                    965                 970                 975

His Asp Leu Cys Gly Leu Pro Val Thr Val Phe Arg Cys Asp Met Ile
                    980                 985                 990

Leu Ala Asp Thr Ser Tyr Ala Gly  Gln Leu Asn Leu Ala  Asp Thr Phe
                    995                 1000                1005

Thr Arg  Leu Met Leu Ser Val  Ala Ala Thr Gly Ile  Ala Pro Ala
            1010                1015                1020

Ser Phe  Tyr Arg Leu Gly Pro  Asp Gly Lys Arg Gln  Pro Ala His
            1025                1030                1035

Phe Asp  Gly Leu Pro Val Glu  Phe Ile Ala Glu Ala  Val Ala Thr
            1040                1045                1050

Leu Gly  Ala Arg Arg His Asp  Gly Phe Gln Val His  His Val Ala
            1055                1060                1065
```

Asn Pro His His Asp Gly Val Gly Leu Asp Glu Tyr Val Asp Trp
    1070                1075                1080

Leu Val Asp Ala Gly Cys Pro Ile Arg Arg Ile Pro Asp Tyr Asp
    1085                1090                1095

Glu Trp Leu Ser Arg Phe Glu Thr Ala Leu His Ala Leu Pro Asp
    1100                1105                1110

Arg Lys Arg Arg His Ser Leu Leu Pro Leu Leu Gln Asn Tyr Arg
    1115                1120                1125

Glu Pro Ala Glu Pro Ile Arg Gly Gly Ile Ala Pro Ala Pro Arg
    1130                1135                1140

Phe Arg Gly Ala Val Arg Gln Ala Lys Ile Gly Arg Asp Asn Asp
    1145                1150                1155

Ile Pro His Val Gly Pro Ala Ile Ile Ala Lys Tyr Ala Ser Asp
    1160                1165                1170

Leu Gln Leu Leu Gly Leu Ala
    1175                1180

<210> SEQ ID NO 70
<211> LENGTH: 1168
<212> TYPE: PRT
<213> ORGANISM: Mycobacterium smegmatis ATCC 700084

<400> SEQUENCE: 70

Met Thr Ile Glu Thr Arg Glu Asp Arg Phe Asn Arg Arg Ile Asp His
1               5                   10                  15

Leu Phe Glu Thr Asp Pro Gln Phe Ala Ala Ala Arg Pro Asp Glu Ala
                20                  25                  30

Ile Ser Ala Ala Ala Ala Asp Pro Glu Leu Arg Leu Pro Ala Ala Val
            35                  40                  45

Lys Gln Ile Leu Ala Gly Tyr Ala Asp Arg Pro Ala Leu Gly Lys Arg
    50                  55                  60

Ala Val Glu Phe Val Thr Asp Glu Glu Gly Arg Thr Thr Ala Lys Leu
65                  70                  75                  80

Leu Pro Arg Phe Asp Thr Ile Thr Tyr Arg Gln Leu Ala Gly Arg Ile
                85                  90                  95

Gln Ala Val Thr Asn Ala Trp His Asn His Pro Val Asn Ala Gly Asp
                100                 105                 110

Arg Val Ala Ile Leu Gly Phe Thr Ser Val Asp Tyr Thr Thr Ile Asp
            115                 120                 125

Ile Ala Leu Leu Glu Leu Gly Ala Val Ser Val Pro Leu Gln Thr Ser
    130                 135                 140

Ala Pro Val Ala Gln Leu Gln Pro Ile Val Ala Glu Thr Glu Pro Lys
145                 150                 155                 160

Val Ile Ala Ser Ser Val Asp Phe Leu Ala Asp Ala Val Ala Leu Val
                165                 170                 175

Glu Ser Gly Pro Ala Pro Ser Arg Leu Val Val Phe Asp Tyr Ser His
                180                 185                 190

Glu Val Asp Asp Gln Arg Glu Ala Phe Glu Ala Ala Lys Gly Lys Leu
            195                 200                 205

Ala Gly Thr Gly Val Val Glu Thr Ile Thr Asp Ala Leu Asp Arg
    210                 215                 220

Gly Arg Ser Leu Ala Asp Ala Pro Leu Tyr Val Pro Asp Glu Ala Asp
225                 230                 235                 240

Pro Leu Thr Leu Leu Ile Tyr Thr Ser Gly Ser Thr Gly Thr Pro Lys
                245                 250                 255

```
Gly Ala Met Tyr Pro Glu Ser Lys Thr Ala Thr Met Trp Gln Ala Gly
            260                 265                 270

Ser Lys Ala Arg Trp Asp Glu Thr Leu Gly Val Met Pro Ser Ile Thr
        275                 280                 285

Leu Asn Phe Met Pro Met Ser His Val Met Gly Arg Gly Ile Leu Cys
    290                 295                 300

Ser Thr Leu Ala Ser Gly Gly Thr Ala Tyr Phe Ala Ala Arg Ser Asp
305                 310                 315                 320

Leu Ser Thr Phe Leu Glu Asp Leu Ala Leu Val Arg Pro Thr Gln Leu
                325                 330                 335

Asn Phe Val Pro Arg Ile Trp Asp Met Leu Phe Gln Glu Tyr Gln Ser
            340                 345                 350

Arg Leu Asp Asn Arg Arg Ala Glu Gly Ser Glu Asp Arg Ala Glu Ala
        355                 360                 365

Ala Val Leu Glu Glu Val Arg Thr Gln Leu Leu Gly Gly Arg Phe Val
    370                 375                 380

Ser Ala Leu Thr Gly Ser Ala Pro Ile Ser Ala Glu Met Lys Ser Trp
385                 390                 395                 400

Val Glu Asp Leu Leu Asp Met His Leu Leu Gly Tyr Gly Ser Thr
                405                 410                 415

Glu Ala Gly Ala Val Phe Ile Asp Gly Gln Ile Gln Arg Pro Pro Val
            420                 425                 430

Ile Asp Tyr Lys Leu Val Asp Val Pro Asp Leu Gly Tyr Phe Ala Thr
        435                 440                 445

Asp Arg Pro Tyr Pro Arg Gly Glu Leu Leu Val Lys Ser Glu Gln Met
    450                 455                 460

Phe Pro Gly Tyr Tyr Lys Arg Pro Glu Ile Thr Ala Glu Met Phe Asp
465                 470                 475                 480

Glu Asp Gly Tyr Tyr Arg Thr Gly Asp Ile Val Ala Glu Leu Gly Pro
                485                 490                 495

Asp His Leu Glu Tyr Leu Asp Arg Arg Asn Asn Val Leu Lys Leu Ser
            500                 505                 510

Gln Gly Glu Phe Val Thr Val Ser Lys Leu Glu Ala Val Phe Gly Asp
        515                 520                 525

Ser Pro Leu Val Arg Gln Ile Tyr Val Tyr Gly Asn Ser Ala Arg Ser
    530                 535                 540

Tyr Leu Leu Ala Val Val Pro Thr Glu Glu Ala Leu Ser Arg Trp
545                 550                 555                 560

Asp Gly Asp Glu Leu Lys Ser Arg Ile Ser Asp Ser Leu Gln Asp Ala
                565                 570                 575

Ala Arg Ala Ala Gly Leu Gln Ser Tyr Glu Ile Pro Arg Asp Phe Leu
            580                 585                 590

Val Glu Thr Thr Pro Phe Thr Leu Glu Asn Gly Leu Leu Thr Gly Ile
        595                 600                 605

Arg Lys Leu Ala Arg Pro Lys Leu Lys Ala His Tyr Gly Glu Arg Leu
    610                 615                 620

Glu Gln Leu Tyr Thr Asp Leu Ala Glu Gly Gln Ala Asn Glu Leu Arg
625                 630                 635                 640

Glu Leu Arg Arg Asn Gly Ala Asp Arg Pro Val Val Glu Thr Val Ser
                645                 650                 655

Arg Ala Ala Val Ala Leu Leu Gly Ala Ser Val Thr Asp Leu Arg Ser
            660                 665                 670
```

```
Asp Ala His Phe Thr Asp Leu Gly Gly Asp Ser Leu Ser Ala Leu Ser
            675                 680                 685

Phe Ser Asn Leu Leu His Glu Ile Phe Asp Val Asp Val Pro Val Gly
        690                 695                 700

Val Ile Val Ser Pro Ala Thr Asp Leu Ala Gly Val Ala Ala Tyr Ile
705                 710                 715                 720

Glu Gly Glu Leu Arg Gly Ser Lys Arg Pro Thr Tyr Ala Ser Val His
            725                 730                 735

Gly Arg Asp Ala Thr Glu Val Arg Ala Arg Asp Leu Ala Leu Gly Lys
                740                 745                 750

Phe Ile Asp Ala Lys Thr Leu Ser Ala Ala Pro Gly Leu Pro Arg Ser
            755                 760                 765

Gly Thr Glu Ile Arg Thr Val Leu Leu Thr Gly Ala Thr Gly Phe Leu
    770                 775                 780

Gly Arg Tyr Leu Ala Leu Glu Trp Leu Glu Arg Met Asp Leu Val Asp
785                 790                 795                 800

Gly Lys Val Ile Cys Leu Val Arg Ala Arg Ser Asp Asp Glu Ala Arg
                805                 810                 815

Ala Arg Leu Asp Ala Thr Phe Asp Thr Gly Asp Ala Thr Leu Leu Glu
                820                 825                 830

His Tyr Arg Ala Leu Ala Ala Asp His Leu Glu Val Ile Ala Gly Asp
            835                 840                 845

Lys Gly Glu Ala Asp Leu Gly Leu Asp His Asp Thr Trp Gln Arg Leu
            850                 855                 860

Ala Asp Thr Val Asp Leu Ile Val Asp Pro Ala Ala Leu Val Asn His
865                 870                 875                 880

Val Leu Pro Tyr Ser Gln Met Phe Gly Pro Asn Ala Leu Gly Thr Ala
                885                 890                 895

Glu Leu Ile Arg Ile Ala Leu Thr Thr Thr Ile Lys Pro Tyr Val Tyr
            900                 905                 910

Val Ser Thr Ile Gly Val Gly Gln Gly Ile Ser Pro Glu Ala Phe Val
            915                 920                 925

Glu Asp Ala Asp Ile Arg Glu Ile Ser Ala Thr Arg Arg Val Asp Asp
            930                 935                 940

Ser Tyr Ala Asn Gly Tyr Gly Asn Ser Lys Trp Ala Gly Glu Val Leu
945                 950                 955                 960

Leu Arg Glu Ala His Asp Trp Cys Gly Leu Pro Val Ser Val Phe Arg
                965                 970                 975

Cys Asp Met Ile Leu Ala Asp Thr Thr Tyr Ser Gly Gln Leu Asn Leu
            980                 985                 990

Pro Asp Met Phe Thr Arg Leu Met Leu Ser Leu Val Ala Thr Gly Ile
            995                 1000                1005

Ala Pro Gly Ser Phe Tyr Glu Leu Asp Ala Asp Gly Asn Arg Gln
    1010                1015                1020

Arg Ala His Tyr Asp Gly Leu Pro Val Glu Phe Ile Ala Glu Ala
    1025                1030                1035

Ile Ser Thr Ile Gly Ser Gln Val Thr Asp Gly Phe Glu Thr Phe
    1040                1045                1050

His Val Met Asn Pro Tyr Asp Asp Gly Ile Gly Leu Asp Glu Tyr
    1055                1060                1065

Val Asp Trp Leu Ile Glu Ala Gly Tyr Pro Val His Arg Val Asp
    1070                1075                1080

Asp Tyr Ala Thr Trp Leu Ser Arg Phe Glu Thr Ala Leu Arg Ala
```

```
                    1085                1090                1095

Leu Pro Glu Arg Gln Arg Gln Ala Ser Leu Leu Pro Leu Leu His
    1100                1105                1110

Asn Tyr Gln Gln Pro Ser Pro Pro Val Cys Gly Ala Met Ala Pro
    1115                1120                1125

Thr Asp Arg Phe Arg Ala Ala Val Gln Asp Ala Lys Ile Gly Pro
    1130                1135                1140

Asp Lys Asp Ile Pro His Val Thr Ala Asp Val Ile Val Lys Tyr
    1145                1150                1155

Ile Ser Asn Leu Gln Met Leu Gly Leu Leu
    1160                1165

<210> SEQ ID NO 71
<211> LENGTH: 835
<212> TYPE: PRT
<213> ORGANISM: Mycobacterium smegmatis ATCC 700084

<400> SEQUENCE: 71

Met Trp Asp Met Leu Phe Gly Thr Phe Gln Ser Glu Val Arg Arg
1               5                   10                  15

Ser Ala Asp Gln Gly Ala His Gly Asp Leu Glu Glu Leu Ala Ala Glu
                20                  25                  30

Val Met Thr Asp Leu Ala Gln His Leu Leu Gly Gly Arg Tyr Leu Leu
            35                  40                  45

Ala Met Thr Gly Ser Ala Pro Ile Ser Asp Glu Asn Lys Ala Phe Val
        50                  55                  60

Glu Leu Leu Asp Leu His Leu Ile Glu Gly Tyr Gly Ser Thr Glu
65                  70                  75                  80

Ala Gly Met Val Phe Val Asp Gly Thr Val Arg Arg Pro Ala Val Ile
                85                  90                  95

Asp Tyr Lys Leu Ala Asp Val Pro Asp Leu Gly Tyr Phe His Thr Asp
            100                 105                 110

Gln Pro His Pro Arg Gly Glu Leu Leu Val Lys Thr Arg Asp Leu Phe
        115                 120                 125

Pro Gly Tyr Tyr Lys Arg Pro Glu Val Thr Ala Ala Val Phe Asp Pro
    130                 135                 140

Asp Gly Phe Tyr His Thr Gly Asp Val Val Ala Glu Val Gly Pro Asp
145                 150                 155                 160

Gln Leu Val Tyr Leu Asp Arg Arg Asn Asn Val Leu Lys Leu Ser Gln
                165                 170                 175

Gly Glu Phe Val Thr Val Ser Lys Leu Glu Pro Leu Phe Gly Asp Ser
            180                 185                 190

Pro Leu Val Arg Gln Ile Tyr Ile Tyr Gly Asn Ser Ala Arg Ala Tyr
        195                 200                 205

Leu Leu Ala Val Val Pro Thr Glu Asp Ala Leu Arg His Ser Gly
    210                 215                 220

Gly Asn Ile Asp Gln Leu Lys Pro Ala Ile Ser Ala Ser Phe Gln Asp
225                 230                 235                 240

Ile Ala Arg Ala Ala Gly Leu Gln Ser Tyr Glu Ile Pro Arg Asp Phe
                245                 250                 255

Leu Val Glu Thr Thr Pro Phe Ser Leu Glu Asn Gly Leu Leu Thr Gly
            260                 265                 270

Ile Arg Lys Leu Ala Arg Pro Lys Leu Lys Ala His Tyr Ala Glu Arg
        275                 280                 285
```

-continued

Leu Glu Ala Leu Tyr Ala Glu Leu Ala Asp Lys Gln Ala Asp Glu Leu
290                 295                 300

Ala Ala Leu Arg Arg Asn Gly Ala Gln Arg Pro Val Leu Glu Thr Val
305                 310                 315                 320

Ser Arg Ala Ala Gly Ala Leu Leu Gly Ala Thr Ala Asp Thr Leu Ala
            325                 330                 335

Pro Asp Ala His Phe Thr Asp Leu Gly Gly Asp Ser Leu Ser Ala Leu
            340                 345                 350

Thr Phe Gly Asn Leu Leu Arg Glu Val Phe Gly Val Asp Val Pro Val
            355                 360                 365

Gly Val Ile Val Ser Pro Ala Ser Asp Leu Arg Ser Ile Ala Asn Tyr
370                 375                 380

Val Glu Ala Gln Arg Gly Ser Gly Ala Ala Gly Pro Ser Phe Ala Ser
385                 390                 395                 400

Val His Gly Arg Asn Ala Thr Gln Val Arg Ala Val Asp Leu Thr Leu
            405                 410                 415

Glu Lys Phe Leu Asp Ser Gln Thr Leu Thr Ala Pro Arg Ser Ala Pro
            420                 425                 430

Ser Ala Asp Val Arg Thr Val Leu Leu Thr Gly Ala Thr Gly Phe Leu
            435                 440                 445

Gly Arg Tyr Leu Ala Leu Glu Trp Leu Glu Arg Met Ser Glu Val Gly
450                 455                 460

Gly Thr Val Ile Cys Leu Val Arg Ala Lys Asp Asp Ala Ser Ala Arg
465                 470                 475                 480

Arg Arg Leu Asp Arg Thr Phe Asp Ser Gly Asp Pro Glu Leu Leu His
            485                 490                 495

His Tyr Leu Asp Leu Ala Asp Arg His Leu Arg Val Ile Ala Gly Ala
            500                 505                 510

Lys Gly Glu Ala Asn Leu Gly Leu Asp Pro Gly Thr Trp Gln Gln Leu
            515                 520                 525

Ala Asp Thr Val Asp Val Ile Val Asp Pro Ala Ala Leu Val Asn His
            530                 535                 540

Val Leu Pro Tyr Gln Glu Leu Phe Gly Pro Asn Val Val Gly Thr Ala
545                 550                 555                 560

Glu Leu Ile Arg Leu Ala Leu Thr Thr Lys Pro Lys Pro Tyr Thr Tyr
            565                 570                 575

Val Ser Thr Ile Gly Val Gly Asp Gln Ile Glu Pro Ser Met Phe Thr
            580                 585                 590

Glu Asp Ala Asp Ile Arg Thr Val Ser Ala Val Arg Ala Ile Asp Asp
            595                 600                 605

Ser Tyr Ala Asn Gly Tyr Gly Asn Ser Lys Trp Ala Gly Glu Val Leu
            610                 615                 620

Leu Arg Glu Ala His Asp Arg Cys Gly Leu Pro Val Ala Val Phe Arg
625                 630                 635                 640

Cys Asp Met Ile Leu Ala Asp Thr Thr Trp Ala Gly Gln Leu Asn Val
            645                 650                 655

Pro Asp Met Phe Thr Arg Leu Met Leu Ser Leu Val Ala Thr Gly Ile
            660                 665                 670

Ala Pro Gly Ser Phe Tyr Glu Leu Asp Ala His Gly Asn Arg Gln Arg
            675                 680                 685

Ala His Tyr Asp Gly Leu Pro Val Gly Phe Ile Ala Glu Ala Ile Ala
            690                 695                 700

Thr Leu Gly Ala Ala Ala Ala Asp Gly Phe Ser Thr Tyr His Val Met

```
                705                 710                 715                 720
Asn Pro His Asp Asp Gly Ile Gly Leu Asp Glu Phe Val Asp Trp Leu
                    725                 730                 735

Asp Glu Ala Gly Tyr Pro Ile Glu Arg Ile Pro Asp Tyr Ala Ala Trp
                740                 745                 750

Leu Gln Arg Phe Asp Thr Ala Leu His Ala Leu Pro Asp Ala Gln Arg
            755                 760                 765

Gln Ala Ser Leu Leu Pro Leu Leu His Asn Tyr Gln His Pro Glu Lys
        770                 775                 780

Pro Ile Arg Gly Ser Gln Ala Pro Thr Asp Arg Phe Arg Ala Ala Val
785                 790                 795                 800

Arg Gln Val Lys Ile Gly Ala Gly Gly Ser Arg Asp Ile Pro Gln
                805                 810                 815

Val Ser Ala Pro Ile Ile Val Lys Tyr Val Thr Asp Leu Gln Lys Val
                820                 825                 830

Gly Leu Leu
        835

<210> SEQ ID NO 72
<211> LENGTH: 1164
<212> TYPE: PRT
<213> ORGANISM: Nocardia brasiliensis NBRC 14402

<400> SEQUENCE: 72

Met Glu Arg Lys Ala Glu Val Leu Ala Ala Arg Arg Val Glu Asp Leu
1               5                   10                  15

Ile Glu Arg Asp Ala Gln Val Arg Ala Ala Ile Pro Asp Pro Val Val
                20                  25                  30

Thr Ala Glu Leu Glu Arg Ala Asp Gly Ser Leu Ala Gln Thr Val Ala
            35                  40                  45

Arg Val Met Ala Gly Tyr Ala Asp Arg Pro Ala Leu Gly Gln Arg Ala
        50                  55                  60

Val Glu Phe Val Pro Asp Glu Asn Gly Cys Arg Arg Thr Arg Leu Leu
65                  70                  75                  80

Pro Trp Phe Asp Thr Ile Thr Phe Gly Glu Leu Trp Gln Arg Val Gly
                85                  90                  95

Thr Val Ala Ala Val Trp Gln Ser Arg Ala Glu Arg Ser Val Arg Ala
            100                 105                 110

Gly Asp Phe Val Ala Val Leu Gly Ser Thr Gly Ile Asp Tyr Thr Val
        115                 120                 125

Val Asp Leu Ala Cys Thr Tyr Ser Gly Ala Val Pro Val Pro Leu Gln
    130                 135                 140

Ala Gly Ala Ser Pro Thr Gln Leu Ala Pro Ile Val Arg Glu Val Glu
145                 150                 155                 160

Pro Lys Val Leu Ala Thr Asp Val Gly Gln Leu Glu Val Ala Val Asp
                165                 170                 175

Leu Ala Ser Ala Gly Asp Ser Val Arg Ser Leu Leu Ile Phe Gly Leu
            180                 185                 190

Tyr Ala Glu Asp Asp Glu His Cys Ala Ala Val Glu Ser Ala Arg Arg
        195                 200                 205

Arg Leu Ala Asp Thr Pro Val Val Glu Thr Ile Val Glu Leu Leu
    210                 215                 220

Ala Ser Gly Gln Asp Arg Pro Ala Ala Ser Leu His Ala Ser Ala Asp
225                 230                 235                 240
```

```
Pro Asp Glu Leu Ala Leu Leu Ile Tyr Thr Ser Gly Ser Thr Gly Thr
                245                 250                 255

Pro Lys Gly Ala Met Tyr Thr Gln Arg Leu Leu Thr Asn Ala Trp Cys
            260                 265                 270

Ala Ala Gly Ala Ser Pro Met Pro Ser Ile Ala Leu Ser Tyr Leu Pro
            275                 280                 285

Met Ser His Thr Met Ala Arg Gln Leu Leu Leu Thr Gly Leu Ala Arg
            290                 295                 300

Gly Gly Thr Val Tyr Phe Ala Ala Arg Asn Asp Met Ser Thr Leu Phe
305                 310                 315                 320

Asp Asp Phe Ala Leu Ala Arg Pro Thr Leu Leu Gly Phe Val Pro Arg
                325                 330                 335

Val Cys Asp Met Val Leu Gln Arg Phe Gln Ser Glu Met Ala Arg Arg
                340                 345                 350

Val Gly Ala Asp Asp Glu Pro Thr Val Val Glu Gln Glu Val Lys Thr
            355                 360                 365

Glu Leu Arg Glu Gln Phe Leu Gly Gly Arg Phe Leu Val Ala Ser Ile
            370                 375                 380

Gly Ser Ala Pro Leu Ser Ala Asp Met Arg Glu Phe Met Gln Ser Val
385                 390                 395                 400

Leu Gly Ile Ala Leu Ile Asp Ala Tyr Gly Ser Thr Glu Thr Gly Gly
                405                 410                 415

Val Leu Met Asn Asn Lys Val Val Arg Thr Ala Ile Leu Asp Tyr Lys
                420                 425                 430

Leu Val Asp Val Pro Glu Leu Gly Tyr Phe Ser Thr Asp Arg Pro His
            435                 440                 445

Pro Arg Gly Glu Leu Leu Ile Lys Ser Arg Thr Leu Ile Pro Gly Tyr
450                 455                 460

Tyr Lys Arg Pro Glu Leu Asn Ser Gln Phe Phe Asp Ala Glu Gly Phe
465                 470                 475                 480

Tyr Arg Thr Gly Asp Val Met Ala Gln Thr Gly Phe Asp Glu Leu Val
                485                 490                 495

Tyr Val Asp Arg Arg Asn Ser Val Leu Lys Leu Ser Gln Gly Glu Phe
            500                 505                 510

Val Ala Val Ser Lys Leu Glu Ala Ile Phe Val Gly Ser Pro Leu Val
            515                 520                 525

Glu Gln Ile Tyr Val Tyr Gly Ser Ser Glu Arg Ala Tyr Leu Leu Ala
            530                 535                 540

Val Ile Val Pro Val Ala Glu Ala Ile Ala Thr His Ala Gly Thr Ala
545                 550                 555                 560

Glu Leu Lys Ala Ala Ile Ser Glu Ser Leu Arg Gln Ile Ala Lys Asp
                565                 570                 575

Ala Glu Leu Ser Ser Tyr Glu Val Pro Arg Asp Phe Leu Leu Glu Ser
            580                 585                 590

Glu Pro Phe Thr Val Asp Asn Gly Leu Leu Ala Gly Leu Ser Lys Leu
            595                 600                 605

Leu Arg Pro Ser Leu Lys Glu Arg Tyr Gly Glu Arg Leu Glu Ala Leu
            610                 615                 620

Tyr Arg Val Ala Glu Ala Gln Thr Gln Glu Leu Ala Ala Leu Arg
625                 630                 635                 640

Gln Gln Ala Gly Met Leu Pro Val Leu Glu Thr Val Ser Arg Ala Ala
                645                 650                 655

Gln Ala Val Leu Gly Val Ser Ala Ala Glu Leu Arg Pro Asp Ala His
```

-continued

```
                660                 665                 670
Phe Thr Asp Leu Gly Gly Asp Ser Leu Ala Ala Leu Ser Phe Ser Thr
                675                 680                 685
Leu Leu Gln Glu Leu Leu Gly Val Gln Val Pro Val Gly Val Ile Ala
            690                 695                 700
Ser Ser Ala Asn Asp Leu Arg Arg Ile Ala Asn Tyr Ala Val Ala Glu
705                 710                 715                 720
Arg Ser Ala Gly Ser Leu Arg Pro Thr Ser Thr Gly Val His Gly Thr
                725                 730                 735
Gly Ser Gln Leu Arg Ala Ile Asp Leu Arg Leu Asp Lys Phe Ile Asp
            740                 745                 750
Pro Ser Thr Leu Ala Ala Ala Thr Thr Leu Pro Arg Ala Gly Glu Pro
            755                 760                 765
Arg Thr Val Leu Leu Thr Gly Ala Asn Gly Tyr Leu Gly Arg Phe Leu
            770                 775                 780
Cys Leu Glu Trp Leu Gln Arg Leu His His Ser Gly Gly Thr Leu Ile
785                 790                 795                 800
Cys Val Val Arg Gly Ile Asp Ala Val Ala Ala Arg Glu Arg Leu Asp
                805                 810                 815
Glu Val Phe Asp Ser Gly Asp Pro Glu Leu Leu His Arg Tyr Arg Glu
                820                 825                 830
Leu Ala Glu Gly Thr Leu Glu Val Leu Cys Gly Asp Ile Ser Glu Pro
            835                 840                 845
Gly Leu Gly Leu Ser Glu Arg Asp Trp Arg Arg Leu Ala Asp Thr Val
            850                 855                 860
Glu Leu Ile Val His Ala Ala Ala Leu Val Asn His Val Leu Pro Tyr
865                 870                 875                 880
Gly Gln Leu Phe Gly Pro Asn Val Val Gly Thr Ala Glu Ile Ile Arg
                885                 890                 895
Leu Ala Met Thr Thr Arg Ile Lys Pro Val Thr Tyr Leu Ser Thr Val
                900                 905                 910
Ala Val Ala Ala Gln Val Ala Pro Glu Gln Phe Thr Glu Asp Gly Asp
            915                 920                 925
Ile Arg Glu Ile Ser Ala Val Arg Ser Leu Asp Glu Gly Tyr Ala Asp
            930                 935                 940
Gly Tyr Gly Thr Ser Lys Trp Ala Gly Glu Val Leu Leu Arg Glu Ala
945                 950                 955                 960
Tyr Asp Leu Cys Gly Leu Pro Val Ala Val Phe Arg Ser Asp Met Ile
                965                 970                 975
Leu Ala His Ser Arg Phe Ala Gly Gln Leu Asn Val Ser Asp Met Phe
                980                 985                 990
Thr Arg Leu Val Leu Ser Val Leu Ala Thr Gly Val Ala Pro Lys Ser
            995                 1000                1005
Phe Tyr Glu Thr Asp Arg Met Gly Asn Arg Gln Arg Ala His Tyr
            1010                1015                1020
Asp Gly Leu Pro Val Asp Phe Thr Ala Gln Ala Ile Thr Val Leu
            1025                1030                1035
Gly Ser Gln Val Val Ser Gly Phe Glu Thr Phe Asp Val Leu Asn
            1040                1045                1050
Pro His Asp Asp Gly Leu Ser Leu Asp Glu Phe Val Asp Trp Leu
            1055                1060                1065
Ile Ala Ala Gly His Ser Ile Asp Arg Ile Asp Gly Tyr Ala Glu
            1070                1075                1080
```

```
Trp Leu Ser Arg Phe Gly Thr Ala Leu Arg Val Leu Ser Glu Arg
    1085                1090                1095

Gln Arg Gln His Ser Val Leu Pro Leu His Ala Tyr Arg Arg
    1100                1105                1110

Ala Ala Val Pro Ile Pro Gly Ala Ala Leu Pro Ala Lys Lys Phe
    1115                1120                1125

Gln Ala Ala Val Gln Asp Ala Gln Leu Gly Pro Gly Arg Asp Ile
    1130                1135                1140

Pro His Leu Thr Pro Asp Leu Ile Glu Lys Tyr Val Ser Asp Leu
    1145                1150                1155

Lys Leu Arg Asn Leu Leu
    1160

<210> SEQ ID NO 73
<211> LENGTH: 1165
<212> TYPE: PRT
<213> ORGANISM: Nocardia brasiliensis NBRC 14402

<400> SEQUENCE: 73

Met Thr Asp Val Glu Val Ala Arg Arg Ile Asp Asp Leu Ser Ala Thr
1               5                   10                  15

Asp Glu Val Leu Ala Gly Ala Leu Pro Asp Pro Ala Val Asn Ala Arg
                20                  25                  30

Ile Gln Asp Pro Ala Val Gly Leu Ala Glu Leu Ile Arg Ile Val Phe
            35                  40                  45

Asp Ala Tyr Gly Gly Arg Pro Ala Val Gly Ala Arg Ala Thr Arg Leu
    50                  55                  60

Val Thr Asp Pro Val Thr Gly Arg Thr Leu His Val Leu Pro Glu
65                  70                  75                  80

Tyr Glu Thr Thr Thr Tyr Ala Glu Leu Gly Arg Gln Val Ala Ala Val
                85                  90                  95

Ala Ala Gly Leu Arg Gly Glu Ala Ala Asp Gly Gly Trp Val Arg Pro
            100                 105                 110

Gly Glu His Val Ala Met Leu Gly Phe Thr Ser Val Glu Tyr Thr Val
        115                 120                 125

Leu Asp Leu Ala Ala Thr Leu Ala Gly Ala Ile Ala Val Pro Met Gln
    130                 135                 140

Ser Asn Ala Pro Ala Val Gln Leu Arg Pro Ile Leu Ala Glu Thr Gln
145                 150                 155                 160

Pro Arg Val Leu Ala Ala Gly Val Asp Gln Leu Ala Glu Ala Leu Asp
                165                 170                 175

Leu Ala Asp Gly Glu His Arg Pro Gly Leu Ile Val Val Leu Asp His
            180                 185                 190

Arg Ala Glu Val Asp Ala His Arg Glu Ala Tyr Glu Ala Ala Ala Ala
        195                 200                 205

Arg Leu Ala Gly Thr Gly Val Ala Leu Lys Thr Leu Ala Glu Leu Ala
    210                 215                 220

Asp Ser Gly Lys Ala Gly Glu Val Ala Pro Glu Ala Ala Asp Ser Glu
225                 230                 235                 240

Arg Ile Val Leu Leu Ile Tyr Thr Ser Gly Ser Thr Gly Thr Pro Lys
                245                 250                 255

Gly Ala Met Tyr Ser Glu Arg Leu Val Ala Asn Leu Trp Gln Gly Lys
            260                 265                 270

Phe Gly Leu Gly Glu Gly Pro His Ala Ala Gly Pro Trp Ile Thr Leu
```

```
            275                 280                 285
Asn Phe Met Pro Met Ser His Leu Met Gly Arg Tyr Thr Leu Tyr Gly
290                 295                 300

Thr Leu Ala Arg Gly Gly Ile Ala Tyr Phe Ala Ser Ser Asp Leu
305                 310                 315                 320

Ser Thr Phe Leu Glu Asp Leu Ser Leu Val Arg Pro Thr Gln Leu Gln
                325                 330                 335

Phe Val Pro Arg Val Trp Asp Leu Leu Tyr Gln Glu Tyr Gln Arg Ala
                340                 345                 350

Leu Asp Gly Val Gly Pro Ala Glu Arg Ser Asp Arg Ala Pro Glu Leu
                355                 360                 365

Leu Ala Glu Leu Arg Arg Asp Leu Leu Gly Arg Ala Leu Gly Ala
370                 375                 380

Val Thr Gly Ser Ala Pro Ile Ser Val Glu Val Arg Glu Phe Val Asp
385                 390                 395                 400

Ala Leu Leu Gly Phe His Leu Pro Asp Gly Tyr Gly Ser Thr Glu Ala
                405                 410                 415

Gly Gly Ile Thr Val Asp Gly Lys Val Ala Arg Pro Val Leu Asp
                420                 425                 430

Tyr Lys Leu Ala Asp Val Pro Glu Leu Gly Tyr Tyr Arg Thr Asp Arg
                435                 440                 445

Pro Tyr Pro Arg Gly Glu Leu Leu Val Lys Thr Gln Asn Ile Phe Pro
450                 455                 460

Gly Tyr Tyr Arg Arg Pro Glu Val Thr Ala Glu Val Phe Asp Pro Asp
465                 470                 475                 480

Gly Tyr Tyr Arg Thr Gly Asp Ile Val Ala Glu Val Gln Pro Asp Glu
                485                 490                 495

Leu Arg Tyr Leu Asp Arg Arg Asn Asn Val Leu Lys Leu Ser Gln Gly
                500                 505                 510

Glu Phe Val Thr Val Ser Lys Leu Glu Ala Ala Tyr Gly Ala Ser Pro
                515                 520                 525

Leu Ile Gln Gln Ile Tyr Ile Tyr Gly Asn Ser Ser Arg Pro Tyr Leu
530                 535                 540

Leu Ala Val Ile Val Pro Asp Asp Ala Val Leu Glu Arg Val Ser Gly
545                 550                 555                 560

Asp Val Gly Ala Ile Gly Pro Leu Leu Thr Glu Ala Leu Arg Ala Val
                565                 570                 575

Ala Ala Asp Ala Gly Leu Gln Ser Tyr Glu Ile Pro Arg Asp Phe Leu
                580                 585                 590

Val Glu Thr Thr Pro Phe Thr Val Glu Asn Gly Leu Leu Thr Gly Ile
                595                 600                 605

Arg Lys Leu Ala Arg Pro Lys Leu Arg Gln Arg Tyr Gly Glu Leu Leu
610                 615                 620

Glu Gln Leu Tyr Gln Arg Leu Ser Asp Gly Gln Ala Glu Glu Leu Arg
625                 630                 635                 640

Ala Leu Arg Thr Gly Ala Ala Asp Arg Pro Val Leu Glu Thr Val Thr
                645                 650                 655

Arg Val Ala Ala Ala Leu Leu Gly Ile Pro Ala Ala Asp Val His Pro
                660                 665                 670

Ala Ala His Phe Thr Glu Leu Gly Gly Asp Ser Leu Ser Ala Leu Thr
                675                 680                 685

Phe Gly Asn Ala Leu His Asp Ile Leu Gly Val Glu Val Pro Val Gly
690                 695                 700
```

```
Val Ile Val Ser Pro Ala Thr Asp Leu Arg Ala Leu Ala Thr Phe Leu
705                 710                 715                 720

Glu Ser Gly Ala Gln Ala Thr Arg Pro Thr Phe Glu Ser Val His Gly
            725                 730                 735

Pro Glu Ala Thr Glu Val Arg Ala Ala Asp Leu Thr Leu Glu Lys Phe
            740                 745                 750

Leu Asp Ala Ala Thr Leu Asp Gly Ala Ala Leu Pro Ala Pro Asn
            755                 760                 765

Tyr Ala Val Arg Thr Val Leu Leu Thr Gly Ala Thr Gly Phe Leu Gly
770                 775                 780

Arg Phe Leu Ala Leu Ala Leu Leu Glu Arg Leu Gly Pro Val Asp Gly
785                 790                 795                 800

Thr Leu Ile Cys Leu Val Arg Ala Thr Asp Ala Ala Ala Arg Gln
                805                 810                 815

Arg Leu Asp Ala Val Phe Asp Ser Gly Asp Pro Gln Leu Leu Thr His
            820                 825                 830

Tyr Arg Arg Leu Ala Glu Arg His Leu Glu Val Val Ala Gly Asp Lys
835                 840                 845

Gly Asp Leu Asp Leu Gly Leu Asp Arg Ala Thr Trp Gln Gln Leu Ala
850                 855                 860

Glu Arg Val Asp Leu Ile Val Asp Cys Ala Ala Leu Val Asn His Val
865                 870                 875                 880

Leu Pro Tyr Arg Gln Leu Phe Gly Pro Asn Val Val Gly Thr Ala Glu
            885                 890                 895

Leu Ile Arg Leu Ala Leu Thr Gly Lys Gln Lys Ile Phe Asp Tyr Ile
            900                 905                 910

Ser Thr Val Gly Val Gly Asp Gln Ile Ala Ala Gly Gln Phe Val Glu
            915                 920                 925

Asp Ala Asp Ile Arg Thr Ile Ser Ala Thr Arg Ser Val Asp Glu Arg
930                 935                 940

Tyr Ala Asn Gly Tyr Gly Asn Ser Lys Trp Ala Gly Glu Val Leu Leu
945                 950                 955                 960

Arg Ala Ala His Glu Arg Tyr Gly Leu Pro Val Ser Val Phe Arg Cys
                965                 970                 975

Asp Met Ile Met Val Asp Gly Arg Tyr Val Gly Gln Leu Asn Val Pro
            980                 985                 990

Asp Met Phe Thr Arg Leu Met Leu Ser Leu Val Ala Thr Gly Val Ala
            995                 1000                1005

Pro Gly Ser Phe Tyr Gln Thr Asp Ala Ala Gly Gln Arg Gln Arg
    1010                1015                1020

Ala His Tyr Asp Gly Leu Pro Val Asp Phe Ile Ala Glu Ala Val
    1025                1030                1035

Thr Glu Leu Gly Val His Glu Gly Phe Ser Thr Tyr His Val Met
    1040                1045                1050

Asn Pro His His Asp Gly Ile Gly Leu Asp Glu Phe Val Asp Trp
    1055                1060                1065

Leu Val Ala Ala Gly Tyr Pro Ile Ala Arg Val Ala Asp Tyr Gln
    1070                1075                1080

Ala Trp Leu Glu Gln Phe Gly Thr Lys Leu Arg Ala Leu Pro Glu
    1085                1090                1095

Gln Gln Arg Arg His Ser Leu Leu Pro Leu Leu His Ser Tyr Ala
    1100                1105                1110
```

His Pro Gln Pro Pro Val Glu Gly Ser Val Ala Pro Ala Asp Arg
    1115                1120                1125

Phe Arg Ala Ala Val Gln Asp Ala Asn Ile Gly Pro Asp Lys Asp
    1130                1135                1140

Ile Pro His Leu Thr Glu Ser Thr Ile Leu Lys Tyr Val Thr Asn
    1145                1150                1155

Leu Glu His Leu Gly Leu Leu
    1160            1165

<210> SEQ ID NO 74
<211> LENGTH: 264
<212> TYPE: PRT
<213> ORGANISM: Bacillus anthracis

<400> SEQUENCE: 74

Met His Met Gln Leu Lys Gly Lys Thr Ala Leu Val Thr Gly Ser Thr
1               5                   10                  15

Ala Gly Ile Gly Lys Ala Ile Ala Thr Ser Leu Val Ala Glu Gly Ala
            20                  25                  30

Asn Val Leu Ile Asn Gly Arg Arg Glu Glu Asn Val Asn Glu Thr Ile
        35                  40                  45

Lys Glu Ile Arg Ala Gln Tyr Pro Asp Ala Ile Leu Gln Pro Val Val
    50                  55                  60

Ala Asp Leu Gly Thr Glu Gln Gly Cys Gln Asp Val Ile Glu Lys Tyr
65                  70                  75                  80

Pro Lys Val Asp Ile Leu Ile Asn Asn Leu Gly Ile Phe Glu Pro Val
                85                  90                  95

Glu Tyr Phe Asp Ile Pro Asp Glu Asp Trp Phe Lys Leu Phe Glu Val
            100                 105                 110

Asn Ile Met Ser Gly Val Arg Leu Thr Arg Ser Tyr Leu Lys Lys Met
        115                 120                 125

Ile Glu Arg Lys Glu Gly Arg Val Ile Phe Ile Ala Ser Glu Ala Ala
    130                 135                 140

Ile Met Pro Ser Gln Glu Met Ala His Tyr Ser Ala Thr Lys Thr Met
145                 150                 155                 160

Gln Leu Ser Leu Ser Arg Ser Leu Ala Glu Leu Thr Thr Gly Thr Asn
                165                 170                 175

Val Thr Val Asn Thr Ile Met Pro Gly Ser Thr Leu Thr Glu Gly Val
            180                 185                 190

Glu Thr Met Leu Asn Ser Leu Tyr Pro Asn Glu Gln Leu Thr Ile Glu
        195                 200                 205

Glu Ala Glu Lys Arg Phe Met Lys Glu Asn Arg Pro Thr Ser Ile Ile
    210                 215                 220

Gln Arg Leu Ile Arg Pro Glu Glu Ile Ala His Leu Val Thr Phe Leu
225                 230                 235                 240

Ser Ser Pro Leu Ser Ser Ala Ile Asn Gly Ser Ala Leu Arg Ile Asp
                245                 250                 255

Gly Gly Leu Val Arg Ser Val Phe
            260

<210> SEQ ID NO 75
<211> LENGTH: 254
<212> TYPE: PRT
<213> ORGANISM: Bacillus anthracis

<400> SEQUENCE: 75

Met Lys Glu Lys Val Ile Ile Thr Gly Ser Ser Gly Met Gly
1               5                   10                  15

Lys Gly Met Ala Thr Arg Phe Ala Lys Glu Gly Ala Arg Val Val Ile
            20                  25                  30

Thr Gly Arg Thr Lys Glu Lys Leu Glu Glu Ala Lys Leu Glu Ile Glu
        35                  40                  45

Gln Phe Pro Gly Gln Ile Leu Thr Val Gln Met Asp Val Arg Asn Thr
50                  55                  60

Asp Asp Ile Gln Lys Met Ile Glu Gln Ile Glu Lys Phe Gly Arg
65              70                  75                  80

Ile Asp Ile Leu Ile Asn Asn Ala Ala Gly Asn Phe Ile Cys Pro Ala
                85                  90                  95

Glu Asp Leu Ser Val Asn Gly Trp Asn Ser Val Ile Asn Ile Val Leu
            100                 105                 110

Asn Gly Thr Phe Tyr Cys Ser Gln Ala Ile Gly Lys Tyr Trp Ile Glu
            115                 120                 125

Lys Gly Ile Lys Gly Asn Ile Ile Asn Met Val Ala Thr Tyr Ala Trp
130                 135                 140

Asp Ala Gly Pro Gly Val Ile His Ser Ala Ala Lys Ala Gly Val
145                 150                 155                 160

Leu Ala Met Thr Lys Thr Leu Ala Val Glu Trp Gly Arg Lys Tyr Gly
                165                 170                 175

Ile Arg Val Asn Ala Ile Ala Pro Gly Pro Ile Glu Arg Thr Gly Gly
                180                 185                 190

Ala Asp Lys Leu Trp Ile Ser Glu Glu Met Ala Lys Arg Thr Ile Gln
            195                 200                 205

Ser Val Pro Leu Gly Arg Leu Gly Thr Pro Glu Glu Ile Ala Gly Leu
210                 215                 220

Ala Tyr Tyr Leu Cys Ser Asp Glu Ala Ala Tyr Ile Asn Gly Thr Cys
225                 230                 235                 240

Met Thr Met Asp Gly Gly Gln His Leu His Gln Tyr Pro Phe
                245                 250

<210> SEQ ID NO 76
<211> LENGTH: 257
<212> TYPE: PRT
<213> ORGANISM: Bordetella parapertussis ATCC BAA-587

<400> SEQUENCE: 76

```
Met Ala Asp His Ser Ile Gln Gly Lys Val Ala Leu Ile Ala Gly Gly
1               5                   10                  15

Ala Lys Asn Leu Gly Gly Leu Ile Ala Arg Asp Leu Ala Ala His Gly
            20                  25                  30

Ala Arg Ala Ile Ala Ile His Tyr Asn Ser Pro Ala Ser Lys Ala Asp
        35                  40                  45

Ala Asp Ala Thr Val Ala Ala Leu Gln Ala Ala Gly Ala Gln Ala Val
    50                  55                  60

Ala Leu Gln Gly Asp Leu Thr Thr Ala Ala Ala Val Glu Lys Leu Tyr
65                  70                  75                  80

Ala Asp Ala Leu Ala Ala Val Gly Arg Pro Asp Ile Ala Ile Asn Thr
                85                  90                  95

Val Gly Lys Val Leu Lys Lys Pro Phe Ser Glu Ile Ser Glu Ala Glu
            100                 105                 110

Tyr Asp Glu Met Ala Ala Val Asn Ala Lys Ser Ala Phe Phe Phe Leu
        115                 120                 125
```

```
Lys Glu Ala Gly Arg His Val Asn Asp His Gly Lys Ile Val Thr Leu
            130                 135                 140

Val Thr Ser Leu Leu Gly Ala Phe Thr Pro Phe Tyr Ser Ala Tyr Ala
145                 150                 155                 160

Gly Thr Lys Ala Pro Val Glu His Tyr Thr Arg Ala Ala Lys Glu
                165                 170                 175

Phe Gly Ala Arg Gly Ile Ser Val Thr Ala Val Gly Pro Gly Pro Met
                180                 185                 190

Asp Thr Pro Phe Phe Tyr Gly Gln Glu Ser Pro Glu Ala Val Ala Tyr
                195                 200                 205

His Gln Ser Ala Ala Ala Leu Ser Pro His Ser Pro Thr Gly Leu Thr
            210                 215                 220

His Ile Glu Asp Val Val Pro Phe Ile Arg His Leu Val Ser Asp Gly
225                 230                 235                 240

Trp Trp Ile Thr Gly Gln Thr Leu Leu Ile Asn Gly Gly Tyr Thr Thr
                245                 250                 255

Lys

<210> SEQ ID NO 77
<211> LENGTH: 253
<212> TYPE: PRT
<213> ORGANISM: Chromobacterium violaceum ATCC 12472

<400> SEQUENCE: 77

Met Thr Met Lys Thr Glu Phe Ala Gln Asp Ala Leu Ala Gly Arg Val
1               5                   10                  15

Ile Leu Ile Thr Gly Ala Ser Gln Gly Ile Gly Arg Glu Ala Ala Leu
                20                  25                  30

Thr Phe Ala Arg His Gly Ala Thr Val Val Leu Leu Ser Arg Ser Val
            35                  40                  45

Lys Gly Leu Glu Lys Val Tyr Asp Glu Ile Val Ala Ala Gly Gly Pro
50                  55                  60

Glu Pro Ala Ala Val Pro Leu Asp Leu Leu Asn Ala Gly Glu Asn Glu
65                  70                  75                  80

Phe Asn Gln Leu Ala Leu Thr Ile Gln Arg Glu Phe Gly Arg Leu Asp
                85                  90                  95

Gly Ile Ala His Cys Ala Ser Phe Tyr Ala Leu Ser Pro Leu Thr
                100                 105                 110

Asn Gln Thr Ile Glu Glu Trp Met Asn Gln Tyr Arg Ile Asn Thr Val
            115                 120                 125

Ala Pro Phe Ala Leu Thr Arg Ala Cys Leu Pro Leu Leu Lys Glu Ala
130                 135                 140

Pro Asp Ala Ser Val Leu Phe Val Gly Glu His Ala Leu His Pro
145                 150                 155                 160

Ala Ala Tyr Trp Gly Gly Phe Gly Ala Ser Asn Ala Gly Leu Pro Tyr
                165                 170                 175

Leu Thr Lys Val Ala Ala Asp Glu Trp Glu Met Leu Pro Ser Leu Arg
            180                 185                 190

Val Asn Leu Leu Leu Pro Gly Pro Val Asn Ser Pro Gln Arg Asn Arg
            195                 200                 205

Thr His Pro Gly Glu Asp Lys Ser Glu Arg Ala Asp Leu Ala Asp Leu
            210                 215                 220

Met Pro His Phe Leu Tyr Trp Leu Gly Ala Asp Ser Arg Gly Arg Ser
225                 230                 235                 240
```

```
Gly Glu Val Val Glu Leu Asp Leu Arg Lys Pro Arg Gly
                245                 250
```

<210> SEQ ID NO 78
<211> LENGTH: 380
<212> TYPE: PRT
<213> ORGANISM: Escherichia coli P12b

<400> SEQUENCE: 78

```
Met Pro His Leu Ala Leu Leu Ile Ser Lys Gly Ala Ile Met Asp Arg
1               5                   10                  15

Ile Ile Gln Ser Pro Gly Lys Tyr Ile Gln Gly Ala Asp Val Ile Asn
            20                  25                  30

Arg Leu Gly Glu Tyr Leu Lys Pro Leu Ala Glu Arg Trp Leu Val Val
        35                  40                  45

Gly Asp Lys Phe Val Leu Gly Phe Ala Gln Ser Thr Val Glu Lys Ser
    50                  55                  60

Phe Lys Asp Ala Gly Leu Val Val Glu Ile Ala Pro Phe Gly Gly Glu
65                  70                  75                  80

Cys Ser Gln Asn Glu Ile Asp Arg Leu Arg Gly Ile Ala Glu Thr Ala
                85                  90                  95

Gln Cys Gly Ala Ile Leu Gly Ile Gly Gly Gly Lys Thr Leu Asp Thr
            100                 105                 110

Ala Lys Ala Leu Ala His Phe Met Gly Val Pro Val Ala Ile Ala Pro
        115                 120                 125

Thr Ile Ala Ser Thr Asp Ala Pro Cys Ser Ala Leu Ser Val Ile Tyr
    130                 135                 140

Thr Asp Glu Gly Glu Phe Asp Arg Tyr Leu Leu Leu Pro Asn Asn Pro
145                 150                 155                 160

Asn Met Val Ile Val Asp Thr Lys Ile Val Ala Gly Ala Pro Ala Arg
                165                 170                 175

Leu Leu Ala Ala Gly Ile Gly Asp Ala Leu Ala Thr Trp Phe Glu Ala
            180                 185                 190

Arg Ala Cys Ser Arg Ser Gly Ala Thr Thr Met Ala Gly Gly Lys Cys
        195                 200                 205

Thr Gln Ala Ala Leu Ala Leu Ala Glu Leu Cys Tyr Asn Thr Leu Leu
    210                 215                 220

Glu Glu Gly Glu Lys Ala Met Leu Ala Ala Glu Gln His Val Val Thr
225                 230                 235                 240

Pro Ala Leu Glu Arg Val Ile Glu Ala Asn Thr Tyr Leu Ser Gly Val
                245                 250                 255

Gly Phe Glu Ser Gly Gly Leu Ala Ala Ala His Ala Val His Asn Gly
            260                 265                 270

Leu Thr Ala Ile Pro Asp Ala His His Tyr Tyr His Gly Glu Lys Val
        275                 280                 285

Ala Phe Gly Thr Leu Thr Gln Leu Val Leu Glu Asn Ala Pro Val Glu
    290                 295                 300

Glu Ile Glu Thr Val Ala Ala Leu Ser His Ala Val Gly Leu Pro Ile
305                 310                 315                 320

Thr Leu Ala Gln Leu Asp Ile Lys Glu Asp Val Pro Ala Lys Met Arg
                325                 330                 335

Ile Val Ala Glu Ala Ala Cys Ala Glu Gly Glu Thr Ile His Asn Met
            340                 345                 350

Pro Gly Gly Ala Thr Pro Asp Gln Val Tyr Ala Ala Leu Leu Val Ala
```

```
                355                 360                 365
Asp Gln Tyr Gly Gln Arg Phe Leu Gln Glu Trp Glu
    370                 375                 380

<210> SEQ ID NO 79
<211> LENGTH: 383
<212> TYPE: PRT
<213> ORGANISM: Escherichia coli

<400> SEQUENCE: 79

Met Met Ala Asn Arg Met Ile Leu Asn Glu Thr Ala Trp Phe Gly Arg
1               5                   10                  15

Gly Ala Val Gly Ala Leu Thr Asp Glu Val Lys Arg Arg Gly Tyr Gln
            20                  25                  30

Lys Ala Leu Ile Val Thr Asp Lys Thr Leu Val Gln Cys Gly Val Val
        35                  40                  45

Ala Lys Val Thr Asp Lys Met Asp Ala Ala Gly Leu Ala Trp Ala Ile
    50                  55                  60

Tyr Asp Gly Val Val Pro Asn Pro Thr Ile Thr Val Val Lys Glu Gly
65                  70                  75                  80

Leu Gly Val Phe Gln Asn Ser Gly Ala Asp Tyr Leu Ile Ala Ile Gly
                85                  90                  95

Gly Gly Ser Pro Gln Asp Thr Cys Lys Ala Ile Gly Ile Ile Ser Asn
            100                 105                 110

Asn Pro Glu Phe Ala Asp Val Arg Ser Leu Glu Gly Leu Ser Pro Thr
        115                 120                 125

Asn Lys Pro Ser Val Pro Ile Leu Ala Ile Pro Thr Thr Ala Gly Thr
    130                 135                 140

Ala Ala Glu Val Thr Ile Asn Tyr Val Ile Thr Asp Glu Glu Lys Arg
145                 150                 155                 160

Arg Lys Phe Val Cys Val Asp Pro His Asp Ile Pro Gln Val Ala Phe
                165                 170                 175

Ile Asp Ala Asp Met Met Asp Gly Met Pro Pro Ala Leu Lys Ala Ala
            180                 185                 190

Thr Gly Val Asp Ala Leu Thr His Ala Ile Glu Gly Tyr Ile Thr Arg
        195                 200                 205

Gly Ala Trp Ala Leu Thr Asp Ala Leu His Ile Lys Ala Ile Glu Ile
    210                 215                 220

Ile Ala Gly Ala Leu Arg Gly Ser Val Ala Gly Asp Lys Asp Ala Gly
225                 230                 235                 240

Glu Glu Met Ala Leu Gly Gln Tyr Val Ala Gly Met Gly Phe Ser Asn
                245                 250                 255

Val Gly Leu Gly Leu Val His Gly Met Ala His Pro Leu Gly Ala Phe
            260                 265                 270

Tyr Asn Thr Pro His Gly Val Ala Asn Ala Ile Leu Leu Pro His Val
        275                 280                 285

Met Arg Tyr Asn Ala Asp Phe Thr Gly Glu Lys Tyr Arg Asp Ile Ala
    290                 295                 300

Arg Val Met Gly Val Lys Val Glu Gly Met Ser Leu Glu Glu Ala Arg
305                 310                 315                 320

Asn Ala Ala Val Glu Ala Val Phe Ala Leu Asn Arg Asp Val Gly Ile
                325                 330                 335

Pro Pro His Leu Arg Asp Val Gly Val Arg Lys Glu Asp Ile Pro Ala
            340                 345                 350
```

```
Leu Ala Gln Ala Ala Leu Asp Asp Val Cys Thr Gly Asn Pro Arg
        355                 360                 365

Glu Ala Thr Leu Glu Asp Ile Val Glu Leu Tyr His Thr Ala Trp
    370                 375                 380

<210> SEQ ID NO 80
<211> LENGTH: 417
<212> TYPE: PRT
<213> ORGANISM: Escherichia coli

<400> SEQUENCE: 80

Met Leu Glu Gln Met Gly Ile Ala Ala Lys Gln Ala Ser Tyr Lys Leu
1               5                   10                  15

Ala Gln Leu Ser Ser Arg Glu Lys Asn Arg Val Leu Glu Lys Ile Ala
            20                  25                  30

Asp Glu Leu Glu Ala Gln Ser Glu Ile Ile Leu Asn Ala Asn Ala Gln
        35                  40                  45

Asp Val Ala Asp Ala Arg Ala Asn Gly Leu Ser Glu Ala Met Leu Asp
    50                  55                  60

Arg Leu Ala Leu Thr Pro Ala Arg Leu Lys Gly Ile Ala Asp Asp Val
65              70                  75                  80

Arg Gln Val Cys Asn Leu Ala Asp Pro Val Gly Gln Val Ile Asp Gly
                85                  90                  95

Gly Val Leu Asp Ser Gly Leu Arg Leu Glu Arg Arg Val Pro Leu
            100                 105                 110

Gly Val Ile Gly Val Ile Tyr Glu Ala Arg Pro Asn Val Thr Val Asp
        115                 120                 125

Val Ala Ser Leu Cys Leu Lys Thr Gly Asn Ala Val Ile Leu Arg Gly
    130                 135                 140

Gly Lys Glu Thr Cys Arg Thr Asn Ala Ala Thr Val Ala Val Ile Gln
145                 150                 155                 160

Asp Ala Leu Lys Ser Cys Gly Leu Pro Ala Gly Ala Val Gln Ala Ile
                165                 170                 175

Asp Asn Pro Asp Arg Ala Leu Val Ser Glu Met Leu Arg Met Asp Lys
            180                 185                 190

Tyr Ile Asp Met Leu Ile Pro Arg Gly Gly Ala Gly Leu His Lys Leu
        195                 200                 205

Cys Arg Glu Gln Ser Thr Ile Pro Val Ile Thr Gly Gly Ile Gly Val
    210                 215                 220

Cys His Ile Tyr Val Asp Glu Ser Val Glu Ile Ala Glu Ala Leu Lys
225                 230                 235                 240

Val Ile Val Asn Ala Lys Thr Gln Arg Pro Ser Thr Cys Asn Thr Val
                245                 250                 255

Glu Thr Leu Leu Val Asn Lys Asn Ile Ala Asp Ser Phe Leu Pro Ala
            260                 265                 270

Leu Ser Lys Gln Met Ala Glu Ser Gly Val Thr Leu His Ala Asp Ala
        275                 280                 285

Ala Ala Leu Ala Gln Leu Gln Ala Gly Pro Ala Lys Val Val Ala Val
    290                 295                 300

Lys Ala Glu Glu Tyr Asp Asp Glu Phe Leu Ser Leu Asp Leu Asn Val
305                 310                 315                 320

Lys Ile Val Ser Asp Leu Asp Asp Ala Ile Ala His Ile Arg Glu His
                325                 330                 335

Gly Thr Gln His Ser Asp Ala Ile Leu Thr Arg Asp Met Arg Asn Ala
            340                 345                 350
```

```
Gln Arg Phe Val Asn Glu Val Asp Ser Ser Ala Val Tyr Val Asn Ala
        355                 360                 365

Ser Thr Arg Phe Thr Asp Gly Gly Gln Phe Gly Leu Gly Ala Glu Val
370                 375                 380

Ala Val Ser Thr Gln Lys Leu His Ala Arg Gly Pro Met Gly Leu Glu
385                 390                 395                 400

Ala Leu Thr Thr Tyr Lys Trp Ile Gly Ile Gly Asp Tyr Thr Ile Arg
                405                 410                 415

Ala

<210> SEQ ID NO 81
<211> LENGTH: 252
<212> TYPE: PRT
<213> ORGANISM: Escherichia coli

<400> SEQUENCE: 81

Met His Tyr Gln Pro Lys Gln Asp Leu Leu Asn Asp Arg Ile Ile Leu
1               5                   10                  15

Val Thr Gly Ala Ser Asp Gly Ile Gly Arg Glu Ala Ala Met Thr Tyr
            20                  25                  30

Ala Arg Tyr Gly Ala Thr Val Ile Leu Leu Gly Arg Asn Glu Glu Lys
        35                  40                  45

Leu Arg Gln Val Ala Ser His Ile Asn Glu Glu Thr Gly Arg Gln Pro
    50                  55                  60

Gln Trp Phe Ile Leu Asp Leu Leu Thr Cys Thr Ser Glu Asn Cys Gln
65                  70                  75                  80

Gln Leu Ala Gln Arg Ile Ala Val Asn Tyr Pro Arg Leu Asp Gly Val
                85                  90                  95

Leu His Asn Ala Gly Leu Leu Gly Asp Val Cys Pro Met Ser Glu Gln
            100                 105                 110

Asn Pro Gln Val Trp Gln Asp Val Met Gln Val Asn Val Asn Ala Thr
        115                 120                 125

Phe Met Leu Thr Gln Ala Leu Leu Pro Leu Leu Leu Lys Ser Asp Ala
    130                 135                 140

Gly Ser Leu Val Phe Thr Ser Ser Ser Val Gly Arg Gln Gly Arg Ala
145                 150                 155                 160

Asn Trp Gly Ala Tyr Ala Ala Ser Lys Phe Ala Thr Glu Gly Met Met
                165                 170                 175

Gln Val Leu Ala Asp Glu Tyr Gln Gln Arg Leu Arg Val Asn Cys Ile
            180                 185                 190

Asn Pro Gly Gly Thr Arg Thr Ala Met Arg Ala Ser Ala Phe Pro Thr
        195                 200                 205

Glu Asp Pro Gln Lys Leu Lys Thr Pro Ala Asp Ile Met Pro Leu Tyr
    210                 215                 220

Leu Trp Leu Met Gly Asp Asp Ser Arg Arg Lys Thr Gly Met Thr Phe
225                 230                 235                 240

Asp Ala Gln Pro Gly Arg Lys Pro Gly Ile Ser Gln
                245                 250

<210> SEQ ID NO 82
<211> LENGTH: 386
<212> TYPE: PRT
<213> ORGANISM: Rhodococcus jostii RHA1

<400> SEQUENCE: 82
```

```
Met Thr Ala His Leu Ser Leu Pro Arg Phe Ala Arg Ile Gly Ala Gly
1               5                   10                  15

Ala Val Asp Glu Ile Gly Ser Val Val Asp Gln Leu Gly Leu Gln Arg
            20                  25                  30

Pro Val Leu Val Thr Asp Ser Tyr Leu Thr Gly Thr Gly Ala Ala Asp
        35                  40                  45

Arg Ile Met Ser Leu Leu Arg Ser Ala Gly Lys Glu Pro Ala Leu Phe
    50                  55                  60

Ser Gly Thr Val Pro Asp Pro Thr Thr Asp Ser Leu Glu Glu Gly Leu
65                  70                  75                  80

Arg Ile Val Ala Glu His Asn Ala Asp Ser Val Ile Gly Phe Gly Gly
                85                  90                  95

Gly Ser Pro Met Asp Thr Ala Lys Ala Leu Ala Val Leu Ser Ala Asn
            100                 105                 110

Gly Gly Glu Met Arg Ser Tyr Lys Ala Pro His Val Tyr Ala Gly Lys
            115                 120                 125

Ala Leu Pro Ile Ile Ala Ile Pro Thr Thr Ala Gly Ser Gly Ser Glu
        130                 135                 140

Ala Thr Gln Phe Thr Val Ile Ser Asp Ser Ala Ser Asp Glu Lys Met
145                 150                 155                 160

Leu Cys Pro Gly Leu Ser Phe Leu Pro Ile Ala Ala Ile Val Asp Phe
                165                 170                 175

Glu Leu Thr Met Ser Met Pro Pro Arg Leu Thr Ala Asp Thr Gly Ile
            180                 185                 190

Asp Ala Leu Thr His Ala Ile Glu Ala Tyr Val Ser Lys Lys Ala Gln
        195                 200                 205

Pro Phe Thr Asp Gly Leu Ala Leu Ser Ala Ile Arg Thr Ile Gly Lys
    210                 215                 220

His Ile Gly Thr Ala Tyr Ala Asp Gly Glu Asp Arg Thr Ala Arg Glu
225                 230                 235                 240

Ala Met Met Val Ala Ser Met Gln Ala Gly Met Ala Phe Ser Asn Ser
                245                 250                 255

Ser Val Ala Leu Val His Gly Met Ser Arg Pro Ile Gly Ala His Phe
            260                 265                 270

His Val Ala His Gly Leu Ser Asn Ala Met Leu Leu Pro Ala Ile Thr
        275                 280                 285

Ala Phe Ser Val Asn Gly Ala Glu Ser Arg Tyr Ala Asp Cys Ala Arg
    290                 295                 300

Ala Phe Gly Ala Ala Pro Glu Ser Ala Gly Asp Ser Val Ala Ala Gln
305                 310                 315                 320

Phe Leu Val Glu Thr Leu Ser Thr Leu Cys His Asp Leu Lys Val Pro
                325                 330                 335

Thr Pro Leu Ala Tyr Gly Ile Asp Arg Asp Ala Trp Asp Gly Leu Ile
            340                 345                 350

Pro Leu Met Ala Glu Gln Ala Leu Ala Ser Gly Ser Pro Gly Asn Asn
        355                 360                 365

Pro Val Val Pro Thr Ala Gly Gln Ile Glu Thr Leu Tyr Ser Glu Val
    370                 375                 380

Phe Ser
385

<210> SEQ ID NO 83
<211> LENGTH: 354
<212> TYPE: PRT
```

<213> ORGANISM: Rhodococcus jostii strain RHA1

<400> SEQUENCE: 83

```
Met Arg Pro Phe Val His Ser Gly Ser Pro Ala Arg Ile Val Phe Gly
1               5                   10                  15
Arg Gly Ala Arg Asp Gly Val Lys Glu Val Glu Arg Leu Gly Ala
            20                  25                  30
Arg Arg Ala Val Val Leu Ser Thr Ala Gln Gln Arg Glu Ser Ala Gly
        35                  40                  45
Arg Leu Ala Asp Asp Leu Gly Ala Leu Gly Val Gly Val Ile Asp Arg
    50                  55                  60
Ala Thr Met His Thr Pro Val Glu Val Thr Ala Gln Ala Leu Val Glu
65                  70                  75                  80
Ile Glu Gln Leu Asp Ala Asp Cys Val Val Ala Leu Gly Gly Gly Ser
                85                  90                  95
Thr Thr Gly Leu Gly Lys Ala Ile Ala Ala Arg Thr Gly Leu Pro Gln
            100                 105                 110
Val Ala Val Pro Thr Thr Tyr Ala Gly Ser Glu Val Thr Pro Ile Leu
        115                 120                 125
Gly Glu Thr Glu Asn Gly Val Lys Thr Thr Arg Arg Gly Pro Glu Ile
    130                 135                 140
Leu Pro Glu Thr Val Val Tyr Asp Pro Ala Leu Thr Asp Ser Leu Pro
145                 150                 155                 160
Ile Pro Leu Ser Ile Ala Ser Gly Leu Asn Ala Met Ala His Ala Ala
                165                 170                 175
Glu Gly Val Tyr Ala Arg Asp Gly Ser Pro Ile Phe Thr Leu Met Ala
            180                 185                 190
Leu Glu Gly Leu Ala Ala Leu Arg Asp Ala Leu Arg Glu Leu Thr Ser
        195                 200                 205
Asp Pro Ala Asp His Asp Ala Arg Asp Arg Ala Leu Tyr Gly Ala Trp
    210                 215                 220
Leu Cys Gly Thr Val Leu Gly Gly Val Gly Met Ser Val His His Lys
225                 230                 235                 240
Leu Cys His Thr Leu Gly Gly Ala Leu Asp Leu Pro His Ala Gln Thr
                245                 250                 255
His Ala Ile Leu Leu Pro His Thr Ile Gly Phe Val Glu Glu Thr Glu
            260                 265                 270
Pro Thr Val Leu Ser Pro Val Ala Asp Leu Phe Gly Gly Ser Ala Gly
        275                 280                 285
Arg Gly Leu His Asp Phe Ala Val Glu Val Gly Ala Pro Leu Arg Leu
    290                 295                 300
Ser Glu Leu Gly Val Thr Pro Glu Gln Leu Asp Arg Val Ala Asp Leu
305                 310                 315                 320
Ala Leu Ala Ala Pro Tyr Trp Ser Pro Arg Pro Leu Asp Arg Asp Ser
                325                 330                 335
Ile Arg Arg Leu Leu Gln His Ala Tyr Asp Gly Thr Arg Pro Glu Ser
            340                 345                 350
Thr Pro
```

<210> SEQ ID NO 84
<211> LENGTH: 358
<212> TYPE: PRT
<213> ORGANISM: Rhodococcus jostii RHA1

<400> SEQUENCE: 84

```
Met Thr Phe Thr Ser Ser Phe His Tyr Gln Ala Leu Pro Met Arg Val
1               5                   10                  15

Ser Phe Glu Val Gly Ala Val Thr Lys Ile Gly Glu Glu Leu Asp Arg
            20                  25                  30

Leu Gly Leu Ser Arg Ala Leu Val Leu Cys Thr Pro Glu Gln Lys His
        35                  40                  45

Leu Ala Asp Leu Val Met Asp His Leu Gly Asp Arg Gly Ala Gly Ile
50                  55                  60

Phe Asp Gln Ala Arg Met His Val Pro Val Glu Thr Ala Asp Arg Ala
65                  70                  75                  80

Arg Asp Arg Ala Arg Lys Leu Gly Ala Asp Ser Cys Val Val Ile Gly
                85                  90                  95

Gly Gly Ser Ser Ile Gly Leu Gly Lys Ala Ile Ala Leu Glu His Gly
            100                 105                 110

Leu Pro Ile Ile Ala Ile Pro Thr Thr Tyr Ala Gly Ser Glu Met Thr
        115                 120                 125

Pro Ile Trp Gly Leu Thr Arg Asp Gly Arg Lys Gln Thr Gly Arg Asp
130                 135                 140

Ala Lys Val Leu Pro Gln Ser Val Ile Tyr Asp Pro Gln Leu Thr Ala
145                 150                 155                 160

Thr Leu Pro Ala Glu Ile Ser Ala Ala Ser Gly Leu Asn Ala Val Ala
                165                 170                 175

His Ala Val Glu Ala Leu Tyr Ala Pro Asp Ala Ser Pro Ile Ile Ser
            180                 185                 190

Leu Met Ala Glu Glu Gly Val Arg Ala Phe Ala Glu Ser Leu Pro Ala
        195                 200                 205

Val Val Ala Asp Gly Asn Asp Leu Asp Ala Arg Ser Lys Ala Leu Tyr
210                 215                 220

Gly Ala Trp Leu Cys Gly Ala Cys Leu Gly Ala Thr Thr Met Ser Leu
225                 230                 235                 240

His His Lys Leu Cys His Val Leu Gly Gly Ser Leu Asp Leu Pro His
                245                 250                 255

Ala Gln Thr His Ala Ile Val Leu Pro His Val Leu Gly Tyr Asn Glu
            260                 265                 270

Ser His Ala Pro Ala Ala Arg Ala Ala Leu Gln Arg Ala Leu Gly Thr
        275                 280                 285

Asp Gly Asp Pro Ser Thr Ala Leu Trp Glu Leu Glu Gln Gln Leu Gln
290                 295                 300

Ile Pro His Ser Leu Glu Glu Leu Gly Val Arg Glu Thr Gln Leu Pro
305                 310                 315                 320

Ala Val Ile Asp Glu Val Leu Ser Asn Pro Tyr Ser Asn Pro Thr Pro
                325                 330                 335

Val Thr Glu Asp Gly Leu Arg His Leu Leu Gly Gln Ala Leu Arg Gly
            340                 345                 350

Asp Arg Pro Thr Arg Arg
        355
```

<210> SEQ ID NO 85
<211> LENGTH: 253
<212> TYPE: PRT
<213> ORGANISM: Streptomyces avermitilis ATCC 31267

<400> SEQUENCE: 85

Met Asp Leu Ser Asn Arg Thr Val Leu Ile Val Gly Gly Thr Ser Gly

```
            1               5                  10                  15
        Ile Gly Arg Glu Leu Ala Arg Arg Phe Ala Ala Gly Ser Thr Val
                       20                  25                  30
        Ala Val Gly Gly Arg Ser Pro Glu Ala Leu Ser Glu Leu Ala Gly Glu
                       35                  40                  45
        Gly Phe Gly Thr Ile Ser Ile Asp Val Thr Asp Ser Ala Ser Val Ala
                50                  55                  60
        Ser Ala Arg Asp Ala Val Leu Ala Arg Tyr Pro Glu Leu Asp Thr Val
         65                  70                  75                  80
        Val Thr Met Pro Gly Ile Met Leu Leu Glu Asp Leu Arg Asp Pro Ala
                            85                  90                  95
        His Phe Glu Ala Ala Ala Thr Thr Ile Asp Thr Asn Leu Val Gly Thr
                        100                 105                 110
        Ile Arg Val Ile Asp Ala Phe Thr Pro His Leu Val Arg Gly Ala
                    115                 120                 125
        Gly Thr Phe Ile Thr Val Thr Ser Gly Ile Ala Phe Leu Pro Phe Pro
                130                 135                 140
        Pro Met Pro Thr Tyr Ala Ala Ser Lys Ala Ala Val His Ala Tyr Ser
        145                 150                 155                 160
        Glu Ala Leu Arg Ala Gln Leu Asp Gly Thr Gly Val Ser Val Val Glu
                        165                 170                 175
        Leu Val Pro Pro Ala Val Ala Thr Ala Gly Gln Glu Lys Val Asn Pro
                    180                 185                 190
        His Ala Leu Pro Leu Asp Asp Phe Ala Thr Glu Val Gln Leu Leu
                    195                 200                 205
        Ser Glu Asp Pro Thr Pro Arg Glu Ile Leu Val Lys Ala Ala Leu Met
        210                 215                 220
        His Arg Trp Ala Glu Arg Asp Gly Thr Tyr Asp Asp Leu Val Ala Gln
        225                 230                 235                 240
        Arg Ser Gln Ala Leu Ala Met Leu Pro Ser Arg Glu Gly
                        245                 250

<210> SEQ ID NO 86
<211> LENGTH: 265
<212> TYPE: PRT
<213> ORGANISM: Streptomyces coelicolor ATCC BAA-471

<400> SEQUENCE: 86

Met Thr Glu Arg Leu Arg Ser Phe Arg Met Thr Ala Leu Thr Asn Lys
         1               5                  10                  15
        Thr Ala Leu Val Thr Gly Gly Ser Arg Gly Ile Gly Arg Ala Ile Ala
                       20                  25                  30
        Gln Arg Leu Gly Lys Glu Gly Ala Leu Val Ala Leu Thr Tyr Ser Ser
                       35                  40                  45
        Asp Glu Ala Ala Ala Lys Glu Thr Val His Ser Ile Glu Ala Ala Gly
                50                  55                  60
        Gly Arg Ala Phe Ala Phe Arg Ser Gln Leu Gly Val Pro Gly Asp Ala
         65                  70                  75                  80
        Glu Ala Leu Trp Gln Ala Phe Asp Ala Gln Ile Gly Gln Tyr Ala Asp
                            85                  90                  95
        Gly Gly Ser Gly Leu Asp Ile Leu Val Asn Asn Ala Gly Ile Ala Gly
                        100                 105                 110
        Pro Gly Leu Ile His Glu Val Glu Glu Ala Glu Tyr Asp Lys Val Phe
                    115                 120                 125
```

```
Ala Val Asn Ala Lys Ala Pro Phe Phe Ile Ile Gln Lys Gly Leu Glu
    130                 135                 140

Arg Leu Arg Asp Gly Gly Arg Ile Val Asn Ile Ser Ser Gly Val Thr
145                 150                 155                 160

Lys Val Ala Phe Pro Gly Met Thr Ser Tyr Ala Ala Lys Gly Ala
                165                 170                 175

Val Glu Val Leu Thr Leu Thr Leu Ala Gln Thr Leu Gly Ser Arg Gly
            180                 185                 190

Ile Thr Val Asn Ala Val Ser Pro Gly Thr Ile Glu Thr Asp Ile His
        195                 200                 205

Pro Trp Met Ala Asp Pro Ala Ala Lys Ala His Ala Ala Gly Phe Ser
210                 215                 220

Val Phe Asn Arg Val Gly Gln Pro Asp Asp Val Ala Asp Val Val Ala
225                 230                 235                 240

Phe Leu Ala Ser Asp Asp Ala Arg Trp Val Thr Gly Gln Asn Ile Asp
                245                 250                 255

Ala Ser Gly Gly Ser Gly Leu Gly Leu
            260                 265

<210> SEQ ID NO 87
<211> LENGTH: 294
<212> TYPE: PRT
<213> ORGANISM: Salmonella enterica subsp. enterica serovar Paratyphi B
      str. ATCC BAA-1585

<400> SEQUENCE: 87

Met Ser His Leu Tyr Asp Pro Thr Thr Gln Tyr Tyr Thr Gly Glu Tyr
1               5                   10                  15

Pro Lys Gln Lys Gln Pro Ala Pro Gly Val Gln Ala Lys Met Thr Pro
            20                  25                  30

Val Pro Asp Cys Gly Glu Lys Ser Tyr Val Gly Ser Gly Arg Leu Lys
        35                  40                  45

Asp Arg Lys Ala Leu Val Thr Gly Gly Asp Ser Gly Ile Gly Arg Ala
    50                  55                  60

Ala Ala Ile Ala Tyr Ala Arg Glu Gly Ala Asp Val Ala Ile Asn Tyr
65                  70                  75                  80

Leu Pro Ala Glu Glu Asp Ala Gln Gln Val Lys Ala Leu Ile Glu
                85                  90                  95

Glu Cys Gly Arg Lys Ala Val Leu Leu Pro Gly Asp Leu Ser Asp Glu
            100                 105                 110

Ser Phe Ala Arg Ser Leu Val His Lys Ala Arg Glu Ala Leu Gly Gly
        115                 120                 125

Leu Asp Ile Leu Ala Leu Val Ala Gly Lys Gln Thr Ala Ile Pro Glu
    130                 135                 140

Ile Lys Asp Leu Thr Ser Glu Gln Phe Gln Gln Thr Phe Ala Val Asn
145                 150                 155                 160

Val Phe Ala Leu Phe Trp Ile Thr Gln Glu Ala Ile Pro Leu Leu Pro
                165                 170                 175

Lys Gly Ala Ser Ile Ile Thr Thr Ser Ser Ile Gln Ala Tyr Gln Pro
            180                 185                 190

Ser Pro His Leu Leu Asp Tyr Ala Ala Thr Lys Ala Ala Ile Leu Asn
        195                 200                 205

Tyr Ser Arg Gly Leu Ala Lys Gln Val Ala Glu Lys Gly Ile Arg Val
    210                 215                 220

Asn Ile Val Ala Pro Gly Pro Ile Trp Thr Ala Leu Gln Ile Ser Gly
```

```
                225                 230                 235                 240
Gly Gln Thr Gln Asp Lys Ile Pro Gln Phe Gly Gln Gln Thr Pro Met
            245                 250                 255
Lys Arg Ala Gly Gln Pro Ala Glu Leu Ala Pro Val Tyr Val Tyr Leu
        260                 265                 270
Ala Ser Gln Glu Ser Ser Tyr Val Thr Ala Glu Val His Gly Val Cys
    275                 280                 285
Gly Gly Glu His Leu Gly
        290

<210> SEQ ID NO 88
<211> LENGTH: 245
<212> TYPE: PRT
<213> ORGANISM: Xanthomonas campestris pv. campestris ATCC 33913

<400> SEQUENCE: 88

Met Thr Asp Ser Ser Lys Val Val Leu Ile Thr Gly Ala Ala Arg Arg
1               5                   10                  15
Ile Gly Ala Gln Ile Ala Thr Thr Leu His Gly Ala Gly Tyr Arg Val
            20                  25                  30
Ala Leu His Ala His Arg Ser Gly Asp Ala Leu Ala Ala Arg Val Ala
        35                  40                  45
Ala Leu Cys Ala Gln Arg Ala Gly Ser Ala Cys Ala Leu Gln Ala Asp
    50                  55                  60
Leu Arg Thr Pro Glu Ala Pro Ala Gln Leu Val Asp Ala Cys Val Ala
65                  70                  75                  80
Ala Phe Gly Arg Leu Asp Ala Val Val Asn Asn Ala Ser Ala Phe Tyr
                85                  90                  95
Pro Thr Val Leu Gly Glu Ala Thr Pro Ala Gln Trp Asp Glu Leu Phe
            100                 105                 110
Ala Val Asn Ala Arg Ala Pro Phe Phe Ile Ala Gln Ala Ala Ala Ala
        115                 120                 125
Gln Leu Arg Ala His His Gly Ala Ile Val Asn Leu Thr Asp Leu His
    130                 135                 140
Ala Glu Gln Pro Met Arg Gln His Pro Leu Tyr Gly Ala Ser Lys Ser
145                 150                 155                 160
Ala Leu Glu Met Leu Thr Arg Ser Leu Ala Leu Glu Leu Ala Pro Gln
                165                 170                 175
Val Arg Val Asn Ala Val Ala Pro Gly Ala Ile Leu Trp Pro Glu Asp
            180                 185                 190
Gly Lys Ala Asp Ala Ala Lys Gln Ala Leu Leu Ala Arg Thr Pro Leu
        195                 200                 205
Ala Arg Ile Gly Thr Pro Glu Glu Val Ala Glu Ala Val Arg Trp Leu
    210                 215                 220
Leu Asp Asp Ala Ser Phe Ile Thr Gly His Thr Leu Arg Val Asp Gly
225                 230                 235                 240
Gly Arg Arg Leu Ser
                245

<210> SEQ ID NO 89
<211> LENGTH: 434
<212> TYPE: PRT
<213> ORGANISM: Bacillus anthracis

<400> SEQUENCE: 89

Met Val Val Lys Phe Thr Lys Ser Glu Ala Leu His Lys Glu Ala Leu
```

-continued

```
1               5                   10                  15
Glu His Ile Val Gly Val Asn Ser Pro Ser Arg Ser Phe Lys Ala
            20                  25                  30
Val Gly Gly Gly Ala Pro Ile Ala Met Glu Arg Gly Lys Gly Ala Tyr
            35                  40                  45
Phe Trp Asp Val Asp Gly Asn Lys Tyr Ile Asp Tyr Leu Ala Ala Tyr
            50                  55                  60
Gly Pro Ile Ile Thr Gly His Ala His Pro His Ile Thr Lys Ala Ile
65                  70                  75                  80
Thr Thr Ala Ala Glu Asn Gly Val Leu Tyr Gly Thr Pro Thr Ala Leu
                85                  90                  95
Glu Val Lys Phe Ala Lys Met Leu Lys Glu Ala Met Pro Ala Leu Asp
                100                 105                 110
Lys Val Arg Phe Val Asn Ser Gly Thr Glu Ala Val Met Thr Thr Ile
                115                 120                 125
Arg Val Ala Arg Ala Tyr Thr Gly Arg Thr Lys Ile Met Lys Phe Ala
130                 135                 140
Gly Cys Tyr His Gly His Ser Asp Leu Val Leu Val Ala Ala Gly Ser
145                 150                 155                 160
Gly Pro Ser Thr Leu Gly Thr Pro Asp Ser Ala Gly Val Pro Gln Ser
                165                 170                 175
Ile Ala Gln Glu Val Ile Thr Val Pro Phe Asn Asn Val Glu Thr Leu
                180                 185                 190
Lys Glu Ala Leu Asp Lys Trp Gly His Glu Val Ala Ala Ile Leu Val
                195                 200                 205
Glu Pro Ile Val Gly Asn Phe Gly Ile Val Glu Pro Lys Pro Gly Phe
                210                 215                 220
Leu Glu Lys Val Asn Glu Leu Val His Glu Ala Gly Ala Leu Val Ile
225                 230                 235                 240
Tyr Asp Glu Val Ile Thr Ala Phe Arg Phe Met Tyr Gly Gly Ala Gln
                245                 250                 255
Asp Leu Leu Gly Val Thr Pro Asp Leu Thr Ala Leu Gly Lys Val Ile
                260                 265                 270
Gly Gly Gly Leu Pro Ile Gly Ala Tyr Gly Gly Lys Lys Glu Ile Met
                275                 280                 285
Glu Gln Val Ala Pro Leu Gly Pro Ala Tyr Gln Ala Gly Thr Met Ala
                290                 295                 300
Gly Asn Pro Ala Ser Met Ala Ser Gly Ile Ala Cys Leu Glu Val Leu
305                 310                 315                 320
Gln Gln Glu Gly Leu Tyr Glu Lys Leu Asp Glu Leu Gly Ala Met Leu
                325                 330                 335
Glu Lys Gly Ile Leu Glu Gln Ala Lys His Asn Ile Asp Ile Thr
                340                 345                 350
Leu Asn Arg Leu Lys Gly Ala Leu Thr Val Tyr Phe Thr Thr Asn Thr
                355                 360                 365
Ile Glu Asp Tyr Asp Ala Ala Gln Asp Thr Asp Gly Glu Met Phe Gly
                370                 375                 380
Lys Phe Phe Lys Leu Met Leu Gln Glu Gly Val Asn Leu Ala Pro Ser
385                 390                 395                 400
Lys Tyr Glu Ala Trp Phe Leu Thr Thr Glu His Thr Lys Glu Asp Ile
                405                 410                 415
Glu Tyr Thr Ile Glu Ala Val Gly Arg Ala Phe Ala Ala Leu Ala Asp
                420                 425                 430
```

Asn Lys

<210> SEQ ID NO 90
<211> LENGTH: 383
<212> TYPE: PRT
<213> ORGANISM: Bacillus anthracis

<400> SEQUENCE: 90

Met Gln Leu Phe His Lys Thr Val Asn Arg Arg Gly Thr His Ser Ile
1               5                   10                  15

Lys Trp Asp Thr Tyr Lys Asn Glu Glu Leu Ile His Ala Trp Ile Ala
                20                  25                  30

Asp Met Asp Phe Glu Val Pro Gln Pro Ile Gln Thr Ala Leu Lys Lys
            35                  40                  45

Arg Ile Glu His Pro Ile Phe Gly Tyr Thr Leu Pro Pro Glu Asn Ile
50                  55                  60

Gly Asp Ile Ile Cys Asn Trp Thr Lys Lys Gln Tyr Asn Trp Asp Ile
65                  70                  75                  80

Gln Lys Glu Trp Ile Val Phe Ser Ala Gly Ile Val Pro Ala Leu Ser
                85                  90                  95

Thr Ser Ile Gln Ala Phe Thr Lys Glu Asn Glu Ser Val Leu Val Gln
                100                 105                 110

Pro Pro Ile Tyr Pro Pro Phe Phe Glu Met Val Thr Thr Asn Asn Arg
            115                 120                 125

Gln Leu Cys Val Ser Pro Leu Gln Lys Gln Asn Asp Thr Tyr Ala Ile
130                 135                 140

Asp Phe Glu His Leu Glu Lys Gln Phe Gln Gln Gly Val Lys Leu Met
145                 150                 155                 160

Leu Leu Cys Ser Pro His Asn Pro Ile Gly Arg Val Trp Lys Lys Glu
                165                 170                 175

Glu Leu Thr Lys Leu Gly Ser Leu Cys Thr Lys Tyr Asn Val Ile Val
                180                 185                 190

Val Ala Asp Glu Ile His Ser Asp Ile Ile Tyr Ala Asp His Thr His
            195                 200                 205

Thr Pro Phe Ala Ser Leu Ser Glu Glu Leu Ala Ala Arg Thr Ile Thr
210                 215                 220

Cys Met Ala Pro Ser Lys Thr Phe Asn Ile Ala Gly Leu Gln Ala Ser
225                 230                 235                 240

Ile Ile Ile Ile Pro Asn Glu Lys Leu Arg Gln Ala Phe Thr Ser Ile
                245                 250                 255

Gln Tyr Arg Gln Gly Phe His Gly Leu Asn Ile Phe Ala Tyr Thr Ala
                260                 265                 270

Met Gln Ser Ala Tyr Thr Glu Cys Asn Asp Trp Leu Asn Glu Ile Arg
            275                 280                 285

Phe Tyr Ile Glu Asp Asn Ala Lys Phe Ala Cys Glu Tyr Ile Lys Asp
290                 295                 300

His Ile Pro Thr Leu Ser Val Met Lys Pro Glu Gly Ser Phe Leu Leu
305                 310                 315                 320

Trp Ile Asp Cys Ser Ala Leu Asn Leu Ser Gln Asp Glu Arg Thr Lys
                325                 330                 335

Leu Leu Glu Glu Lys Gly Lys Ile Ile Val Glu Pro Gly Glu Lys Tyr
                340                 345                 350

Gly Leu Gly Gly Glu Glu His Ile Gly Ile Asn Ile Gly Cys Pro Arg
            355                 360                 365

```
Ser Val Leu Glu Glu Ile Leu Asn Arg Leu Arg His Thr Phe Ser
        370                 375                 380

<210> SEQ ID NO 91
<211> LENGTH: 425
<212> TYPE: PRT
<213> ORGANISM: Marinobacter hydrocarbonoclasticus strain ATCC 700491

<400> SEQUENCE: 91

Met Ser Asn Lys Glu Leu Gln Ala Leu Lys Glu Arg Tyr Val Ala Ala
1               5                   10                  15

Gly Ala Ala Ser Pro Asn Asp Gln Phe Ala Asp His Ala Leu Asn Ala
            20                  25                  30

Glu Val Trp Asp Ala Asp Gly Lys Arg Met Ile Asp Phe Ala Gly Gly
        35                  40                  45

Ile Gly Val Leu Asn Ile Gly His Arg His Pro Arg Val Val Glu Ala
    50                  55                  60

Val Lys Ala Gln Leu Asp Lys Leu Met His Thr Cys Gln Thr Val Met
65                  70                  75                  80

Pro Tyr Glu Gly Tyr Val Lys Leu Ala Gln Lys Leu Ser Glu Val Val
                85                  90                  95

Pro Val Lys Gly His Gly Lys Val Met Leu Ala Asn Ser Gly Ala Glu
            100                 105                 110

Ala Leu Glu Asn Ala Val Lys Ile Ala Arg Ala Ala Thr Gly Lys Asn
        115                 120                 125

Asn Val Ile Cys Phe Asp Gly Gly Tyr His Gly Arg Thr Phe Phe Thr
    130                 135                 140

Met Ala Met Asn Gly Lys Ala Ala Pro Tyr Gln Thr Ser Phe Gly Pro
145                 150                 155                 160

Met Pro Gly Leu Val Tyr Arg Ala Pro Tyr Pro Val Pro Tyr His Gly
                165                 170                 175

Ile Ser Glu Glu Glu Ser Leu Arg Gly Leu Ala Met Thr Met Lys Ala
            180                 185                 190

Asp Ser Pro Ala His Glu Thr Ala Ala Ile Val Leu Glu Pro Val Leu
        195                 200                 205

Gly Glu Gly Gly Phe Tyr Pro Ala Pro Pro Ser Phe Leu Lys Ala Ile
    210                 215                 220

Arg Lys Ile Cys Asp Glu Asn Asp Ile Met Met Ile Val Asp Glu Val
225                 230                 235                 240

Gln Ser Gly Phe Gly Arg Thr Gly Lys Leu Phe Ala Ile Glu His Ser
                245                 250                 255

Gly Ile Glu Pro Asp Ile Met Thr Met Ala Lys Ser Met Ala Asp Gly
            260                 265                 270

Met Pro Ile Ser Ala Ile Val Gly Thr Asp Lys Val Met Asp Ser Ser
        275                 280                 285

Gly Pro Asn Ser Leu Gly Gly Thr Tyr Thr Gly Ser Pro Thr Ala Cys
    290                 295                 300

Ala Ala Ala Leu Ala Val Phe Asp Val Ile Lys Glu Glu Asp Ile Leu
305                 310                 315                 320

Gly Arg Ser Gln Arg Leu Gly Glu Lys Leu Arg Ala Arg Phe Asp Gln
                325                 330                 335

Trp Gln Glu Gln Phe Thr His Val Asp Asn Ala Arg Asn Leu Gly Pro
            340                 345                 350

Met Ala Ala Phe Glu Leu Val Glu Ser Lys Asp Ser His Lys Pro Met
```

```
            355                 360                 365
Pro Glu Leu Ala Gly Ala Ile Thr Lys Lys Ala Lys Glu Lys Gly Leu
    370                 375                 380

Ile Leu Leu Ser Cys Gly Met His Gly Asn Thr Leu Arg Phe Leu Met
385                 390                 395                 400

Pro Val Thr Ile Glu Asp Glu Val Leu Glu Gly Leu Asn Ile Val
                    405                 410                 415

Glu Glu Cys Leu Lys Glu Val Gly Ala
                420                 425

<210> SEQ ID NO 92
<211> LENGTH: 460
<212> TYPE: PRT
<213> ORGANISM: Pseudomonas aeruginosa ATCC 15692

<400> SEQUENCE: 92

Met Thr Ala Gln Leu Asn Pro Gln Arg Asp Thr Arg Asp Tyr Gln Gln
1               5                   10                  15

Leu Asp Ala Ala His His Ile His Ala Phe Leu Asp Gln Lys Ala Leu
                20                  25                  30

Asn Arg Glu Gly Pro Arg Val Met Val Arg Gly Asp Gly Leu Gln Leu
            35                  40                  45

Trp Asp Asn Asp Gly Lys Arg Tyr Leu Asp Gly Met Ser Gly Leu Trp
    50                  55                  60

Cys Thr Asn Leu Gly Tyr Gly Arg Gln Asp Leu Ala Ala Ala Ala Ser
65                  70                  75                  80

Arg Gln Leu Glu Gln Leu Pro Tyr Tyr Asn Met Phe Phe His Thr Thr
                85                  90                  95

His Pro Ala Val Val Glu Leu Ser Glu Met Leu Phe Ser Leu Leu Pro
            100                 105                 110

Asp His Tyr Ser His Ala Ile Tyr Thr Asn Ser Gly Ser Glu Ala Asn
        115                 120                 125

Glu Val Leu Ile Arg Thr Val Arg Arg Tyr Trp Gln Ile Leu Gly Lys
    130                 135                 140

Pro Gln Lys Lys Ile Met Ile Gly Arg Trp Asn Gly Tyr His Gly Ser
145                 150                 155                 160

Thr Leu Gly Ser Thr Ala Leu Gly Gly Met Lys Phe Met His Glu Met
                165                 170                 175

Gly Gly Met Leu Pro Asp Phe Ala His Ile Asp Glu Pro Tyr Trp Tyr
            180                 185                 190

Ala Asn Gly Gly Glu Leu Ser Pro Ala Glu Phe Gly Arg Arg Ala Ala
        195                 200                 205

Leu Gln Leu Glu Glu Lys Ile Leu Glu Leu Gly Ala Glu Asn Val Ala
    210                 215                 220

Ala Phe Val Ala Glu Pro Phe Gln Gly Ala Gly Gly Met Ile Phe Pro
225                 230                 235                 240

Pro Gln Ser Tyr Trp Pro Glu Ile Gln Arg Ile Cys Arg Gln Tyr Asp
                245                 250                 255

Val Leu Leu Cys Ala Asp Glu Val Ile Gly Gly Phe Gly Arg Thr Gly
            260                 265                 270

Glu Trp Phe Ala His Glu His Phe Gly Phe Gln Pro Asp Thr Leu Ser
        275                 280                 285

Ile Ala Lys Gly Leu Thr Ser Gly Tyr Ile Pro Met Gly Gly Leu Val
    290                 295                 300
```

```
Leu Gly Lys Arg Ile Ala Glu Val Leu Val Glu Gln Gly Gly Val Phe
305                 310                 315                 320

Ala His Gly Leu Thr Tyr Ser Gly His Pro Val Ala Ala Val Ala
            325                 330                 335

Ile Ala Asn Leu Lys Ala Leu Arg Asp Glu Gly Val Val Thr Arg Val
            340                 345                 350

Arg Glu Glu Thr Gly Pro Tyr Leu Gln Arg Cys Leu Arg Glu Val Phe
            355                 360                 365

Gly Asp His Pro Leu Val Gly Glu Val Gln Gly Ala Gly Phe Val Ala
            370                 375                 380

Ala Leu Gln Phe Ala Glu Asp Lys Val Thr Arg Lys Arg Phe Ala Asn
385                 390                 395                 400

Glu Asn Asp Leu Ala Trp Arg Cys Arg Thr Ile Gly Phe Glu Glu Gly
            405                 410                 415

Val Ile Ile Arg Ser Thr Leu Gly Arg Met Ile Met Ala Pro Ala Leu
            420                 425                 430

Val Ala Gly Arg Ala Glu Ile Asp Glu Leu Ile Asp Lys Thr Arg Ile
            435                 440                 445

Ala Val Asp Arg Thr Ala Arg Glu Ile Gly Val Leu
            450                 455                 460

<210> SEQ ID NO 93
<211> LENGTH: 468
<212> TYPE: PRT
<213> ORGANISM: Pseudomonas aeruginosa ATCC 15692

<400> SEQUENCE: 93

Met Asn Ala Arg Leu His Ala Thr Ser Pro Leu Gly Asp Ala Asp Leu
1               5                   10                  15

Val Arg Ala Asp Gln Ala His Tyr Met His Gly Tyr His Val Phe Asp
            20                  25                  30

Asp His Arg Val Asn Gly Ser Leu Asn Ile Ala Ala Gly Asp Gly Ala
            35                  40                  45

Tyr Ile Tyr Asp Thr Ala Gly Asn Arg Tyr Leu Asp Ala Val Gly Gly
    50                  55                  60

Met Trp Cys Thr Asn Ile Gly Leu Gly Arg Glu Glu Met Ala Arg Thr
65              70                  75                  80

Val Ala Glu Gln Thr Arg Leu Leu Ala Tyr Ser Asn Pro Phe Cys Asp
            85                  90                  95

Met Ala Asn Pro Arg Ala Ile Glu Leu Cys Arg Lys Leu Ala Glu Leu
            100                 105                 110

Ala Pro Gly Asp Leu Asp His Val Phe Leu Thr Thr Gly Gly Ser Thr
            115                 120                 125

Ala Val Asp Thr Ala Ile Arg Leu Met His Tyr Tyr Gln Asn Cys Arg
            130                 135                 140

Gly Lys Arg Ala Lys Lys His Val Ile Thr Arg Ile Asn Ala Tyr His
145                 150                 155                 160

Gly Ser Thr Phe Leu Gly Met Ser Leu Gly Gly Lys Ser Ala Asp Arg
            165                 170                 175

Pro Ala Glu Phe Asp Phe Leu Asp Glu Arg Ile His His Leu Ala Cys
            180                 185                 190

Pro Tyr Tyr Tyr Arg Ala Pro Glu Gly Leu Gly Glu Ala Glu Phe Leu
            195                 200                 205

Asp Gly Leu Val Asp Glu Phe Glu Arg Lys Ile Leu Glu Leu Gly Ala
            210                 215                 220
```

```
Asp Arg Val Gly Ala Phe Ile Ser Glu Pro Val Phe Gly Ser Gly
225                 230                 235                 240

Val Ile Val Pro Pro Ala Gly Tyr His Arg Arg Met Trp Glu Leu Cys
            245                 250                 255

Gln Arg Tyr Asp Val Leu Tyr Ile Ser Asp Glu Val Val Thr Ser Phe
            260                 265                 270

Gly Arg Leu Gly His Phe Phe Ala Ser Gln Ala Val Phe Gly Val Gln
            275                 280                 285

Pro Asp Ile Ile Leu Thr Ala Lys Gly Leu Thr Ser Gly Tyr Gln Pro
            290                 295                 300

Leu Gly Ala Cys Ile Phe Ser Arg Arg Ile Trp Glu Val Ile Ala Glu
305                 310                 315                 320

Pro Asp Lys Gly Arg Cys Phe Ser His Gly Phe Thr Tyr Ser Gly His
            325                 330                 335

Pro Val Ala Cys Ala Ala Ala Leu Lys Asn Ile Glu Ile Ile Glu Arg
            340                 345                 350

Glu Gly Leu Leu Ala His Ala Asp Glu Val Gly Arg Tyr Phe Glu Glu
            355                 360                 365

Arg Leu Gln Ser Leu Arg Asp Leu Pro Ile Val Gly Asp Val Arg Gly
    370                 375                 380

Met Arg Phe Met Ala Cys Val Glu Phe Val Ala Asp Lys Ala Ser Lys
385                 390                 395                 400

Ala Leu Phe Pro Glu Ser Leu Asn Ile Gly Glu Trp Val His Leu Arg
            405                 410                 415

Ala Gln Lys Arg Gly Leu Leu Val Arg Pro Ile Val His Leu Asn Val
            420                 425                 430

Met Ser Pro Pro Leu Ile Leu Thr Arg Glu Gln Val Asp Thr Val Val
            435                 440                 445

Arg Val Leu Arg Glu Ser Ile Glu Glu Thr Val Glu Asp Leu Val Arg
    450                 455                 460

Ala Gly His Arg
465

<210> SEQ ID NO 94
<211> LENGTH: 444
<212> TYPE: PRT
<213> ORGANISM: Pseudomonas aeruginosa ATCC 15692

<400> SEQUENCE: 94

Met Thr Met Asn Asp Glu Pro Gln Ser Ser Leu Asp Asn Phe Trp
1               5                   10                  15

Met Pro Phe Thr Ala Asn Arg Gln Phe Lys Ala Arg Pro Arg Leu Leu
            20                  25                  30

Glu Ser Ala Glu Gly Ile His Tyr Ile Ala Gln Gly Arg Arg Ile
            35                  40                  45

Leu Asp Gly Thr Ala Gly Leu Trp Cys Cys Asn Ala Gly His Gly Arg
    50                  55                  60

Arg Glu Ile Ser Glu Ala Val Ala Arg Gln Ile Ala Thr Leu Asp Tyr
65                  70                  75                  80

Ala Pro Pro Phe Gln Met Gly His Pro Leu Pro Phe Glu Leu Ala Ala
            85                  90                  95

Arg Leu Thr Glu Ile Ala Pro Pro Ser Leu Asn Lys Val Phe Phe Thr
            100                 105                 110

Asn Ser Gly Ser Glu Ser Ala Asp Thr Ala Leu Lys Ile Ala Leu Ala
```

```
            115                 120                 125
Tyr Gln Arg Ala Ile Gly Gln Gly Thr Arg Thr Arg Leu Ile Gly Arg
    130                 135                 140

Glu Leu Gly Tyr His Gly Val Gly Phe Gly Gly Leu Ser Val Gly Gly
145                 150                 155                 160

Met Val Asn Asn Arg Lys Ala Phe Ser Ala Asn Leu Leu Pro Gly Val
                165                 170                 175

Asp His Leu Pro His Thr Leu Asp Val Ala Arg Asn Ala Phe Thr Val
                180                 185                 190

Gly Leu Pro Glu His Gly Val Glu Lys Ala Glu Glu Leu Glu Arg Leu
            195                 200                 205

Val Thr Leu His Gly Ala Glu Asn Ile Ala Ala Val Ile Val Glu Pro
        210                 215                 220

Met Ser Gly Ser Ala Gly Val Val Leu Pro Pro Lys Gly Tyr Leu Gln
225                 230                 235                 240

Arg Leu Arg Glu Ile Thr Arg Lys His Gly Ile Leu Leu Ile Phe Asp
                245                 250                 255

Glu Val Ile Thr Gly Phe Gly Arg Val Gly Glu Ala Phe Ala Ala Gln
                260                 265                 270

Arg Trp Gly Val Val Pro Asp Leu Leu Thr Cys Ala Lys Gly Leu Thr
            275                 280                 285

Asn Gly Ser Ile Pro Met Gly Ala Val Phe Val Asp Glu Lys Ile His
        290                 295                 300

Ala Ala Phe Met Gln Gly Pro Gln Gly Ala Ile Glu Phe Phe His Gly
305                 310                 315                 320

Tyr Thr Tyr Ser Gly His Pro Val Ala Cys Ala Ala Ala Leu Ala Thr
                325                 330                 335

Leu Asp Ile Tyr Arg Arg Asp Asp Leu Phe Gln Arg Ala Val Glu Leu
                340                 345                 350

Glu Gly Tyr Trp Gln Asp Ala Leu Phe Ser Leu Arg Asp Leu Pro Asn
            355                 360                 365

Val Val Asp Ile Arg Ala Val Gly Leu Val Gly Gly Val Gln Leu Ala
        370                 375                 380

Pro His Ala Asp Gly Pro Gly Lys Arg Gly Tyr Asp Val Phe Glu Arg
385                 390                 395                 400

Cys Phe Trp Glu His Asp Leu Met Val Arg Val Thr Gly Asp Ile Ile
                405                 410                 415

Ala Met Ser Pro Pro Leu Ile Ile Asp Lys Pro His Ile Asp Gln Ile
                420                 425                 430

Val Glu Arg Leu Ala Gln Ala Ile Arg Ala Ser Val
            435                 440

<210> SEQ ID NO 95
<211> LENGTH: 452
<212> TYPE: PRT
<213> ORGANISM: Pseudomonas putida KT2440

<400> SEQUENCE: 95

Met Ser Glu Gln Asn Ser Gln Thr Leu Ala Trp Gln Thr Met Ser Arg
1               5                   10                  15

Asp His His Leu Ala Pro Phe Ser Asp Val Arg Gln Leu Ala Glu Lys
                20                  25                  30

Gly Pro Arg Ile Ile Thr Ser Ala Lys Gly Val Tyr Leu Trp Asp Ser
            35                  40                  45
```

```
Glu Gly Asn Lys Ile Leu Asp Gly Met Ala Gly Leu Trp Cys Val Ala
 50                  55                  60
Val Gly Tyr Gly Arg Glu Leu Ala Glu Val Ala Ser Gln Gln Met
 65                  70                  75                  80
Lys Gln Leu Pro Tyr Tyr Asn Leu Phe Gln Thr Ala His Pro Pro
                 85                  90                  95
Ala Leu Glu Leu Ala Lys Ala Ile Ala Glu Val Ala Pro Gln Gly Met
                100                 105                 110
Asn His Val Phe Phe Thr Gly Ser Gly Ser Glu Gly Asn Asp Thr Val
                115                 120                 125
Leu Arg Met Val Arg His Tyr Trp Ala Leu Lys Gly Gln Lys Asn Lys
 130                 135                 140
Lys Val Ile Ile Gly Arg Ile Asn Gly Tyr His Gly Ser Thr Val Ala
145                 150                 155                 160
Gly Ala Ala Leu Gly Gly Met Ser Gly Met His Gln Gln Gly Gly Val
                165                 170                 175
Ile Pro Asp Val Val His Ile Pro Gln Pro Tyr Trp Phe Gly Glu Gly
                180                 185                 190
Gly Asp Met Thr Glu Ala Asp Phe Gly Val Trp Ala Ala Glu Gln Leu
                195                 200                 205
Glu Lys Lys Ile Leu Glu Val Gly Val Asp Asn Val Ala Ala Phe Ile
 210                 215                 220
Ala Glu Pro Ile Gln Gly Ala Gly Gly Val Ile Ile Pro Pro Gln Thr
225                 230                 235                 240
Tyr Trp Pro Lys Ile Lys Glu Ile Leu Ala Arg Tyr Asp Ile Leu Phe
                245                 250                 255
Val Ala Asp Glu Val Ile Cys Gly Phe Gly Arg Thr Gly Glu Trp Phe
                260                 265                 270
Gly Thr Asp Tyr Tyr Asp Leu Lys Pro Asp Leu Met Thr Ile Ala Lys
                275                 280                 285
Gly Leu Thr Ser Gly Tyr Ile Pro Met Gly Gly Val Ile Val Arg Asp
                290                 295                 300
Glu Val Ala Lys Val Ile Ser Glu Gly Gly Asp Phe Asn His Gly Phe
305                 310                 315                 320
Thr Tyr Ser Gly His Pro Val Ala Ala Val Gly Leu Glu Asn Leu
                325                 330                 335
Arg Ile Leu Arg Asp Glu Gln Ile Ile Gln Gln Val His Asp Lys Thr
                340                 345                 350
Ala Pro Tyr Leu Gln Gln Arg Leu Arg Glu Leu Ala Asp His Pro Leu
                355                 360                 365
Val Gly Glu Val Arg Gly Leu Gly Met Leu Gly Ala Ile Glu Leu Val
                370                 375                 380
Lys Asp Lys Ala Thr Arg Ala Arg His Glu Gly Lys Gly Val Gly Met
385                 390                 395                 400
Ile Cys Arg Gln His Cys Phe Asp Asn Gly Leu Ile Met Arg Ala Val
                405                 410                 415
Gly Asp Thr Met Ile Ile Ala Pro Pro Leu Val Ile Ser Ile Glu Glu
                420                 425                 430
Ile Asp Glu Leu Val Glu Lys Ala Arg Lys Cys Leu Asp Leu Thr Tyr
                435                 440                 445
Glu Ala Val Arg
450
```

```
<210> SEQ ID NO 96
<211> LENGTH: 470
<212> TYPE: PRT
<213> ORGANISM: Pseudomonas putida KT2440

<400> SEQUENCE: 96

Met Ala Thr Pro Ser Lys Ala Phe Ala Ile Ala His Asp Pro Leu Val
1               5                   10                  15

Glu Ala Asp Lys Ala His Tyr Met His Gly Tyr His Val Phe Asp Glu
            20                  25                  30

His Arg Glu Gln Gly Ala Leu Asn Ile Val Ala Gly Glu Gly Ala Tyr
        35                  40                  45

Ile Arg Asp Thr His Gly Asn Arg Phe Leu Asp Ala Val Gly Gly Met
    50                  55                  60

Trp Cys Thr Asn Ile Gly Leu Gly Arg Glu Glu Met Ala Leu Ala Ile
65                  70                  75                  80

Val Asp Gln Val Arg Gln Leu Ala Tyr Ser Asn Pro Phe Ser Asp Met
                85                  90                  95

Ala Asn Asp Val Ala Ile Glu Leu Cys Gln Lys Leu Ala Gln Leu Ala
            100                 105                 110

Pro Gly Asp Leu Asn His Val Phe Leu Thr Thr Gly Gly Ser Thr Ala
        115                 120                 125

Val Asp Thr Ala Tyr Arg Leu Ile Gln Tyr Tyr Gln Asn Cys Arg Gly
    130                 135                 140

Lys Pro His Lys Lys His Ile Ile Ala Arg Tyr Asn Ala Tyr His Gly
145                 150                 155                 160

Ser Thr Thr Leu Thr Met Ser Ile Gly Asn Lys Ala Ala Asp Arg Val
                165                 170                 175

Pro Glu Phe Asp Tyr His His Asp Leu Ile His His Val Ser Asn Pro
            180                 185                 190

Asn Pro Tyr Arg Ala Pro Asp Asp Met Asp Glu Ala Glu Phe Leu Asp
        195                 200                 205

Phe Leu Val Ala Glu Phe Glu Asp Lys Ile Leu Ser Leu Gly Ala Asp
    210                 215                 220

Asn Val Ala Ala Phe Phe Ala Glu Pro Ile Met Gly Ser Gly Gly Val
225                 230                 235                 240

Ile Ile Pro Pro Glu Gly Tyr Phe Gln Arg Met Trp Gln Leu Cys Gln
                245                 250                 255

Thr Tyr Asp Ile Leu Phe Val Ala Asp Glu Val Val Thr Ser Phe Gly
            260                 265                 270

Arg Leu Gly Thr Phe Phe Ala Ser Glu Glu Leu Phe Gly Val Thr Pro
        275                 280                 285

Asp Ile Ile Thr Thr Ala Lys Gly Leu Thr Ser Ala Tyr Leu Pro Leu
    290                 295                 300

Gly Ala Cys Ile Phe Ser Glu Arg Ile Trp Gln Val Ile Ala Glu Pro
305                 310                 315                 320

Gly Lys Gly Arg Cys Phe Thr His Gly Phe Thr Tyr Ser Gly His Pro
                325                 330                 335

Val Cys Cys Thr Ala Ala Leu Lys Asn Ile Glu Ile Ile Glu Arg Glu
            340                 345                 350

Gln Leu Leu Asp His Val Asn Asp Val Gly Ser Tyr Leu Glu Gln Arg
        355                 360                 365

Leu Gln Ser Leu Arg Asp Leu Pro Leu Val Gly Asp Val Arg Cys Met
    370                 375                 380
```

```
Lys Leu Met Ala Cys Val Glu Phe Val Ala Asn Lys Ala Ser Lys Ala
385                 390                 395                 400

Leu Phe Ala Asp Glu Val Asn Ile Gly Glu Arg Ile His Ser Lys Ala
            405                 410                 415

Gln Glu Lys Gly Leu Leu Val Arg Pro Ile Met His Leu Asn Val Met
        420                 425                 430

Ser Pro Pro Leu Ile Ile Thr His Ala Gln Val Asp Glu Ile Val Glu
        435                 440                 445

Thr Leu Arg Gln Cys Ile Ile Glu Thr Ala Arg Glu Leu Thr Ala Leu
    450                 455                 460

Gly Leu Tyr Gln Gly Arg
465                 470

<210> SEQ ID NO 97
<211> LENGTH: 453
<212> TYPE: PRT
<213> ORGANISM: Pseudomonas putida KT2440

<400> SEQUENCE: 97

Met Ser Val Asn Asn Pro Gln Thr Arg Glu Trp Gln Thr Leu Ser Gly
1               5                   10                  15

Glu His His Leu Ala Pro Phe Ser Asp Tyr Lys Gln Leu Lys Glu Lys
            20                  25                  30

Gly Pro Arg Ile Ile Thr Lys Ala Gln Gly Val His Leu Trp Asp Ser
        35                  40                  45

Glu Gly His Lys Ile Leu Asp Gly Met Ala Gly Leu Trp Cys Val Ala
    50                  55                  60

Val Gly Tyr Gly Arg Glu Glu Leu Val Gln Ala Ala Glu Lys Gln Met
65                  70                  75                  80

Arg Glu Leu Pro Tyr Tyr Asn Leu Phe Phe Gln Thr Ala His Pro Pro
                85                  90                  95

Ala Leu Glu Leu Ala Lys Ala Ile Thr Asp Val Ala Pro Lys Gly Met
            100                 105                 110

Thr His Val Phe Phe Thr Gly Ser Gly Ser Glu Gly Asn Asp Thr Val
        115                 120                 125

Leu Arg Met Val Arg His Tyr Trp Ala Leu Lys Gly Lys Pro His Lys
    130                 135                 140

Gln Thr Ile Ile Gly Arg Ile Asn Gly Tyr His Gly Ser Thr Phe Ala
145                 150                 155                 160

Gly Ala Cys Leu Gly Gly Met Ser Gly Met His Glu Gln Gly Gly Leu
                165                 170                 175

Pro Ile Pro Gly Ile Val His Ile Pro Gln Pro Tyr Trp Phe Gly Glu
            180                 185                 190

Gly Gly Asp Met Thr Pro Asp Glu Phe Gly Val Trp Ala Ala Glu Gln
        195                 200                 205

Leu Glu Lys Lys Ile Leu Glu Val Gly Glu Asp Asn Val Ala Ala Phe
    210                 215                 220

Ile Ala Glu Pro Ile Gln Gly Ala Gly Gly Val Ile Ile Pro Pro Glu
225                 230                 235                 240

Thr Tyr Trp Pro Lys Val Lys Glu Ile Leu Ala Arg Tyr Asp Ile Leu
                245                 250                 255

Phe Val Ala Asp Glu Val Ile Cys Gly Phe Gly Arg Thr Gly Glu Trp
            260                 265                 270

Phe Gly Ser Asp Tyr Tyr Asp Leu Lys Pro Asp Leu Met Thr Ile Ala
        275                 280                 285
```

-continued

```
Lys Gly Leu Thr Ser Gly Tyr Ile Pro Met Gly Gly Val Ile Val Arg
    290                 295                 300

Asp Thr Val Ala Lys Val Ile Ser Glu Gly Gly Asp Phe Asn His Gly
305                 310                 315                 320

Phe Thr Tyr Ser Gly His Pro Val Ala Ala Val Gly Leu Glu Asn
                325                 330                 335

Leu Arg Ile Leu Arg Asp Glu Lys Ile Val Glu Lys Ala Arg Thr Glu
            340                 345                 350

Ala Ala Pro Tyr Leu Gln Lys Arg Leu Arg Glu Leu Gln Asp His Pro
        355                 360                 365

Leu Val Gly Glu Val Arg Gly Leu Gly Met Leu Gly Ala Ile Glu Leu
    370                 375                 380

Val Lys Asp Lys Ala Thr Arg Ser Arg Tyr Glu Gly Lys Gly Val Gly
385                 390                 395                 400

Met Ile Cys Arg Thr Phe Cys Phe Glu Asn Gly Leu Ile Met Arg Ala
                405                 410                 415

Val Gly Asp Thr Met Ile Ile Ala Pro Pro Leu Val Ile Ser His Ala
            420                 425                 430

Glu Ile Asp Glu Leu Val Glu Lys Ala Arg Lys Cys Leu Asp Leu Thr
        435                 440                 445

Leu Glu Ala Ile Gln
    450

<210> SEQ ID NO 98
<211> LENGTH: 413
<212> TYPE: PRT
<213> ORGANISM: Rhodococcus jostii RHA1

<400> SEQUENCE: 98

Met Thr Arg Leu Ser Pro Leu Leu Ala Gln Ala Thr Pro Val Thr Val
1               5                   10                  15

Asp His Gly Glu Gly Cys Tyr Leu Tyr Gly Thr Asp Gly Arg Arg Tyr
            20                  25                  30

Leu Asp Phe Thr Ala Gly Ile Gly Val Thr Ser Thr Gly His Cys His
        35                  40                  45

Pro His Val Val Glu Ala Ala Arg Arg Gln Ile Gly Ser Leu Ile His
    50                  55                  60

Gly Gln Tyr Thr Thr Val Met His Gln Pro Met Leu Glu Leu Val Asp
65                  70                  75                  80

Arg Leu Gly Ser Val Leu Pro Ala Gly Leu Asp Ser Leu Phe Phe Ala
                85                  90                  95

Asn Ser Gly Ser Glu Ala Val Glu Ala Ser Leu Arg Leu Ser Arg Gln
            100                 105                 110

Ala Thr Gly Arg Pro Asn Val Ile Val Phe His Gly Gly Phe His Gly
        115                 120                 125

Arg Thr Val Ala Thr Ala Thr Met Thr Thr Ser Gly Thr Arg Phe Ser
    130                 135                 140

Ala Gly Phe Ser Pro Leu Met Gly Gly Val His Val Ala Pro Phe Pro
145                 150                 155                 160

Asn Ala Tyr Arg Tyr Gly Trp Ser Glu Glu Ala Thr Ala Phe Ala
                165                 170                 175

Leu Lys Glu Leu Asp Tyr Ile Phe Ala Thr Leu Thr Ala Pro Asn Glu
            180                 185                 190

Thr Ala Ala Phe Val Val Glu Pro Val Leu Gly Glu Gly Gly Tyr Val
```

```
            195                 200                 205
Pro Gly Asn Thr Ala Phe Phe Gln Gly Leu Arg Glu Arg Ala Asp Arg
210                 215                 220

Tyr Gly Ile Leu Leu Val Ile Asp Glu Ile Gln Thr Gly Phe Gly Arg
225                 230                 235                 240

Thr Gly Lys Phe Phe Gly His Gln His Phe Asp Val Arg Pro Asp Ile
                245                 250                 255

Ile Thr Ile Ala Lys Gly Leu Ala Ser Gly Phe Pro Leu Ser Gly Ile
            260                 265                 270

Ala Ala Ser Glu Ala Leu Met Ala Lys Gly Trp Pro Gly Ser Gln Gly
        275                 280                 285

Gly Thr Tyr Gly Gly Asn Ala Val Ser Cys Ala Ala Val Ala Thr
290                 295                 300

Leu Glu Val Ile Glu Lys Glu Asp Leu Val Ala Asn Ala Ala Arg
305                 310                 315                 320

Gly Val Gln Leu Leu Asp Gly Ala Arg Thr Arg Ala Ile Asp Gly Ile
                325                 330                 335

Gly Asp Val Arg Gly Leu Gly Leu Leu Val Gly Ser Glu Phe Thr Ala
            340                 345                 350

Ala Asp Gly Ser Ala Asp Arg Thr Lys Ala Ser Ala Ala Gln Gln Leu
        355                 360                 365

Ala Ala Lys Lys Gly Leu Leu Leu Thr Cys Gly Ala His Met Asn
370                 375                 380

Val Val Arg Met Ile Pro Pro Leu Ile Val Thr Ala Glu Gln Ile Glu
385                 390                 395                 400

Asp Ala Leu Lys Ile Trp Ser Glu Val Leu Asp Glu Val
                405                 410

<210> SEQ ID NO 99
<211> LENGTH: 461
<212> TYPE: PRT
<213> ORGANISM: Rhodococcus jostii RHA1

<400> SEQUENCE: 99

Met Thr Thr Val Thr Asn Ser Ser Pro Thr Thr Ala His Leu Glu Ala
1               5                   10                  15

Ala Ala Arg Arg His Leu Trp Gly His Phe Ser Arg His Gly Gln Asn
            20                  25                  30

Ile Thr Pro Pro Ile Ile Thr Arg Gly Glu Gly Ala Arg Ile Trp Asp
        35                  40                  45

Thr Ala Gly Lys Ser Tyr Leu Asp Gly Leu Ser Gly Leu Phe Val Val
50                  55                  60

Gln Ala Gly His Gly Arg Thr Glu Leu Ala Glu Ala Ala Lys Gln
65                  70                  75                  80

Ala Glu Gln Leu Ala Phe Phe Pro Leu Trp Ser Tyr Ala Thr Glu Pro
                85                  90                  95

Ala Ile Glu Leu Ala Glu Arg Leu Ala Gly Tyr Ala Pro Gly Asp Leu
            100                 105                 110

Asn Arg Val Phe Phe Thr Thr Gly Gly Gly Glu Ala Val Glu Ser Ala
        115                 120                 125

Trp Lys Leu Ala Lys Gln Tyr Phe Lys Lys Val Gly Lys Pro Gly Lys
130                 135                 140

His Lys Val Ile Ser Arg Ser Ile Ala Tyr His Gly Thr Pro Gln Gly
145                 150                 155                 160
```

Ala Leu Ala Ile Thr Gly Ile Pro Ala Leu Lys Ala Pro Phe Glu Pro
                165                 170                 175

Leu Thr Pro Gly Ala Phe Arg Val Pro Asn Thr Asn Ile Tyr Arg Ala
            180                 185                 190

Pro Glu Pro Leu Gly Ser Asp Pro Lys Ala Phe Gly Ile Trp Ala Ala
        195                 200                 205

Asp Arg Ile Ala Glu Ala Ile Glu Phe Glu Gly Pro Asp Thr Val Ala
    210                 215                 220

Ala Val Phe Leu Glu Pro Val Gln Asn Ala Gly Cys Phe Pro Pro
225                 230                 235                 240

Pro Pro Gly Tyr Phe Glu Arg Val Arg Gln Ile Cys Asp Glu Tyr Asp
            245                 250                 255

Val Leu Leu Val Ser Asp Glu Val Ile Cys Ala Phe Gly Arg Ile Gly
        260                 265                 270

Ser Met Phe Ala Cys Asp Asp Phe Gly Tyr Val Pro Asp Ile Ile Thr
    275                 280                 285

Cys Ala Lys Gly Leu Thr Ser Gly Tyr Ser Pro Ile Gly Ala Met Ile
290                 295                 300

Ala Ser Asp Arg Leu Phe Glu Pro Phe Ser Asp Gly Thr Ser Met Phe
305                 310                 315                 320

Ala His Gly Tyr Thr Phe Gly Gly His Pro Val Ser Ala Ala Val Ala
            325                 330                 335

Leu Ala Asn Leu Asp Ile Phe Glu Arg Glu Gly Leu Asn Ala His Val
        340                 345                 350

Ala Glu Gln Ala Pro Ala Phe Arg Ala Thr Leu Asp Lys Leu Thr Asp
    355                 360                 365

Leu Pro Met Val Gly Asp Val Arg Gly Glu Gly Phe Phe Tyr Gly Ile
370                 375                 380

Glu Leu Val Lys Asp Lys Thr Thr Lys Glu Ser Phe Thr Asp Asp Glu
385                 390                 395                 400

Ala Glu Arg Ile Leu His Gly Phe Leu Ser Thr Ala Leu Phe Asp Ala
            405                 410                 415

Gly Leu Tyr Cys Arg Ala Asp Asp Arg Gly Asp Pro Val Ile Gln Leu
        420                 425                 430

Ala Pro Pro Leu Ile Cys Gly Gln Ala Glu Phe Asp Glu Ile Glu His
    435                 440                 445

Ile Leu Arg Ser Val Leu Thr Glu Ala Trp Thr Leu Leu
450                 455                 460

<210> SEQ ID NO 100
<211> LENGTH: 459
<212> TYPE: PRT
<213> ORGANISM: Streptomyces avermitilis ATCC 31267

<400> SEQUENCE: 100

Met Gly Asn Pro Ile Ala Val Ser Lys Asp Leu Ser Arg Thr Ala Tyr
1               5                   10                  15

Asp His Leu Trp Met His Phe Thr Arg Met Ser Ser Tyr Glu Asn Ala
            20                  25                  30

Pro Val Pro Thr Ile Val Arg Gly Glu Gly Thr Tyr Ile Tyr Asp Asp
        35                  40                  45

Lys Gly Lys Arg Tyr Leu Asp Gly Leu Ser Gly Leu Phe Val Val Gln
    50                  55                  60

Ala Gly His Gly Arg Thr Glu Leu Ala Glu Thr Ala Phe Lys Gln Ala
65                  70                  75                  80

Gln Glu Leu Ala Phe Phe Pro Val Trp Ser Tyr Ala His Pro Lys Ala
                85                  90                  95

Val Glu Leu Ala Glu Arg Leu Ala Asn Tyr Ala Pro Gly Asp Leu Asn
            100                 105                 110

Lys Val Phe Phe Thr Thr Gly Gly Glu Ala Val Glu Thr Ala Trp
        115                 120                 125

Lys Leu Ala Lys Gln Tyr Phe Lys Leu Gln Gly Lys Pro Thr Lys Tyr
        130                 135                 140

Lys Val Ile Ser Arg Ala Val Ala Tyr His Gly Thr Pro Gln Gly Ala
145                 150                 155                 160

Leu Ser Ile Thr Gly Leu Pro Ala Leu Lys Ala Pro Phe Glu Pro Leu
                165                 170                 175

Val Pro Gly Ala His Lys Val Pro Asn Thr Asn Ile Tyr Arg Ala Pro
            180                 185                 190

Leu Phe Gly Asp Asp Pro Glu Ala Phe Gly Arg Trp Ala Ala Asp Gln
        195                 200                 205

Ile Glu Gln Gln Ile Leu Phe Glu Gly Pro Glu Thr Val Ala Ala Val
        210                 215                 220

Phe Leu Glu Pro Val Gln Asn Ala Gly Gly Cys Phe Pro Pro Pro
225                 230                 235                 240

Gly Tyr Phe Gln Arg Val Arg Glu Ile Cys Asp Gln Tyr Asp Val Leu
                245                 250                 255

Leu Val Ser Asp Glu Val Ile Cys Ala Phe Gly Arg Leu Gly Thr Met
                260                 265                 270

Phe Ala Cys Asp Lys Phe Gly Tyr Val Pro Asp Met Ile Thr Cys Ala
        275                 280                 285

Lys Gly Met Thr Ser Gly Tyr Ser Pro Ile Gly Ala Cys Ile Val Ser
        290                 295                 300

Asp Arg Ile Ala Glu Pro Phe Tyr Lys Gly Asp Asn Thr Phe Leu His
305                 310                 315                 320

Gly Tyr Thr Phe Gly Gly His Pro Val Ser Ala Ala Val Gly Val Ala
                325                 330                 335

Asn Leu Asp Leu Phe Glu Arg Glu Gly Leu Asn Gln His Val Leu Asp
            340                 345                 350

Asn Glu Ser Ala Phe Leu Thr Thr Leu Gln Lys Leu His Asp Leu Pro
        355                 360                 365

Ile Val Gly Asp Val Arg Gly Asn Gly Phe Phe Tyr Gly Ile Glu Leu
        370                 375                 380

Val Lys Asp Lys Ala Thr Lys Glu Thr Phe Thr Asp Glu Glu Ser Glu
385                 390                 395                 400

Arg Val Leu Tyr Gly Phe Val Ser Lys Lys Leu Phe Glu Tyr Gly Leu
                405                 410                 415

Tyr Cys Arg Ala Asp Asp Arg Gly Asp Pro Val Ile Gln Leu Ser Pro
            420                 425                 430

Pro Leu Ile Ser Asn Gln Ser Thr Phe Asp Glu Ile Glu Ser Ile Ile
        435                 440                 445

Arg Gln Val Leu Thr Glu Ala Trp Thr Lys Leu
450                 455

<210> SEQ ID NO 101
<211> LENGTH: 458
<212> TYPE: PRT
<213> ORGANISM: Rhizobium meliloti 1021

```
<400> SEQUENCE: 101

Met Tyr Ser Asn Ser Leu Ile Glu Leu Asp Arg Ala His Leu Ile His
1               5                   10                  15

Pro Val Ala Ser Tyr Arg Gly His Glu Lys Leu Gly Val Arg Val Leu
            20                  25                  30

Ala Ser Ala Lys Gly Ala Thr Val Thr Asp Ala Ser Gly Arg Gln Leu
        35                  40                  45

Ile Asp Gly Phe Ala Gly Leu Trp Cys Val Asn Ala Gly Tyr Gly Gln
    50                  55                  60

Glu Thr Ile Val Glu Ala Ala Lys Gln Met Arg Glu Leu Ser Tyr
65                  70                  75                  80

Ala Thr Ala Tyr Phe Gly Leu Gly Ser Glu Pro Ala Ile Arg Leu Ala
                85                  90                  95

Ser Glu Leu Ala Glu Arg Ala Pro Gly Asn Leu Asn His Val Tyr Phe
            100                 105                 110

Thr Leu Gly Gly Ser Asp Ala Val Asp Ser Thr Ile Arg Phe Ile Arg
        115                 120                 125

Tyr Tyr Trp Thr Ala Arg Gly Glu Pro Gln Arg Asp Gln Phe Ile Ser
    130                 135                 140

Val Glu Gln Gly Tyr His Gly Ser Ser Thr Val Gly Ala Gly Leu Thr
145                 150                 155                 160

Ala Leu Pro Ala Phe His Thr Gly Phe Gly Ile Pro Phe Asp Trp Gln
                165                 170                 175

His Lys Ile Pro Ser His Tyr Ala Tyr Arg Asn Pro Val Gly Asp Asp
            180                 185                 190

Pro Gln Ala Ile Ile Ala Ala Ser Leu Thr Ala Leu Arg Arg Lys Val
        195                 200                 205

Glu Glu Ile Gly Pro Glu Arg Val Ala Ala Phe Tyr Ala Glu Pro Ile
210                 215                 220

Gln Gly Ser Gly Gly Val Leu Val Pro Pro Arg Gly Trp Met Lys Ala
225                 230                 235                 240

Met Arg Glu Leu Cys Arg Asp Leu Gly Ile Leu Phe Val Ala Asp Glu
                245                 250                 255

Val Ile Thr Gly Phe Gly Arg Thr Gly Pro Leu Phe Ala Ser Thr Glu
            260                 265                 270

Asn Glu Ile Val Pro Asp Phe Ile Thr Thr Ala Lys Gly Leu Thr Ser
        275                 280                 285

Gly Tyr Val Pro Met Gly Ala Val Phe Met Ala Asp His Ile Tyr Gln
    290                 295                 300

Thr Ile Ala Asp Gly Ala Gly Ala Ser Ala Val Gly His Gly Tyr Thr
305                 310                 315                 320

Tyr Ser Ala His Pro Val Ser Ala Val Gly Leu Glu Val Leu Arg
                325                 330                 335

Leu Tyr Glu Asn Gly Leu Leu Glu Asn Gly Val Lys Ala Gly Ala Arg
            340                 345                 350

Leu Met Glu Gly Leu Gly Ser Leu Arg Asp His Pro Leu Val Gly Asp
        355                 360                 365

Val Arg Gly Arg Gly Met Leu Ala Ala Ile Glu Leu Val Val Asp Lys
    370                 375                 380

Ala Gln Lys Thr Pro Leu Pro Ala Ala Ala Glu Pro Ala Arg Ile
385                 390                 395                 400

Phe Asp Arg Ala Trp Glu Asn Gly Leu Val Ile Arg Ala Phe Ala Asn
                405                 410                 415
```

```
Gly Val Leu Gly Tyr Ala Pro Pro Leu Cys Cys Ser Glu Thr Glu Ile
                420                 425                 430

Asp Ala Ile Ile Glu Arg Thr Arg Gln Ser Leu Asp Glu Thr Leu Glu
            435                 440                 445

Asp Pro Asp Val Arg Arg Ala Leu Lys Thr
        450                 455

<210> SEQ ID NO 102
<211> LENGTH: 447
<212> TYPE: PRT
<213> ORGANISM: Sinorhizobium meliloti

<400> SEQUENCE: 102

Met Thr His Leu Leu His Arg Ala Ile His Ala Lys Leu Pro Val Ala
1               5                   10                  15

Val Arg Gly Glu Gly Ile Arg Leu Phe Asp Ala Glu Gly Arg Ala Tyr
            20                  25                  30

Ile Asp Ala Ser Gly Gly Ala Ala Val Ser Cys Leu Gly His Ala His
        35                  40                  45

Pro Asp Val Leu Ala Ala Leu His Ala Gln Leu Asp Arg Ile Ala Tyr
    50                  55                  60

Ala His Thr Gly Phe Phe Thr Thr Glu Ala Ala Glu Arg Leu Ala Asp
65                  70                  75                  80

Arg Leu Val Ala Asp Ala Pro Asp Gly Leu Asp His Val Tyr Leu Val
                85                  90                  95

Ser Gly Gly Ser Glu Ala Val Glu Ala Ala Leu Lys Met Ala Arg Gln
            100                 105                 110

Tyr Phe Val Glu Lys Gly Glu Pro Gln Arg Arg His Ile Ile Ala Arg
        115                 120                 125

Arg Gln Ser Tyr His Gly Asn Thr Leu Gly Ala Leu Ala Ala Gly Gly
130                 135                 140

Asn Glu Trp Arg Arg Ala Gln Phe Arg Pro Leu Leu Val Glu Thr His
145                 150                 155                 160

His Ile Asp Pro Cys Phe Ala Tyr Arg Leu Gln Gln Ala Gly Glu Ser
                165                 170                 175

Asp Thr Asp Tyr Ala Ala Arg Ala Ala Gly Gln Leu Glu Ala Lys Ile
            180                 185                 190

Leu Glu Leu Gly Ala Asp Gln Val Ile Ala Phe Val Ala Glu Thr Val
        195                 200                 205

Val Gly Ala Thr Ala Gly Ala Val Pro Pro Val Ala Asp Tyr Leu Lys
    210                 215                 220

Arg Val Arg Ala Ile Cys Asp Lys Tyr Gly Val Leu Leu Ile Leu Asp
225                 230                 235                 240

Glu Val Met Cys Gly Met Gly Arg Thr Gly Thr Leu His Ala Cys Glu
                245                 250                 255

Gln Asp Gly Val Val Pro Asp Leu Met Thr Ile Ala Lys Gly Leu Gly
            260                 265                 270

Gly Gly Tyr Gln Pro Val Gly Ala Val Leu Leu Ser Ser Ala Ile Phe
        275                 280                 285

Gln Ala Phe Ser Glu Gly Ser Gly Phe Phe Gln His Gly His Thr Tyr
    290                 295                 300

Met Gly His Pro Met Ala Ala Ala Ala Gly Leu Ala Val Gln Glu Val
305                 310                 315                 320

Ile Arg Arg Asp Gly Leu Leu Glu Asn Val Val Ser Met Gly Asp Tyr
```

|  |  |  | 325 |  |  |  | 330 |  |  |  | 335 |  |
|--|--|--|--|--|--|--|--|--|--|--|--|--|

Leu Glu Arg Cys Leu Val Glu Arg Leu Gly Asn His His His Val Gly
            340            345            350

Asp Ile Arg Gly Arg Gly Leu Phe Arg Ala Val Glu Leu Val Ala Asp
            355            360            365

Arg Ala Thr Lys Ser Pro Phe Asp Pro Gly Leu Lys Leu Asn Ala Arg
    370                375            380

Ile Lys Lys Glu Ala Met Ala Arg Gly Leu Met Val Tyr Pro Met Gly
385                390            395            400

Gly Thr Ile Asp Gly Gln Arg Gly Asp His Val Leu Leu Ala Pro Pro
            405            410            415

Phe Ile Leu Asn Arg Glu Asp Val Gly Gln Ile Val Glu Arg Leu Gly
            420            425            430

Asp Ala Val Asp Ala Ala Ile Ala Ser Leu Thr Lys Ala Ala Gly
            435            440            445

<210> SEQ ID NO 103
<211> LENGTH: 445
<212> TYPE: PRT
<213> ORGANISM: Mesorhizobium sp. LUK

<400> SEQUENCE: 103

Met Asn Glu Pro Ile Gly Glu Pro Gly Arg Ser Pro Ala Ser Asp Thr
1              5              10            15

Ala Glu Lys Ala Gln Ala Ile Ala Ala Arg Asn Thr Phe Ala Arg
            20            25            30

Asp Asn Pro Val Ser Ala Gly His His Glu Arg Ala Arg Arg Ser Met
            35            40            45

Pro Gly Gly Asn Thr Arg Ser Ile Leu Phe His Arg Pro Phe Pro Leu
    50                55            60

Val Ile Ala Gln Gly Thr Gly Ser Arg Phe Gln Asp Val Asp Gly His
65                70            75            80

Ala Tyr Val Asn Phe Leu Gly Glu Tyr Thr Ala Gly Leu Phe Gly His
              85            90            95

Ser His Pro Val Ile Arg Ala Ala Val Glu Arg Ala Leu Ala Val Gly
            100           105          110

Leu Asn Leu Ser Thr Gln Thr Glu Asn Glu Ala Leu Phe Ala Glu Ala
            115           120          125

Val Cys Asp Arg Phe Pro Ser Ile Asp Leu Val Arg Phe Thr Asn Ser
    130               135          140

Gly Thr Glu Ala Asn Leu Met Ala Leu Ala Thr Ala Thr Ala Ile Thr
145              150           155          160

Gly Arg Lys Thr Val Leu Ala Phe Asp Gly Gly Tyr His Gly Gly Leu
            165           170          175

Leu Asn Phe Ala Ser Gly His Ala Pro Thr Asn Ala Pro Tyr His Val
            180           185          190

Val Leu Gly Val Tyr Asn Asp Val Glu Gly Thr Ala Asp Leu Leu Lys
            195           200          205

Arg His Gly His Asp Cys Ala Ala Ile Leu Val Glu Pro Met Leu Gly
    210                215          220

Ala Gly Gly Cys Val Pro Ala Glu Arg Ala Phe Leu Asp Leu Leu Arg
225              230           235          240

Ala Glu Ala Ser Arg Cys Gly Ala Leu Leu Ile Phe Asp Glu Val Met
            245           250          255

```
Thr Ser Arg Leu Ser Gly Gly Ala Gln Glu Met Leu Gly Ile Ser
        260             265             270

Ala Asp Leu Thr Thr Leu Gly Lys Tyr Ile Gly Gly Met Ser Phe
        275             280             285

Gly Ala Phe Gly Gly Arg Arg Asp Leu Met Glu Arg Phe Asp Pro Ala
    290             295             300

Arg Asp Gly Ala Phe Ala His Ala Gly Thr Phe Asn Asn Asn Ile Leu
305             310             315             320

Thr Met Ser Ala Gly His Ala Ala Leu Thr Gln Ile Tyr Thr Arg Gln
                325             330             335

Ala Ala Ser Asp Leu Ser Ala Ser Gly Asp Arg Phe Arg Ala Asn Leu
        340             345             350

Asn Arg Ile Ala Val Glu Asn Gln Ala Pro Leu Gln Phe Thr Gly Leu
        355             360             365

Gly Ser Leu Gly Thr Ile His Phe Ser Arg Ala Pro Ile Arg Ser Ala
        370             375             380

Gly Asp Val Arg Ala Ala Asp Gln Gln Leu Lys Glu Leu Phe Phe
385             390             395             400

His Met Leu Arg Lys Gly Ile Tyr Leu Ala Pro Arg Gly Met Tyr Ala
                405             410             415

Leu Ser Leu Glu Ile Ala Asp Ala Gly Arg Asp Ala Phe Ala Glu Ala
                420             425             430

Leu Ala Asp Phe Ile Gly Glu Gln Arg Ala Leu Leu Met
        435             440             445

<210> SEQ ID NO 104
<211> LENGTH: 496
<212> TYPE: PRT
<213> ORGANISM: Pseudomonas aeruginosa ATCC 15692

<400> SEQUENCE: 104

Met Phe Glu Ser Ala Glu Val Gly His Ser Ile Asp Lys Asp Thr Tyr
1               5               10              15

Glu Lys Ala Val Ile Glu Leu Arg Glu Ala Leu Leu Glu Ala Gln Phe
                20              25              30

Glu Leu Lys Gln Gln Ala Arg Phe Pro Val Ile Ile Leu Ile Asn Gly
        35              40              45

Ile Glu Gly Ala Gly Lys Gly Glu Thr Val Lys Leu Leu Asn Glu Trp
    50              55              60

Met Asp Pro Arg Leu Ile Glu Val Gln Ser Phe Leu Arg Pro Ser Asp
65              70              75              80

Glu Glu Leu Glu Arg Pro Pro Gln Trp Arg Phe Trp Arg Arg Leu Pro
                85              90              95

Pro Lys Gly Arg Thr Gly Ile Phe Phe Gly Asn Trp Tyr Ser Gln Met
            100             105             110

Leu Tyr Ala Arg Val Glu Gly His Ile Lys Glu Ala Lys Leu Asp Gln
        115             120             125

Ala Ile Asp Ala Ala Glu Arg Phe Glu Arg Met Leu Cys Asp Glu Gly
    130             135             140

Ala Leu Leu Phe Lys Phe Trp Phe His Leu Ser Lys Lys Gln Leu Lys
145             150             155             160

Glu Arg Leu Lys Ala Leu Glu Lys Asp Pro Gln His Ser Trp Lys Leu
                165             170             175

Ser Pro Leu Asp Trp Lys Gln Ser Glu Val Tyr Asp Arg Phe Val His
            180             185             190
```

```
Tyr Gly Glu Arg Val Leu Arg Arg Thr Ser Arg Asp Tyr Ala Pro Trp
        195                 200                 205

Tyr Val Val Glu Gly Ala Asp Glu Arg Tyr Arg Ala Leu Thr Val Gly
    210                 215                 220

Arg Ile Leu Leu Glu Gly Leu Gln Ala Ala Leu Ala Thr Lys Glu Arg
225                 230                 235                 240

Ala Lys Arg Gln Pro His Ala Ala Pro Leu Val Ser Ser Leu Asp Asn
                245                 250                 255

Arg Gly Leu Leu Asp Ser Leu Asp Leu Gly Gln Tyr Leu Asp Lys Asp
            260                 265                 270

Ala Tyr Lys Glu Gln Leu Ala Ala Glu Gln Ala Arg Leu Ala Gly Leu
        275                 280                 285

Ile Arg Asp Lys Arg Phe Arg Gln His Ser Leu Val Ala Val Phe Glu
    290                 295                 300

Gly Asn Asp Ala Ala Gly Lys Gly Gly Ala Ile Arg Arg Val Thr Asp
305                 310                 315                 320

Ala Leu Asp Pro Arg Gln Tyr His Ile Val Pro Ile Ala Ala Pro Thr
                325                 330                 335

Glu Glu Glu Arg Ala Gln Pro Tyr Leu Trp Arg Phe Trp Arg His Ile
            340                 345                 350

Pro Ala Arg Arg Gln Phe Thr Ile Phe Asp Arg Ser Trp Tyr Gly Arg
        355                 360                 365

Val Leu Val Glu Arg Ile Glu Gly Phe Cys Ala Pro Ala Asp Trp Leu
    370                 375                 380

Arg Ala Tyr Gly Glu Ile Asn Asp Phe Glu Glu Gln Leu Ser Glu Tyr
385                 390                 395                 400

Gly Ile Ile Val Val Lys Phe Trp Leu Ala Ile Asp Lys Gln Thr Gln
                405                 410                 415

Met Glu Arg Phe Lys Glu Arg Glu Lys Thr Pro Tyr Lys Arg Tyr Lys
            420                 425                 430

Ile Thr Glu Glu Asp Trp Arg Asn Arg Asp Lys Trp Asp Gln Tyr Val
        435                 440                 445

Asp Ala Val Gly Asp Met Val Asp Arg Thr Ser Thr Glu Ile Ala Pro
    450                 455                 460

Trp Thr Leu Val Glu Ala Asn Asp Lys Arg Phe Ala Arg Val Lys Val
465                 470                 475                 480

Leu Arg Thr Ile Asn Asp Ala Ile Glu Ala Tyr Lys Lys Asp Lys
                485                 490                 495

<210> SEQ ID NO 105
<211> LENGTH: 300
<212> TYPE: PRT
<213> ORGANISM: Rhizobium meliloti strain 1021

<400> SEQUENCE: 105

Met Ala Leu Asp Glu Ala Pro Ala Glu Ala Arg Pro Gly Ser Arg Ala
1               5                   10                  15

Val Glu Leu Glu Ile Asp Gly Arg Ser Arg Ile Phe Asp Ile Asp Asp
            20                  25                  30

Pro Asp Leu Pro Lys Trp Ile Asp Glu Ala Phe Arg Ser Asp Asp
        35                  40                  45

Tyr Pro Tyr Lys Lys Leu Asp Arg Glu Glu Tyr Glu Glu Thr Leu
    50                  55                  60

Thr Lys Leu Gln Ile Glu Leu Val Lys Val Gln Phe Trp Met Gln Ala
```

```
              65                  70                  75                  80
Thr Gly Lys Arg Val Met Ala Val Phe Glu Gly Arg Asp Ala Ala Gly
                85                  90                  95

Lys Gly Gly Ala Ile His Ala Thr Thr Ala Asn Met Asn Pro Arg Ser
            100                 105                 110

Ala Arg Val Val Ala Leu Thr Lys Pro Thr Glu Thr Glu Arg Gly Gln
        115                 120                 125

Trp Tyr Phe Gln Arg Tyr Val Ala Thr Phe Pro Thr Ala Gly Glu Phe
    130                 135                 140

Val Leu Phe Asp Arg Ser Trp Tyr Asn Arg Ala Gly Val Glu Pro Val
145                 150                 155                 160

Met Gly Phe Cys Thr Pro Asp Gln Tyr Glu Gln Phe Leu Lys Glu Ala
                165                 170                 175

Pro Arg Phe Glu Glu Met Ile Ala Asn Glu Gly Ile His Leu Phe Lys
            180                 185                 190

Phe Trp Ile Asn Ile Gly Arg Glu Met Gln Leu Lys Arg Phe His Asp
        195                 200                 205

Arg Arg His Asp Pro Leu Lys Ile Trp Lys Leu Ser Pro Met Asp Ile
    210                 215                 220

Ala Ala Leu Ser Lys Trp Asp Asp Tyr Thr Gly Lys Arg Asp Arg Met
225                 230                 235                 240

Leu Lys Glu Thr His Thr Glu His Gly Pro Trp Ala Val Ile Arg Gly
                245                 250                 255

Asn Asp Lys Arg Arg Ser Arg Ile Asn Val Ile Arg His Met Leu Thr
            260                 265                 270

Lys Leu Asp Tyr Asp Gly Lys Asp Glu Ala Ala Ile Gly Glu Val Asp
        275                 280                 285

Glu Lys Ile Leu Gly Ser Gly Pro Gly Phe Leu Arg
    290                 295                 300

<210> SEQ ID NO 106
<211> LENGTH: 378
<212> TYPE: PRT
<213> ORGANISM: Bacillus subtilis 168

<400> SEQUENCE: 106

Met Ile Ile Gly Val Pro Lys Glu Ile Lys Asn Asn Glu Asn Arg Val
1               5                  10                  15

Ala Leu Thr Pro Gly Gly Val Ser Gln Leu Ile Ser Asn Gly His Arg
            20                  25                  30

Val Leu Val Glu Thr Gly Ala Gly Leu Gly Ser Gly Phe Glu Asn Glu
        35                  40                  45

Ala Tyr Glu Ser Ala Gly Ala Glu Ile Ile Ala Asp Pro Lys Gln Val
    50                  55                  60

Trp Asp Ala Glu Met Val Met Lys Val Lys Glu Pro Leu Pro Glu Glu
65                  70                  75                  80

Tyr Val Tyr Phe Arg Lys Gly Leu Val Leu Phe Thr Tyr Leu His Leu
                85                  90                  95

Ala Ala Glu Pro Glu Leu Ala Gln Ala Leu Lys Asp Lys Gly Val Thr
            100                 105                 110

Ala Ile Ala Tyr Glu Thr Val Ser Glu Gly Arg Thr Leu Pro Leu Leu
        115                 120                 125

Thr Pro Met Ser Glu Val Ala Gly Arg Met Ala Ala Gln Ile Gly Ala
    130                 135                 140
```

```
Gln Phe Leu Glu Lys Pro Lys Gly Gly Lys Gly Ile Leu Leu Ala Gly
145                 150                 155                 160

Val Pro Gly Val Ser Arg Gly Lys Val Thr Ile Ile Gly Gly Gly Val
            165                 170                 175

Val Gly Thr Asn Ala Ala Lys Met Ala Val Gly Leu Gly Ala Asp Val
            180                 185                 190

Thr Ile Ile Asp Leu Asn Ala Asp Arg Leu Arg Gln Leu Asp Asp Ile
            195                 200                 205

Phe Gly His Gln Ile Lys Thr Leu Ile Ser Asn Pro Val Asn Ile Ala
            210                 215                 220

Asp Ala Val Ala Glu Ala Asp Leu Leu Ile Cys Ala Val Leu Ile Pro
225                 230                 235                 240

Gly Ala Lys Ala Pro Thr Leu Val Thr Glu Glu Met Val Lys Gln Met
            245                 250                 255

Lys Pro Gly Ser Val Ile Val Asp Val Ala Ile Asp Gln Gly Gly Ile
            260                 265                 270

Val Glu Thr Val Asp His Ile Thr Thr His Asp Gln Pro Thr Tyr Glu
            275                 280                 285

Lys His Gly Val Val His Tyr Ala Val Ala Asn Met Pro Gly Ala Val
            290                 295                 300

Pro Arg Thr Ser Thr Ile Ala Leu Thr Asn Val Thr Val Pro Tyr Ala
305                 310                 315                 320

Leu Gln Ile Ala Asn Lys Gly Ala Val Lys Ala Leu Ala Asp Asn Thr
            325                 330                 335

Ala Leu Arg Ala Gly Leu Asn Thr Ala Asn Gly His Val Thr Tyr Glu
            340                 345                 350

Ala Val Ala Arg Asp Leu Gly Tyr Glu Tyr Val Pro Ala Glu Lys Ala
            355                 360                 365

Leu Gln Asp Glu Ser Ser Val Ala Gly Ala
            370                 375

<210> SEQ ID NO 107
<211> LENGTH: 454
<212> TYPE: PRT
<213> ORGANISM: Saccharomyces cerevisiae

<400> SEQUENCE: 107

Met Ser Glu Pro Glu Phe Gln Gln Ala Tyr Glu Glu Val Val Ser Ser
1               5                   10                  15

Leu Glu Asp Ser Thr Leu Phe Glu Gln His Pro Glu Tyr Arg Lys Val
            20                  25                  30

Leu Pro Ile Val Ser Val Pro Glu Arg Ile Ile Gln Phe Arg Val Thr
        35                  40                  45

Trp Glu Asn Asp Lys Gly Glu Gln Glu Val Ala Gln Gly Tyr Arg Val
    50                  55                  60

Gln Tyr Asn Ser Ala Lys Gly Pro Tyr Lys Gly Gly Leu Arg Phe His
65                  70                  75                  80

Pro Ser Val Asn Leu Ser Ile Leu Lys Phe Leu Gly Phe Glu Gln Ile
                85                  90                  95

Phe Lys Asn Ser Leu Thr Gly Leu Asp Met Gly Gly Gly Lys Gly Gly
            100                 105                 110

Leu Cys Val Asp Leu Lys Gly Arg Ser Asn Asn Glu Ile Arg Arg Ile
        115                 120                 125

Cys Tyr Ala Phe Met Arg Glu Leu Ser Arg His Ile Gly Gln Asp Thr
    130                 135                 140
```

```
Asp Val Pro Ala Gly Asp Ile Gly Val Gly Gly Arg Glu Ile Gly Tyr
145                 150                 155                 160

Leu Phe Gly Ala Tyr Arg Ser Tyr Lys Asn Ser Trp Glu Gly Val Leu
            165                 170                 175

Thr Gly Lys Gly Leu Asn Trp Gly Gly Ser Leu Ile Arg Pro Glu Ala
        180                 185                 190

Thr Gly Tyr Gly Leu Val Tyr Tyr Thr Gln Ala Met Ile Asp Tyr Ala
    195                 200                 205

Thr Asn Gly Lys Glu Ser Phe Glu Gly Lys Arg Val Thr Ile Ser Gly
210                 215                 220

Ser Gly Asn Val Ala Gln Tyr Ala Ala Leu Lys Val Ile Glu Leu Gly
225                 230                 235                 240

Gly Thr Val Val Ser Leu Ser Asp Ser Lys Gly Cys Ile Ile Ser Glu
                245                 250                 255

Thr Gly Ile Thr Ser Glu Gln Val Ala Asp Ile Ser Ser Ala Lys Val
            260                 265                 270

Asn Phe Lys Ser Leu Glu Gln Ile Val Asn Glu Tyr Ser Thr Phe Ser
        275                 280                 285

Glu Asn Lys Val Gln Tyr Ile Ala Gly Ala Arg Pro Trp Thr His Val
    290                 295                 300

Gln Lys Val Asp Ile Ala Leu Pro Cys Ala Thr Gln Asn Glu Val Ser
305                 310                 315                 320

Gly Glu Glu Ala Lys Ala Leu Val Ala Gln Gly Val Lys Phe Ile Ala
                325                 330                 335

Glu Gly Ser Asn Met Gly Ser Thr Pro Glu Ala Ile Ala Val Phe Glu
            340                 345                 350

Thr Ala Arg Ser Thr Ala Thr Gly Pro Ser Glu Ala Val Trp Tyr Gly
        355                 360                 365

Pro Pro Lys Ala Ala Asn Leu Gly Gly Val Ala Val Ser Gly Leu Glu
    370                 375                 380

Met Ala Gln Asn Ser Gln Arg Ile Thr Trp Thr Ser Glu Arg Val Asp
385                 390                 395                 400

Gln Glu Leu Lys Arg Ile Met Ile Asn Cys Phe Asn Glu Cys Ile Asp
                405                 410                 415

Tyr Ala Lys Lys Tyr Thr Lys Asp Gly Lys Val Leu Pro Ser Leu Val
            420                 425                 430

Lys Gly Ala Asn Ile Ala Ser Phe Ile Lys Val Ser Asp Ala Met Phe
        435                 440                 445

Asp Gln Gly Asp Val Phe
    450

<210> SEQ ID NO 108
<211> LENGTH: 401
<212> TYPE: PRT
<213> ORGANISM: Pseudomonas sp. strain 101
<220> FEATURE:
<221> NAME/KEY: point_mutation_D222Q
<222> LOCATION: (222)..(222)
<223> OTHER INFORMATION: D mutated to Q
<220> FEATURE:
<221> NAME/KEY: point_mutation_H224N
<222> LOCATION: (224)..(224)
<223> OTHER INFORMATION: H mutated to N

<400> SEQUENCE: 108

Met Ala Lys Val Leu Cys Val Leu Tyr Asp Asp Pro Val Asp Gly Tyr
1               5                   10                  15
```

Pro Lys Thr Tyr Ala Arg Asp Asp Leu Pro Lys Ile Asp His Tyr Pro
            20                  25                  30

Gly Gly Gln Thr Leu Pro Thr Pro Lys Ala Ile Asp Phe Thr Pro Gly
        35                  40                  45

Gln Leu Leu Gly Ser Val Ser Gly Glu Leu Gly Leu Arg Lys Tyr Leu
50                  55                  60

Glu Ser Asn Gly His Thr Leu Val Val Thr Ser Asp Lys Asp Gly Pro
65                  70                  75                  80

Asp Ser Val Phe Glu Arg Glu Leu Val Asp Ala Asp Val Val Ile Ser
                85                  90                  95

Gln Pro Phe Trp Pro Ala Tyr Leu Thr Pro Glu Arg Ile Ala Lys Ala
            100                 105                 110

Lys Asn Leu Lys Leu Ala Leu Thr Ala Gly Ile Gly Ser Asp His Val
            115                 120                 125

Asp Leu Gln Ser Ala Ile Asp Arg Asn Val Thr Val Ala Glu Val Thr
130                 135                 140

Tyr Cys Asn Ser Ile Ser Val Ala Glu His Val Val Met Met Ile Leu
145                 150                 155                 160

Ser Leu Val Arg Asn Tyr Leu Pro Ser His Glu Trp Ala Arg Lys Gly
                165                 170                 175

Gly Trp Asn Ile Ala Asp Cys Val Ser His Ala Tyr Asp Leu Glu Ala
            180                 185                 190

Met His Val Gly Thr Val Ala Ala Gly Arg Ile Gly Leu Ala Val Leu
            195                 200                 205

Arg Arg Leu Ala Pro Phe Asp Val His Leu His Tyr Thr Asp Arg His
210                 215                 220

Arg Leu Pro Glu Ser Val Glu Lys Glu Leu Asn Leu Thr Trp His Ala
225                 230                 235                 240

Thr Arg Glu Asp Met Tyr Pro Val Cys Asp Val Val Thr Leu Asn Cys
                245                 250                 255

Pro Leu His Pro Glu Thr Glu His Met Ile Asn Asp Glu Thr Leu Lys
            260                 265                 270

Leu Phe Lys Arg Gly Ala Tyr Ile Val Asn Thr Ala Arg Gly Lys Leu
            275                 280                 285

Cys Asp Arg Asp Ala Val Ala Arg Ala Leu Glu Ser Gly Arg Leu Ala
290                 295                 300

Gly Tyr Ala Gly Asp Val Trp Phe Pro Gln Pro Ala Pro Lys Asp His
305                 310                 315                 320

Pro Trp Arg Thr Met Pro Tyr Asn Gly Met Thr Pro His Ile Ser Gly
                325                 330                 335

Thr Thr Leu Thr Ala Gln Ala Arg Tyr Ala Ala Gly Thr Arg Glu Ile
            340                 345                 350

Leu Glu Cys Phe Phe Glu Gly Arg Pro Ile Arg Asp Glu Tyr Leu Ile
            355                 360                 365

Val Gln Gly Gly Ala Leu Ala Gly Thr Gly Ala His Ser Tyr Ser Lys
370                 375                 380

Gly Asn Ala Thr Gly Gly Ser Glu Glu Ala Ala Lys Phe Lys Lys Ala
385                 390                 395                 400

Val

<210> SEQ ID NO 109
<211> LENGTH: 1174
<212> TYPE: PRT

<213> ORGANISM: Nocardia iowensis

<400> SEQUENCE: 109

```
Met Ala Val Asp Ser Pro Asp Glu Arg Leu Gln Arg Arg Ile Ala Gln
1               5                   10                  15

Leu Phe Ala Glu Asp Glu Gln Val Lys Ala Ala Arg Pro Leu Glu Ala
            20                  25                  30

Val Ser Ala Ala Val Ser Ala Pro Gly Met Arg Leu Ala Gln Ile Ala
        35                  40                  45

Ala Thr Val Met Ala Gly Tyr Ala Asp Arg Pro Ala Ala Gly Gln Arg
    50                  55                  60

Ala Phe Glu Leu Asn Thr Asp Asp Ala Thr Gly Arg Thr Ser Leu Arg
65                  70                  75                  80

Leu Leu Pro Arg Phe Glu Thr Ile Thr Tyr Arg Glu Leu Trp Gln Arg
                85                  90                  95

Val Gly Glu Val Ala Ala Ala Trp His His Asp Pro Glu Asn Pro Leu
            100                 105                 110

Arg Ala Gly Asp Phe Val Ala Leu Leu Gly Phe Thr Ser Ile Asp Tyr
        115                 120                 125

Ala Thr Leu Asp Leu Ala Asp Ile His Leu Gly Ala Val Thr Val Pro
    130                 135                 140

Leu Gln Ala Ser Ala Ala Val Ser Gln Leu Ile Ala Ile Leu Thr Glu
145                 150                 155                 160

Thr Ser Pro Arg Leu Leu Ala Ser Thr Pro Glu His Leu Asp Ala Ala
                165                 170                 175

Val Glu Cys Leu Leu Ala Gly Thr Thr Pro Glu Arg Leu Val Val Phe
            180                 185                 190

Asp Tyr His Pro Glu Asp Asp Gln Arg Ala Ala Phe Glu Ser Ala
        195                 200                 205

Arg Arg Arg Leu Ala Asp Ala Gly Ser Leu Val Ile Val Glu Thr Leu
    210                 215                 220

Asp Ala Val Arg Ala Arg Gly Arg Asp Leu Pro Ala Ala Pro Leu Phe
225                 230                 235                 240

Val Pro Asp Thr Asp Asp Pro Leu Ala Leu Leu Ile Tyr Thr Ser
                245                 250                 255

Gly Ser Thr Gly Thr Pro Lys Gly Ala Met Tyr Thr Asn Arg Leu Ala
            260                 265                 270

Ala Thr Met Trp Gln Gly Asn Ser Met Leu Gln Gly Asn Ser Gln Arg
        275                 280                 285

Val Gly Ile Asn Leu Asn Tyr Met Pro Met Ser His Ile Ala Gly Arg
    290                 295                 300

Ile Ser Leu Phe Gly Val Leu Ala Arg Gly Gly Thr Ala Tyr Phe Ala
305                 310                 315                 320

Ala Lys Ser Asp Met Ser Thr Leu Phe Glu Asp Ile Gly Leu Val Arg
                325                 330                 335

Pro Thr Glu Ile Phe Phe Val Pro Arg Val Cys Asp Met Val Phe Gln
            340                 345                 350

Arg Tyr Gln Ser Glu Leu Asp Arg Arg Ser Val Ala Gly Ala Asp Leu
        355                 360                 365

Asp Thr Leu Asp Arg Glu Val Lys Ala Asp Leu Arg Gln Asn Tyr Leu
    370                 375                 380

Gly Gly Arg Phe Leu Val Ala Val Val Gly Ser Ala Pro Leu Ala Ala
385                 390                 395                 400
```

```
Glu Met Lys Thr Phe Met Glu Ser Val Leu Asp Leu Pro Leu His Asp
                405                 410                 415

Gly Tyr Gly Ser Thr Glu Ala Gly Ala Ser Val Leu Leu Asp Asn Gln
        420                 425                 430

Ile Gln Arg Pro Pro Val Leu Asp Tyr Lys Leu Val Asp Val Pro Glu
            435                 440                 445

Leu Gly Tyr Phe Arg Thr Asp Arg Pro His Pro Arg Gly Glu Leu Leu
    450                 455                 460

Leu Lys Ala Glu Thr Thr Ile Pro Gly Tyr Tyr Lys Arg Pro Glu Val
465                 470                 475                 480

Thr Ala Glu Ile Phe Asp Glu Asp Gly Phe Tyr Lys Thr Gly Asp Ile
                485                 490                 495

Val Ala Glu Leu Glu His Asp Arg Leu Val Tyr Val Asp Arg Arg Asn
        500                 505                 510

Asn Val Leu Lys Leu Ser Gln Gly Glu Phe Val Thr Val Ala His Leu
            515                 520                 525

Glu Ala Val Phe Ala Ser Ser Pro Leu Ile Arg Gln Ile Phe Ile Tyr
    530                 535                 540

Gly Ser Ser Glu Arg Ser Tyr Leu Leu Ala Val Ile Val Pro Thr Asp
545                 550                 555                 560

Asp Ala Leu Arg Gly Arg Asp Thr Ala Thr Leu Lys Ser Ala Leu Ala
                565                 570                 575

Glu Ser Ile Gln Arg Ile Ala Lys Asp Ala Asn Leu Gln Pro Tyr Glu
        580                 585                 590

Ile Pro Arg Asp Phe Leu Ile Glu Thr Glu Pro Phe Thr Ile Ala Asn
            595                 600                 605

Gly Leu Leu Ser Gly Ile Ala Lys Leu Leu Arg Pro Asn Leu Lys Glu
    610                 615                 620

Arg Tyr Gly Ala Gln Leu Glu Gln Met Tyr Thr Asp Leu Ala Thr Gly
625                 630                 635                 640

Gln Ala Asp Glu Leu Leu Ala Leu Arg Arg Glu Ala Ala Asp Leu Pro
                645                 650                 655

Val Leu Glu Thr Val Ser Arg Ala Ala Lys Ala Met Leu Gly Val Ala
        660                 665                 670

Ser Ala Asp Met Arg Pro Asp Ala His Phe Thr Asp Leu Gly Gly Asp
            675                 680                 685

Ser Leu Ser Ala Leu Ser Phe Ser Asn Leu Leu His Glu Ile Phe Gly
    690                 695                 700

Val Glu Val Pro Val Gly Val Val Ser Pro Ala Asn Glu Leu Arg
705                 710                 715                 720

Asp Leu Ala Asn Tyr Ile Glu Ala Glu Arg Asn Ser Gly Ala Lys Arg
                725                 730                 735

Pro Thr Phe Thr Ser Val His Gly Gly Gly Ser Glu Ile Arg Ala Ala
        740                 745                 750

Asp Leu Thr Leu Asp Lys Phe Ile Asp Ala Arg Thr Leu Ala Ala Ala
            755                 760                 765

Asp Ser Ile Pro His Ala Pro Val Pro Ala Gln Thr Val Leu Leu Thr
    770                 775                 780

Gly Ala Asn Gly Tyr Leu Gly Arg Phe Leu Cys Leu Glu Trp Leu Glu
785                 790                 795                 800

Arg Leu Asp Lys Thr Gly Gly Thr Leu Ile Cys Val Val Arg Gly Ser
                805                 810                 815

Asp Ala Ala Ala Ala Arg Lys Arg Leu Asp Ser Ala Phe Asp Ser Gly
```

```
                820                 825                 830
Asp Pro Gly Leu Leu Glu His Tyr Gln Gln Leu Ala Ala Arg Thr Leu
            835                 840                 845
Glu Val Leu Ala Gly Asp Ile Gly Asp Pro Asn Leu Gly Leu Asp Asp
        850                 855                 860
Ala Thr Trp Gln Arg Leu Ala Glu Thr Val Asp Leu Ile Val His Pro
865                 870                 875                 880
Ala Ala Leu Val Asn His Val Leu Pro Tyr Thr Gln Leu Phe Gly Pro
                885                 890                 895
Asn Val Val Gly Thr Ala Glu Ile Val Arg Leu Ala Ile Thr Ala Arg
            900                 905                 910
Arg Lys Pro Val Thr Tyr Leu Ser Thr Val Gly Val Ala Asp Gln Val
        915                 920                 925
Asp Pro Ala Glu Tyr Gln Glu Asp Ser Asp Val Arg Glu Met Ser Ala
    930                 935                 940
Val Arg Val Val Arg Glu Ser Tyr Ala Asn Gly Tyr Gly Asn Ser Lys
945                 950                 955                 960
Trp Ala Gly Glu Val Leu Leu Arg Glu Ala His Asp Leu Cys Gly Leu
                965                 970                 975
Pro Val Ala Val Phe Arg Ser Asp Met Ile Leu Ala His Ser Arg Tyr
            980                 985                 990
Ala Gly Gln Leu Asn Val Gln Asp Val Phe Thr Arg Leu Ile Leu Ser
        995                1000                1005
Leu Val Ala Thr Gly Ile Ala Pro Tyr Ser Phe Tyr Arg Thr Asp
    1010                1015                1020
Ala Asp Gly Asn Arg Gln Arg Ala His Tyr Asp Gly Leu Pro Ala
    1025                1030                1035
Asp Phe Thr Ala Ala Ala Ile Thr Ala Leu Gly Ile Gln Ala Thr
    1040                1045                1050
Glu Gly Phe Arg Thr Tyr Asp Val Leu Asn Pro Tyr Asp Asp Gly
    1055                1060                1065
Ile Ser Leu Asp Glu Phe Val Asp Trp Leu Val Glu Ser Gly His
    1070                1075                1080
Pro Ile Gln Arg Ile Thr Asp Tyr Ser Asp Trp Phe His Arg Phe
    1085                1090                1095
Glu Thr Ala Ile Arg Ala Leu Pro Glu Lys Gln Arg Gln Ala Ser
    1100                1105                1110
Val Leu Pro Leu Leu Asp Ala Tyr Arg Asn Pro Cys Pro Ala Val
    1115                1120                1125
Arg Gly Ala Ile Leu Pro Ala Lys Glu Phe Gln Ala Ala Val Gln
    1130                1135                1140
Thr Ala Lys Ile Gly Pro Glu Gln Asp Ile Pro His Leu Ser Ala
    1145                1150                1155
Pro Leu Ile Asp Lys Tyr Val Ser Asp Leu Glu Leu Leu Gln Leu
    1160                1165                1170
Leu

<210> SEQ ID NO 110
<211> LENGTH: 206
<212> TYPE: PRT
<213> ORGANISM: Escherichia coli K12

<400> SEQUENCE: 110

Met Lys Thr Thr His Thr Ser Leu Pro Phe Ala Gly His Thr Leu His
```

```
            1               5                  10                 15
          Phe Val Glu Phe Asp Pro Ala Asn Phe Cys Glu Gln Asp Leu Leu Trp
                          20                  25                 30

Leu Pro His Tyr Ala Gln Leu Gln His Ala Gly Arg Lys Arg Lys Thr
                          35                  40                 45

Glu His Leu Ala Gly Arg Ile Ala Ala Val Tyr Ala Leu Arg Glu Tyr
                  50                  55                 60

Gly Tyr Lys Cys Val Pro Ala Ile Gly Glu Leu Arg Gln Pro Val Trp
          65                  70                  75                 80

Pro Ala Glu Val Tyr Gly Ser Ile Ser His Cys Gly Thr Thr Ala Leu
                          85                  90                 95

Ala Val Val Ser Arg Gln Pro Ile Gly Ile Asp Ile Glu Glu Ile Phe
                          100                 105                110

Ser Val Gln Thr Ala Arg Glu Leu Thr Asp Asn Ile Ile Thr Pro Ala
                          115                 120                125

Glu His Glu Arg Leu Ala Asp Cys Gly Leu Ala Phe Ser Leu Ala Leu
                          130                 135                140

Thr Leu Ala Phe Ser Ala Lys Glu Ser Ala Phe Lys Ala Ser Glu Ile
          145                 150                 155                160

Gln Thr Asp Ala Gly Phe Leu Asp Tyr Gln Ile Ile Ser Trp Asn Lys
                          165                 170                175

Gln Gln Val Ile Ile His Arg Glu Asn Glu Met Phe Ala Val His Trp
                          180                 185                190

Gln Ile Lys Glu Lys Ile Val Ile Thr Leu Cys Gln His Asp
                          195                 200                205

<210> SEQ ID NO 111
<211> LENGTH: 224
<212> TYPE: PRT
<213> ORGANISM: Bacillus subtilis strain 168

<400> SEQUENCE: 111

Met Lys Ile Tyr Gly Ile Tyr Met Asp Arg Pro Leu Ser Gln Glu Glu
1               5                   10                  15

Asn Glu Arg Phe Met Ser Phe Ile Ser Pro Lys Arg Glu Lys Cys
                20                  25                  30

Arg Arg Phe Tyr His Lys Glu Asp Ala His Arg Thr Leu Leu Gly Asp
                35                  40                  45

Val Leu Val Arg Ser Val Ile Ser Arg Gln Tyr Gln Leu Asp Lys Ser
        50                  55                  60

Asp Ile Arg Phe Ser Thr Gln Glu Tyr Gly Lys Pro Cys Ile Pro Asp
65                  70                  75                  80

Leu Pro Asp Ala His Phe Asn Ile Ser His Ser Gly Arg Trp Val Ile
                85                  90                  95

Cys Ala Phe Asp Ser Gln Pro Ile Gly Ile Asp Ile Glu Lys Thr Lys
                100                 105                 110

Pro Ile Ser Leu Glu Ile Ala Lys Arg Phe Phe Ser Lys Thr Glu Tyr
                115                 120                 125

Ser Asp Leu Leu Ala Lys Asp Lys Asp Glu Gln Thr Asp Tyr Phe Tyr
                130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
                165                 170                 175
```

-continued

```
Gln Val Ser Ile Glu Leu Pro Asp Ser His Ser Pro Cys Tyr Ile Lys
            180                 185                 190

Thr Tyr Glu Val Asp Pro Gly Tyr Lys Met Ala Val Cys Ala Ala His
        195                 200                 205

Pro Asp Phe Pro Glu Asp Ile Thr Met Val Ser Tyr Glu Glu Leu Leu
    210                 215                 220
```

UNITED STATES PATENT AND TRADEMARK OFFICE
CERTIFICATE OF CORRECTION

PATENT NO. : 12,371,675 B2
APPLICATION NO. : 17/479722
DATED : July 29, 2025
INVENTOR(S) : Alexander Yakunin et al.

Page 1 of 1

It is certified that error appears in the above-identified patent and that said Letters Patent is hereby corrected as shown below:

In the Claims

In Claim 2, Column 327, Line 27, delete "-substrate"

Signed and Sealed this
Sixteenth Day of September, 2025

Coke Morgan Stewart
*Acting Director of the United States Patent and Trademark Office*